US010272148B2

(12) United States Patent
Couture et al.

(10) Patent No.: US 10,272,148 B2
(45) Date of Patent: Apr. 30, 2019

(54) CHIMERIC INFLUENZA VIRUS-LIKE PARTICLES COMPRISING HEMAGGLUTININ

(75) Inventors: Manon Couture, St-Augustin-de-Desmaures (CA); Michele Dargis, Quebec (CA); Pierre-Olivier Lavoie, Quebec (CA); Louis-Philippe Vezina, Neuville (CA); Marc-Andre D'Aoust, Quebec (CA)

(73) Assignee: MEDICAGO INC., Quebec (CA)

(*) Notice: Subject to any disclaimer, the term of this patent is extended or adjusted under 35 U.S.C. 154(b) by 0 days.

(21) Appl. No.: 13/380,346

(22) PCT Filed: Jun. 25, 2010

(86) PCT No.: PCT/CA2010/000983

§ 371 (c)(1), (2), (4) Date: Apr. 17, 2012

(87) PCT Pub. No.: WO2010/148511

PCT Pub. Date: Dec. 29, 2010

(65) Prior Publication Data

US 2012/0189658 A1 Jul. 26, 2012

Related U.S. Application Data

(60) Provisional application No. 61/220,161, filed on Jun. 24, 2009.

(51) Int. Cl.

| | |
|---|---|
| ***A61K 39/145*** | (2006.01) |
| ***C07K 14/11*** | (2006.01) |
| ***C12N 15/09*** | (2006.01) |
| ***C12N 15/82*** | (2006.01) |
| ***C07K 14/005*** | (2006.01) |
| ***A61K 39/12*** | (2006.01) |
| *A61K 39/00* | (2006.01) |

(52) U.S. Cl.

CPC ............ *A61K 39/145* (2013.01); *A61K 39/12* (2013.01); *C07K 14/005* (2013.01); *C12N 15/8257* (2013.01); *A61K 2039/5258* (2013.01); *C07K 2319/00* (2013.01); *C07K 2319/02* (2013.01); *C12N 2760/16122* (2013.01); *C12N 2760/16123* (2013.01); *C12N 2760/16134* (2013.01); *C12N 2760/16222* (2013.01); *C12N 2760/16223* (2013.01); *C12N 2760/16234* (2013.01)

(58) Field of Classification Search

None

See application file for complete search history.

(56) References Cited

U.S. PATENT DOCUMENTS

| | | | | |
|---|---|---|---|---|
| 5,232,833 | A | 8/1993 | Sanders et al. | |
| 5,486,510 | A | 1/1996 | Bouic et al. | |
| 5,762,939 | A | 6/1998 | Smith et al. | |
| 5,858,368 | A | 1/1999 | Smith et al. | |
| 5,958,422 | A | 9/1999 | Lomonossoff | |
| 6,020,169 | A | 2/2000 | Lee et al. | |
| 6,042,832 | A | 3/2000 | Koprowski et al. | |
| 6,284,875 | B1 | 9/2001 | Turpen et al. | |
| 6,287,570 | B1 | 9/2001 | Foley | |
| 6,326,470 | B1 | 12/2001 | Cosgrove | |
| 6,489,537 | B1 | 12/2002 | Rea et al. | |
| 6,867,293 | B2 * | 3/2005 | Andrews et al. | 536/23.6 |
| 7,125,978 | B1 | 10/2006 | Vezina et al. | |
| 7,132,291 | B2 | 11/2006 | Cardineau et al. | |
| 7,763,450 | B2 | 7/2010 | Robinson et al. | |
| 8,124,103 | B2 | 2/2012 | Yusibov et al. | |
| 8,519,113 | B2 | 8/2013 | Lomonossoff | |
| 8,697,088 | B2 | 4/2014 | Smith et al. | |
| 8,771,703 | B2 | 7/2014 | Couture et al. | |
| 9,546,375 | B2 | 1/2017 | Couture et al. | |
| 2001/0006950 | A1 | 7/2001 | Punnonen et al. | |
| 2003/0079248 | A1 | 4/2003 | Mason et al. | |
| 2004/0002061 | A1 | 1/2004 | Kawaoka | |
| 2005/0048074 | A1 * | 3/2005 | Cardineau et al. | 424/186.1 |
| 2005/0223430 | A1 | 10/2005 | Bakker et al. | |
| 2006/0252132 | A1 | 11/2006 | Yang et al. | |
| 2007/0286873 | A1 | 12/2007 | Williams et al. | |
| 2008/0008725 | A1 | 1/2008 | Weeks-Levy et al. | |
| 2008/0057538 | A1 | 3/2008 | Belyaev | |

(Continued)

FOREIGN PATENT DOCUMENTS

| | | | |
|---|---|---|---|
| CA | 2 693 956 | A1 | 1/2009 |
| CA | 2615 372 | A1 | 1/2009 |

(Continued)

OTHER PUBLICATIONS

Horimoto et al (Journal of Virology, 77(14), pp. 8031-8038, 2003).*
Kaverin et al (J. of Virol, 78(1), pp. 240-249, 2004).*
Doyle et al (JCB, 103, pp. 1193-1204, 1986).*
Chen et al (J. Virol. 81(13), pp. 7111-7123, 2007); cited on IDS.*
Gomord et al (TRENDS in Biotechnology, 23(11), pp. 559-565, 2005).*
Giddings et al (Nature Biotechnology, 18, pp. 1151-1155, 2000).*
Copeland et al (J. Virol., 79(10), pp. 6549-6471, 2005).*
Yang et al (Science, 317(5839), pp. 8250828, 2007).*
Wang et al (J. Virol., 2007, 81(20): 10869-10878).*
Horimoto et al (Microbes and Infection, 2004, 6(6): 579-583).*

(Continued)

*Primary Examiner* — Stephen Uyeno
(74) *Attorney, Agent, or Firm* — Sterne, Kessler, Goldstein & Fox P.L.L.C.

(57) ABSTRACT

A method for synthesizing chimeric influenza virus-like particles (VLPs) within a plant or a portion of a plant is provided. The method involves expression of chimeric influenza HA in a plant or a portion of a plant. The invention is also directed towards a VLP comprising chimeric influenza HA protein and plants lipids. The invention is also directed to a nucleic acid encoding chimeric influenza HA as well as vectors. The VLPs may be used to formulate influenza vaccines, or may be used to enrich existing vaccines.

17 Claims, 49 Drawing Sheets

Specification includes a Sequence Listing.

(56) References Cited

U.S. PATENT DOCUMENTS

| | | | |
|---|---|---|---|
| 2009/0311669 | A1 | 12/2009 | Kawaoka |
| 2010/0143406 | A1 | 6/2010 | Smith et al. |
| 2010/0167376 | A1 | 7/2010 | Hogan et al. |
| 2010/0239610 | A1 | 9/2010 | D'Aoust et al. |
| 2010/0310604 | A1 | 12/2010 | D'Aoust et al. |
| 2011/0191915 | A1 | 8/2011 | Couture et al. |
| 2011/0293650 | A1 | 12/2011 | D'Aoust et al. |
| 2012/0189658 | A1 | 7/2012 | Couture et al. |

FOREIGN PATENT DOCUMENTS

| | | | |
|---|---|---|---|
| CA | 2 707 235 | A1 | 6/2009 |
| JP | 5551780 | B2 | 7/2014 |
| NZ | 598508 | A | 2/2014 |
| WO | WO 86/03224 | A1 | 6/1986 |
| WO | WO 00/56906 | A1 | 9/2000 |
| WO | WO 02/074795 | A2 | 9/2002 |
| WO | WO 03/068163 | A2 | 8/2003 |
| WO | WO 03/068923 | A2 | 8/2003 |
| WO | WO 03/068993 | A1 | 8/2003 |
| WO | WO 2004/003207 | A1 | 1/2004 |
| WO | WO 2004/098530 | A2 | 11/2004 |
| WO | WO 2004/098533 | A2 | 11/2004 |
| WO | WO 2005/020889 | A2 | 3/2005 |
| WO | WO 2006/119516 | A2 | 11/2006 |
| WO | WO 2007/011904 | A2 | 1/2007 |
| WO | WO 2007/019094 | A2 | 2/2007 |
| WO | WO 2007/047831 | A2 | 4/2007 |
| WO | WO 2007/095318 | A2 | 8/2007 |
| WO | WO 2007/130327 | A2 | 11/2007 |
| WO | WO 2008/005777 | A2 | 1/2008 |
| WO | WO 2008/054540 | A2 | 5/2008 |
| WO | WO 2008/060669 | A2 | 5/2008 |
| WO | WO 2008/061243 | A2 | 5/2008 |
| WO | WO 2008/087391 | A1 | 7/2008 |
| WO | WO 2008/148104 | A1 | 12/2008 |
| WO | WO 2008/151440 | A1 | 12/2008 |
| WO | WO 2009/008573 | A1 | 1/2009 |
| WO | WO 2009/009876 | A1 | 1/2009 |
| WO | WO 2009/026397 | A2 | 2/2009 |
| WO | WO 2009/076778 | A1 | 6/2009 |
| WO | WO 2009/087391 | A1 | 7/2009 |
| WO | WO 2010/003225 | A1 | 1/2010 |
| WO | WO 2010/006452 | A1 | 1/2010 |
| WO | WO 2010/025285 | A1 | 3/2010 |
| WO | WO 2010/077712 | A1 | 7/2010 |
| WO | WO 2011/035423 | A1 | 3/2011 |

OTHER PUBLICATIONS

Spitsin et al (Vaccine, 27, pp. 1289-1292, 2009; cited on IDS dated Dec. 31, 2014).*

Li et al (Journal of Virology, 1992, 66(1): 399-404; cited on IDS dated Dec. 31, 2014).*

Sainsbury et al (Plant Biotechnology Journal, 2008, 6(1): 82-92; cited on IDS dated Aug. 7, 2012).*

Sagawa et al (Journal of General Virology, 1996, 77: 1483-1487).*

Air, G.M., "Sequence relationships among the hemagglutinin genes of 12 subtypes of influenza A virus," *Proc. Natl. Acad. Sci. USA* 78(12):7639-7643, National Academy of Sciences, United States (1981).

Arntzen, C. and Dodet, B., "Plant-derived vaccines and antibodies: potential and limitations," *Vaccine* 23:1753-1756, Elsevier Ltd., England (2005).

Bao, Y., et al., "The Influenza Virus Resource at the National Center for Biotechnology Information," *J. Virol.* 82(2):596-601, American Society for Microbiology, United States (2007).

Berger, A., et al., "Plant sterols: factors affecting their efficacy and safety as functional food ingredients," *Lipids Health Dis.* 3:5, 19 pages, BioMed Central Ltd., England (2004).

Berman, H., et al., "Announcing the worldwide Protein Data Bank," *Nat. Struct. Biol.* 10(12):980, Nature Publishing Group, England (2003).

Borisjuk et al., "Expression of avian flu antigen for bird immunization," *Plant Biology & Botany 2007 Joint Commission*, 2 pages, Botanical Society of America, United States (2007) available at <http://2007.botanyconference.org/engine/search/index.php?func=detail&aid=1410>.

Bouic, P.J.D. and Lamprecht, J.H., "Plant Sterols and Sterolins: A Review of Their Immune-Modulating Properties", *Alter. Med. Rev.* 4:170-177, Alternative Medicine Review, United States (1999).

Bouic, P., "The role of phytosterols and phytosterolins in immune modulation: a review of the past 10 years," *Current Opinion in Clinical Nutrition & Metabolic Care*, 4(3):471-475, Thorne Research, Inc., England (2001).

Bouic, P.J.D., "Sterols and sterolins: new drugs for the immune system?" *Drug Discovery Today*, 7:775-778, Lippincott Williams & Wilkins, United States (2002).

Brigneti, G., et al., "Viral pathogenicity determinants are suppressors of transgenesilencing in *Nicotiana benthamiana*," *The EMBO Journal* 17(22):6739-6746, Oxford University Press England (1998).

Chandler, G.L., "Influenza Hemagglutinin Expression in Nicotiana trabacum and Nicotiana benthamiana," Masters in Science Thesis, Baylor University, Waco, Texas, 2007, 70 pages.

Chandrasekaran, A., et al., "Glycan topology determines human adaptation of avian H5N1 virus hemagglutinin," *Nature Biotechnology*, 26(1):107-113, Nature Publishing Group, England (Jan. 2008).

Charland, N., et al., "An Innovative VLP-based Technology to Respond to Global Influenza Vaccine Needs," Poster Abstracts, IDSA Seasonal and Pandemic Influenza Meeting, Arlington, Virginia, USA (May 2008).

Chen, B.J., et al., "Influenza Virus Hemagglutinin and Neuraminidase, but Not the Matrix Protein, Are Required for Assembly and Budding of Plasmid-Derived Virus-Like Particles," *J. Virol.* 81(13):7111-7123, American Society for Microbiology, United States (2007).

Chen, Z., et al., "Stabilizing the glycosylation pattern of influenza B hemagglutinin following adaptation to growth in eggs," *Vaccine* 26:361-371, Elsevier Ltd., England (Jan. 2008).

Chiba, M., et al., "Diverse suppressors of RNA silencing enhance agroinfection by a viral replicon," *Virology* 34627-14, Elsevier Inc., United States (2005).

Crawford, J ., et al,. "Baculovirus-derived hemagglutinin vaccines protect against lethal influenza infections by avian H5 and H7 subtypes," *Vaccine* 17:2265-2274, Elsevier Science Ltd., England(1999).

Cross, K.J., et 1., "Studies on influenza haemagglutinin fusion peptide mutants generated by reverse genetics," *EMBO J.* 20(16):4432-4442, European Molecular Biology Organization, England (2001).

D'Aoust, M-A., et al., "Influenza Virus-like particles produced by transient expression in Nicotiana benthamiana induce a protective immune response against a lethal viral challenge in mice," *Plant Biotechnol. J.* 6930-940, Blackwell Publishing Ltd., England (Dec. 2008).

D'Aoust, M-A., et al., "The production of hemagglutinin-based virus-like particles in plants: a rapid, efficient and safe response to pandemic influenza," *Plant Biotechnol. J.* 8:1-13, Blackwell Publishing Ltd., England (Jun. 2010).

Diaz-Vivancos, P., et al., "The apoplastic antioxidant system in *Prunus*: response to long-term plum pox virus infection," *J. Exp. Bot.* 57(14):38 13-3 824, Oxford University Press, England (2006).

Fischer, R, et al., "Towards molecular farming in the future: transient protein expression in plants," *Biotechnol. Appl. Biochem.* 302113-116, Portland Press Ltd., England (1999).

Fischer, R., et al., "Affinity-purification of a TMV-specific recombinant full-size antibody from a transgenic tobacco suspension culture," *J. Immunol. Methods* 226:1-10, Elsevier Science B.V., Netherlands (1999).

Flandorfer, A., et al., "Chimeric Influenza A Viruses with a Functional Influenza B Virus Neuraminidase or Hemagglutinin," *J. Virol.* 77(17):9116-9123, American Society for Microbiology, United States (2003).

Frugis, G., et al., "MsJ1, an alfalfa DnaJ-like gene, is tissue-specific and transcriptionally regulated during cell cycle," *Plant Mol. Biol.* 40:397-408, Kluwer Academic Publishers, Netherlands (1999).

(56) References Cited

OTHER PUBLICATIONS

Galarza, J.M., et al., "Virus-Like Particle (VLP) Vaccine Conferred Complete Protection against a Lethal Influenza Virus Challenge," *Viral Immunol.* 18(1):244-251, Mary Ann Liebert, Inc., United States (2005).
Gallagher, P., et al., "Addition of Carbohydrate Side Chains at Novel Sites on Influenza Virus Hamagglutinin Can Modulate the Folding, Transport, and Activity of the Molecule,"*J. Cell Biol.* 107(6):2059-2073, The Rockefeller University Press, United States (1988).
Gallagher, P.J., et al., "Glycosylation Requirements for Intracellular Transport and Function of the Hemagglutinin of Influenza Virus," *J. Virol.* 66(12):7136-7145, American Society for Microbiology, United States (1992).
Gamblin, S.J., et al., "The Structure and Receptor Binding Properties of the 1918 Influenza Hemagglutinin,"*Science* 303:1838-1842, American Association for the Advancement of Science, United States (2004).
Garcea, R.L. and Gissmann, L., "Virus-like particles as vaccines and vessels for the delivery of small molecules," *Curr. Opin. Biotechnol.* 15:513-517, Elsevier Ltd., England (2004).
Garten, R.J., et al., "Influenza A Virus (A/California/04/2009(H1N1)) segment 4 hemagglutinin (HA) gene, complete cds," GenBank Accession No. FJ966082, NCBI Entrez Nucleotide, 2 pages, accessed Aug. 28, 2010 at <www.ncbi.nlm.nih.gov/nuccore/227809829>.
Gillim-Ross, L. and Subbarao, K., "Emerging Respiratory Viruses: Challenges and Vaccine Strategies," *Clin. Microbiol. Rev.* 19(4):614-636, American Society for Microbiology, United States (2006).
Gömez-Puertas, P., et al., "Efficient formation of influenza virus-like particles: dependence on the expression levels of viral proteins," *J. Gen. Vir.* 80:1635-1645, SGM, England (1999).
Gömez-Puertas, P., et al., "Influenza Virus Matrix Protein is the Major Driving Force in Virus Budding," *J. Virol.* 74(24):11538-11547, American Society for Microbiology, United States (2000).
Grgacic, E.V.L. and Anderson, D.A., "Virus-like particles: Passport to immune recognition," *Methods* 40:60-65, Elsevier Inc., United States (2006).
Gupta, R., et al., "O-GLYCBASE version 4.0: a revised database of O-glycosylated proteins," *Nucleic Acids Res.* 27(1):370-372, Oxford University Press, England (1999).
Hahn, B-S., et al., "Expression of hemagglutinin-neuraminidase protein of Newcastle disease virus in transgenic tobacco," *Plant Biotechnol. Rep.* 1:85-92, Korean Scociety for Plant Technology and Springer, Japan (2007).
Hamilton, A., et al., "Two classes of short interfering RNA in RNA silencing," *EMBO J.* 21(17):4671-4679, European Molecular Biology Organization, England (2002).
Harbury, P.B., et al., "A Switch Between Two-, Three-, and Four-Stranded Coiled Coils in GCN4 Leucine Zipper Mutants," *Science* 262:1401-1407, American Association for the Advancement of Science, Untied States (1993).
Hartl, F.U., "Molecular chaperones in cellular protein folding," *Nature* 381(13):571-580, Nature Publishing Group, England (1996).
NCBI Entrez, Genbank Report, Accession No. FJ966082, Influenza A Virus (A/California/04/2009 H1N1), Dawood et al., collection date Apr. 2009, 3 pages.
Horimoto, T., et al., "Generation of Influenza A Viruses with Chimeric (Type A/B) Hemagglutinins," *J. Virol.* 77(14):8031-8038, American Society for Microbiology, United States (2003).
Huang, Z., et al., "Plant-derived measles virus hamagglutinin protein induces neutralizing antibodies in mice," *Vaccine* 19:2163-2171, Elsevier Science Ltd., England (2001).
Huang, Z., et al., "Virus-like Particle expression and assembly in plants: hepatitis B and Norwalk viruses," *Vaccine* 23:1851-1858, Elsevier Ltd., England (2005).
Ito, T., et al., "Receptor Specificity of Influenza A Viruses Correlates with the Agglutination of Erythrocytes from Different Animal Species," *Virology* 227:493-499, Academic Press, United States (1997).
Johansson, B.E., "Immunization with influenza A virus hemagglutinin and neuraminidase produced in recombinant baculovirus results in a balanced and broadened immune response superior to conventional vaccine," *Vaccine* 17:2073-2080, Elsevier Science Ltd., England (1999).
Knossow, M. and SkeheL, J.J., "Variation and infectivity neutralization in influenza," *Immunology* 119:1-7, Blackwell Publishing Ltd,, England (2006).
Latham, T. and Galarza, J.M., "Formation of Wild-Type and Chimeric Influenza Virus-Like Particles following Simultaneous Expression of Only Four Structural Proteins," *J. Virol.* 75(13):6154-6165, American Society for Microbiology, United States (2001).
Lefebvre, B., et al., "Characterization of Lipid rafts from *Medicago truncatula* Root Plasma Membranes: A Proteomic Study Reveals the Presence of a Raft-Associated Redox System," *Plant Physiology* 144:402-418, American Society of Plant Biologists, United States (2007).
Lin, B-L., et al., "Genomic analysis of the Hsp70 superfamily in *Arabidopsis thaliana," Cell Stress Chaperones* 6(3):201-208, Cell Stress Society International, Netherlands (2001).
Liu, L. and Lomonossoff, G.P., "Agroinfection as a rapid method for prepagating *Cowpea mosaic* virus-based constructs," *J. Virol. Methods* 105:343-348, Eisevier Science B.V., Netheriands (2002).
Low, D., et al., "Future of antibody purification," *J. Chromatogr. B* 848:48-63, Elsevier B.V., Netherlands (2006).
Macala, L.J., et al., "Analysis of brain lipids by high performance thin-layer chromatography and densitometry," *J. Lipid Res.* 24:1243-1250, American Society for Biochemistry and Molecular Biology, United States (1983).
Macario, A.J.L., "Heat-shock proteins and molecular chaperones: implications for pathogenesis, diagnostics, and therapeutics," *Int. J. Clin. Lab. Res.* 25:59-70, Springer-Verlag, Germany (1995).
Mansour, M.M.F., et al., "Plasma membrane lipid alterations induced by NaCl in winter wheat roots," *Physiol. Plant.* 92:473-478, Physiologia Plantarum, Denmark (1994).
Marozin, S., et al., "Antigenic and genetic diversity among swine influencza A H1N1 and H1N2 viruses in Europe," *J. Gen. Virol.* 83 :735-745, SGM, England (2002).
Mason, H.S., et al., "Expression of Norwalk virus capsid protein in transgenic tobacco and potato and its oral immunogenicity in mice," *Proc. Natl. Acad, Sci. USA* 93:5335-5340, National Academy of Sciences, United States (1996).
McCauley, J.W. and Mahy, W.J., "Structure and function of the influenza virus genome," *Biochem. J.* 211:281-294, Portland Press, England (1983).
Medeiros, R., et al., "Hemagglutinin Residues of Recent Human A(H3N2) Influenza Viruses That Contribute to the Inability to Agglutinate Chicken Erythrocytes," *Virology* 289:74-85, Academic Press, United States (2001).
Mena, I., et al., "Rescue of a Synthetic Chloramphenicol Acetyltransferase RNA into Influenza Virus-Like Particles Obtained from Recombinant Plasmids," *J. Virol.* 70(8):5016-5024, American Society of Microbiology, United States (1996).
Meshcheryakova, Y.A., et al., "Cowpea Mosaic Virus Chimeric Particles Bearing the Ectodomain of Matrix Protein 2 (M2E) of the Influenza A Virus: Production and Characterization," *Mol. Biol.* 43(4):685-694, Pleiades Publishing, Inc., Russia (Jul. 2008).
Mett, V., et al., "A plant-produced influenza subunit vaccine protects ferrets against virus challenge," *Influenza Other Respi. Viruses* 2:33-40, Blackwell Publishing Ltd., England (Jan. 2008).
Mongrand, S., et a1., "Lipid Rafts in Higher Plant Cells," *J. Biol. Chem.* 279(35):36277-36286, The American Society for Biochemistry and Molecular Biology, Inc., United States (2004).
Musiychuk, K., et al., "A launch vector for the production of vaccine antigens in plants," *Influenza Other Respi. Viruses* 1:19-25, Blackwell Publishing Ltd., England (2007).
Nakahara, T., et al., "Glycoconjugate Data Bank: Structures—an annotated glycan structure database and N-glycan primary structure verification service," *Nucleic Acids Res.* 36:D368-D371, Oxford University Press, England (2007).

(56) References Cited

OTHER PUBLICATIONS

Nemchinov, L.G. and Natilla, A., "Transient expression of the ectodomain of matrix protein 2 (M2e) of avian influenza A Virus in plants," *Protein Expr. Purif.* 56:153-159, Elsevier Inc., United States (2007).
Neumann, G., et al., "Plasmid-Driven Formation of Influenza Virus-Like Particle," *J. Virol.* 74(1):1547-551, American Society for Microbiology, United States (2000).
Nuttall, J., et al., "ER-resident chaperone interactions with recombinant antibodies in transgenic plants," *Eur. J. Biochem.* 269:6042-6051, FEBS, England (2002).
Olsen, C.W., et al., "Immunogenicity and efficacy of baculovirus-expressed and DNA-based equine influenza virus hemagglutinin vaccines in mice," *Vaccine* 15(10):1149-1156, Elsevier Science Ltd., England (1997).
Parsell, D.A. and Lindquist, S., et al., "Tile Function Of Heat-Shock Proteins in Stress Tolerance: Degradation and Reactivation of Damaged Proteins," *Annu. Rev. Genet.* 27:2437-496, Annual Reviews Inc., United States. (1993).
Plotkin, J .B., et al., "Hemagglutinin sequence clusters and the antigenic evolution of influenza A Virus," *Proc. Natl. Acad. Sci.* 99(9):6263-6268, American Association for the Advancement of Science, United States (2002).
Pushko, P., et al., "Influenza virus-like particles comprised of the HA, NA, and M1 proteins of H9N2 influenza virus induce protective immune responses in BALB/c mice," *Vaccine* 23:5751-5759, Elsevier Science Ltd., England (2005).
Pwee, K-H. and GRAY, J.C., "The pea plastocyanin promoter directs cell-specific but not full light-regulated expression in transgenic tobacco plants," *Plant J* 3(3):437-449, Blackwell Scientific Publishers, England (1993).
Quan, F-S., et al., "Virus-Like Partile Vaccine Induces Protective Immunity against Homologous and Heterologous Strains of Influenza Virus," *J. Virol.* 81(7):3514-3524, American Society for Microbiology, United States (2007).
Regnard, G.L., et al., "High level protein expression in plants through the use of a novel autonomously replicating geminivirus shuttle vector," *Plant Biotechnol. J.* 8:38-46, Blackwell Publishing Ltd., England (Jan. 2010).
Rowe, T., et al., "Detection of Antibody to Avian Influenza A (H5N1) Virus in Human Serum by Using a Combination of Serologic Assays," *Journal of Clinical Microbiology* 37(4):937-943, American Society for Microbiology, United States (1999).
Roy, P. and Noad, R., "Virus-like particles as a vaccine delivery system," *Hum. Vaccin.* 4(6):5-8, Landes Bioscience, United States (Jan. 2008).
Sainsbury, F. and Lomonossoff, G.P., et al., "Extremely High-Level and Rapid Transient Protein Production in Plants without the Use of Viral Replication," *Plant Physiol.* 148:1212-1218, American Society of Plant Biologists, United States (Nov. 2008).
Sainsbury, F., et al., "Expression of multiple proteins using full-length and deleted versions of cowpea mosaic virus RNA-2," *Plant Biotechnol. J.* 6:82-92, Blackwell Publishing Ltd., England (2007).
Saint-Jore-Dupas, C., et al., "From planta to pharma with glycosylation in the toolbox," *Trends Biotechnol.* 25(7):317-323, Elsevier Ltd., England (2007).
Salzberg, S.L., et al., "Gamma Analysis Linking Recent European and African Influenza (H5N1) Viruses," *Emerg. Infect. Dis.* 13(5):733-718, National Center for Infectious Diseases, United States (2007).
Schillberg, S., et al., "Apoplastic and cytosolic expression of full-size antibodies and antibody fragments in *Nicotiana tabacum," Trangsgenic Res.* 8:255-263, Kluwer Academic Publishers, Netherlands (1999).
Schillberg, S., et al., "Molecular farming of recombinant antibodies in plants," *Cell. Mol. Life Sci.* 60:433-445, Birkhäuser Verlag, Switzerland (2003).
Shoji, Y., et al., "Plant-expressed HA as a seasonal influenza vaccine candidate," *Vaccine* 26:2930-2934, Elsevier Ltd., England (Jun. 2008).
Skehel, J.J . and Wiley, D.C., "Receptor Binding and Membrane Fusion in Virus Entry: The Influenza Hemagglutinin," *Annu. Rev. Biochem.* 69:2531-569, Annual Reviews, United States (2000).
Staehelin, L.A., "The plant ER: a dynamic organelle composed of a large number of discrete functional domains," *Plant J.* 11(6):1151-1165, Blackwell Scientific Publishers, England (1997).
Toukach, P., et al., "Sharing of worldwide distributed carbohydrate-related digital resources: online connection of the *Bacterial Carbohydrate Structure DataBase* and *GLYCOSCIENCES.de," Nucleic Acids Res.* 35 :D280-D286, Oxford University Press, England (2007).
Treanor, J.J ., et al., "Safety and Immunogenicity of a Baculovirus-Expressed Hemagglutinin Influenza Vaccine," *JAMA* 297(14):1577-1582, American Medical Association, United States (2007).
Vaccaro, L., et al., "Plasticity of Influenza Haemagglutinin Fusion Peptides and Their Interaction with Lipid Bilayers," *Biophys. J.* 88:25-36, The Biophysical Society, United States (2005).
Van Ree, R., et al., "β(1,2)-Xylose and α(1,3)-Fucose Residues Have a Strong Contriubtion in IgE Binding to Plant Glycoallergens," *J Biol. Chem.* 275(15):11451-11458, The American Society for Biochemistry and Molecular Biology, Inc., United States (2000).
Wagner, R., et al., "Interdependence of Hemagglutinin Glycosylation and Neuraminidase as Regulators of Influenza Virus Growth: a Study by Reverse Genetics," *J. Virol.* 74(14):6316-6323, American Society for Microbiology, United States (2000).
Wakefield, L. and Brownlee, G.G., "RNA-binding properties of influenza A virus matrix protein M1," *Nucleic Acids Res.* 17(21):8569-8580, IRL Press, England (1989).
Wang, K., et al., "Expression and purification of an influenza hemagglutinin—one step closer to a recombinant protein-based influenza vaccine," *Vaccine* 24:2176-2185, Elsevier Ltd., England (2006).
Wei, C-J., et al., "Comparative Efficacy of Neutralizing Antibodies Elicited by Recombinant Hemagglutinin Proteins from Avian H5N1 Influenza Virus," *J. Virol.* 82(13):6200-6208, American Society for Microbiology, United States (Jul. 2008).
Weldon, W.C., et al., "Enhanced Immunogenicity of Stabilized Trimeric Soluble Influenza Hemagglutinin," *PLoS One* 5(9):e12466, 8 pages, Public Library of Science, United States (Sep. 2010).
Wilson, I.B.H., et al., "Core α1,3-fucose is a key part of the epitope recognized by antibodies reacting against plant N-inked oligosaccharides and is present in a wide variety of plant extracts," *Glycobiology* 8(7):651-661, Oxford University Press, England (1998).
Office Action dated Jan. 20, 2012 in Canadian Patent Application No. 2,693,956, assignee Medicago Inc., filed Jul. 11, 2008.
Office Action dated Jan. 26, 2011 in Canadian Patent Application No. 2,693,956, assignee Medicago Inc., filed Jul. 11, 2008.
Office Action dated Sep. 22, 2011 in Canadian Patent Application No. 2,693,956, assignee Medicago Inc., filed Jul. 11, 2008.
Office Action dated Jun. 1, 2011 in Canadian Patent Application No. 2,707,235, assignee Medicago Inc., filed Jan. 12, 2009.
Office Action dated Oct. 28, 2011 in Canadian Patent Application No. 2,707,235, assignee Medicago Inc., filed Jan. 12, 2009.
Office Action dated Nov. 30, 2011 in Canadian Patent Application No. 2,730,185, assignee Medicago Inc., filed Nov. 30, 2011.
Office Action dated Apr. 27, 2012 in Canadian Patent Application No. 2,730,185, assignee Medicago Inc., filed Nov. 30, 2011.
Office Action dated Jun. 28, 2011 in Canadian Patent Application No. 2,730,185, assignee assignee Medicago Inc., filed Nov. 30, 2011.
Office Action dated Feb. 16, 2012 in Canadian Patent Application No. 2,762,042, assignee Medicago Inc., filed Jun. 25, 20101.
Translation of Office Action dated Apr. 6, 2012 in Chinese Patent Application No. 200980126670.5, assignee Medicago Inc., filed Jul. 7, 2009.
Translation of Office Action dated Sep. 27, 2011 in Chinese Patent Application No. 200880107072.9, assignee Medicago Inc., filed Jul. 11, 2008.
Translation of Office Action dated Jan. 21, 2012 in Chinese Patent Application No. 200980109781.5, Medicago, Inc., filed Jan. 12, 2009.

(56) References Cited

OTHER PUBLICATIONS

Supplementary European Search Report for European Patent Application No. EP 08 78 3201, European Patent Office, Germany, dated Sep. 13, 2010.
Supplementary European Search Report for European Patent Application No. EP 09 70 0061, European Patent Office, Germany, dated Mar. 7, 2011.
Supplementary European Search Report for European Patent Application No. EP 09 79 3741, Munich, European Patent Office, Germany, dated Aug. 9, 2011.
International Preliminary Report on Patentability for International Patent Application No. PCT/CA2009/000032, The International Bureau of WIPO, Switzerland, dated Jul. 27, 2010.
International Preliminary Report on Patentability for International Patent Application No. PCT/CA2009/00094l, The International Bureau of WIPO, Switzerland, dated Jan. 11, 2011.
International Preliminary Report on Patentability for International Patent Application No. PCT/CA2009/000926, Canadian Intellectual Property Office, Canadian Intellectual Property Office, Canada, dated Nov. 5, 2010.
International Search Report for International Patent Application No. PCT/CA2009/000926, Canadian Intellectual Property Office, Canada, dated Oct. 1, 2009.
International Search Report for International Patent Application No. PCT/CA2008/001281, Canadian Intellectual Property Office, Canada, dated Oct. 7, 2008.
International Search Report for International Patent Application No. PCT/CA2009/000032, Canadian Intellectual Property Office, Canada, dated Apr. 30, 2009.
International Search Report for International Patent Application No. PCT/CA2010/001489, Canadian Intellectual Property Office, Canada, dated Nov. 30, 2010.
International Search Report for International Patent Application No. PCT/CA2011/001427, Canadian Intellectual Property Office, Canada, dated Mar. 20, 2012.
International Search Report for International Patent Application No. PCT/CA2011/001228, Canadian Intellectual Property Office, Canada, dated Jan. 18, 2012.
International Preliminary Report on Patentability for International Application No. PCT/CA2008/001281, Canadian Intellectual Property Office, Canada, dated Nov. 12, 2009.
International Search Report for International Patent Application No. PCT/CA2009/000041, Canadian Intellectual Property Office, Canada, dated Sep. 10, 2009.
Communication pursuant to Article 94(3) EPC for European Patent Application No. EP 08 783 201.0, Canadian Intellectual Property Office, Canada, dated May 26, 2011.
Office Action dated Mar. 8, 2011 in Vietnamese Patent Application No. 1-2012-00186, assignee Medicago Inc., filed Jan. 19, 2012.
Office Action dated Nov. 8, 2010 in New Zealand Patent Application No. 582360, assignee Medicago Inc., filed Feb. 13, 2010.
Office Action dated Apr. 15, 2011 in New Zealand Patent Application No. 590144, assignee Medicago Inc., filed Feb. 11, 2011.
Office Action dated Apr. 18, 2012 in Singapore Patent Application No. 201009568-5, assignee Medicago Inc., filed Jul. 2, 2009.
Office Action dated Mar. 2, 2011 in Singapore Patent Application No. 201000090-9, assignee Medicago Inc., filed Jul. 11, 2008.
Office Action dated Feb. 11, 2010 in Eurasian Patent Organization (EAPO) Patent Application No. 201000195/28, Russia.
Supplementary European Search Report for European Patent Application No. EP 09 79 3751, European Patent Office, Germany, completed Sep. 19, 2011.
Office Action dated Nov. 27, 2011 in Egyptian Patent Application No. PCT1222/2010, assignee Medicago Inc., Cairo, Egypt.
Asahi-Ozaki et al., "Intranasal administration of adjuvant-combined recombinant influenza virus HA vaccine protects mice from the lethal H5N1 virus infection," *Microbes and Infection* (2006) 8:2706-2714, Elsevier Masson SAS, France.
Bilang, R. et al. "The 3'-terminal region of the hygromycin-B-resistance gene is important for its activity in *Escherichia coli* and *Nicotiana tabacum," Gene* (1991) 100:247-250, Elsevier Science Publishers B.V., Netherlands.
Bright, R.A., et al., "Influenza virus-like particles elicit broader immune responses than whole virion inactivated influenza virus or recombinant hemagglutinin," *Vaccine* (2007) 25:3871-3878, Elsevier Ltd., England.
Bright, R.A., et al. "Impact of glycosylation on the immunogenicity of a DNA-based influenza H5 HA vaccine," *Virology* (2003) 308: 270-278, Elsevier Science, United States.
Firek, S., et al. "Secretion of a functional single-chain Fv protein in transgenic tobacco plants and cell suspension cultures," *Plant Molecular Biology* (1993) 23:861-870, Kluwer Academic Publishers, Belgium.
Garten, R.J., et al. "Antigenic and Genetic Characteristics of Swine-Origin 2009 A(H1N1) Influenza Viruses Circulating in Humans," *Science* (Jul. 2009) 325:197-201, American Association for the Advancement of Science, United States.
Giritch, A. et al. "Rapid high-yield expression of full-size IgG antibodies in plants coinfected with noncompeting viral vectors," *Proc. Natl. Acad. Sci. U.S.A.* (2006) 103:14701-14706, The National Academy of Science of the USA, United States.
Hiatt, A. and Pauly, M., "Monoclonal antibodies from plants: A new speed record," *Proc. Natl. Acad. Sci. U.S.A.* (2006) 103:14645-14646, The National Academy of Science of the USA, United States.
Hiatt, A., et al. "Production of antibodies in transgenic plants" *Nature* (1989) 342:76-78, Nature Publishing Group, England.
Houston, N.L., et al. "Phylogenetic Analyses Identify 10 Classes of the Protein Disulfide Isomerase Family in Plants, Including Single-Domain Protein Disulfide Isomerase-Related Proteins," *Plant Physiology* (2005) 137:762-778, American Society of Plant Biologists, United States.
Huang, Z., et al. "A DNA Replicon System for Rapid High-Level Production of Virus-Like Particles in Plants," *Biotechnol. Bioeng.* (Jul. 2009) 103(4):706-714, Wiley Periodicals, Inc., United States.
Huang, Z., et al. "High-Level Rapid Production of Full-Size Monoclonal Antibodies in Plants by a Single-Vector DNA Replicon System," *Biotechnol. Bioeng.* (May 2010) 106(1):9-17, Wiley Periodicals, Inc., United States.
Certificate of granted patent 2011/01231 of Republic of South Africa dated Oct. 26, 2011.
Richter, L.J., et al. "Production of hepatitis B surface antigen in transgenic plants for oral immunization," *Nature Biotechnology* (2000) 18:1167-1171, Nature America Inc., United States.
Shorrosh, B.S. and Dixon, R.A., "Molecular cloning of a putative plant endomembrane protein resembling vertebrate protein disulfide-isomerase and a phosphatidylinositol-specific phospholipase C," *Proc. Natl. Acad. Sci. USA* (1991) 88(23):10941-10945, National Academy of Sciences, United States.
Certificate of granted patent from The Registry of Patents Singapore, Patent No. 158301 dated Apr. 30, 2012.
Twyman, R.M., et al. "Molecular farming in plants: host systems and expression technology," *TRENDS in Biotechnology* (2003) 21(12) :570-578, Elsevier Ltd., England.
Vézina, L-P. et al. "Transient co-expression for fast and high-yield production of antibodies with human-like N-glycans in plants," *Plant Biotechnology Journal* (Jun. 2009) 7(5):442-455, Blackwell Publishing Ltd., England.
Weissenhorn, W., et al. "Assembly of a rod-shaped chimera of a trimeric GCN4 zipper and the HIV-1 gp41 ectodomain expressed in *Escherichia coli," Proc. Natl. Acad. Sci. USA* (1997) 94:6065-6069, The National Academy of Sciences, United States.
Wydro, M. et al. "Optimization of transient *Agrobacterium*-mediated gene expression system in leaves of *Nicotiana bentharniana," Acta Biochimica Polonica* (2006) 53(2):289-298, Panstwowe Wydawnictwo Naukowe, Poland.
Nucleotide sequence of"Influenza A virus (A/New Caledonia/20/99(H1N1)) hemagglutinin (HA) gene, complete cds," GenBank Accession No. AY289929 (2003).
Nucleotide sequence of "M.sativa mRNA for protein disulfide isomerase," GenBank Accession No. Z11499 (2006).

(56) References Cited

OTHER PUBLICATIONS

Office Action dated Sep. 6, 2012 in Canadian application CA 2,615,372.
Office Action dated Oct. 16, 2012 in Canadian application CA 2,693,956.
Office Action dated Mar. 1, 2013 in Canadian application CA 2,693,956.
Office Action dated Jun. 7, 2012 in Canadian application CA 2,707,235.
Office Action dated Sep. 28, 2012 in Canadian application CA 2,707,235.
Office Action dated Mar. 1, 2013 in Canadian application CA 2,707,235.
Office Action dated Sep. 6, 2012 in Canadian application CA 2,730,185.
Notice of Allowance dated Jun. 29, 2012 in Canadian application CA 2,762,042.
English translation of Chinese Office Action dated Nov. 27, 2012 in Chinese application CN 200980109781.5.
English translation of Chinese Office Action dated Nov. 5, 2012 in Chinese application CN 200980126670.5.
English translation of Chinese Office Action dated Mar. 15, 2013 in Chinese application CN 200980126670.5.
English translation of Chinese Office Action dated Jul. 24, 2012 in Chinese application CN 200880107072.9.
English translation of Chinese Office Action dated Feb. 21, 2013 in Chinese application CN 200880107072.9.
English translation of Chinese Office Action dated Jul. 16, 2012 in Chinese Application CN 200980134868.8.
English translation of Chinese Office Action dated Jan. 15, 2013 in Chinese application CN 200980134868.8.
English translation of Chinese Office Action dated Mar. 8, 2013 in Chinese application CN 200980136376.2.
English translation of Russian Office Action in Eurasian application EA 20100195/28.
English translation of Russian Office Action dated Aug. 28, 2012 in Eurasian application EA 201001198.
European Office Action dated Oct. 26, 2012 in European application EP 08783201.0.
European Decision to Grant dated Aug. 17, 2012 in European application EP 09700061.6.
European Search Report dated Dec. 20, 2011 in European application EP 09797336.
European Examination Report dated Aug. 23, 2012 in European application EP 09793751.0.
European Extended Search Report dated Jan. 3, 2013 in European application EP 10818191.8.
European Extended Search Report dated Feb. 15, 2013 in European application EP 12181077.4.
English translation of Office Action dated Oct. 8, 2012 in Indonesian application ID W-00201002481.
English translation of Office Action dated May 8, 2012 in Israeli application IL 203018.
English translation of Office Action dated May 9, 2012 in Israeli application IL 206967.
English translation of Office Action dated Oct. 25, 2012 in Israeli application IL 210215.
English translation of Office Action dated Nov. 25, 2012 in Israeli application IL 210451.
International Preliminary Report on Patentability in PCT/CA2011/001228 dated Dec. 4, 2012.
International Search Report in PCT/CA2009/001040 dated Nov. 10, 2009.
English translation of Office Action dated Mar. 6, 2013 (together with untranslated version) in Mexican application MX/a/2010/000525.
English translation of Office Action dated Mar. 6, 2013 (together with untranslated version) in Mexican application MX/a/2010/007962.
English translation of Office Action dated Mar. 6, 2013 (together with untranslated version) in Mexican application MX/a/2011/000459.
English translation of Office Action dated Sep. 19, 2012 (together with untranslated version) in Mexican application MX/a/2011/000657.
New Zealand 582360 Letters Patent Aug. 6, 2012.
New Zealand 587108 Examination Report dated Mar. 21, 2011.
New Zealand 587108 Examination Report dated Jun. 27, 2012.
New Zealand 587108 Examination Report dated Jan. 28, 2013.
New Zealand 590351 Examination Report dated May 4, 2011.
New Zealand 597401 Examination Report dated Jul. 9, 2012.
New Zealand 598508 Examination Report dated Nov. 15, 2012.
English translation of Office Action dated Mar. 13, 2013 in Thailand application TH 1101003761.
Restriction Requirement dated Aug. 13, 2012 in U.S. Appl. No. 12/669,033.
Office Action dated Oct. 4, 2012 in U.S. Appl. No. 12/669,033.
Restriction Requirement dated Sep. 27, 2012 in U.S. Appl. No. 12/863,772.
Office Action dated Dec. 14, 2012 in U.S. Appl. No. 12/863,772.
Restriction Requirement dated Dec. 6, 2012 in U.S. Appl. No. 13/001,111.
Office Action dated Apr. 2, 2013 in U.S. Appl. No. 13/001,111.
Restriction Requirement dated Mar. 25, 2013 in U.S. Appl. No. 13/748,531.
D'Aoust, M-A., et al., "The production of hemagglutinin-based virus-like particles in plants: a rapid, efficient and safe response to pandemic influenza," *Plant Biotechnology Journal* 8:607-619, Blackwell Publishing Ltd., England (Jun. 2010).
Novel Swine-Origin Influenza A (H1N1) Virus Investigation Team, "Emergence of a Novel Swine-Origin Influenza A (H1N1) Virus in Humans," *N Engl J Med* 360(25):2605-2615, Massachusetts Medical Society, United States (Jun. 2009).
Shorrosh, B.S. and Dixon, R.A., "Sequence analysis and developpment expression of an alfalfa protein disulfide isomerase," *Plant Molecular Biology* 19:2319-321, Kluwer Academic Publishers, Belgium (1992).
Bertioli, D.J., et al., "Transgenic plants and insect cells expressing the coat protein of arabis mosaic virus produce empty virus-like particles," *J. Gen Virol.* 72(8): 1801-1809, SGM, England (1991).
Eckert, D., et al., "Crystal Structure of GCN4-pIQI, a Trimeric Coiled Coil with Buried Polar Residues," *Journal of Molecular Biology* 284:859-865, Academic Press, United States (1998).
Ellis, R.J., "The molecular chaperone concept," *Semin Cell Biol* 1(1):1-9, Saunders Scientific Publications, United States (1990).
Klopfleisch, R., et al., "Neurotropism of Highly Pathogenic Avian Influenza Virus A/Chicken/Indonesia/2003 (H5N1) in Experimentally Infected Pigeons (*Columbia livia* f. *domestica*)," *Vet Pathol* 43:463-470, Karger, United States (2006).
Kobayashi, Y, et al., "Chaperones Hsp70 and Hsp40 Suppress Aggregate Formation and Apoptosis in Cultured Neuronal cells Expressing Truncated Androgen Receptor Protein with Expanded Polyglutamine Tract," *J Biol. Chem.* 25(12):8772-8778, The American Society for Biochemistry and Molecular Biology, Inc., United States (2000).
Lelivelt, C.L.C., et al., "Stable plastid transformation in lettuce (*Lactuca sativa* L.)," *Plant Molecular Biology* 58:763-774, Springer, Germany (2005).
Li, S., et al., "Influenza A Virus Transfectants with Chimeric Hemagglutinins Containing Epitopes from Different Subtypes," *Journal of Virology* 66(3):399-404, American Society for Microbiology, United States (1992).
Liu, L., et al., "Cowpea mosaic virus-based systems for the production of antigens and antibodies in plants," *Vaccine* 23:1788-1792, Elsevier Ltd., England (2004).
Ma, J.K.C., et al., "The Production of Recombinant Pharmaceutical Proteins in Plants," *Nature Reviews Genetics* 4(10):794-805, Nature Publishing Group, England (2003).
Mishin, V., et al., "Effect of Hemagglutinin Glycosylation on Influenza Virus Susceptibility to Neuraminidase Inhibitors," *Journal of Virology* 79(19):12416-12424, American Society for Microbiology, United States (2005).

(56) References Cited

OTHER PUBLICATIONS

Mori, S.I., et al., "A novel amino acid substitution at the receptor-bindnig site on the hemagglutinin of H3N2 influenza A viruses isolated from 6 cases with acute encephalopathy during the 1997-1998 season in Tokyo," *Archives of Virology* 144:147-155, Springer Verlag, Austria (1999).
Nobusawa, E., "Protective antigen of influenza virus," *Nihon Rinsho Japanese Journal of Clinical Medicine* 55(1):2719-2724, Nippon Rinsho Co., Japan (1997).
Rivard, D., et al., "An in-built proteinase inhibitor system for the protection of recombinant proteins recovered from transgenic plants," *Plant Biotechnology Journal* 4:359-368, Blackwell Publishing Ltd., England (2006).
Spitsin, S., et al., "Immunological assessment of plant-derived avian flu H5/HA1 variants," *Vaccine* 27:1289-1292, Elsevier Ltd., England (Feb. 2009).
Tatulian, S.A. and Tamm, L.K., "Secondary Structure, Orientation, Oligomerization, and Lipid Interactions of the Transmembrane Domain of Influenza Hemagglutinin," *Biochemistry* 39:496-507, American Chemical Society, United Sttaes (2000).
Warzecha, H., "Biopharmaceuticals from Plants: A Multitude of Options for Posttranslational Modifications," *Biotechnology and Genetic Engineering Reviews* 25:315-330, Taylor & Francis Ltd., England (Feb. 2008).
Whitelam, G.C., "The Production of Recombinant Proteins in Plants," *J Sci Food Agric* 68:1-9, SCI, England (1995).
Wiley, D.C. and Skehel, J.J., "The Structure and Function of the Hemagglutinin Membrane Glycoprotein of Influenza Virus," *Ann Rev Biochem* 56(1):365-394, Annual Reviews Inc., United States (1987).
Yang, Z., et al., "Immunization by Avian H5 Influenza Hemagglutinin Mutants with Altered Receptor Binding Specificity," *Science* 317:825-828, American Association for the Advancement of Science, United States (2007).
GenBank Report, Accession No. AFU70328, published Jul. 26, 2007, accessed at http://ibis.internal.epo/org/exam/dbfetch.jsp?id=GSP:AFU70328, accessed on Jan. 24, 2014.
GenBank Report, Accession No. EF541394.1, accessed at http://www.ncbi.nlm.nih/gov/nuccore/EF541394, accessed on Jul. 30, 2013.
Office Action dated May 21, 2013 in Australian Patent Application No. 2008278222, applicant Medicago Inc., filed Jul. 11, 2008.
Office Action dated Jun. 13, 2013 in Australian Patent Application No. 2009202819, applicant Medicago Inc., filed Jan. 12, 2009.
Office Action dated Mar. 26, 2014 in Australian Patent Application No. 2009267769, applicant Medicago Inc., filed Jul. 7, 2009.
Office Action dated Dec. 18, 2013 in Australian Patent Application No. 2010265766, applicant Medicago Inc., filed Jun. 25, 2010.
Notice of Allowance dated Aug. 14, 2013 in Canadian Patent Application No. 2,707,235, applicant Medicago Inc., filed Jan. 12, 2009.
Office Action dated Jun. 2, 2014 in Canadian Patent Application No. 2,730,185, applicant Medicago Inc., filed Jun. 2, 2014.
Notice of Allowance dated Aug. 7, 2013 in Canadian Patent Application No. 2,815,887, applicant Medicago Inc., filed Nov. 3, 2011.
Office Action dated Jul. 23, 2014 in Canadian Patent Application No. 2,821,574, applicant Medicago Inc., filed Dec. 22, 2011.
Office Action dated Jul. 23, 2013 in Chinese Patent Application No. 200980126670.5, applicant Medicago Inc., filed Jan. 7, 2011.
Office Action dated May 30, 2013 in Chinese Patent Application No. 200980134868.8, applicant Medicago Inc., filed Jul. 2, 2009.
Decision on Rejection dated Feb. 20, 2014 in Chinese Patent Application No. 200980134868.8, applicant Medicago Inc., filed Jul. 2, 2009.
Office Action dated Mar. 4, 2014 in Chinese Patent Application No. 201180064127.4, applicant Medicago Inc., filed Nov. 3, 2011.
Office Action dated Jun. 13, 2012 in Chinese Patent Application No. 200980136376.2, applicant Medicago Inc., filed Jul. 15, 2009.
Office Action dated Oct. 10, 2013 in Chinese Patent Application No. 200980136376.2, filed Jul. 15, 2009.
Office Action dated Jul. 1, 2014 in Chinese Patent Application No. 200980136376.2, filed Jul. 15, 2009.
Office Action dated Jun. 28, 2013 in Chinese Patent Application No. 201080035066.4, filed Jun. 25, 2010.
Office Action dated Feb. 19, 2014 in Chinese Patent Application No. 201080035066.4, filed Jun. 25, 2010.
Office Action dated Aug. 20, 2014 in Chinese Patent Application No. 201080035066.4, filed Jun. 25, 2010.
Office Action dated Jan. 13, 2014 in Chinese Patent Application No. 2013100216938, filed Jan. 12, 2009.
Office Action dated Sep. 23, 2014 in Chinese Patent Application No. 201310021693.8, filed Jan. 12, 2009.
Office Action dated Mar. 14, 2014 in Chinese Patent Application No. 201180065696.0, filed Dec. 22, 2011.
Office Action dated Dec. 26, 2013 in Eurasian Patent Application No. 201001198, filed Dec. 26, 2012.
Office Action dated Sep. 3, 2014 in Eurasian Patent Application No. 201001198, filed Dec. 26, 2012.
Office Action dated Aug. 27, 2013 in Egyptian Patent Application 2010010061, filed Dec. 1, 2010.
Office Action dated Sep. 3, 2014 in Egyptian Patent Application 2010010061, filed Dec. 1, 2010.
European Search Report dated Oct. 8, 2013 in European Patent Application No. 10 791 119, having an international filing date of Jun. 25, 2010.
Office Action dated May 31, 2013 in European Patent Application No. 08 78 3201, having an international filing date of Jul. 8, 2011.
Office Action dated Aug. 1, 2013 in European Patent Application No. 09 793 751, having an international filing date of Jul. 7, 2009.
Supplementary European Search Report dated Apr. 10, 2014 in European Patent Application No. 11 83 7364, having an international filed of Nov. 3, 2011.
Office Action dated Feb. 6, 2014 in European Patent Application No. 09 797 336, having an international filing date of Jul. 15, 2009.
Office Action dated Jul. 4, 2014 in European Patent Application No. 10 791 119, having an international filing date of Jun. 25, 2010.
Supplementary European Search Report dated Apr. 8, 2014 in European Patent Application No. 11 85 1176, having an international filing date of Dec. 22, 2011.
Office Action dated May 10, 2013 in Indonesian Patent Application No. W-00201002481, having an international filing date of Jan. 12, 2009.
Office Action dated Aug. 18, 2013 in Israeli Patent Application No. 203018, filed Jul. 11, 2008.
Office Action dated Mar. 30, 2014 in Israeli Patent Application No. 216937, filed Jun. 25, 2010.
Office Action dated Jan. 15, 2014 in Japanese Patent Application No. 2011-516934, filing date Oct. 27, 2011.
Office Action dated Jul. 17, 2013 in Japanese Patent Application No. 2010-516334, filing date Oct. 21, 2010.
Office Action dated Jan. 15, 2014 in Japanese Patent Application No. 2010-516334, filed Oct. 21, 2010.
Office Action dated Aug. 30, 2013 in Japanese Patent Application No. 2010-542486, filed Mar. 31, 2011.
Office Action dated Jan. 6, 2014 in Japanese Patent Application No. 2011-516935, filed Oct. 27, 2011.
Office Action dated Feb. 13, 2014 in Japanese Patent Application No. 2011-517725, filed Nov. 17, 2011.
Office Action dated May 28, 2013 in Japanese Patent Application No. 2012-516452, filed Dec. 6, 2012.
Office Action dated Dec. 3, 2013 in Japanese Patent Application No. 2012-516452, filed Dec. 6, 2012.
Office Action dated Jul. 18, 2014 in Japanese Patent Application No. 2012-516452, filed Dec. 6, 2012.
Office Action dated Aug. 7, 2013 in Korean Patent Application No. 10-2012-7001798, filed Jan. 20, 2012.
Office Action dated Sep. 15, 2014 in Malaysian Patent Application No. PI201000142, filed Jul. 11, 2008.
Office Action dated Dec. 5, 2013 in Mexican Patent Application No. MX/a/2010/007962, filed Jul. 7, 2009.
Office Action dated May 20, 2013 in Mexican Patent Application No. MX/a/2011/000657, filed Jul. 15, 2009.

(56) References Cited

OTHER PUBLICATIONS

Office Action dated Oct. 29, 2013 in Mexican Patent Application No. MX/a/2011/000657, filed Jul. 15, 2009.
Office Action dated Jul. 2, 2014 in Mexican Patent Application No. MX/a/2011/000657, filed Jul. 15, 2009.
Office Action dated Nov. 29, 2013 in New Zealand Patent Application No. 612603, filed Jun. 27, 2013.
Office Action dated Apr. 5, 2013 in Russian Patent Application No. 2011105073/10, filed Jul. 2, 2009.
Office Action dated Oct. 21, 2013 in Russian Patent Application No. 2011105073/10, filed Jul. 2, 2009.
Office Action dated Aug. 1, 2013 in Russian Patent Application No. 2011105885/10, filed Jul. 15, 2009.
Office Action dated Feb. 27, 2014 in Russian Patent Application No. 2011105885/10, filed Jul. 15, 2009.
Office Action dated Jun. 26, 2014 in Russian Patent Application No. 2012101946/10, filed Jun. 25, 2010.
Written Opinion in Singaporean Patent Application No. 201304594-3, filed Dec. 22, 2011.
Certificate of South African Patent, issued Oct. 30, 2013 in South African Patent Application No. 2010/05917, filed Aug. 19, 2010.
Office Action dated Sep. 18, 2014 in Thailand Patent Application No. 1101003761, filed Dec. 21, 2011.
Notice of Allowance dated Oct. 28, 2013 in U.S. Appl. No. 13/001,111, § 371 (c) date Dec. 23, 2010.
Office Action dated Jul. 12, 2013 in U.S. Appl. No. 13/054,452, § 371 (c) date Apr. 19, 2011.
Office Action dated May 8, 2014 in U.S. Appl. No. 13/054,452, § 371 (c) date Apr. 19, 2011.
Office Action dated Nov. 25, 2013 in U.S. Appl. No. 13/734,886, filed Jan. 4, 2013.
Office Action dated Mar. 20, 2014 in U.S. Appl. No. 13/734,886, filed Jan. 4, 2013.
Office Action dated Sep. 12, 2013 in U.S. Appl. No. 13/748,531, filed Jan. 23, 2013.
Office Action dated Jun. 18, 2014 in U.S. Appl. No. 13/748,531, filed Jan. 23, 2013.
Office Action dated Jul. 17, 2013 in U.S. Appl. No. 13/003,570, § 371 (c) date Apr. 26, 2011.
Office Action dated May 8, 2014 in U.S. Appl. No. 13/003,570, § 371 (c) date Apr. 26, 2011.
English language abstract of Chinese Patent Application No. CN 1861793A, Chinese Patent Office, espacenet database—Worldwide (2006).
Office Action dated Apr. 24, 2013 in Eurasian Patent Application No. 201001198, filed Dec. 26, 2012.
Communication under Rule 71(3) EPC, Intention to Grant, dated Oct. 7, 2016, in EP Application No. 10791119.0, applicant Medicago, Inc., filed Jun. 25, 2010.
Denis, J., et al., "Immunogenicity of papaya mosaic virus-like particles fused to a hepatitis C virus epitope: Evidence for the critical function of multimerization," *Virology* 363:59-68, Elsevier Inc., United States (2007).
GenBank, "Influenza A virus (A/Indonesia/5/05(H5N1)) segment 4 hemagglutinin (HA) gene, complete cds," Accession No. EF541394.1, accessed at www.ncbi.nlm.nih.gov/nuccore/145284449?sat=12&satkey=4030144, accessed on Jun. 1, 2016, 2 pages.
Naito, T., et al., "Involvement of Hsp90 in Assembly and Nuclear Import of Influenza Virus RNA Polymerase Subunits," *Journal of Virology* 81(3):1339-1349, American Society for Microbiology, United States (2007).
Office Action dated Aug. 12, 2016, in Chinese Patent Application No. 201310021693.8, applicant Medicago, Inc., filed Jan. 12, 2009.
Office Action dated May 18, 2016, in Egyptian Patent Application No. PCT 61/2010, applicant Medicago, Inc.
Office Action dated Oct. 1, 2015, in Eurasian Patent Application No. 201001198, applicant Medicago, Inc., filed Jan. 12, 2009.
Foreign Associate Letter dated Aug. 24, 2016, regarding Office Action in Indonesian Patent Application No. W-00201000109, applicant Medicago, Inc.
Office Action, Notice of Final Rejection, dated Jan. 22, 2016, in Korean Patent Application No. 10-2010-7018343, applicant Medicago, Inc., filed Jan. 12, 2009.
Office Action, Reexamination, dated Jun. 2 2016, in Korean Patent Application No. 10-2010-7018343, applicant Medicago, Inc., filed Jan. 12, 2009.
Office Action dated Feb. 12, 2016, in U.S. Appl. No. 13/734,886, applicant Medicago, Inc., filed Jan. 4, 2013.
Notice of Allowance dated May 31, 2016, in U.S. Appl. No. 13/734,886, applicant Medicago, Inc., filed Jan. 4, 2013.
Notice of Allowance dated May 26, 2016, in U.S. Appl. No. 13/748,531, applicant Medicago, Inc., filed Jan. 23, 2013.
Notice of Allowance dated Jun. 29, 2016, in U.S. Appl. No. 13/003,570, applicant Medicago, Inc., filed Apr. 26, 2011.
Notice of Allowance dated May 31, 2016, in Canadian Patent Application No. 2,730,171, applicant Medicago, Inc., filed Jul. 7, 2009.
Waterhouse, P.M. and Helms, K., "Purification of Particles of Subterranean Clover Red Leaf Virus Using an Industrial-Grade Cellulase," *Journal of Virological Methods* 8:321-329, Elsevier Science Publishers B.V., Netherlands (1984).
Office Action dated Oct. 4, 2016, in Canadian Patent Application No. 2,772,964, applicant Medicago, Inc., filed Sep. 21, 2010.
Notice of Reexamination issued Sep. 20, 2016, in Chinese Patent Application No. 201080042336.4, applicant Medicago, Inc., filed Sep. 21, 2010.
Communication pursuant to Article 94(3) EPC dated Nov. 17, 2015, in European Patent Application No. 10818191.8, applicant Medicago, Inc., filed Sep. 21, 2010.
Communication pursuant to Article 94(3) EPC dated Jul. 26, 2016, in European Patent Application No. 10818191.8, applicant Medicago, Inc., filed Sep. 21, 2010.
Foreign Associate Letter dated Jan. 22, 2016, regarding Office Action in Indonesian Patent Application No. W-00201201507, filed Aug. 1, 2007, applicant Medicago, Inc.
Notification of Defects dated May 23, 2016, in Israeli Patent Application No. 218422, applicant Medicago, Inc., filed Mar. 1, 2012.
GenBank, "hemagglutinin, partial [Influenza A virus (A/Indonesia/5/2005(H5N1))]," Accession No. ABW06108.1, accessed at https://www.ncbi.nlm.nih.gov/protein/157955423/, accessed on Dec. 20, 2016, 2 pages.
Kost, T.A., et al., "Baculovirus as versatile vectors for protein expression in insect and mammalian cells," *Nature Biotechnology* 23(5):567-575, Nature Publishing Group, United States (2005).
Ma, J.K-C., et al., "Antibody processing and engineering in plants, and new strategies for vaccine production," *Vaccine* 23:1814-1818, Elsevier Ltd., England (2005).
UniProt, "P09345 (HEMA_159A0)," accessed at http://www.uniprot.org/uniprot/P09345, accessed on Dec. 20, 2016, 9 pages.
Examination Report dated Sep. 7, 2016, in Australian Patent Application No. 2011349031, applicant Medicago, Inc., filed Dec. 22, 2011.
Notice of Allowance dated Nov. 2, 2016, in Canadian Patent Application No. 2,821,574, applicant Medicago, Inc., filed Dec. 22, 2011.
Communication under Rule 71(3) EPC, Intention to Grant, dated Aug. 10, 2016, in European Patent Application No. 11851176.5, applicant Medicago, Inc., filed Dec. 22, 2011.
Decision to Grant a Patent dated Oct. 11, 2016, in Japanese Patent Application No. 2013-544982, applicant Medicago, Inc., filed Dec. 22, 2011.
Substantive Examination Adverse Report dated Sep. 30, 2016, in Malaysian Patent Application No. PI 2013701052, applicant Medicago, Inc., filed Dec. 22, 2011.
Foreign Associate Letter dated May 11, 2016, regarding Office Action, in Mexican Patent Application No. MX/a/2013/007270, applicant Medicago, Inc., filed Jun. 21, 2013.
Office Action dated Nov. 21, 2016, in Russian Patent Application No. 2013133734, applicant Medicago, Inc., filed Dec. 22, 2011.
Office Action dated Jun. 16, 2016, in U.S. Appl. No. 13/992,893, applicant Medicago, Inc., filed Aug. 23, 2013.

(56) References Cited

OTHER PUBLICATIONS

Foreign Associate Letter dated Jun. 16, 2016, regarding Office Action, Paper No. 08, dated Jun. 10, 2016, in Philippine Patent Application No. 1-2012-500565, applicant Medicago, Inc., filed Mar. 20, 2012.
Written Opinion dated May 17, 2016, in Singaporean Patent Application No. 201201471-8, applicant Medicago, Inc., filed Sep. 21, 2010.
Office Action dated Jan. 12, 2016, in U.S. Appl. No. 13/497,767, applicant Medicago, Inc., filed Mar. 22, 2012.
Communication under Rule 71(3) EPC, Intention to Grant, dated Feb. 5, 2016, in European Patent Application No. 09797336.6, applicant Medicago, Inc., filed Jul. 15, 2009.
Decision to grant a European patent pursuant to Article 97(1) EPC dated May 27, 2016, in European Patent Application No. 09797336.6, applicant Medicago, Inc., filed Jul. 15, 2009.
Office Action dated Jun. 24, 2016, in Korean Patent Application No. 10-2011-7002827, applicant Medicago, Inc., filed Feb. 7, 2011.
Office Action dated Mar. 31, 2016, in Malyasian Patent Application No. PI2011000210, applicant Medicago, Inc., filed Jul. 15, 2009.
Office Action dated Jan. 7, 2016, in U.S. Appl. No. 13/054,452, applicant Medicago, Inc., filed Apr. 19, 2011.
Notice of Allowance dated Oct. 4, 2016, in U.S. Appl. No. 13/054,452, applicant Medicago, Inc., filed Apr. 19, 2011.
GenBank, "Binary vector pEAQ-HT, complete sequence," Accession No. GQ497234.1, accessed at https://www.ncbi.nlm.nih.gov/nuccore/GQ497234, accessed on Dec. 20, 2016, 5 pages.
Sainsbury, F., et al., "pEAQ: versatile expression vectors for easy and quick transient expression of heterologous proteins in plants," Plant Biotechnology Journal 7:682-693, Blackwell Publishing Ltd., England (2009).
Examination Report dated Apr. 22, 2016, in Australian Patent Application No. 2011325827, applicant Medicago, Inc., filed Nov. 3, 2011.
Notice of Acceptance dated Jul. 22, 2016, in Australian Patent Application No. 2011325827, applicant Medicago, Inc., filed Nov. 3, 2011.
Decision on Rejection issued May 31, 2016, in Chinese Patent Application No. 201180064127.4, applicant Medicago, Inc., filed Nov. 3, 2011.
Communication under Rule 71(3) EPC, Intention to Grant, dated Feb. 4, 2016, in European Patent Application No. 11837364.6, applicant Medicago, Inc., filed Nov. 3, 2011.
Communication under Rule 71(3) EPC, Intention to Grant, dated May 19, 2016, in European Patent Application No. 11837364.6, applicant Medicago, Inc., filed Nov. 3, 2011.
Decision to grant a European patent pursuant to Article 97(1) EPC dated Sep. 29, 2016, in European Patent Application No. 11837364.6, applicant Medicago, Inc., filed Nov. 3, 2011.
Decision to Grant dated Sep. 6, 2016 in Japanese Patent Application No. 2013-536965, applicant Medicago, Inc., filed Nov. 3, 2011.
Office Action dated Mar. 14, 2016, in U.S. Appl. No. 13/883,439, applicant Medicago, Inc., filed Jul. 17, 2013.
Orlic, I.J.D., "Protoplast preparation (from plant tissue)," Ivaan.com, accessed at http://www.ivaan.com/protocols/128.html, Dec. 2006, accessed on May 8, 2014, 1 page.
Cover Page of Australian Patent, issued Mar. 19, 2015, in Australian Patent No. 2010265766, applicant Medicago, Inc., filed Jun. 25, 2010.
Certificate of Australian Patent, dated Nov. 12, 2015, in Australian Patent No. 2010300034, applicant Medicago, Inc., filed Sep. 21, 2010.
Notification of Reexamination dated May 26, 2015, in Chinese Patent Application No. 200980126670.5, applicant Medicago, Inc., filed Jul. 7, 2009.
Office Action dated Sep. 7, 2015, in Chinese Patent Application No. 201180064127.4, applicant Medicago, Inc., filed Nov. 3, 2011.
Decision on rejection issued Dec. 14, 2015, in Chinese Patent Application No. 200980136376.2, applicant Medicago, Inc., filed Jul. 15, 2009.
Office Action dated Nov. 26, 2015, in Chinese Patent Application No. 201310021693.8, applicant Medicago, Inc., filed Jan. 12, 2009.
Communication pursuant to Article 94(3) EPC dated Aug. 12, 2015, in European Patent Application No. 09797336.6, applicant Medicago, Inc., filed Jul. 15, 2009.
Summons to attend oral proceedings pursuant to Rule 115(1) EPC mailed Oct. 30, 2015, in European Patent Application No. 10791119.0, applicant Medicago, Inc., filed Jun. 25, 2010.
Notice of Allowability dated Sep. 18, 2015, in Indonesian Patent Application No. W-00201002481, applicant Medicago, Inc., filed Jan. 12, 2009.
Certificate of Israeli Patent, granted May 27, 2015, in Israeli Patent No. 230708, applicant Medicago, Inc., filed Nov. 7, 2008.
Office Action dated Oct. 27, 2015, in Japanese Patent Application No. 2013-536965, applicant Medicago, Inc., filed Nov. 3, 2011.
Office Action dated Dec. 8, 2015, in Japanese Patent Application No. 2013-544982, applicant Medicago, Inc., filed Dec. 22, 2011.
Office Action dated Oct. 21, 2014, in Israeli Patent Application No. 218422, applicant Medicago, Inc., filed Sep. 21, 2010.
Office Action dated Aug. 6, 2015, in Indian Patent Application No. 212/DELNP/2010, applicant Medicago, Inc., filed Jan. 12, 2010.
Decision of Grant dated Aug. 17, 2015, in Japanese Patent Application No. 2011-516935, applicant Medicago, Inc., filed Jul. 7, 2009.
Decision of Grant dated Aug. 17, 2015, in Japanese Patent Application No. 2011-517725, applicant Medicago, Inc., filed Jul. 15, 2009.
Office Action dated Jun. 16, 2015, in Japanese Patent Application No. 2012-516452, applicant Medicago, Inc., filed Jun. 25, 2010.
Office Action dated Jun. 2, 2015, in Japanese Patent Application No. 2014-076395, applicant Medicago, Inc., filed Apr. 2, 2014.
Office Action dated Aug. 19, 2015, in Korean Patent Application No. 10-2011-7002827, applicant Medicago, Inc., filed Feb. 7, 2011.
Foreign Associate Letter regarding Office Action dated Dec. 7, 2015, in Mexican Patent Application No. MX/a/2011/013517, applicant Medicago, Inc., filed Jun. 25, 2010.
Foreign Associate Letter regarding Office Action dated Jun. 15, 2015, in Mexican Patent Application No. MX/a/2011/013517, applicant Medicago, Inc., filed Jun. 25, 2010.
Office Action dated Jan. 22, 2015, in Russian Patent Application No. 2012101946/10(002681), applicant Medicago, Inc., filed Jun. 25, 2010.
Notice of Allowance dated Apr. 21, 2015, in Russian Patent Application No. 2012101946/10(002681), applicant Medicago, Inc., filed Jun. 25, 2010.
Office Action dated Oct. 7, 2015, in Russian Patent Application No. 2013133734, applicant Medicago, Inc., filed Dec. 22, 2011.
Office Action dated Aug. 14, 2015, in Singaporean Patent Application No. 2013053467, applicant Medicago, Inc., filed Jul. 15, 2009.
Notice of Allowance dated Nov. 27, 2015, in Taiwanese Patent Application No. 100147730, applicant Medicago, Inc., filed Dec. 21, 2011.
Office Action dated Feb. 9, 2015, in U.S. Appl. No. 13/054,452, applicant Medicago, Inc., filed Apr. 19, 2011.
Advisory Action dated Nov. 3, 2015, in U.S. Appl. No. 13/734,886, applicant Medicago, Inc., filed Jan. 4, 2013.
Office Action dated Oct. 6, 2015, in U.S. Appl. No. 13/748,531, applicant Medicago, Inc., filed Jan. 23, 2013.
Office Action dated Dec. 2, 2015, in U.S. Appl. No. 13/003,570, applicant Medicago, Inc., filed Apr. 26, 2011.
Search Report completed Jul. 28, 2015, in Singaporean Patent Application No. 2013053467, applicant Medicago, Inc., filed Jul. 15, 2009.
Office action dated Sep. 15, 2017, for India Patent Application No. 650/DELNP/2012, Intellectual Property India, New Delhi, India.
Office action dated Jun. 8, 2017, for Vietnamese Patent Application No. 1-2012-00186, National Office of Intellectual Property, Hanoi, Vietnam.
Office action dated May 1, 2017, for India Patent Application No. 9255/DELNP/2010, Intellectual Property India, New Delhi, India.
Siminis, C.I., et al., "Catalase Is Differentially Expressed in Dividing and Nondividing Protoplasts," Plant Physiol. Aug. 1994;105(4):1375-1383, Am. Soc. Plant Biologists, Rockville, MD.

(56) References Cited

OTHER PUBLICATIONS

Excerpted file history, U.S. Appl. No. 13/497,767, USPTO Office actions dated Jun. 30, 2017 and Nov. 25, 2016, U.S. Patent and Trademark Office, Alexandria, VA.
"Notification of Patent Registration Formalities" and "Notification on Grant of Patent Right for Invention," for CN application No. 200980136376.2, dispatched Jun. 8, 2017, The State Intellectual Property Office of the People's Republic of China, Beijing, China.
"Decision for Patent Grant," for KR Appl. No. 10-2011-7002827, dated Apr. 25, 2017, KIPO, Daejeon, South Korea.
"Notification of Reexamination," for CN application No. 20110064127.4, dated May 8, 2017, The State Intellectual Property Office of the People's Republic of China, Beijing, China.
"Notification of defects" for Israeli patent application No. 251338, dated Jul. 26, 2017, The Registrar of Patents, Jerusalem, Israel.
"Substantive Examination Report" for Philippine application No. 1-2013-501230, dated Sep. 4, 2017, Intellectual Property Office of the Philippines, Taguig City, Philippines.
Office action for Russian Application No. 2013133734, dated Jun. 15, 2017, Federal Service for Intellectual Property (ROSPATENT), Moscow, Russia.
Communication under Rule 71(3) EPC, Intention to Grant, dated Apr. 3, 2017, in EP Application No. 10791119.0, European Patent Office, Munich, Germany.
Office action dated May 17, 2016, for Japanese Patent Application No. 2014-076395, Japanese Patent Office, Tokyo, Japan.
Foreign Associate Letter dated Feb. 20, 2017 regarding Office Action dated Feb. 15, 2017, in Mexican Patent Application No. MX/a/2011/013517, Mexican Institute of Industrial Property, Mexico City, Mexico.
Office action dated Apr. 5, 2017, for Vietnamese Patent Application No. 1-2012-00186, National Office of Intellectual Property, Hanoi, Vietnam.
Examination Report dated Oct. 28, 2016, for Korean Patent Application No. UAE/P/0043/2010, KIPO, Daejeon, South Korea.
Office Action dated Mar. 28, 2017, for Chinese Patent Application No, 201310021693.8, The State Intellectual Property Office of the People's Republic of China, Beijing, China.
Office action dated Dec. 26, 2016, for Japanese Patent Application No. 2016-000233, Japanese Patent Office, Tokyo, Japan.
Excerpted file history, U.S. Appl. No. 15/256,119, USPTO Office action dated Apr. 6, 2017, U.S. Patent and Trademark Office, Alexandria, VA.
Park, Kwan-Hwa, "Microbial production of yeast and plant cell wall lytic enzyme," Research Report from University of Seoul, Research conducted from Oct. 1, 1984 to Sep. 30, 1987 (1988).
Examination Report dated Oct. 28, 2016, for Korean Patent Application No. UAE/P/0287/2012, KIPO, Daejeon, South Korea.
Communication under Rule 71(3) EPC, Intention to Grant, dated Apr. 10, 2017, in European Patent Application No. 10818191.8, European Patent Office, Munich, Germany.
Foreign Associate Letter dated Jan. 22, 2016, regarding Office action issued Dec. 3, 2015 in Indonesian Patent Application No. W-00201201507, Directorate General of Intellectual Property (DGIP), Jakarta Selatan, Indonesia.
Office action forwarded dated Mar. 15, 2017 in Korean Patent Application No. 10-2012-7010044, KIPO, Daejeon, South Korea.
Examination Report dated Nov. 10, 2016, in Singaporean Patent Application No. 201201471-8, Hungarian Intellectual Property Office, Budapest, Hungary.
De Vries, R.P., et al., "The Influenza A virus hemagglutinin glycosylation state affects receptor-binding specificity," Virology 403:17-25, Elsevier Inc., United States (2010).
Search Report dated Apr. 6, 2016, for Korean Patent Application No. UAE/P/0065/2011, KIPO, Daejeon, South Korea.
Examination Report No. 1 dated Sep. 28, 2016, for Australian Patent Application No. 2015202195, Australian Patent Office, Sydney, Australia.
Office Action dated Dec. 7, 2016, for Canadian Patent Application No. 2,730,668, Canadian Intellectual Property Office, Vancouver, Canada.
Office Action dated Nov. 24, 2016, for Indonesian Patent Application No. W00201100221, General of Intellectual Property (DGIP), Jakarta Selatan, Indonesia.
Certificate of Grant dated Nov. 24, 2016, for Australian Patent Application No. 2011325827, Australian Patent Office, Sydney, Australia.
Excerpted file history, U.S. Appl. No. 13/883,439, USPTO Office action dated Jan. 19, 2017, U.S. Patent and Trademark Office, Alexandria, VA.
Office Action dated Feb. 23, 2017, for Chinese Patent Application No. 201180065696.0, The State Intellectual Property Office of the People's Republic of China, Beijing, China.
Decision to grant a European patent pursuant to Article 97(1) EPC, dated Jan. 19, 2017, for European Patent Application No. 11851176.5, European Patent Office, Munich, Germany.
Letters Patent dated Nov. 11, 2016, for Japanese Patent 6038041 (Patent Application No. 2013-544982), Japanese Patent Office, Tokyo, Japan.
Invitation to Respond to Written Opinion dated Apr. 13, 2017 and Written Opinion dated Feb. 28, 2017 for Singapore Patent Application No. 10201605096Q, Intellectual Property Office of Singapore, Singapore.
Excerpted file history, U.S. Appl. No. 13/992,893, USPTO Office action dated Mar. 30, 2017, U.S. Patent and Trademark Office, Alexandria, VA.
Davey, M.R., et al., "Plant protoplasts: status and biotechnological perspectives," *Biotechnology Advances* 23(2):131-171, Elsevier Science, England (2005).
Gomord, V., et al., "Plant-specific glycosylation patterns in the context of therapeutic protein production," *Plant Biotechnology Journal* 8(5):564-587, Oxford Wiley on behalf of the Society for Experimental Biology, Association of Applied Biologists, England (Jun. 2010).
Helenius, A. and Aebi, M., "Roles of N-Linked Glycans in the Endoplasmic Reticulum," *Annu. Rev. Biochem* 73:1019-1049, Annual Reviews, United States (2004).
Power, J.B. and Cocking, E.C., "A Simple Method for the Isolation of Very Large Number of Leaf Protoplasts by using Mixtures of Cellulase and Pectinase," *Biochem J.* 111(5):33P, Portland Press on behalf of the Biochemical Society, England (1969).
Sørensen, H.P. and Mortensen, K.K., "Advanced genetic strategies for recombinant protein expression in *Escherichia coil,*" *Journal of Biotechnology* 115(2):113-128, Elsevier Science Publishers, Netherlands (2005).
Takahashi, Y., et al., "A high-throughput screen of cell-death-inducing factors in *Nicotiana benthamiana* identifies a novel MAPKK that mediates INF1-induced cell death signaling and non-host resistance to *Pseudomonas cichorii,*" *The Plant Journal* 49(6):1030-1040, Oxford : Blackwell Scientific Publishers and BIOS Scientific Publishers in association with the Society for Experimental Biology, England (2007).
Wang, W., et al., "Role of plant heat-shock proteins and molecular chaperones in the abiotic stress response," *TRENDS in Plant Science* 9(5):244-252, Oxford : Elsevier Science, Ltd., England (2004).
Yigzaw, Y., et al., "Exploitation of the Adsorptive Properties of Depth Filters for Host Cell Protein Removal during Monoclonal Antibody Purification," *Biotechnol. Prog.* 22(1):288-96, American Institute of Chemical Engineers, United States (2006).
Yokoyama, N., et al., "Co-expression of human chaperone Hsp70 and Hsdj or Hsp40 co-factor increases solubility of overexpressed target proteins in insect cells," *Biochimica et Biophysica Acta* 1493:119-124, Elsevier Pub Co., Netherlands (2000).
Notice of Acceptance dated Jul. 2, 2015, in Australian Patent Application No. 2009267769, applicant Medicago Inc., filed Dec. 16, 2010.
Australian 2009270404 Examination Report dated Dec. 16, 2014.
Australian 2009270404 Examination Report dated May 7, 2015.
Australian 2010300034 Examination Report dated Nov. 6, 2013.
Australian 2010300034 Examination Report dated Dec. 24, 2014.

(56) References Cited

OTHER PUBLICATIONS

Office Action dated May 4, 2015, in Canadian Patent Application No. 2,730,171, applicant Medicago, Inc., filed Jul. 7, 2009.
Notice of Allowance dated Jun. 1, 2015, in Canadian Patent Application No. 2,730,185, applicant Medicago, Inc., filed Jul. 2, 2009.
Office Action dated Apr. 14, 2015, in Canadian Patent Application No. 2,730,668, applicant Medicago, Inc., filed Jul. 15, 2009.
Office Action dated Jul. 16, 2015, in Canadian Patent Application No. 2,821,574, applicant Medicago, Inc., filed Dec. 22, 2011.
Office Action dated May 26, 2015, in Chinese Patent Application No. 201310021693.8, applicant Medicago, Inc., filed Jan. 12, 2009.
Office Action dated Nov. 26, 2014, in Chinese Patent Application No. 201180064127.4, applicant Medicago, Inc., filed Nov. 3, 2011.
Office Action dated Mar. 25, 2015, in Chinese Patent Application No. 200980136376.2, applicant Medicago, Inc., filed Jul. 15, 2009.
Office Action dated Jul. 29, 2013, in Chinese Patent Application No. 201080042336.4, applicant Medicago, Inc., filed Sep. 21, 2010.
Office Action dated Apr. 24, 2014, in Chinese Patent Application No. 201080042336.4, applicant Medicago, Inc., filed Sep. 21, 2010.
Office Action dated Nov. 15, 2014, in Chinese Patent Application No. 201080042336.4, applicant Medicago, Inc., filed Sep. 21, 2010.
Decision on Rejection dated May 28, 2015, in Chinese Patent Application No. 201080042336.4, applicant Medicago, Inc., filed Sep. 21, 2010.
Office Action dated Dec. 23, 2014, in Chinese Patent Application No. 201180065696.0, applicant Medicago, Inc., filed Dec. 22, 2011.
Decision on Rejection dated Jun. 26, 2015, in Chinese Patent Application No. 201180065696.0, applicant Medicago, Inc., filed Dec. 22, 2011.
Office Action dated Jun. 24, 2015, in Chinese Patent Application No. 201280047819.2, applicant Medicago, Inc., filed Sep. 28, 2012.
Decision to Grant dated Apr. 23, 2015, in European Patent No. 2294202, filed Jul. 7, 2009.
Office Action dated Mar. 27, 2015, in European Patent Application No. 11837364.6, applicant Medicago, Inc., filed Nov. 3, 2011.
European Patent Application No. 10818191.8 Examination Report dated Oct. 23, 2013.
Office Action dated Aug. 18, 2014, in European Patent Application No. 10818191.8, applicant Medicago, Inc., filed Sep. 21, 2010.
Office Action dated Jan. 20, 2015, in European Patent Application No. 11 851 176.5, applicant Medicago, Inc., filed Dec. 22, 2011.
Office Action dated Sep. 22, 2014, in Indonesian Patent Application No. W-00201002481, applicant Medicago, Inc., filed Jan. 12, 2009.
Office Action dated Jan. 9, 2015, in Indonesian Patent Application No. W-00201002481, applicant Medicago, Inc., filed Jan. 12, 2009.
Office Action dated Jan. 13, 2015, in Japanese Patent Application No. 2011- 516934, applicant Medicago, Inc., filed Oct. 27, 2011.
Final Office Action dated Dec. 24, 2014, Japanese Patent Application No. 2011-516935, applicant Medicago, Inc., filed Oct. 27, 2011.
Office Action dated Jan. 26, 2015, Japanese Patent Application No. 2011-517725, applicant Medicago, Inc., filed Nov. 17, 2011.
Office Action dated Oct. 29, 2013, in Japanese Patent Application No. 2012-530060, applicant Medicago, Inc., filed Feb. 14, 2013.
Office Action dated May 27, 2015, in Japanese Patent Application No. 2014-039035, applicant Medicago, Inc., filed May 29, 2014.
Office Action dated Dec. 22, 2014, in Korean Patent Application No. 10-2010-7002538, applicant Medicago, Inc., filed Jul. 11, 2008.
Decision of Grant dated Jul. 20, 2015, in Korean Patent Application No. 10-2010-7002538, applicant Medicago, Inc., filed Jul. 11, 2008.
Office Action dated May 21, 2015, in Korean Patent Application No. 10-2010-7018343, applicant Medicago, Inc., filed Jan. 12, 2009.
Office Action dated Feb. 11, 2014, in Mexican Patent Application No. MX/a/20I2/003372, applicant Medicago, Inc., filed Sep. 21, 2010.
Office Action dated Aug. 27, 2014, in Mexican Patent Application No. MX/a/2012/003372, applicant Medicago, Inc., filed Sep. 21, 2010.
New Zealand 612603 Examination Report dated Mar. 19, 2015.
Notice of Acceptance dated Jul. 1, 2015, in New Zealand Patent Application No. 612603, applicant Medicago, Inc., filed Dec. 22, 2011.
Decision of Grant dated Jan. 23, 2015, in Russian Patent Application No. 2011105885/10, applicant Medicago, Inc., filed Jul. 15, 2009.
Office Action dated Jun. 19, 2014, in Russian Patent Application No. 2012115996/10, applicant Medicago, Inc., filed Sep. 21, 2010.
Office Action dated Nov. 12, 2014, in Russian Patent Application No. 2012115996/10, applicant Medicago, Inc., filed Sep. 21, 2010.
Notice of Allowance dated May 5, 2015, in Russian Patent Application No. 2012115996/10, applicant Medicago, Inc., filed Sep. 21, 2010.
Certificate of Singaporean Patent, issued Aug. 26, 2014, in Singaporean Patent No. 187500, filed Jan. 12, 2009.
Search Report and Written Opinion dated Apr. 16, 2014, in Singaporean Patent Application No. 201201471-8, filed Sep. 21, 2010.
Office Action dated Apr. 27, 2015, in Taiwanese Patent Application No. 100147730, applicant Medicago, Inc.
Office Action dated Dec. 5, 2014, in U.S. Appl. No. 13/734,886, filed Jan. 4, 2013.
Office Action dated Jun. 25, 2015, in U.S. Appl. No. 13/734,886, filed Jan. 4, 2013.
Office Action dated Jan. 5, 2015, in U.S. Appl. No. 13/748,531, filed Jan. 23, 2013.
Final Office Action dated Jun. 23, 2015, in U.S. Appl. No. 13/748,531, filed Jan. 23, 2013.
Office Action dated Sep. 4, 2014, in U.S. Appl. No. 13/497,767, 371 Date Mar. 22, 2012.
Office Action dated Jun. 24, 2015, in U.S. Appl. No. 13/497,767, 371 Date Mar. 22, 2012.
Office Action dated Feb. 11, 2015, in U.S. Appl. No. 13/003,570, 371 Date Apr. 26, 2011.

* cited by examiner

Figure 2

Swapping of receptor binding subdomain on HA stem. Sequence of mature proteins.

| Construct No. | N-terminal Stem: - F'1+E1 | RB head | C-terminal Stem: E2+F'2-Stop |
|---|---|---|---|
| 690 and 734 | **H5/Indo**<br>DQICIGYHANNS<br>TEQVDTIMEKNV<br>TVTHAQDILEKT<br>HNGKLCDLDGV<br>KPLILRDCSVAG<br>WLLGNPMCDEF<br>INVPEWSYIVEK<br>ANPTNDLCYP | **H1/Brisbane**<br>GHFADYEELREQLSSVSSFERFEIF<br>PKESSWPNHTVTGVSASCSHNGES<br>SFYRNLLWLTGKNGLYPNLSKSYA<br>NNKEKEVLVLWGVHHPPNIGDQKA<br>LYHTENAYVSVVSSHYSRKFTPEIA<br>KRPKVRDQEGRINYYWTLLEPGDTI<br>IFEANGNLIAPRYAFALSRGFGSG | **H5/Indo**<br>IMKSELEYGNCNTKCQTPMGAINSSM<br>PFHNIHPLTIGECPKYVKSNRLVLATGL<br>RNSPQRESRRKKRGLFGAIAGFIEGG<br>WQGMVDGWYGYHHSNEQGSGYAAD<br>KESTQKAIDGVTNKVNSIIDKMNTQFE<br>AVGREFNNLERRIENLNKKMEDGFLDV<br>WTYNAELLVLMENERTLDFHDSNVKN<br>LYDKVRLQLRDNAKELGNGCFEFYHK<br>CDNECMESIRNGTYNYPQYSEEARLK<br>REEISGVKLESIGTYQILSIYSTVASSLA<br>LAIMMAGLSLWMCSNGSLQCRICI |
| 696 | **H1/NC**<br>DTICIGYHANNS<br>TDTVDTVLEKNV<br>TVTHSVNLLEDS<br>HNGKLCLLKGIA<br>PLQLGNCSVAG<br>WILGNPECELLI<br>SKESWSYIVETP<br>NPENGTCYP | **H5/Indo**<br>GSFNDYEELKHLLSRINHFEKIQIIP<br>KSSWSDHEASSGVSSACPYLGSPS<br>FFRNVVWLIKKNSTYPTIKKSYNNT<br>NQEDLLVLWGIHHPNDAAEQTRLY<br>QNPTTYISIGTSTLNQRLVPKIATRS<br>KVNGQSGRMEFFWTILKPNDAINFE<br>SNGNFIAPEYAYKIVKKGDSA | **H1/NC**<br>IITSNAPMDECDAKCQTPQGAINSSLP<br>FQNVHPVTIGECPKYVRSAKLRMVTGL<br>RNIPSIQSRGLFGAIAGFIEGGWTGMV<br>DGWYGYHHQNEQGSGYAADQKSTQ<br>NAINGITNKVNSVIEKMNTQFTAVGKEF<br>NKLERRMENLNKKVDDGFLDIWTYNA<br>ELLVLLENERTLDFHDSNVKNLYEKVK<br>SQLKNNAKEIGNGCFEFYHKCNNECM<br>ESVKNGTYDYPKYSEESKLNREKIDGV<br>KLESMGVYQILAIYSTVASSLVLLVSLG<br>AISFWMCSNGSLQCRICI |

Swapping of receptor binding and esterase subdomains on HA stem. Sequence of mature protein.

| Construct No. | N-terminal Stem: F'1 | E1-RB-E2 head | C-terminal stem: F'2- Stop |
|---|---|---|---|
| 691 | **H5/Indo**<br>DQICIGYHANNS<br>TEQVDTIMEKNV<br>TVTHAQDILEKT<br>HNGKLC | **H1/Brisbane**<br>LLKGIAPLQLGNCSVAGWIL<br>GNPECELLISKESWSYIVEK<br>PNPENGTCYPGHFADYEEL<br>REQLSSVSSFERFEIFPKES<br>SWPNHTVTGVSASCSHNG<br>ESSFYRNLLWLTGKNGLYP<br>NLSKSYANNKEKEVLVLWG<br>VHHPPNIGDQKALYHTENA<br>YVSVVSSHYSRKFTPEIAKR<br>PKVRDQEGRINYYWTLLEP<br>GDTIIFEANGNLIAPRYAFAL<br>SRGFGSGIINSNAPMDK | **H5/Indo**<br>CNTKCQTPMGAINSSMPFHNIHPLTIGECPKYVKSN<br>RLVLATGLRNSPQRESRRKKRGLFGAIAGFIEGGW<br>QGMVDGWYGYHHSNEQGSGYAADKESTQKAIDG<br>VTNKVNSIIDKMNTQFEAVGREFNNLERRIENLNKK<br>MEDGFLDVWTYNAELLVLMENERTLDFHDSNVKNL<br>YDKVRLQLRDNAKELGNGCFEFYHKCDNECMESIR<br>NGTYNYPQYSEEARLKREEISGVKLESIGTYQILSIY<br>STVASSLALAIMMAGLSLWMCSNGSLQCRICI |

Figure 3

Amino acid translation of coding sequence in construct 690 and 734 expression cassette (SEQ ID NO: 80):

MEKIVLLLAIVSLVKSDQICIGYHANNSTEQVDTIMEKNVTVTHAQDILEKTHNGKLCDLDGVKPLILR
DCSVAGWLLGNPMCDEFINVPEWSYIVEKANPTNDLCYPGHFADYEELREQLSSVSSFERFEIFPK
ESSWPNHTVTGVSASCSHNGESSFYRNLLWLTGKNGLYPNLSKSYANNKEKEVLVLWGVHHPPNI
GDQKALYHTENAYVSVVSSHYSRKFTPEIAKRPKVRDQEGRINYYWTLLEPGDTIIFEANGNLIAPRY
AFALSRGFGSGIMKSELEYGNCNTKCQTPMGAINSSMPFHNIHPLTIGECPKYVKSNRLVLATGLRN
SPQRESRRKKRGLFGAIAGFIEGGWQGMVDGWYGYHHSNEQGSGYAADKESTQKAIDGVTNKVN
SIIDKMNTQFEAVGREFNNLERRIENLNKKMEDGFLDVWTYNAELLVLMENERTLDFHDSNVKNLYD
KVRLQLRDNAKELGNGCFEFYHKCDNECMESIRNGTYNYPQYSEEARLKREEISGVKLESIGTYQIL
SIYSTVASSLALAIMMAGLSLWMCSNGSLQCRICI

Figure 4

Amino acid translation of coding sequence in construct 691 expression cassette (SEQ ID NO: 81):

MEKIVLLLAIVSLVKSDQICIGYHANNSTEQVDTIMEKNVTVTHAQDILEKTHNGKLCLLKGIAPLQL
GNCSVAGWILGNPECELLISKESWSYIVEKPNPENGTCYPGHFADYEELREQLSSVSSFERFEIF
PKESSWPNHTVTGVSASCSHNGESSFYRNLLWLTGKNGLYPNLSKSYANNKEKEVLVLWGVHH
PPNIGDQKALYHTENAYVSVVSSHYSRKFTPEIAKRPKVRDQEGRINYYWTLLEPGDTIIFEANGN
LIAPRYAFALSRGFGSGIINSNAPMDKCNTKCQTPMGAINSSMPFHNIHPLTIGECPKYVKSNRLV
LATGLRNSPQRESRRKKRGLFGAIAGFIEGGWQGMVDGWYGYHHSNEQGSGYAADKESTQKAI
DGVTNKVNSIIDKMNTQFEAVGREFNNLERRIENLNKKMEDGFLDVWTYNAELLVLMENERTLDF
HDSNVKNLYDKVRLQLRDNAKELGNGCFEFYHKCDNECMESIRNGTYNYPQYSEEARLKREEIS
GVKLESIGTYQILSIYSTVASSLALAIMMAGLSLWMCSNGSLQCRICI

Figure 5

Amino acid translation of coding sequence in construct 696 expression cassette (SEQ ID NO: 82):

MAKNVAIFGLLFSLLVLVPSQIFADTICIGYHANNSTDTVDTVLEKNVTVTHSVNLLEDSHNGKLCLLKGIA
PLQLGNCSVAGWILGNPECELLISKESWSYIVETPNPENGTCYPGSFNDYEELKHLLSRINHFEKIQIIPK
SSWSDHEASSGVSSACPYLGSPSFFRNVVWLIKKNSTYPTIKKSYNNTNQEDLLVLWGIHHPNDAAEQT
RLYQNPTTYISIGTSTLNQRLVPKIATRSKVNGQSGRMEFFWTILKPNDAINFESNGNFIAPEYAYKIVKK
GDSAIITSNAPMDECDAKCQTPQGAINSSLPFQNVHPVTIGECPKYVRSAKLRMVTGLRNIPSIQSRGLF
GAIAGFIEGGWTGMVDGWYGYHHQNEQGSGYAADQKSTQNAINGITNKVNSVIEKMNTQFTAVGKEF
NKLERRMENLNKKVDDGFLDIWTYNAELLVLLENERTLDFHDSNVKNLYEKVKSQLKNNAKEIGNGCFE
FYHKCNNECMESVKNGTYDYPKYSEESKLNREKIDGVKLESMGVYQILAIYSTVASSLVLLVSLGAISFW
MCSNGSLQCRICI

Anti H1-Brisbane

Anti H5-Indonesia

Anti H1-Brisbane

Construct No.

E1-RB-E2

SP   RB   TMD/CT 736   35S pro → CPMV HT | PDI | H3 Brisbane | CPMV HT | NOS ter 737   35S pro → CPMV HT | PDI | H3 Brisbane | H5 Indo | CPMV HT | NOS ter 739   35S pro → CPMV HT | PDI | B Florida | CPMV HT | NOS ter 745   35S pro → CPMV HT | PDI | B Florida | H5 Indo | CPMV HT | NOS ter Construct number 745   —B/Florida—  —H5/Indo—
      ...LNDDGLDN | Y | QILSIYSTVA
      SEQ ID NO: 115    SEQ ID NO: 114

737   —H3/Brisbane—  —H5/Indo—
      ...KGVELKS | IGTY | QILSIYSTVA
      SEQ ID NO: 116          SEQ ID NO: 114
               SEQ ID NO: 117

Figure 12

Amino acid translation of coding sequence in construct 737 expression cassette (SEQ ID NO: 83):

MAKNVAIFGLLFSLLVLVPSQIFAQKLPGNDNSTATLCLGHHAVPNGTIVKTITNDQIEVTNATELVQSS
STGEICDSPHQILDGENCTLIDALLGDPQCDGFQNKKWDLFVERSKAYSNCYPYDVPDYASLRSLVA
SSGTLEFNNESFNWTGVTQNGTSSACIRRSNNSFFSRLNWLTHLKFKYPALNVTMPNNEKFDKLYIW
GVHHPGTDNDQIFLYAQASGRITVSTKRSQQTVIPNIGSRPRVRNIPSRISIYWTIVKPGDILLINSTGNL
IAPRGYFKIRSGKSSIMRSDAPIGKCNSECITPNGSIPNDKPFQNVNRITYGACPRYVKQNTLKLATGM
RNVPEKQTRGIFGAIAGFIENGWEGMVDGWYGFRHQNSEGIGQAADLKSTQAAIDQINGKLNRLIGK
TNEKFHQIEKEFSEVEGRIQDLEKYVEDTKIDLWSYNAELLVALENQHTIDLTDSEMNKLFEKTKKQLR
ENAEDMGNGCFKIYHKCDNACIGSIRNGTYDHDVYRDEALNNRFQIKGVELKSIGTYQILSIYSTVASS
LALAIMMAGLSLWMCSNGSLQCRICI

Figure 13

Amino acid translation of coding sequence in construct 745 expression cassette (SEQ IDNO: 84):

MAKNVAIFGLLFSLLVLVPSQIFADRICTGITSSNSPHVVKTATQGEVNVTGVIPLTTTPTKSYFANLKGTR
TRGKLCPDCLNCTDLDVALGRPMCVGTTPSAKASILHEVKPVTSGCFPIMHDRTKIRQLPNLLRGYENI
RLSTQNVIDAEKAPGGPYRLGTSGSCPNATSKSGFFATMAWAVPKDNNKNATNPLTVEVPYICTEGED
QITVWGFHSDNKTQMKNLYGDSNPQKFTSSANGVTTHYVSQIGSFPDQTEDGGLPQSGRIVVDYMMQ
KPGKTGTIVYQRGVLLPQKVWCASGRSKVIKGSLPLIGEADCLHEKYGGLNKSKPYYTGEHAKAIGNCP
IWVKTPLKLANGTKYRPPAKLLKERGFFGAIAGFLEGGWEGMIAGWHGYTSHGAHGVAVAADLKSTQE
AINKITKNLNSLSELEVKNLQRLSGAMDELHNEILELDEKVDDLRADTISSQIELAVLLSNEGIINSEDEHLL
ALERKLKKMLGPSAVEIGNGCFETKHKCNQTCLDRIAAGTFNAGEFSLPTFDSLNITAASLNDDGLDNY
QILSIYSTVASSLALAIMMAGLSLWMCSNGSLQCRICI

Anti B-Florida

Anti H3-Brisbane

Figure 17

SEQ. ID. NO. 52.

B-Plasto-Native SP-H5 A/Indonesia/5/05 (HindIII-Native Sp-H5 A/Indo/5/05-SacI)

AAGCTTATGGAGAAAATAGTGCTTCTTCTTGCAATAGTCAGTCTTGTTAAAAGTGATCAGATT
TGCATTGGTTACCATGCAAACAATTCAACAGAGCAGGTTGACACAATCATGGAAAAGAACGT
TACTGTTACACATGCCCAAGACATACTGGAAAAGACACACAACGGGAAGCTCTGCGATCTAG
ATGGAGTGAAGCCTCTAATTTTAAGAGATTGTAGTGTAGCTGGATGGCTCCTCGGGAACCCA
ATGTGTGACGAATTCATCAATGTACCGGAATGGTCTTACATAGTGGAGAAGGCCAATCCAAC
CAATGACCTCTGTTACCCAGGGAGTTTCAACGACTATGAAGAACTGAAACACCTATTGAGCA
GAATAAACCATTTTGAGAAAATTCAAATCATCCCCAAAAGTTCTTGGTCCGATCATGAAGCCT
CATCAGGAGTTAGCTCAGCATGTCCATACCTGGGAAGTCCCTCCTTTTTTAGAAATGTGGTA
TGGCTTATCAAAAAGAACAGTACATACCCAACAATAAAGAAAAGCTACAATAATACCAACCAA
GAGGATCTTTTGGTACTGTGGGGAATTCACCATCCTAATGATGCGGCAGAGCAGACAAGGC
TATATCAAAACCCAACCACCTATATTTCCATTGGGACATCAACACTAAACCAGAGATTGGTAC
CAAAAATAGCTACTAGATCCAAAGTAAACGGGCAAAGTGGAAGGATGGAGTTCTTCTGGACA
ATTTTAAAACCTAATGATGCAATCAACTTCGAGAGTAATGGAAATTTCATTGCTCCAGAATAT
GCATACAAAATTGTCAAGAAAGGGGACTCAGCAATTATGAAAAGTGAATTGGAATATGGTAA
CTGCAACACCAAGTGTCAAACTCCAATGGGGGCGATAAACTCTAGTATGCCATTCCACAACA
TACACCCTCTCACCATCGGGGAATGCCCCAAATATGTGAAATCAAACAGATTAGTCCTTGCA
ACAGGGCTCAGAAATAGCCCTCAAAGAGAGAGCAGAAGAAAAAAGAGAGGACTATTTGGAG
CTATAGCAGGTTTTATAGAGGGAGGATGGCAGGGAATGGTAGATGGTTGGTATGGGTACCA
CCATAGCAATGAGCAGGGGAGTGGGTACGCTGCAGACAAAGAATCCACTCAAAAGGCAATA
GATGGAGTCACCAATAAGGTCAACTCAATCATTGACAAAATGAACACTCAGTTTGAGGCCGT
TGGAAGGGAATTTAATAACTTAGAAAGGAGAATAGAGAATTTAAACAAGAAGATGGAAGACG
GGTTTCTAGATGTCTGGACTTATAATGCCGAACTTCTGGTTCTCATGGAAAATGAGAGAACTC
TAGACTTTCATGACTCAAATGTTAAGAACCTCTACGACAAGGTCCGACTACAGCTTAGGGAT
AATGCAAAGGAGCTGGGTAACGGTTGTTTCGAGTTCTATCACAAATGTGATAATGAATGTATG
GAAAGTATAAGAAACGGAACGTACAACTATCCGCAGTATTCAGAAGAAGCAAGATTAAAAG
AGAGGAAATAAGTGGGGTAAAATTGGAATCAATAGGAACTTACCAAATACTGTCAATTTATTC
AACAGTGGCGAGTTCCCTAGCACTGGCAATCATGATGGCTGGTCTATCTTTATGGATGTGCT
CCAATGGATCGTTACAATGCAGAATTTGCATTTAAGAGCTC

Figure 18

SEQ. ID. NO. 53

660 expression cassette from HindIII (in the multiple cloning site, upstream of the Plastocyanin promoter) to EcoRI (immediately downstream of the Plastocyanin terminator). H5 from A/Indonesia/5/2005 coding sequence underlined.

AAGCTTGCTAGCGGCCTCAATGGCCCTGCAGGTCGACTCTAGAGGTACCCCGGGCTGGTATATTTATA
TGTTGTCAAATAACTCAAAAACCATAAAAGTTTAAGTTAGCAAGTGTGTACATTTTTACTTGAACAAAAAT
ATTCACCTACTACTGTTATAAATCATTATTAAACATTAGAGTAAAGAAATATGGATGATAAGAACAAGAGT
AGTGATATTTTGACAACAATTTTGTTGCAACATTTGAGAAAATTTTGTTGTTCTCTCTTTTCATTGGTCAA
AAACAATAGAGAGAGAAAAAGGAAGAGGGAGAATAAAAACATAATGTGAGTATGAGAGAGAAAGTTGTA
CAAAAGTTGTACCAAAATAGTTGTACAAATATCATTGAGGAATTTGACAAAAGCTACACAAATAAGGGTT
AATTGCTGTAAATAAATAAGGATGACGCATTAGAGAGATGTACCATTAGAGAATTTTTGGCAAGTCATTA
AAAAGAAAGAATAAATTATTTTTAAAATTAAAAGTTGAGTCATTTGATTAAACATGTGATTATTTAATGAAT
TGATGAAAGAGTTGGATTAAAGTTGTATTAGTAATTAGAATTTGGTGTCAAATTTAATTTGACATTTGATC
TTTTCCTATATATTGCCCCATAGAGTCAGTTAACTCATTTTTATATTTCATAGATCAAATAAGAGAAATAA
CGGTATATTAATCCCTCCAAAAAAAAAAAACGGTATATTTACTAAAAAATCTAAGCCACGTAGGAGGATA
ACAGGATCCCCGTAGGAGGATAACATCCAATCCAACCAATCACAACAATCCTGATGAGATAACCCACTT
TAAGCCCACGCATCTGTGGCACATCTACATTATCTAAATCACACATTCTTCCACACATCTGAGCCACACA
AAAACCAATCCACATCTTTATCACCCATTCTATAAAAAATCACACTTTGTGAGTCTACACTTTGATTCCCT
TCAAACACATACAAAGAGAAGAGACTAATTAATTAATTAATCATCTTGAGAGAAAATGGAGAAAATAGTG
CTTCTTCTTGCAATAGTCAGTCTTGTTAAAAGTGATCAGATTTGCATTGGTTACCATGCAAACAATTCAA
CAGAGCAGGTTGACACAATCATGGAAAAGAACGTTACTGTTACACATGCCCAAGACATACTGGAAAAGA
CACACAACGGGAAGCTCTGCGATCTAGATGGAGTGAAGCCTCTAATTTTAAGAGATTGTAGTGTAGCTG
GATGGCTCCTCGGGAACCCAATGTGTGACGAATTCATCAATGTACCGGAATGGTCTTACATAGTGGAG
AAGGCCAATCCAACCAATGACCTCTGTTACCCAGGGAGTTTCAACGACTATGAAGAACTGAAACACCTA
TTGAGCAGAATAAACCATTTTGAGAAAATTCAAATCATCCCCAAAAGTTCTTGGTCCGATCATGAAGCCT
CATCAGGAGTTAGCTCAGCATGTCCATACCTGGGAAGTCCCTCCTTTTTTAGAAATGTGGTATGGCTTA
TCAAAAAGAACAGTACATACCCAACAATAAAGAAAAGCTACAATAATACCAACCAAGAGGATCTTTTGGT
ACTGTGGGGAATTCACCATCCTAATGATGCGGCAGAGCAGACAAGGCTATATCAAAACCCAACCACCT
ATATTTCCATTGGGACATCAACACTAAACCAGAGATTGGTACCAAAAATAGCTACTAGATCCAAAGTAAA
CGGGCAAAGTGGAAGGATGGAGTTCTTCTGGACAATTTTAAAACCTAATGATGCAATCAACTTCGAGAG
TAATGGAAATTTCATTGCTCCAGAATATGCATACAAAATTGTCAAGAAAGGGGACTCAGCAATTATGAAA
AGTGAATTGGAATATGGTAACTGCAACACCAAGTGTCAAACTCCAATGGGGGCGATAAACTCTAGTATG
CCATTCCACAACATACACCCTCTCACCATCGGGGAATGCCCCAAATATGTGAAATCAAACAGATTAGTC
CTTGCAACAGGGCTCAGAAATAGCCCTCAAAGAGAGAGCAGAAGAAAAAAGAGAGGACTATTTGGAGC
TATAGCAGGTTTTATAGAGGGAGGATGGCAGGGAATGGTAGATGGTTGGTATGGGTACCACCATAGCA
ATGAGCAGGGGAGTGGGTACGCTGCAGACAAAGAATCCACTCAAAAGGCAATAGATGGAGTCACCAAT
AAGGTCAACTCAATCATTGACAAAATGAACACTCAGTTTGAGGCCGTTGGAAGGGAATTTAATAACTTA
GAAAGGAGAATAGAGAATTTAAACAAGAAGATGGAAGACGGGTTTCTAGATGTCTGGACTTATAATGCC
GAACTTCTGGTTCTCATGGAAAATGAGAGAACTCTAGACTTTCATGACTCAAATGTTAAGAACCTCTACG
ACAAGGTCCGACTACAGCTTAGGGATAATGCAAAGGAGCTGGGTAACGGTTGTTTCGAGTTCTATCACA
AATGTGATAATGAATGTATGGAAAGTATAAGAAACGGAACGTACAACTATCCGCAGTATTCAGAAGAAG
CAAGATTAAAAAGAGAGGAAATAAGTGGGGTAAAATTGGAATCAATAGGAACTTACCAAATACTGTCAAT
TTATTCAACAGTGGCGAGTTCCCTAGCACTGGCAATCATGATGGCTGGTCTATCTTTATGGATGTGCTC
CAATGGATCGTTACAATGCAGAATTTGCATTTAAGAGCTCTAAGTTAAAATGCTTCTTCGTCTCCTATTTA
TAATATGGTTTGTTATTGTTAATTTTGTTCTTGTAGAAGAGCTTAATTAATCGTTGTTGTTATGAAATACTA
TTTGTATGAGATGAACTGGTGTAATGTAATTCATTTACATAAGTGGAGTCAGAATCAGAATGTTTCCTCC
ATAACTAACTAGACATGAAGACCTGCCGCGTACAATTGTCTTATATTTGAACAACTAAAATTGAACATCT
TTTGCCACAACTTTATAAGTGGTTAATATAGCTCAAATATATGGTCAAGTTCAATAGATTAATAATGGAAA
TATCAGTTATCGAAATTCATTAACAATCAACTTAACGTTATTAACTACTAATTTTATATCATCCCCTTTGAT
AAATGATAGTACACCAATTAGGAAGGAGCATGCTCGAGGCCTGGCTGGCCGAATTC

Figure 19

SEQ. ID. NO. 54.

Wild-type H1/NC (H1N1) coding sequence lacking TmD and Ctail (GenBank acc. No. AY289929)

ATGAAAGCAAAACTACTGGTCCTGTTATGTACATTTACAGCTACATATGCAGACACAATATGTAT
AGGCTACCATGCCAACAACTCAACCGACACTGTTGACACAGTACTTGAGAAGAATGTGACAGT
GACACACTCTGTCAACCTACTTGAGGACAGTCACAATGGAAAACTATGTCTACTAAAAGGAATA
GCCCCACTACAATTGGGTAATTGCAGCGTTGCCGGATGGATCTTAGGAAACCCAGAATGCGAA
TTACTGATTTCCAAGGAATCATGGTCCTACATTGTAGAAACACCAAATCCTGAGAATGGAACAT
GTTACCCAGGGTATTTCGCCGACTATGAGGAACTGAGGGAGCAATTGAGTTCAGTATCTTCAT
TTGAGAGATTCGAAATATTCCCCAAAGAAAGCTCATGGCCCAACCACACCGTAACCGGAGTAT
CAGCATCATGCTCCCATAATGGGAAAAGCAGTTTTTACAGAAATTTGCTATGGCTGACGGGGA
AGAATGGTTTGTACCCAAACCTGAGCAAGTCCTATGTAAACAACAAAGAGAAAGAAGTCCTTGT
ACTATGGGGTGTTCATCACCCGCCTAACATAGGGAACCAAAGGGCCCTCTATCATACAGAAAA
TGCTTATGTCTCTGTAGTGTCTTCACATTATAGCAGAAGATTCACCCCAGAAATAGCCAAAAGA
CCCAAAGTAAGAGATCAGGAAGGAAGAATCAACTACTACTGGACTCTGCTGGAACCTGGGGAT
ACAATAATATTTGAGGCAAATGGAAATCTAATAGCGCCATGGTATGCTTTTGCACTGAGTAGAG
GCTTTGGATCAGGAATCATCACCTCAAATGCACCAATGGATGAATGTGATGCGAAGTGTCAAA
CACCTCAGGGAGCTATAAACAGCAGTCTTCCTTTCCAGAATGTACACCCAGTCACAATAGGAG
AGTGTCCAAAGTATGTCAGGAGTGCAAAATTAAGGATGGTTACAGGACTAAGGAACATCCCAT
CCATTCAATCCAGAGGTTTGTTTGGAGCCATTGCCGGTTTCATTGAAGGGGGGTGGACTGGAA
TGGTAGATGGGTGGTATGGTTATCATCATCAGAATGAGCAAGGATCTGGCTATGCTGCAGATC
AAAAAAGTACACAAAATGCCATTAACGGGATTACAAACAAGGTGAATTCTGTAATTGAGAAAAT
GAACACTCAATTCACAGCTGTGGGCAAAGAATTCAACAAATTGGAAAGAAGGATGGAAAACTTA
AATAAAAAAGTTGATGATGGGTTTCTAGACATTTGGACATATAATGCAGAATTGTTGGTTCTACT
GGAAAATGAAAGGACTTTGGATTTCCATGACTCCAATGTGAAGAATCTGTATGAGAAAGTAAAA
AGCCAATTAAAGAATAATGCCAAAGAAATAGGAAACGGGTGTTTTGAATTCTATCACAAGTGTA
ACAATGAATGCATGGAGAGTGTGAAAAATGGAACTTATGACTATCCAAAATATTCCGAAGAATC
AAAGTTAAACAGGGAGAAAATTGATGGAGTGAAATTGGAATCAATGGGAGTCTATCAGATTCTG
GCGATCTACTCAACTGTCGCCAGTTCCCTGGTTCTTTTGGTCTCCCTGGGGGCAATCAGCTTC
TGGATGTGTTCCAATGGGTCTTTGCAGTGTAGAATATGCATCTGAGACCAGAATTTCA

Figure 20

SEQ. ID. NO. 55.

Synthesized BglII-H1 A/NC/20/99-SacI/StuI.

AGATCTTCGCTGACACAATATGTATAGGCTACCATGCCAACAACTCAACCGACACTGTTGACAC
AGTACTTGAGAAGAATGTGACAGTGACACACTCTGTCAACCTACTTGAGGACAGTCACAATGGA
AAACTATGTCTACTAAAAGGAATAGCCCCACTACAATTGGGTAATTGCAGCGTTGCCGGATGGA
TCTTAGGAAACCCAGAATGCGAATTACTGATTTCCAAGGAATCATGGTCCTACATTGTAGAAACA
CCAAATCCTGAGAATGGAACATGTTACCCAGGGTATTTCGCCGACTATGAGGAACTGAGGGAGC
AATTGAGTTCAGTATCTTCATTTGAGAGATTCGAAATATTCCCCAAAGAAAGCTCATGGCCCAAC
CACACCGTAACCGGAGTATCAGCATCATGCTCCCATAATGGGAAAAGCAGTTTTTACAGAAATTT
GCTATGGCTGACGGGGAAGAATGGTTTGTACCCAAACCTGAGCAAGTCCTATGTAAACAACAAA
GAGAAAGAAGTCCTTGTACTATGGGGTGTTCATCACCCGCCTAACATAGGGAACCAAAGGGCAC
TCTATCATACAGAAAATGCTTATGTCTCTGTAGTGTCTTCACATTATAGCAGAAGATTCACCCCA
GAAATAGCCAAAAGACCCAAAGTAAGAGATCAGGAAGGAAGAATCAACTACTACTGGACTCTGC
TGGAACCTGGGGATACAATAATATTTGAGGCAAATGGAAATCTAATAGCGCCATGGTATGCTTTT
GCACTGAGTAGAGGCTTTGGATCAGGAATCATCACCTCAAATGCACCAATGGATGAATGTGATG
CGAAGTGTCAAACACCTCAGGGAGCTATAAACAGCAGTCTTCCTTTCCAGAATGTACACCCAGT
CACAATAGGAGAGTGTCCAAAGTATGTCAGGAGTGCAAAATTAAGGATGGTTACAGGACTAAGG
AACATCCCATCCATTCAATCCAGAGGTTTGTTTGGAGCCATTGCCGGTTTCATTGAAGGGGGGT
GGACTGGAATGGTAGATGGGTGGTATGGTTATCATCATCAGAATGAGCAAGGATCTGGCTATGC
TGCAGATCAAAAAAGTACACAAAATGCCATTAACGGGATTACAAACAAGGTCAATTCTGTAATTG
AGAAAATGAACACTCAATTCACAGCTGTGGGCAAAGAGTTCAACAAATTGGAAAGAAGGATGGA
AAACTTAAATAAAAAAGTTGATGATGGGTTTCTAGACATTTGGACATATAATGCAGAATTGTTGGT
TCTACTGGAAAATGAAAGGACTTTGGATTTCCATGACTCCAATGTGAAGAATCTGTATGAGAAAG
TAAAAAGCCAATTAAAGAATAATGCCAAAGAAATAGGAAACGGGTGTTTTGAGTTCTATCACAAG
TGTAACAATGAATGCATGGAGAGTGTGAAAAATGGTACCTATGACTATCCAAAATATTCCGAAGA
ATCAAAGTTAAACAGGGAGAAAATTGATGGAGTGAAATTGGAATCAATGGGAGTATACTAAGAG
CTCAGGCCT

Figure 21

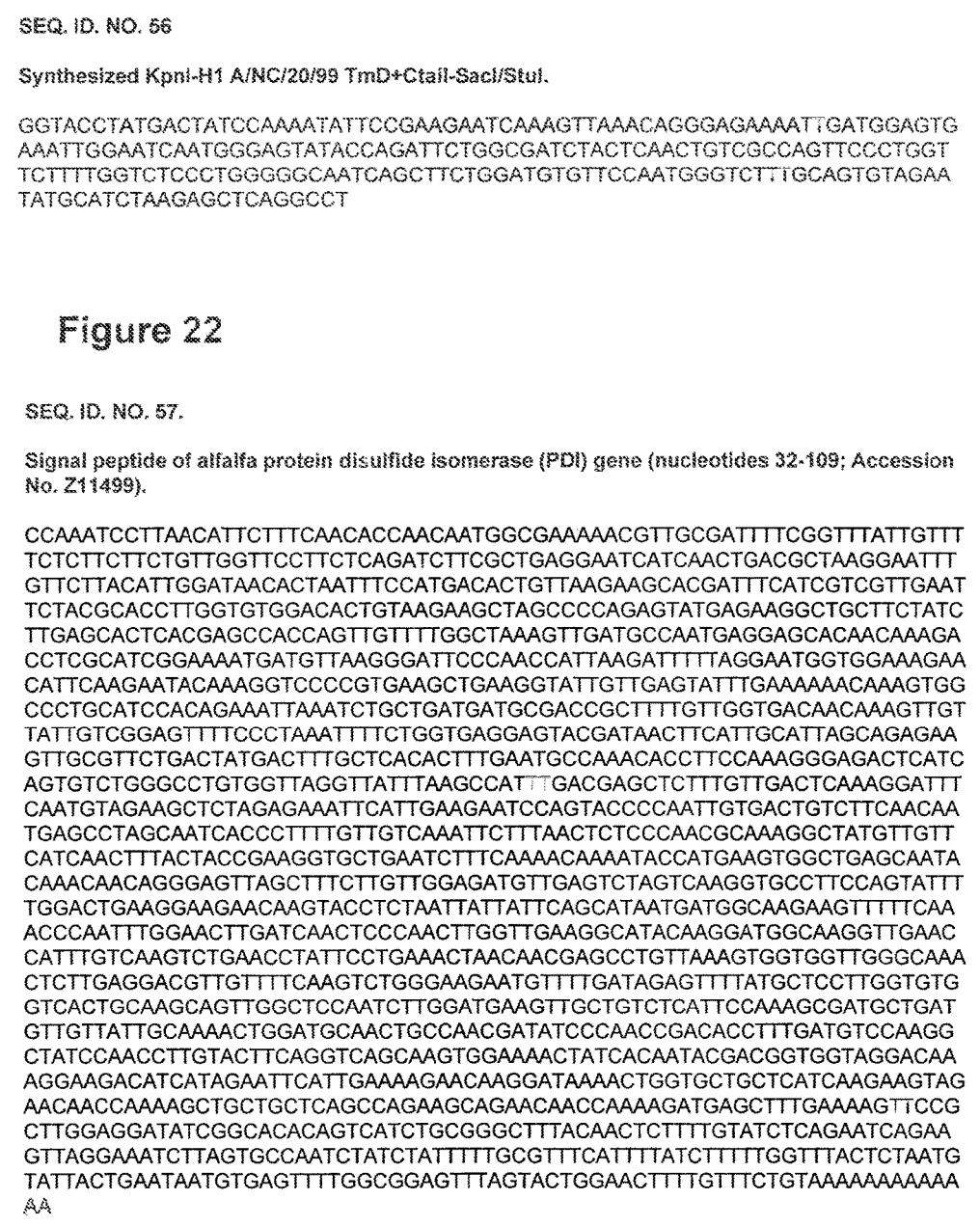

SEQ. ID. NO. 56

Synthesized KpnI-H1 A/NC/20/99 TmD+Ctail-SacI/StuI.

GGTACCTATGACTATCCAAAATATTCCGAAGAATCAAAGTTAAACAGGGAGAAAATTGATGGAGTG
AAATTGGAATCAATGGGAGTATACCAGATTCTGGCGATCTACTCAACTGTCGCCAGTTCCCTGGT
TCTTTTGGTCTCCCTGGGGGCAATCAGCTTCTGGATGTGTTCCAATGGGTCTTTGCAGTGTAGAA
TATGCATCTAAGAGCTCAGGCCT

Figure 22

SEQ. ID. NO. 57.

Signal peptide of alfalfa protein disulfide isomerase (PDI) gene (nucleotides 32-109; Accession No. Z11499).

CCAAATCCTTAACATTCTTTCAACACCAACAATGGCGAAAAACGTTGCGATTTTCGGTTTATTGTTT
TCTCTTCTTCTGTTGGTTCCTTCTCAGATCTTCGCTGAGGAATCATCAACTGACGCTAAGGAATTT
GTTCTTACATTGGATAACACTAATTTCCATGACACTGTTAAGAAGCACGATTTCATCGTCGTTGAAT
TCTACGCACCTTGGTGTGGACACTGTAAGAAGCTAGCCCCAGAGTATGAGAAGGCTGCTTCTATC
TTGAGCACTCACGAGCCACCAGTTGTTTTGGCTAAAGTTGATGCCAATGAGGAGCACAACAAAGA
CCTCGCATCGGAAAATGATGTTAAGGGATTCCCAACCATTAAGATTTTTAGGAATGGTGGAAAGAA
CATTCAAGAATACAAAGGTCCCCGTGAAGCTGAAGGTATTGTTGAGTATTTGAAAAAACAAAGTGG
CCCTGCATCCACAGAAATTAAATCTGCTGATGATGCGACCGCTTTTGTTGGTGACAACAAAGTTGT
TATTGTCGGAGTTTTCCCTAAATTTTCTGGTGAGGAGTACGATAACTTCATTGCATTAGCAGAGAA
GTTGCGTTCTGACTATGACTTTGCTCACACTTTGAATGCCAAACACCTTCCAAAGGGAGACTCATC
AGTGTCTGGGCCTGTGGTTAGGTTATTTAAGCCATTTGACGAGCTCTTTGTTGACTCAAAGGATTT
CAATGTAGAAGCTCTAGAGAAATTCATTGAAGAATCCAGTACCCCAATTGTGACTGTCTTCAACAA
TGAGCCTAGCAATCACCCTTTTGTTGTCAAATTCTTTAACTCTCCCAACGCAAAGGCTATGTTGTT
CATCAACTTTACTACCGAAGGTGCTGAATCTTTCAAAACAAAATACCATGAAGTGGCTGAGCAATA
CAAACAACAGGGAGTTAGCTTTCTTGTTGGAGATGTTGAGTCTAGTCAAGGTGCCTTCCAGTATTT
TGGACTGAAGGAAGAACAAGTACCTCTAATTATTATTCAGCATAATGATGGCAAGAAGTTTTTCAA
ACCCAATTTGGAACTTGATCAACTCCCAACTTGGTTGAAGGCATACAAGGATGGCAAGGTTGAAC
CATTTGTCAAGTCTGAACCTATTCCTGAAACTAACAACGAGCCTGTTAAAGTGGTGGTTGGGCAAA
CTCTTGAGGACGTTGTTTTCAAGTCTGGGAAGAATGTTTTGATAGAGTTTTATGCTCCTTGGTGTG
GTCACTGCAAGCAGTTGGCTCCAATCTTGGATGAAGTTGCTGTCTCATTCCAAAGCGATGCTGAT
GTTGTTATTGCAAAACTGGATGCAACTGCCAACGATATCCCAACCGACACCTTTGATGTCCAAGG
CTATCCAACCTTGTACTTCAGGTCAGCAAGTGGAAAACTATCACAATACGACGGTGGTAGGACAA
AGGAAGACATCATAGAATTCATTGAAAAGAACAAGGATAAAACTGGTGCTGCTCATCAAGAAGTAG
AACAACCAAAAGCTGCTGCTCAGCCAGAAGCAGAACAACCAAAAGATGAGCTTTGAAAAGTTCCG
CTTGGAGGATATCGGCACACAGTCATCTGCGGGCTTTACAACTCTTTTGTATCTCAGAATCAGAA
GTTAGGAAATCTTAGTGCCAATCTATCTATTTTTGCGTTTCATTTTATCTTTTTGGTTTACTCTAATG
TATTACTGAATAATGTGAGTTTTGGCGGAGTTTAGTACTGGAACTTTTGTTTCTGTAAAAAAAAAA
AA

Figure 23A

SEQ. ID. NO. 58.

PromPlasto-PDI SP-BglII

*CTGGTATATTTATATGTTGTCAAATAACTCAAAAACCATAAAAGTTTAAGTTAGCAAGTGTGTACATT*
*TTTACTTGAACAAAAATATTCACCTACTACTGTTATAAATCATTATTAAACATTAGAGTAAAGAAATA*
*TGGATGATAAGAACAAGAGTAGTGATATTTTGACAACAATTTTGTTGCAACATTTGAGAAAATTTTG*
*TTGTTCTCTCTTTTCATTGGTCAAAAACAATAGAGAGAGAAAAAGGAAGAGGGAGAATAAAAACATA*
*ATGTGAGTATGAGAGAGAAAGTTGTACAAAAGTTGTACCAAAATAGTTGTACAAATATCATTGAGGA*
*ATTTGACAAAAGCTACACAAATAAGGGTTAATTGCTGTAAATAAATAAGGATGACGCATTAGAGAGA*
*TGTACCATTAGAGAATTTTTGGCAAGTCATTAAAAAGAAAGAATAAATTATTTTTAAAATTAAAAGTT*
*GAGTCATTTGATTAAACATGTGATTATTTAATGAATTGATGAAAGAGTTGGATTAAAGTTGTATTAGT*
*AATTAGAATTTGGTGTCAAATTTAATTTGACATTTGATCTTTTCCTATATATTGCCCCATAGAGTCAG*
*TTAACTCATTTTTATATTTCATAGATCAAATAAGAGAAATAACGGTATATTAATCCCTCCAAAAAAAA*
*AAAACGGTATATTTACTAAAAAATCTAAGCCACGTAGGAGGATAACAGGATCCCCGTAGGAGGATA*
*ACATCCAATCCAACCAATCACAACAATCCTGATGAGATAACCCACTTTAAGCCCACGCATCTGTGG*
*CACATCTACATTATCTAAATCACACATTCTTCCACACATCTGAGCCACACAAAAACCAATCCACATC*
*TTTATCACCCATTCTATAAAAAATCACACTTTGTGAGTCTACACTTTGATTCCCTTCAAACACATACA*
*AAGAGAAGAGACTAATTAATTAATTAATCATCTTGAGAGAAA*ATGGCGAAAAACGTTGCGATTTTCG
GCTTATTGTTTTCTCTTCTTGTGTTGGTTCCTTCTCAGATCT

Figure 23B

SEQ. ID. NO. 85.

SacI-Plasto 3'UTR plasmid sequence

GAGCTCTAAGTTAAAATGCTTCTTCGTCTCCTATTTATAATATGGTTTGTTATTGTTAATTTTGTTCT
TGTAGAAGAGCTTAATTAATCGTTGTTGTTATGAAATACTATTTGTATGAGATGAACTGGTGTAATG
TAATTCATTTACATAAGTGGAGTCAGAATCAGAATGTTTCCTCCATAACTAACTAGACATGAAGACC
TGCCGCGTACAATTGTCTTATATTTGAACAACTAAAATTGAACATCTTTTGCCACAACTTTATAAGT
GGTTAATATAGCTCAAATATATGGTCAAGTTCAATAGATTAATAATGGAAATATCAGTTATCGAAATT
CATTAACAATCAACTTAACGTTATTAACTACTAATTTTATATCATCCCCTTTGATAAATGATAGTACA

Figure 24

SEQ ID NO: 59.

540 expression cassette from HindIII (in the multiple cloning site, upstream of the Plastocyanin promoter) to EcoRI (immediately downstream of the Plastocyanin terminator). H1 from A/New Caledonia/20/1999 coding sequence underlined.

AAGCTTGCTAGCGGCCTCAATGGCCCTGCAGGTCGACTCTAGAGGTACCCCGGGCTGGTATATTTATATGTTGT
CAAATAACTCAAAAACCATAAAAGTTTAAGTTAGCAAGTGTGTACATTTTTACTTGAACAAAAATATTCACCTACTA
CTGTTATAAATCATTATTAAACATTAGAGTAAAGAAATATGGATGATAAGAACAAGAGTAGTGATATTTTGACAAC
AATTTTGTTGCAACATTTGAGAAAATTTTGTTGTTCTCTCTTTTCATTGGTCAAAAACAATAGAGAGAGAAAAAGG
AAGAGGGAGAATAAAAACATAATGTGAGTATGAGAGAGAAAGTTGTACAAAAGTTGTACCAAAATAGTTGTACAA
ATATCATTGAGGAATTTGACAAAAGCTACACAAATAAGGGTTAATTGCTGTAAATAAATAAGGATGACGCATTAGA
GAGATGTACCATTAGAGAATTTTTGGCAAGTCATTAAAAAGAAAGAATAAATTATTTTTAAAATTAAAAGTTGAGTC
ATTTGATTAAACATGTGATTATTTAATGAATTGATGAAAGAGTTGGATTAAAGTTGTATTAGTAATTAGAATTTGGT
GTCAAATTTAATTTGACATTTGATCTTTTCCTATATATTGCCCCATAGAGTCAGTTAACTCATTTTTATATTTCATAG
ATCAAATAAGAGAAATAACGGTATATTAATCCCTCCAAAAAAAAAAAACGGTATATTTACTAAAAAATCTAAGCCA
CGTAGGAGGATAACAGGATCCCCGTAGGAGGATAACATCCAATCCAACCAATCACAACAATCCTGATGAGATAA
CCCACTTTAAGCCCACGCATCTGTGGCACATCTACATTATCTAAATCACACATTCTTCCACACATCTGAGCCACA
CAAAAACCAATCCACATCTTTATCACCCATTCTATAAAAAATCACACTTTGTGAGTCTACACTTTGATTCCCTTCAA
ACACATACAAAGAGAAGAGACTAATTAATTAATTAATCATCTTGAGAGAAAATGGCGAAAAACGTTGCGATTTTCG
GCTTATTGTTTTCTCTTCTTGTGTTGGTTCCTTCTCAGATCTTCGCTGACACAATATGTATAGGCTACCATGCCAA
CAACTCAACCGACACTGTTGACACAGTACTTGAGAAGAATGTGACAGTGACACACTCTGTCAACCTACTTGAGG
ACAGTCACAATGGAAAACTATGTCTACTAAAAGGAATAGCCCCACTACAATTGGGTAATTGCAGCGTTGCCGGAT
GGATCTTAGGAAACCCAGAATGCGAATTACTGATTTCCAAGGAATCATGGTCCTACATTGTAGAAACACCAAATC
CTGAGAATGGAACATGTTACCCAGGGTATTTCGCCGACTATGAGGAACTGAGGGAGCAATTGAGTTCAGTATCT
TCATTTGAGAGATTCGAAATATTCCCCAAAGAAAGCTCATGGCCCAACCACACCGTAACCGGAGTATCAGCATCA
TGCTCCCATAATGGGAAAAGCAGTTTTTACAGAAATTTGCTATGGCTGACGGGGAAGAATGGTTTGTACCCAAAC
CTGAGCAAGTCCTATGTAAACAACAAAGAGAAAGAAGTCCTTGTACTATGGGGTGTTCATCACCCGCCTAACATA
GGGAACCAAAGGGCACTCTATCATACAGAAAATGCTTATGTCTCTGTAGTGTCTTCACATTATAGCAGAAGATTC
ACCCCAGAAATAGCCAAAAGACCCAAAGTAAGAGATCAGGAAGGAAGAATCAACTACTACTGGACTCTGCTGGA
ACCTGGGGATACAATAATATTTGAGGCAAATGGAAATCTAATAGCGCCATGGTATGCTTTTGCACTGAGTAGAGG
CTTTGGATCAGGAATCATCACCTCAAATGCACCAATGGATGAATGTGATGCGAAGTGTCAAACACCTCAGGGAG
CTATAAACAGCAGTCTTCCTTTCCAGAATGTACACCCAGTCACAATAGGAGAGTGTCCAAAGTATGTCAGGAGTG
CAAAATTAAGGATGGTTACAGGACTAAGGAACATCCCATCCATTCAATCCAGAGGTTTGTTTGGAGCCATTGCCG
GTTTCATTGAAGGGGGGTGGACTGGAATGGTAGATGGGTGGTATGGTTATCATCATCAGAATGAGCAAGGATCT
GGCTATGCTGCAGATCAAAAAAGTACACAAAATGCCATTAACGGGATTACAAACAAGGTCAATTCTGTAATTGAG
AAAATGAACACTCAATTCACAGCTGTGGGCAAAGAGTTCAACAAATTGGAAAGAAGGATGGAAAACTTAAATAAA
AAAGTTGATGATGGGTTTCTAGACATTTGGACATATAATGCAGAATTGTTGGTTCTACTGGAAAATGAAAGGACTT
TGGATTTCCATGACTCCAATGTGAAGAATCTGTATGAGAAAGTAAAAAGCCAATTAAAGAATAATGCCAAAGAAAT
AGGAAACGGGTGTTTTGAGTTCTATCACAAGTGTAACAATGAATGCATGGAGAGTGTGAAAAATGGTACCTATGA
CTATCCAAAATATTCCGAAGAATCAAAGTTAAACAGGGAGAAAATTGATGGAGTGAAATTGGAATCAATGGGAGT
ATACCAGATTCTGGCGATCTACTCAACTGTCGCCAGTTCCCTGGTTCTTTTGGTCTCCCTGGGGGCAATCAGCTT
CTGGATGTGTTCCAATGGGTCTTTGCAGTGTAGAATATGCATCTAAGAGCTCTAAGTTAAAATGCTTCTTCGTCT
CCTATTTATAATATGGTTTGTTATTGTTAATTTTGTTCTTGTAGAAGAGCTTAATTAATCGTTGTTGTTATGAAATAC
TATTTGTATGAGATGAACTGGTGTAATGTAATTCATTTACATAAGTGGAGTCAGAATCAGAATGTTTCCTCCATAA
CTAACTAGACATGAAGACCTGCCGCGTACAATTGTCTTATATTTGAACAACTAAAATTGAACATCTTTTGCCACAA
CTTTATAAGTGGTTAATATAGCTCAAATATATGGTCAAGTTCAATAGATTAATAATGGAAATATCAGTTATCGAAAT
TCATTAACAATCAACTTAACGTTATTAACTACTAATTTTATATCATCCCCTTTGATAAATGATAGTACACCAATTAG
GAAGGAGCATGCTCGAGGCCTGGCTGGCCGAATTC

Figure 25

SEQ ID NO: 60

Synthesized fragment DraIII-Plasto(-84+1)-H1 A/Brisbane/59/07-SacI.

CACTTTGTGAGTCTACACTTTGATTCCCTTCAAACACATACAAAGAGAAGAGACTAATTAATTAAT
TAATCATCTTGAGAGAAAATGAAAGTAAAACTACTGGTCCTGTTATGCACATTTACAGCTACATAT
GCAGACACAATATGTATAGGCTACCATGCTAACAACTCGACCGACACTGTTGACACAGTACTTGA
AAAGAATGTGACAGTGACACACTCTGTCAACCTGCTTGAGAACAGTCACAATGGAAAACTATGTC
TATTAAAAGGAATAGCCCCACTACAATTGGGTAATTGCAGCGTTGCCGGGTGGATCTTAGGAAAC
CCAGAATGCGAATTACTGATTTCCAAGGAGTCATGGTCCTACATTGTAGAAAAACCAAATCCTGA
GAATGGAACATGTTACCCAGGGCATTTCGCTGACTATGAGGAACTGAGGGAGCAATTGAGTTCA
GTATCTTCATTTGAGAGGTTCGAAATATTCCCCAAAGAAAGCTCATGGCCCAACCACACCGTAAC
CGGAGTGTCAGCATCATGCTCCCATAATGGGGAAAGCAGTTTTTACAGAAATTTGCTATGGCTGA
CGGGGAAGAATGGTTTGTACCCAAACCTGAGCAAGTCCTATGCAAACAACAAAGAAAAAGAAGT
CCTTGTACTATGGGGTGTTCATCACCCGCCAAACATAGGTGACCAAAAGGCCCTCTATCATACA
GAAAATGCTTATGTCTCTGTAGTGTCTTCACATTATAGCAGAAAATTCACCCCAGAAATAGCCAAA
AGACCCAAAGTAAGAGATCAAGAAGGAAGAATCAATTACTACTGGACTCTGCTTGAACCCGGGG
ATACAATAATATTTGAGGCAAATGGAAATCTAATAGCGCCAAGATATGCTTTCGCACTGAGTAGA
GGCTTTGGATCAGGAATCATCAACTCAAATGCACCAATGGATAAATGTGATGCGAAGTGCCAAAC
ACCTCAGGGAGCTATAAACAGCAGTCTTCCTTTCCAGAACGTACACCCAGTCACAATAGGAGAG
TGTCCAAAGTATGTCAGGAGTGCAAAATTAAGGATGGTTACAGGACTAAGGAACATCCCATCCAT
TCAATCCAGAGGTTTGTTTGGAGCCATTGCCGGTTTCATTGAAGGGGGGTGGACTGGAATGGTA
GATGGTTGGTATGGTTATCATCATCAGAATGAGCAAGGATCTGGCTATGCTGCAGATCAAAAAAG
CACACAAAATGCCATTAATGGGATTACAAACAAGGTCAATTCTGTAATTGAGAAAATGAACACTCA
ATTCACAGCAGTGGGCAAAGAGTTCAACAAATTGGAAAGAAGGATGGAAAACTTGAATAAAAAAG
TTGATGATGGGTTTATAGACATTTGGACATATAATGCAGAACTGTTGGTTCTACTGGAAAATGAAA
GGACTTTGGATTTCCATGACTCCAATGTGAAGAATCTGTATGAGAAAGTAAAAAGCCAGTTAAAG
AATAATGCTAAAGAAATAGGAAATGGGTGTTTTGAGTTCTATCACAAGTGTAACGATGAATGCAT
GGAGAGTGTAAAGAATGGAACTTATGACTATCCAAAATATTCCGAAGAATCAAAGTTAAACAGGG
AGAAAATTGATGGAGTGAAATTGGAATCAATGGGAGTCTATCAGATTCTGGCGATCTACTCAACA
GTCGCCAGTTCTCTGGTTCTTTTGGTCTCCCTGGGGGCAATCAGCTTCTGGATGTGTTCCAATG
GGTCTTTACAGTGTAGAATATGCATCTAAGAGCTC

Figure 26

SEQ ID NO: 61

774 expression cassette from HindIII (in the multiple cloning site, upstream of the Plastocyanin promoter) to EcoRI (immediately downstream of the Plastocyanin terminator). H1 from A/Brisbane/59/2007 coding sequence underlined.

AAGCTTGCTAGCGGCCTCAATGGCCCTGCAGGTCGACTCTAGAGGTACCCCGGGCTGGTATATTTATATGTT
GTCAAATAACTCAAAAACCATAAAAGTTTAAGTTAGCAAGTGTGTACATTTTTACTTGAACAAAAATATTCACC
TACTACTGTTATAAATCATTATTAAACATTAGAGTAAAGAAATATGGATGATAAGAACAAGAGTAGTGATATTTT
GACAACAATTTTGTTGCAACATTTGAGAAAATTTTGTTGTTCTCTCTTTTCATTGGTCAAAAACAATAGAGAGA
GAAAAAGGAAGAGGGAGAATAAAAACATAATGTGAGTATGAGAGAGAAAGTTGTACAAAAGTTGTACCAAAA
TAGTTGTACAAATATCATTGAGGAATTTGACAAAAGCTACACAAATAAGGGTTAATTGCTGTAAATAAATAAGG
ATGACGCATTAGAGAGATGTACCATTAGAGAATTTTTGGCAAGTCATTAAAAAGAAAGAATAAATTATTTTTAA
AATTAAAAGTTGAGTCATTTGATTAAACATGTGATTATTTAATGAATTGATGAAAGAGTTGGATTAAAGTTGTAT
TAGTAATTAGAATTTGGTGTCAAATTTAATTTGACATTTGATCTTTTCCTATATATTGCCCCATAGAGTCAGTTA
ACTCATTTTTATATTTCATAGATCAAATAAGAGAAATAACGGTATATTAATCCCTCCAAAAAAAAAAAACGGTAT
ATTTACTAAAAAATCTAAGCCACGTAGGAGGATAACAGGATCCCCGTAGGAGGATAACATCCAATCCAACCA
ATCACAACAATCCTGATGAGATAACCCACTTTAAGCCCACGCATCTGTGGCACATCTACATTATCTAAATCAC
ACATTCTTCCACACATCTGAGCCACACAAAAACCAATCCACATCTTTATCACCCATTCTATAAAAAATCACACT
TTGTGAGTCTACACTTTGATTCCCTTCAAACACATACAAAGAGAAGAGACTAATTAATTAATTAATCATCTTGA
GAGAAAATGAAAGTAAAACTACTGGTCCTGTTATGCACATTTACAGCTACATATGCAGACACAATATGTATAG
GCTACCATGCTAACAACTCGACCGACACTGTTGACACAGTACTTGAAAAGAATGTGACAGTGACACACTCTG
TCAACCTGCTTGAGAACAGTCACAATGGAAAACTATGTCTATTAAAAGGAATAGCCCCACTACAATTGGGTAA
TTGCAGCGTTGCCGGGTGGATCTTAGGAAACCCAGAATGCGAATTACTGATTTCCAAGGAGTCATGGTCCTA
CATTGTAGAAAAACCAAATCCTGAGAATGGAACATGTTACCCAGGGCATTTCGCTGACTATGAGGAACTGAG
GGAGCAATTGAGTTCAGTATCTTCATTTGAGAGGTTCGAAATATTCCCCAAAGAAAGCTCATGGCCCAACCA
CACCGTAACCGGAGTGTCAGCATCATGCTCCCATAATGGGGAAAGCAGTTTTTACAGAAATTTGCTATGGCT
GACGGGGAAGAATGGTTTGTACCCAAACCTGAGCAAGTCCTATGCAAACAACAAAGAAAAAGAAGTCCTTGT
ACTATGGGGTGTTCATCACCCGCCAAACATAGGTGACCAAAAGGCCCTCTATCATACAGAAAATGCTTATGT
CTCTGTAGTGTCTTCACATTATAGCAGAAAATTCACCCCAGAAATAGCCAAAAGACCCAAAGTAAGAGATCAA
GAAGGAAGAATCAATTACTACTGGACTCTGCTTGAACCCGGGGATACAATAATATTTGAGGCAAATGGAAAT
CTAATAGCGCCAAGATATGCTTTCGCACTGAGTAGAGGCTTTGGATCAGGAATCATCAACTCAAATGCACCA
ATGGATAAATGTGATGCGAAGTGCCAAACACCTCAGGGAGCTATAAACAGCAGTCTTCCTTTCCAGAACGTA
CACCCAGTCACAATAGGAGAGTGTCCAAAGTATGTCAGGAGTGCAAAATTAAGGATGGTTACAGGACTAAGG
AACATCCCATCCATTCAATCCAGAGGTTTGTTTGGAGCCATTGCCGGTTTCATTGAAGGGGGGTGGACTGGA
ATGGTAGATGGTTGGTATGGTTATCATCATCAGAATGAGCAAGGATCTGGCTATGCTGCAGATCAAAAAAGC
ACACAAAATGCCATTAATGGGATTACAAACAAGGTCAATTCTGTAATTGAGAAAATGAACACTCAATTCACAG
CAGTGGGCAAAGAGTTCAACAAATTGGAAAGAAGGATGGAAAACTTGAATAAAAAAGTTGATGATGGGTTTAT
AGACATTTGGACATATAATGCAGAACTGTTGGTTCTACTGGAAAATGAAAGGACTTTGGATTTCCATGACTCC
AATGTGAAGAATCTGTATGAGAAAGTAAAAAGCCAGTTAAAGAATAATGCTAAAGAAATAGGAAATGGGTGTT
TTGAGTTCTATCACAAGTGTAACGATGAATGCATGGAGAGTGTAAAGAATGGAACTTATGACTATCCAAAATA
TTCCGAAGAATCAAAGTTAAACAGGGAGAAAATTGATGGAGTGAAATTGGAATCAATGGGAGTCTATCAGATT
CTGGCGATCTACTCAACAGTCGCCAGTTCTCTGGTTCTTTTGGTCTCCCTGGGGGCAATCAGCTTCTGGATG
TGTTCCAATGGGTCTTTACAGTGTAGAATATGCATCTAAGAGCTCTAAGTTAAAATGCTTCTTCGTCTCCTATT
TATAATATGGTTTGTTATTGTTAATTTTGTTCTTGTAGAAGAGCTTAATTAATCGTTGTTGTTATGAAATACTATT
TGTATGAGATGAACTGGTGTAATGTAATTCATTTACATAAGTGGAGTCAGAATCAGAATGTTTCCTCCATAACT
AACTAGACATGAAGACCTGCCGCGTACAATTGTCTTATATTTGAACAACTAAAATTGAACATCTTTTGCCACAA
CTTTATAAGTGGTTAATATAGCTCAAATATATGGTCAAGTTCAATAGATTAATAATGGAAATATCAGTTATCGA
AATTCATTAACAATCAACTTAACGTTATTAACTACTAATTTTATATCATCCCCTTTGATAAATGATAGTACACCA
ATTAGGAAGGAGCATGCTCGAGGCCTGGCTGGCCGAATTC

Figure 27

SEQ ID NO: 62

Expression cassette number 828, from PacI (upstream of the promoter) to AscI (immediately downstream of the NOS terminator). CPMV HT 3'UTR sequence underlined with mutated ATG in bold. ApaI restriction site (immediately downstream ATG for protein coding sequence, in this case C5-1 kappa light chain, is underlined italic).

TTAATTAAGAATTCGAGCTCCACCGCGGAAACCTCCTCGGATTCCATTGCCCAGCTATCTGTCACTT
TATTGAGAAGATAGTGGAAAAGGAAGGTGGCTCCTACAAATGCCATCATTGCGATAAAGGAAAGGC
CATCGTTGAAGATGCCTCTGCCGACAGTGGTCCCAAAGATGGACCCCCACCCACGAGGAGCATCG
TGGAAAAAGAAGACGTTCCAACCACGTCTTCAAAGCAAGTGGATTGATGTGATATCTCCACTGACGT
AAGGGATGACGCACAATCCCACTATCCTTCGCAAGACCCTTCCTCTATATAAGGAAGTTCATTTCAT
TTGGAGAGGTATTAAAATCTTAATAGGTTTTGATAAAAGCGAACGTGGGGAAACCCGAACCAAACCT
TCTTCTAAACTCTCTCTCATCTCTCTTAAAGCAAACTTCTCTCTTGTCTTTCTTGCGTGAGCGATCTT
CAACGTTGTCAGATCGTGCTTCGGCACCAGTACAACGTTTTCTTTCACTGAAGCGAAATCAAAGATC
TCTTTGTGGACACGTAGTGCGGCGCCATTAAATAACGTGTACTTGTCCTATTCTTGTCGGTGTGGTC
TTGGGAAAAGAAAGCTTGCTGGAGGCTGCTGTTCAGCCCCATACATTACTTGTTACGATTCTGCTGA
CTTTCGGCGGGTGCAATATCTCTACTTCTGCTTGACGAGGTATTGTTGCCTGTACTTCTTTCTTCTT
CTTCTTGCTGATTGGTTCTATAAGAAATCTAGTATTTTCTTTGAAACAGAGTTTTCCCGTGGTTTTCG
AACTTGGAGAAAGATTGTTAAGCTTCTGTATATTCTGCCCAAATTTGTC*GGGCCC*ATGGTTTTCACA
CCTCAGATACTTGGACTTATGCTTTTTTGGATTTCAGCCTCCAGAGGTGATATTGTGCTAACTCAGT
CTCCAGCCACCCTGTCTGTGACTCCAGGAGATAGTGTCAGTCTTTCCTGCAGGGCCAGCCAAAGTA
TTAGCAACAACCTACACTGGTTTCAACAAAAATCGCATGAGTCTCCAAGGCTTCTCATCAAGTATGC
TTCCCAGTCCATATCTGGGATCCCCTCCAGGTTCAGTGGCAGTGGATCTGGGACAGATTTCACTCT
CAGTATCAACAGTGTGAAGACTGAAGATTTTGGAATGTTTTTCTGTCAACAGAGTAACAGCTGGCCT
CTCACGTTCGGTGATGGGACAAAGCTGGAGCTGAAACGGGCTGATGCTGCACCAACTGTATCCAT
CTTCCCACCATCCAGTGAGCAGTTAACATCTGGAGGTGCCTCAGTCGTGTGCTTCTTGAACAACTT
CTACCCCAAAGACATCAATGTCAAGTGGAAGATTGATGGCAGTGAACGACAAAATGGCGTCCTGAA
CAGTTGGACTGATCAGGACAGCAAAGACAGCACCTACAGCATGAGCAGCACCCTCACGTTGACCA
AGGACGAGTATGAACGACATAACAGCTATACCTGTGAGGCCACTCACAAGACATCAACTTCACCCA
TTGTCAAGAGCTTCAACAGGAATGAGTGTTAGAGGCCTATTTTCTTTAGTTTGAATTTACTGTTATTC
GGTGTGCATTTCTATGTTTGGTGAGCGGTTTTCTGTGCTCAGAGTGTGTTTATTTTATGTAATTTAAT
TTCTTTGTGAGCTCCTGTTTAGCAGGTCGTCCCTTCAGCAAGGACACAAAAAGATTTTAATTTTATTA
AAAAAAAAAAAAAAAAAGACCGGGAATTCGATATCAAGCTTATCGACCTGCAGATCGTTCAAACATT
TGGCAATAAAGTTTCTTAAGATTGAATCCTGTTGCCGGTCTTGCGATGATTATCATATAATTTCTGTT
GAATTACGTTAAGCATGTAATAATTAACATGTAATGCATGACGTTATTTATGAGATGGGTTTTTATGA
TTAGAGTCCCGCAATTATACATTTAATACGCGATAGAAAACAAAATATAGCGCGCAAACTAGGATAA
ATTATCGCGCGCGGTGTCATCTATGTTACTAGATTCTAGAGTCTCAAGCTTCGGCGCGCC

Figure 28

SEQ. ID. NO. 63

Construct number 690, from HindIII (in the multiple cloning site, upstream of the Plastocyanin promoter) to EcoRI (immediately downstream of the Plastocyanin terminator). Chimeric HA coding sequence is underlined.

AAGCTTGCTAGCGGCCTCAATGGCCCTGCAGGTCGACTCTAGAGGTACCCCGGGCTGGTATATTTATATGTT
GTCAAATAACTCAAAAACCATAAAAGTTTAAGTTAGCAAGTGTGTACATTTTTACTTGAACAAAAATATTCACCT
ACTACTGTTATAAATCATTATTAAACATTAGAGTAAAGAAATATGGATGATAAGAACAAGAGTAGTGATATTTTG
ACAACAATTTTGTTGCAACATTTGAGAAAATTTTGTTGTTCTCTCTTTTCATTGGTCAAAAACAATAGAGAGAGA
AAAAGGAAGAGGGAGAATAAAAACATAATGTGAGTATGAGAGAGAAAGTTGTACAAAAGTTGTACCAAAATAG
TTGTACAAATATCATTGAGGAATTTGACAAAAGCTACACAAATAAGGGTTAATTGCTGTAAATAAATAAGGATG
ACGCATTAGAGAGATGTACCATTAGAGAATTTTTGGCAAGTCATTAAAAAGAAAGAATAAATTATTTTTAAAATT
AAAAGTTGAGTCATTTGATTAAACATGTGATTATTTAATGAATTGATGAAAGAGTTGGATTAAAGTTGTATTAGT
AATTAGAATTTGGTGTCAAATTTAATTTGACATTTGATCTTTTCCTATATATTGCCCCATAGAGTCAGTTAACTC
ATTTTTATATTTCATAGATCAAATAAGAGAAATAACGGTATATTAATCCCTCCAAAAAAAAAAAACGGTATATTT
ACTAAAAAATCTAAGCCACGTAGGAGGATAACAGGATCCCCGTAGGAGGATAACATCCAATCCAACCAATCA
CAACAATCCTGATGAGATAACCCACTTTAAGCCCACGCATCTGTGGCACATCTACATTATCTAAATCACACATT
CTTCCACACATCTGAGCCACACAAAAACCAATCCACATCTTTATCACCCATTCTATAAAAAATCACACTTTGTG
AGTCTACACTTTGATTCCCTTCAAACACATACAAAGAGAAGAGACTAATTAATTAATTAATCATCTTGAGAGAA
AATGGAGAAAATAGTGCTTCTTCTTGCAATAGTCAGTCTTGTTAAAAGTGATCAGATTTGCATTGGTTACCATG
CAAACAATTCAACAGAGCAGGTTGACACAATCATGGAAAAGAACGTTACTGTTACACATGCCCAAGACATACT
GGAAAAGACACACAACGGGAAGCTCTGCGATCTAGATGGAGTGAAGCCTCTAATTTTAAGAGATTGTAGTGT
AGCTGGATGGCTCCTCGGGAACCCAATGTGTGACGAATTCATCAATGTACCGGAATGGTCTTACATAGTGGA
GAAGGCCAATCCAACCAATGACCTCTGTTACCCAGGGCATTTCGCTGACTATGAGGAACTGAGGGAGCAATT
GAGTTCAGTATCTTCATTTGAGAGGTTCGAAATATTCCCCAAAGAAAGCTCATGGCCCAACCACACCGTAACC
GGAGTGTCAGCATCATGCTCCCATAATGGGGAAAGCAGTTTTTACAGAAATTTGCTATGGCTGACGGGGAAG
AATGGTTTGTACCCAAACCTGAGCAAGTCCTATGCAAACAACAAAGAAAAAGAAGTCCTTGTACTATGGGGTG
TTCATCACCCGCCAAACATAGGTGACCAAAAGGCCCTCTATCATACAGAAAATGCTTATGTCTCTGTAGTGTC
TTCACATTATAGCAGAAAATTCACCCCAGAAATAGCCAAAAGACCCAAAGTAAGAGATCAAGAAGGAAGAATC
AATTACTACTGGACTCTGCTTGAACCCGGGGATACAATAATATTTGAGGCAAATGGAAATCTAATAGCGCCAA
GATATGCTTTCGCACTGAGTAGAGGCTTTGGATCAGGAATTATGAAAAGTGAATTGGAATATGGTAACTGCAA
CACCAAGTGTCAAACTCCAATGGGGGCGATAAACTCTAGTATGCCATTCCACAACATACACCCTCTCACCATC
GGGGAATGCCCCAAATATGTGAAATCAAACAGATTAGTCCTTGCAACAGGGCTCAGAAATAGCCCTCAAAGA
GAGAGCAGAAGAAAAAAGAGAGGACTATTTGGAGCTATAGCAGGTTTTATAGAGGGAGGATGGCAGGGAAT
GGTAGATGGTTGGTATGGGTACCACCATAGCAATGAGCAGGGGAGTGGGTACGCTGCAGACAAAGAATCCA
CTCAAAAGGCAATAGATGGAGTCACCAATAAGGTCAACTCAATCATTGACAAAATGAACACTCAGTTTGAGGC
CGTTGGAAGGGAATTTAATAACTTAGAAAGGAGAATAGAGAATTTAAACAAGAAGATGGAAGACGGGTTTCTA
GATGTCTGGACTTATAATGCCGAACTTCTGGTTCTCATGGAAAATGAGAGAACTCTAGACTTTCATGACTCAA
ATGTTAAGAACCTCTACGACAAGGTCCGACTACAGCTTAGGGATAATGCAAAGGAGCTGGGTAACGGTTGTT
TCGAGTTCTATCACAAATGTGATAATGAATGTATGGAAAGTATAAGAAACGGAACGTACAACTATCCGCAGTA
TTCAGAAGAAGCAAGATTAAAAAGAGAGGAAATAAGTGGGGTAAAATTGGAATCAATAGGAACTTACCAAATA
CTGTCAATTTATTCAACAGTGGCGAGTTCCCTAGCACTGGCAATCATGATGGCTGGTCTATCTTTATGGATGT
GCTCCAATGGATCGTTACAATGCAGAATTTGCATTTAAGAGCTCTAAGTTAAAATGCTTCTTCGTCTCCTATTT
ATAATATGGTTTGTTATTGTTAATTTTGTTCTTGTAGAAGAGCTTAATTAATCGTTGTTGTTATGAAATACTATTT
GTATGAGATGAACTGGTGTAATGTAATTCATTTACATAAGTGGAGTCAGAATCAGAATGTTTCCTCCATAACTA
ACTAGACATGAAGACCTGCCGCGTACAATTGTCTTATATTTGAACAACTAAAATTGAACATCTTTTGCCACAAC
TTTATAAGTGGTTAATATAGCTCAAATATATGGTCAAGTTCAATAGATTAATAATGGAAATATCAGTTATCGAAA
TTCATTAACAATCAACTTAACGTTATTAACTACTAATTTTATATCATCCCCTTTGATAAATGATAGTACACCAATT
AGGAAGGAGCATGCTCGAGGCCTGGCTGGCCGAATTC

Figure 29

SEQ. ID. NO. 64

Construct number 691, from HindIII (in the multiple cloning site, upstream of the Plastocyanin promoter) to EcoRI (immediately downstream of the Plastocyanin terminator). Chimeric HA coding sequence is underlined.

AAGCTTGCTAGCGGCCTCAATGGCCCTGCAGGTCGACTCTAGAGGTACCCCGGGCTGGTATATTTATATGTTGTC
AAATAACTCAAAAACCATAAAAGTTTAAGTTAGCAAGTGTGTACATTTTTACTTGAACAAAAATATTCACCTACTACT
GTTATAAATCATTATTAAACATTAGAGTAAAGAAATATGGATGATAAGAACAAGAGTAGTGATATTTTGACAACAATT
TTGTTGCAACATTTGAGAAAATTTTGTTGTTCTCTCTTTTCATTGGTCAAAAACAATAGAGAGAGAAAAAGGAAGAG
GGAGAATAAAAACATAATGTGAGTATGAGAGAGAAAGTTGTACAAAAGTTGTACCAAAATAGTTGTACAAATATCAT
TGAGGAATTTGACAAAAGCTACACAAATAAGGGTTAATTGCTGTAAATAAATAAGGATGACGCATTAGAGAGATGT
ACCATTAGAGAATTTTTGGCAAGTCATTAAAAAGAAAGAATAAATTATTTTTAAAATTAAAAGTTGAGTCATTTGATT
AAACATGTGATTATTTAATGAATTGATGAAAGAGTTGGATTAAAGTTGTATTAGTAATTAGAATTTGGTGTCAAATTT
AATTTGACATTTGATCTTTTCCTATATATTGCCCCATAGAGTCAGTTAACTCATTTTTATATTTCATAGATCAAATAAG
AGAAATAACGGTATATTAATCCCTCCAAAAAAAAAAAACGGTATATTTACTAAAAAATCTAAGCCACGTAGGAGGAT
AACAGGATCCCCGTAGGAGGATAACATCCAATCCAACCAATCACAACAATCCTGATGAGATAACCCACTTTAAGCC
CACGCATCTGTGGCACATCTACATTATCTAAATCACACATTCTTCCACACATCTGAGCCACACAAAAACCAATCCAC
ATCTTTATCACCCATTCTATAAAAAATCACACTTTGTGAGTCTACACTTTGATTCCCTTCAAACACATACAAAGAGAA
GAGACTAATTAATTAATTAATCATCTTGAGAGAAAATGGAGAAAATAGTGCTTCTTCTTGCAATAGTCAGTCTTGTTA
AAAGTGATCAGATTTGCATTGGTTACCATGCAAACAATTCAACAGAGCAGGTTGACACAATCATGGAAAAGAACGT
TACTGTTACACATGCCCAAGACATACTGGAAAAGACACACAACGGGAAGCTCTGCCTATTAAAAGGAATAGCCCC
ACTACAATTGGGTAATTGCAGCGTTGCCGGGTGGATCTTAGGAAACCCAGAATGCGAATTACTGATTTCCAAGGA
GTCATGGTCCTACATTGTAGAAAAACCAAATCCTGAGAATGGAACATGTTACCCAGGGCATTTCGCTGACTATGAG
GAACTGAGGGAGCAATTGAGTTCAGTATCTTCATTTGAGAGGTTCGAAATATTCCCCAAAGAAAGCTCATGGCCCA
ACCACACCGTAACCGGAGTGTCAGCATCATGCTCCCATAATGGGGAAAGCAGTTTTTACAGAAATTTGCTATGGCT
GACGGGGAAGAATGGTTTGTACCCAAACCTGAGCAAGTCCTATGCAAACAACAAAGAAAAAGAAGTCCTTGTACT
ATGGGGTGTTCATCACCCGCCAAACATAGGTGACCAAAAGGCCCTCTATCATACAGAAAATGCTTATGTCTCTGTA
GTGTCTTCACATTATAGCAGAAAATTCACCCCAGAAATAGCCAAAAGACCCAAAGTAAGAGATCAAGAAGGAAGAA
TCAATTACTACTGGACTCTGCTTGAACCCGGGGATACAATAATATTTGAGGCAAATGGAAATCTAATAGCGCCAAG
ATATGCTTTCGCACTGAGTAGAGGCTTTGGATCAGGAATCATCAACTCAAATGCACCAATGGATAAATGCAACACC
AAGTGTCAAACTCCAATGGGGGCGATAAACTCTAGTATGCCATTCCACAACATACACCCTCTCACCATCGGGGAAT
GCCCCAAATATGTGAAATCAAACAGATTAGTCCTTGCAACAGGGCTCAGAAATAGCCCTCAAAGAGAGAGCAGAA
GAAAAAAGAGAGGACTATTTGGAGCTATAGCAGGTTTTATAGAGGGAGGATGGCAGGGAATGGTAGATGGTTGGT
ATGGGTACCACCATAGCAATGAGCAGGGGAGTGGGTACGCTGCAGACAAAGAATCCACTCAAAAGGCAATAGAT
GGAGTCACCAATAAGGTCAACTCAATCATTGACAAAATGAACACTCAGTTTGAGGCCGTTGGAAGGGAATTTAATA
ACTTAGAAAGGAGAATAGAGAATTTAAACAAGAAGATGGAAGACGGGTTTCTAGATGTCTGGACTTATAATGCCGA
ACTTCTGGTTCTCATGGAAAATGAGAGAACTCTAGACTTTCATGACTCAAATGTTAAGAACCTCTACGACAAGGTC
CGACTACAGCTTAGGGATAATGCAAAGGAGCTGGGTAACGGTTGTTTCGAGTTCTATCACAAATGTGATAATGAAT
GTATGGAAAGTATAAGAAACGGAACGTACAACTATCCGCAGTATTCAGAAGAAGCAAGATTAAAAAGAGAGGAAAT
AAGTGGGGTAAAATTGGAATCAATAGGAACTTACCAAATACTGTCAATTTATTCAACAGTGGCGAGTTCCCTAGCA
CTGGCAATCATGATGGCTGGTCTATCTTTATGGATGTGCTCCAATGGATCGTTACAATGCAGAATTTGCATTTAAG
AGCTCTAAGTTAAAATGCTTCTTCGTCTCCTATTTATAATATGGTTTGTTATTGTTAATTTTGTTCTTGTAGAAGAGC
TTAATTAATCGTTGTTGTTATGAAATACTATTTGTATGAGATGAACTGGTGTAATGTAATTCATTTACATAAGTGGAG
TCAGAATCAGAATGTTTCCTCCATAACTAACTAGACATGAAGACCTGCCGCGTACAATTGTCTTATATTTGAACAAC
TAAAATTGAACATCTTTTGCCACAACTTTATAAGTGGTTAATATAGCTCAAATATATGGTCAAGTTCAATAGATTAAT
AATGGAAATATCAGTTATCGAAATTCATTAACAATCAACTTAACGTTATTAACTACTAATTTTATATCATCCCCTTTGA
TAAATGATAGTACACCAATTAGGAAGGAGCATGCTCGAGGCCTGGCTGGCCGAATTC

Figure 30

SEQ. ID. NO. 65

Construct number 696, from HindIII (in the multiple cloning site, upstream of the Plastocyanin promoter) to EcoRI (immediately downstream of the Plastocyanin terminator). Chimeric HA coding sequence is underlined.

AAGCTTGCTAGCGGCCTCAATGGCCCTGCAGGTCGACTCTAGAGGTACCCCGGGCTGGTATATTTATATGTTG
TCAAATAACTCAAAAACCATAAAAGTTTAAGTTAGCAAGTGTGTACATTTTTACTTGAACAAAAATATTCACCTAC
TACTGTTATAAATCATTATTAAACATTAGAGTAAAGAAATATGGATGATAAGAACAAGAGTAGTGATATTTTGAC
AACAATTTTGTTGCAACATTTGAGAAAATTTTGTTGTTCTCTCTTTTCATTGGTCAAAAACAATAGAGAGAGAAA
AAGGAAGAGGGAGAATAAAAACATAATGTGAGTATGAGAGAGAAAGTTGTACAAAAGTTGTACCAAAATAGTT
GTACAAATATCATTGAGGAATTTGACAAAAGCTACACAAATAAGGGTTAATTGCTGTAAATAAATAAGGATGAC
GCATTAGAGAGATGTACCATTAGAGAATTTTTGGCAAGTCATTAAAAAGAAAGAATAAATTATTTTTAAAATTAA
AAGTTGAGTCATTTGATTAAACATGTGATTATTTAATGAATTGATGAAAGAGTTGGATTAAAGTTGTATTAGTAAT
TAGAATTTGGTGTCAAATTTAATTTGACATTTGATCTTTTCCTATATATTGCCCCATAGAGTCAGTTAACTCATTT
TTATATTTCATAGATCAAATAAGAGAAATAACGGTATATTAATCCCTCCAAAAAAAAAAAACGGTATATTTACTAA
AAAATCTAAGCCACGTAGGAGGATAACAGGATCCCCGTAGGAGGATAACATCCAATCCAACCAATCACAACAA
TCCTGATGAGATAACCCACTTTAAGCCCACGCATCTGTGGCACATCTACATTATCTAAATCACACATTCTTCCA
CACATCTGAGCCACACAAAAACCAATCCACATCTTTATCACCCATTCTATAAAAAATCACACTTTGTGAGTCTAC
ACTTTGATTCCCTTCAAACACATACAAAGAGAAGAGACTAATTAATTAATTAATCATCTTGAGAGAAAATGGCGA
AAAACGTTGCGATTTTCGGCTTATTGTTTTCTCTTCTTGTGTTGGTTCCTTCTCAGATCTTCGCTGACACAATAT
GTATAGGCTACCATGCCAACAACTCAACCGACACTGTTGACACAGTACTTGAGAAGAATGTGACAGTGACACA
CTCTGTCAACCTACTTGAGGACAGTCACAATGGAAAACTATGTCTACTAAAAGGAATAGCCCCACTACAATTGG
GTAATTGCAGCGTTGCCGGATGGATCTTAGGAAACCCAGAATGCGAATTACTGATTTCCAAGGAATCATGGTC
CTACATTGTAGAAACACCAAATCCTGAGAATGGAACATGTTACCCAGGGAGTTTCAACGACTATGAAGAACTG
AAACACCTATTGAGCAGAATAAACCATTTTGAGAAAATTCAAATCATCCCCAAAAGTTCTTGGTCCGATCATGA
AGCCTCATCAGGAGTTAGCTCAGCATGTCCATACCTGGGAAGTCCCTCCTTTTTTAGAAATGTGGTATGGCTTA
TCAAAAAGAACAGTACATACCCAACAATAAAGAAAAGCTACAATAATACCAACCAAGAGGATCTTTTGGTACTG
TGGGGAATTCACCATCCTAATGATGCGGCAGAGCAGACAAGGCTATATCAAAACCCAACCACCTATATTTCCA
TTGGGACATCAACACTAAACCAGAGATTGGTACCAAAAATAGCTACTAGATCCAAAGTAAACGGGCAAAGTGG
AAGGATGGAGTTCTTCTGGACAATTTTAAAACCTAATGATGCAATCAACTTCGAGAGTAATGGAAATTTCATTG
CTCCAGAATATGCATACAAAATTGTCAAGAAAGGGGACTCAGCAATCATCACCTCAAATGCACCAATGGATGA
ATGTGATGCGAAGTGTCAAACACCTCAGGGAGCTATAAACAGCAGTCTTCCTTTCCAGAATGTACACCCAGTC
ACAATAGGAGAGTGTCCAAAGTATGTCAGGAGTGCAAAATTAAGGATGGTTACAGGACTAAGGAACATCCCAT
CCATTCAATCCAGAGGTTTGTTTGGAGCCATTGCCGGTTTCATTGAAGGGGGGTGGACTGGAATGGTAGATG
GGTGGTATGGTTATCATCATCAGAATGAGCAAGGATCTGGCTATGCTGCAGATCAAAAAAGTACACAAAATGC
CATTAACGGGATTACAAACAAGGTCAATTCTGTAATTGAGAAAATGAACACTCAATTCACAGCTGTGGGCAAAG
AGTTCAACAAATTGGAAAGAAGGATGGAAAACTTAAATAAAAAAGTTGATGATGGGTTTCTAGACATTTGGACA
TATAATGCAGAATTGTTGGTTCTACTGGAAAATGAAAGGACTTTGGATTTCCATGACTCCAATGTGAAGAATCT
GTATGAGAAAGTAAAAAGCCAATTAAAGAATAATGCCAAAGAAATAGGAAACGGGTGTTTTGAGTTCTATCACA
AGTGTAACAATGAATGCATGGAGAGTGTGAAAAATGGTACCTATGACTATCCAAAATATTCCGAAGAATCAAAG
TTAAACAGGGAGAAAATTGATGGAGTGAAATTGGAATCAATGGGAGTATACCAGATTCTGGCGATCTACTCAA
CTGTCGCCAGTTCCCTGGTTCTTTTGGTCTCCCTGGGGGCAATCAGCTTCTGGATGTGTTCCAATGGGTCTTT
GCAGTGTAGAATATGCATCTAAGAGCTCTAAGTTAAAATGCTTCTTCGTCTCCTATTTATAATATGGTTTGTTAT
TGTTAATTTTGTTCTTGTAGAAGAGCTTAATTAATCGTTGTTGTTATGAAATACTATTTGTATGAGATGAACTGGT
GTAATGTAATTCATTTACATAAGTGGAGTCAGAATCAGAATGTTTCCTCCATAACTAACTAGACATGAAGACCT
GCCGCGTACAATTGTCTTATATTTGAACAACTAAAATTGAACATCTTTTGCCACAACTTTATAAGTGGTTAATAT
AGCTCAAATATATGGTCAAGTTCAATAGATTAATAATGGAAATATCAGTTATCGAAATTCATTAACAATCAACTTA
ACGTTATTAACTACTAATTTTATATCATCCCCTTTGATAAATGATAGTACACCAATTAGGAAGGAGCATGCTCGA
GGCCTGGCTGGCCGAATTC

Figure 31

SEQ. ID. NO. 66

Construct 732, from PacI (upstream of the 35S promoter) to AscI (immediately downstream of the NOS terminator). Coding sequence of H1 A/Brisbane/59/2007 is underlined.

TTAATTAAGAATTCGAGCTCCACCGCGGAAACCTCCTCGGATTCCATTGCCCAGCTATCTGTCACTTTATTGAGAA
GATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGT
CTTCAAAGCAAGTGGATTGATGTGATATCTCCACTGACGTAAGGGATGACGCACAATCCCACTATCCTTCGCAAGA
CCCTTCCTCTATATAAGGAAGTTCATTTCATTTGGAGAGGTATTAAAATCTTAATAGGTTTTGATAAAAGCGAACGT
GGGGAAACCCGAACCAAACCTTCTTCTAAACTCTCTCTCATCTCTCTTAAAGCAAACTTCTCTCTTGTCTTTCTTGC
GTGAGCGATCTTCAACGTTGTCAGATCGTGCTTCGGCACCAGTACAACGTTTTCTTTCACTGAAGCGAAATCAAAG
ATCTCTTTGTGGACACGTAGTGCGGCGCCATTAAATAACGTGTACTTGTCCTATTCTTGTCGGTGTGGTCTTGGGA
AAAGAAAGCTTGCTGGAGGCTGCTGTTCAGCCCCATACATTACTTGTTACGATTCTGCTGACTTTCGGCGGGTGCA
ATATCTCTACTTCTGCTTGACGAGGTATTGTTGCCTGTACTTCTTTCTTCTTCTTCTTGCTGATTGGTTCTATAAGAA
ATCTAGTATTTTCTTTGAAACAGAGTTTTCCCGTGGTTTTCGAACTTGGAGAAAGATTGTTAAGCTTCTGTATATTCT
GCCCAAATTTGTCGGGCCCATGAAAGTAAAACTACTGGTCCTGTTATGCACATTTACAGCTACATATGCAGACACA
ATATGTATAGGCTACCATGCTAACAACTCGACCGACACTGTTGACACAGTACTTGAAAAGAATGTGACAGTGACAC
ACTCTGTCAACCTGCTTGAGAACAGTCACAATGGAAAACTATGTCTATTAAAAGGAATAGCCCCACTACAATTGGG
TAATTGCAGCGTTGCCGGGTGGATCTTAGGAAACCCAGAATGCGAATTACTGATTTCCAAGGAGTCATGGTCCTAC
ATTGTAGAAAAACCAAATCCTGAGAATGGAACATGTTACCCAGGGCATTTCGCTGACTATGAGGAACTGAGGGAG
CAATTGAGTTCAGTATCTTCATTTGAGAGGTTCGAAATATTCCCCAAAGAAAGCTCATGGCCCAACCACACCGTAA
CCGGAGTGTCAGCATCATGCTCCCATAATGGGGAAAGCAGTTTTTACAGAAATTTGCTATGGCTGACGGGGAAGA
ATGGTTTGTACCCAAACCTGAGCAAGTCCTATGCAAACAACAAAGAAAAAGAAGTCCTTGTACTATGGGGTGTTCA
TCACCCGCCAAACATAGGTGACCAAAAGGCCCTCTATCATACAGAAAATGCTTATGTCTCTGTAGTGTCTTCACATT
ATAGCAGAAAATTCACCCCAGAAATAGCCAAAAGACCCAAAGTAAGAGATCAAGAAGGAAGAATCAATTACTACTG
GACTCTGCTTGAACCCGGGGATACAATAATATTTGAGGCAAATGGAAATCTAATAGCGCCAAGATATGCTTTCGCA
CTGAGTAGAGGCTTTGGATCAGGAATCATCAACTCAAATGCACCAATGGATAAATGTGATGCGAAGTGCCAAACAC
CTCAGGGAGCTATAAACAGCAGTCTTCCTTTCCAGAACGTACACCCAGTCACAATAGGAGAGTGTCCAAAGTATGT
CAGGAGTGCAAAATTAAGGATGGTTACAGGACTAAGGAACATCCCATCCATTCAATCCAGAGGTTTGTTTGGAGCC
ATTGCCGGTTTCATTGAAGGGGGGTGGACTGGAATGGTAGATGGTTGGTATGGTTATCATCATCAGAATGAGCAA
GGATCTGGCTATGCTGCAGATCAAAAAAGCACACAAAATGCCATTAATGGGATTACAAACAAGGTCAATTCTGTAA
TTGAGAAAATGAACACTCAATTCACAGCAGTGGGCAAAGAGTTCAACAAATTGGAAAGAAGGATGGAAAACTTGAA
TAAAAAAGTTGATGATGGGTTTATAGACATTTGGACATATAATGCAGAACTGTTGGTTCTACTGGAAAATGAAAGGA
CTTTGGATTTCCATGACTCCAATGTGAAGAATCTGTATGAGAAAGTAAAAAGCCAGTTAAAGAATAATGCTAAAGAA
ATAGGAAATGGGTGTTTTGAGTTCTATCACAAGTGTAACGATGAATGCATGGAGAGTGTAAAGAATGGAACTTATG
ACTATCCAAAATATTCCGAAGAATCAAAGTTAAACAGGGAGAAAATTGATGGAGTGAAATTGGAATCAATGGGAGT
CTATCAGATTCTGGCGATCTACTCAACAGTCGCCAGTTCTCTGGTTCTTTTGGTCTCCCTGGGGGCAATCAGCTTC
TGGATGTGTTCCAATGGGTCTTTACAGTGTAGAATATGCATCTAAAGGCCTATTTTCTTTAGTTTGAATTTACTGTTA
TTCGGTGTGCATTTCTATGTTTGGTGAGCGGTTTTCTGTGCTCAGAGTGTGTTTATTTTATGTAATTTAATTTCTTTG
TGAGCTCCTGTTTAGCAGGTCGTCCCTTCAGCAAGGACACAAAAAGATTTTAATTTTATTAAAAAAAAAAAAAAAAA
AGACCGGGAATTCGATATCAAGCTTATCGACCTGCAGATCGTTCAAACATTTGGCAATAAAGTTTCTTAAGATTGAA
TCCTGTTGCCGGTCTTGCGATGATTATCATATAATTTCTGTTGAATTACGTTAAGCATGTAATAATTAACATGTAATG
CATGACGTTATTTATGAGATGGGTTTTTATGATTAGAGTCCCGCAATTATACATTTAATACGCGATAGAAAACAAAAT
ATAGCGCGCAAACTAGGATAAATTATCGCGCGCGGTGTCATCTATGTTACTAGATTCTAGAGTCTCAAGCTTCGGC
GCGCC

Figure 32

SEQ. ID. NO. 67

Coding sequence, from ATG to stop, of intermediate construct number 787.

ATGGCGAAAAACGTTGCGATTTTCGGCTTATTGTTTTCTCTTCTTGTGTTGGTTCCTTCTCAGATCTTCG
CTGACACAATATGTATAGGCTACCATGCTAACAACTCGACCGACACTGTTGACACAGTACTTGAAAAGA
ATGTGACAGTGACACACTCTGTCAACCTGCTTGAGAACAGTCACAATGGAAAACTATGTCTATTAAAAGG
AATAGCCCCACTACAATTGGGTAATTGCAGCGTTGCCGGGTGGATCTTAGGAAACCCAGAATGCGAATT
ACTGATTTCCAAGGAGTCATGGTCCTACATTGTAGAAAAACCAAATCCTGAGAATGGAACATGTTACCCA
GGGCATTTCGCTGACTATGAGGAACTGAGGGAGCAATTGAGTTCAGTATCTTCATTTGAGAGGTTCGAA
ATATTCCCCAAAGAAAGCTCATGGCCCAACCACACCGTAACCGGAGTGTCAGCATCATGCTCCCATAAT
GGGGAAAGCAGTTTTTACAGAAATTTGCTATGGCTGACGGGGAAGAATGGTTTGTACCCAAACCTGAGC
AAGTCCTATGCAAACAACAAAGAAAAAGAAGTCCTTGTACTATGGGGTGTTCATCACCCGCCAAACATA
GGTGACCAAAAGGCCCTCTATCATACAGAAAATGCTTATGTCTCTGTAGTGTCTTCACATTATAGCAGAA
AATTCACCCCAGAAATAGCCAAAAGACCCAAAGTAAGAGATCAAGAAGGAAGAATCAATTACTACTGGA
CTCTGCTTGAACCCGGGGATACAATAATATTTGAGGCAAATGGAAATCTAATAGCGCCAAGATATGCTTT
CGCACTGAGTAGAGGCTTTGGATCAGGAATCATCAACTCAAATGCACCAATGGATAAATGTGATGCGAA
GTGCCAAACACCTCAGGGAGCTATAAACAGCAGTCTTCCTTTCCAGAACGTACACCCAGTCACAATAGG
AGAGTGTCCAAAGTATGTCAGGAGTGCAAAATTAAGGATGGTTACAGGACTAAGGAACATCCCATCCAT
TCAATCCAGAGGTTTGTTTGGAGCCATTGCCGGTTTCATTGAAGGGGGGTGGACTGGAATGGTAGATG
GTTGGTATGGTTATCATCATCAGAATGAGCAAGGATCTGGCTATGCTGCAGATCAAAAAAGCACACAAA
ATGCCATTAATGGGATTACAAACAAGGTCAATTCTGTAATTGAGAAAATGAACACTCAATTCACAGCAGT
GGGCAAAGAGTTCAACAAATTGGAAAGAAGGATGGAAAACTTGAATAAAAAAGTTGATGATGGGTTTATA
GACATTTGGACATATAATGCAGAACTGTTGGTTCTACTGGAAAATGAAAGGACTTTGGATTTCCATGACT
CCAATGTGAAGAATCTGTATGAGAAAGTAAAAAGCCAGTTAAAGAATAATGCTAAAGAAATAGGAAATGG
GTGTTTTGAGTTCTATCACAAGTGTAACGATGAATGCATGGAGAGTGTAAAGAATGGAACTTATGACTAT
CCAAAATATTCCGAAGAATCAAAGTTAAACAGGGAGAAAATTGATGGAGTGAAATTGGAATCAATGGGA
GTCTATCAGATTCTGGCGATCTACTCAACAGTCGCCAGTTCTCTGGTTCTTTTGGTCTCCCTGGGGGCA
ATCAGCTTCTGGATGTGTTCCAATGGGTCTTTACAGTGTAGAATATGCATCTAA

Figure 33

SEQ. ID. NO. 68

Construct number 733, from PacI (upstream of the 35S promoter) to AscI (immediately downstream of the NOS terminator). Coding sequence of SpPDI-H1 A/Brisbane/59/2007 is underlined.

TTAATTAAGAATTCGAGCTCCACCGCGGAAACCTCCTCGGATTCCATTGCCCAGCTATCTGTCACTTTATTGAGAAG
ATAGTGGAAAAGGAAGGTGGCTCCTACAAATGCCATCATTGCGATAAAGGAAAGGCCATCGTTGAAGATGCCTCTG
CCGACAGTGGTCCCAAAGATGGACCCCCACCCACGAGGAGCATCGTGGAAAAAGAAGACGTTCCAACCACGTCTT
CAAAGCAAGTGGATTGATGTGATATCTCCACTGACGTAAGGGATGACGCACAATCCCACTATCCTTCGCAAGACCCT
TCCTCTATATAAGGAAGTTCATTTCATTTGGAGAGGTATTAAAATCTTAATAGGTTTTGATAAAAGCGAACGTGGGGA
AACCCGAACCAAACCTTCTTCTAAACTCTCTCTCATCTCTCTTAAAGCAAACTTCTCTCTTGTCTTTCTTGCGTGAGC
GATCTTCAACGTTGTCAGATCGTGCTTCGGCACCAGTACAACGTTTTCTTTCACTGAAGCGAAATCAAAGATCTCTTT
GTGGACACGTAGTGCGGCGCCATTAAATAACGTGTACTTGTCCTATTCTTGTCGGTGTGGTCTTGGGAAAAGAAAGC
TTGCTGGAGGCTGCTGTTCAGCCCCATACATTACTTGTTACGATTCTGCTGACTTTCGGCGGGTGCAATATCTCTAC
TTCTGCTTGACGAGGTATTGTTGCCTGTACTTCTTTCTTCTTCTTCTTGCTGATTGGTTCTATAAGAAATCTAGTATTT
TCTTTGAAACAGAGTTTTCCCGTGGTTTTCGAACTTGGAGAAAGATTGTTAAGCTTCTGTATATTCTGCCCAAATTTGT
CGGGCCCATGGCGAAAAACGTTGCGATTTTCGGCTTATTGTTTTCTCTTCTTGTGTTGGTTCCTTCTCAGATCTTCGC
TGACACAATATGTATAGGCTACCATGCTAACAACTCGACCGACACTGTTGACACAGTACTTGAAAAGAATGTGACAG
TGACACACTCTGTCAACCTGCTTGAGAACAGTCACAATGGAAAACTATGTCTATTAAAAGGAATAGCCCCACTACAAT
TGGGTAATTGCAGCGTTGCCGGGTGGATCTTAGGAAACCCAGAATGCGAATTACTGATTTCCAAGGAGTCATGGTC
CTACATTGTAGAAAAACCAAATCCTGAGAATGGAACATGTTACCCAGGGCATTTCGCTGACTATGAGGAACTGAGGG
AGCAATTGAGTTCAGTATCTTCATTTGAGAGGTTCGAAATATTCCCCAAAGAAAGCTCATGGCCCAACCACACCGTA
ACCGGAGTGTCAGCATCATGCTCCCATAATGGGGAAAGCAGTTTTTACAGAAATTTGCTATGGCTGACGGGGAAGA
ATGGTTTGTACCCAAACCTGAGCAAGTCCTATGCAAACAACAAAGAAAAAGAAGTCCTTGTACTATGGGGTGTTCAT
CACCCGCCAAACATAGGTGACCAAAAGGCCCTCTATCATACAGAAAATGCTTATGTCTCTGTAGTGTCTTCACATTAT
AGCAGAAAATTCACCCCAGAAATAGCCAAAAGACCCAAAGTAAGAGATCAAGAAGGAAGAATCAATTACTACTGGAC
TCTGCTTGAACCCGGGGATACAATAATATTTGAGGCAAATGGAAATCTAATAGCGCCAAGATATGCTTTCGCACTGA
GTAGAGGCTTTGGATCAGGAATCATCAACTCAAATGCACCAATGGATAAATGTGATGCGAAGTGCCAAACACCTCAG
GGAGCTATAAACAGCAGTCTTCCTTTCCAGAACGTACACCCAGTCACAATAGGAGAGTGTCCAAAGTATGTCAGGAG
TGCAAAATTAAGGATGGTTACAGGACTAAGGAACATCCCATCCATTCAATCCAGAGGTTTGTTTGGAGCCATTGCCG
GTTTCATTGAAGGGGGGTGGACTGGAATGGTAGATGGTTGGTATGGTTATCATCATCAGAATGAGCAAGGATCTGG
CTATGCTGCAGATCAAAAAAGCACACAAAATGCCATTAATGGGATTACAAACAAGGTCAATTCTGTAATTGAGAAAAT
GAACACTCAATTCACAGCAGTGGGCAAAGAGTTCAACAAATTGGAAAGAAGGATGGAAAACTTGAATAAAAAAGTTG
ATGATGGGTTTATAGACATTTGGACATATAATGCAGAACTGTTGGTTCTACTGGAAAATGAAAGGACTTTGGATTTCC
ATGACTCCAATGTGAAGAATCTGTATGAGAAAGTAAAAAGCCAGTTAAAGAATAATGCTAAAGAAATAGGAAATGGGT
GTTTTGAGTTCTATCACAAGTGTAACGATGAATGCATGGAGAGTGTAAAGAATGGAACTTATGACTATCCAAAATATT
CCGAAGAATCAAAGTTAAACAGGGAGAAAATTGATGGAGTGAAATTGGAATCAATGGGAGTCTATCAGATTCTGGCG
ATCTACTCAACAGTCGCCAGTTCTCTGGTTCTTTTGGTCTCCCTGGGGGCAATCAGCTTCTGGATGTGTTCCAATGG
GTCTTTACAGTGTAGAATATGCATCTAAAGGCCTATTTTCTTTAGTTTGAATTTACTGTTATTCGGTGTGCATTTCTAT
GTTTGGTGAGCGGTTTTCTGTGCTCAGAGTGTGTTTATTTTATGTAATTTAATTTCTTTGTGAGCTCCTGTTTAGCAGG
TCGTCCCTTCAGCAAGGACACAAAAAGATTTTAATTTTATTAAAAAAAAAAAAAAAAAAAGACCGGGAATTCGATATCAA
GCTTATCGACCTGCAGATCGTTCAAACATTTGGCAATAAAGTTTCTTAAGATTGAATCCTGTTGCCGGTCTTGCGATG
ATTATCATATAATTTCTGTTGAATTACGTTAAGCATGTAATAATTAACATGTAATGCATGACGTTATTTATGAGATGGG
TTTTTATGATTAGAGTCCCGCAATTATACATTTAATACGCGATAGAAAACAAAATATAGCGCGCAAACTAGGATAAATT
ATCGCGCGCGGTGTCATCTATGTTACTAGATTCTAGAGTCTCAAGCTTCGGCGCGCC

Figure 34

SEQ. ID. NO. 69

Construct 734, from PacI (upstream of the 35S promoter) to AscI (immediately downstream of the NOS terminator). Coding sequence of chimeric HA is underlined.

TTAATTAAGAATTCGAGCTCCACCGCGGAAACCTCCTCGGATTCCATTGCCCAGCTATCTGTCACTTTATTGAGAAG
ATAGTGGAAAAGGAAGGTGGCTCCTACAAATGCCATCATTGCGATAAAGGAAAGGCCATCGTTGAAGATGCCTCTG
CCGACAGTGGTCCCAAAGATGGACCCCCACCCACGAGGAGCATCGTGGAAAAAGAAGACGTTCCAACCACGTCTT
CAAAGCAAGTGGATTGATGTGATATCTCCACTGACGTAAGGGATGACGCACAATCCCACTATCCTTCGCAAGACCC
TTCCTCTATATAAGGAAGTTCATTTCATTTGGAGAGGTATTAAAATCTTAATAGGTTTTGATAAAAGCGAACGTGGGG
AAACCCGAACCAAACCTTCTTCTAAACTCTCTCTCATCTCTCTTAAAGCAAACTTCTCTCTTGTCTTTCTTGCGTGAG
CGATCTTCAACGTTGTCAGATCGTGCTTCGGCACCAGTACAACGTTTTCTTTCACTGAAGCGAAATCAAAGATCTCT
TTGTGGACACGTAGTGCGGCGCCATTAAATAACGTGTACTTGTCCTATTCTTGTCGGTGTGGTCTTGGGAAAAGAA
AGCTTGCTGGAGGCTGCTGTTCAGCCCCATACATTACTTGTTACGATTCTGCTGACTTTCGGCGGGTGCAATATCT
CTACTTCTGCTTGACGAGGTATTGTTGCCTGTACTTCTTTCTTCTTCTTCTTGCTGATTGGTTCTATAAGAAATCTAG
TATTTTCTTTGAAACAGAGTTTTCCCGTGGTTTTCGAACTTGGAGAAAGATTGTTAAGCTTCTGTATATTCTGCCCAA
ATTTGTCGGGCCCATGGAGAAAATAGTGCTTCTTCTTGCAATAGTCAGTCTTGTTAAAAGTGATCAGATTTGCATTG
GTTACCATGCAAACAATTCAACAGAGCAGGTTGACACAATCATGGAAAAGAACGTTACTGTTACACATGCCCAAGA
CATACTGGAAAAGACACACAACGGGAAGCTCTGCGATCTAGATGGAGTGAAGCCTCTAATTTTAAGAGATTGTAGT
GTAGCTGGATGGCTCCTCGGGAACCCAATGTGTGACGAATTCATCAATGTACCGGAATGGTCTTACATAGTGGAGA
AGGCCAATCCAACCAATGACCTCTGTTACCCAGGGCATTTCGCTGACTATGAGGAACTGAGGGAGCAATTGAGTTC
AGTATCTTCATTTGAGAGGTTCGAAATATTCCCCAAAGAAAGCTCATGGCCCAACCACACCGTAACCGGAGTGTCA
GCATCATGCTCCCATAATGGGGAAAGCAGTTTTTACAGAAATTTGCTATGGCTGACGGGGAAGAATGGTTTGTACC
CAAACCTGAGCAAGTCCTATGCAAACAACAAAGAAAAAGAAGTCCTTGTACTATGGGGTGTTCATCACCCGCCAAA
CATAGGTGACCAAAAGGCCCTCTATCATACAGAAAATGCTTATGTCTCTGTAGTGTCTTCACATTATAGCAGAAAAT
TCACCCCAGAAATAGCCAAAAGACCCAAAGTAAGAGATCAAGAAGGAAGAATCAATTACTACTGGACTCTGCTTGA
ACCCGGGGATACAATAATATTTGAGGCAAATGGAAATCTAATAGCGCCAAGATATGCTTTCGCACTGAGTAGAGGC
TTTGGATCAGGAATTATGAAAAGTGAATTGGAATATGGTAACTGCAACACCAAGTGTCAAACTCCAATGGGGGCGA
TAAACTCTAGTATGCCATTCCACAACATACACCCTCTCACCATCGGGGAATGCCCCAAATATGTGAAATCAAACAGA
TTAGTCCTTGCAACAGGGCTCAGAAATAGCCCTCAAAGAGAGAGCAGAAGAAAAAAGAGAGGACTATTTGGAGCTA
TAGCAGGTTTTATAGAGGGAGGATGGCAGGGAATGGTAGATGGTTGGTATGGGTACCACCATAGCAATGAGCAGG
GGAGTGGGTACGCTGCAGACAAAGAATCCACTCAAAAGGCAATAGATGGAGTCACCAATAAGGTCAACTCAATCAT
TGACAAAATGAACACTCAGTTTGAGGCCGTTGGAAGGGAATTTAATAACTTAGAAAGGAGAATAGAGAATTTAAACA
AGAAGATGGAAGACGGGTTTCTAGATGTCTGGACTTATAATGCCGAACTTCTGGTTCTCATGGAAAATGAGAGAAC
TCTAGACTTTCATGACTCAAATGTTAAGAACCTCTACGACAAGGTCCGACTACAGCTTAGGGATAATGCAAAGGAG
CTGGGTAACGGTTGTTTCGAGTTCTATCACAAATGTGATAATGAATGTATGGAAAGTATAAGAAACGGAACGTACAA
CTATCCGCAGTATTCAGAAGAAGCAAGATTAAAAAGAGAGGAAATAAGTGGGGTAAAATTGGAATCAATAGGAACT
TACCAAATACTGTCAATTTATTCAACAGTGGCGAGTTCCCTAGCACTGGCAATCATGATGGCTGGTCTATCTTTATG
GATGTGCTCCAATGGATCGTTACAATGCAGAATTTGCATTTAAAGGCCTATTTTCTTTAGTTTGAATTTACTGTTATT
CGGTGTGCATTTCTATGTTTGGTGAGCGGTTTTCTGTGCTCAGAGTGTGTTTATTTTATGTAATTTAATTTCTTTGTG
AGCTCCTGTTTAGCAGGTCGTCCCTTCAGCAAGGACACAAAAAGATTTTAATTTTATTAAAAAAAAAAAAAAAAAAGA
CCGGGAATTCGATATCAAGCTTATCGACCTGCAGATCGTTCAAACATTTGGCAATAAAGTTTCTTAAGATTGAATCC
TGTTGCCGGTCTTGCGATGATTATCATATAATTTCTGTTGAATTACGTTAAGCATGTAATAATTAACATGTAATGCAT
GACGTTATTTATGAGATGGGTTTTTATGATTAGAGTCCCGCAATTATACATTTAATACGCGATAGAAAACAAAATATA
GCGCGCAAACTAGGATAAATTATCGCGCGCGGTGTCATCTATGTTACTAGATTCTAGAGTCTCAAGCTTCGGCGCG
CC

Figure 35

SEQ. ID. NO. 70

Synthesized fragment DraIII-Plasto(-84+1)-H3 A/Brisbane/10/07-SacI

CACTTTGTGAGTCTACACTTTGATTCCCTTCAAACACATACAAAGAGAAGAGACTAATTAATTAATTAAT
CATCTTGAGAGAAAATGAAGACTATCATTGCTTTGAGCTACATTCTATGTCTGGTTTTCACTCAAAAACT
TCCCGGAAATGACAACAGCACGGCAACGCTGTGCCTTGGGCACCATGCAGTACCAAACGGAACGATA
GTGAAAACAATCACGAATGACCAAATTGAAGTTACTAATGCTACTGAGCTGGTTCAGAGTTCCTCAACA
GGTGAAATATGCGACAGTCCTCATCAGATCCTTGATGGAGAAAACTGCACACTAATAGATGCTCTATTG
GGAGACCCTCAGTGTGATGGCTTCCAAAATAAGAAATGGGACCTTTTTGTTGAACGCAGCAAAGCCTA
CAGCAACTGTTACCCTTATGATGTGCCGGATTATGCCTCCCTTAGGTCACTAGTTGCCTCATCCGGCA
CACTGGAGTTTAACAATGAAAGTTTCAATTGGACTGGAGTCACTCAAAACGGAACAAGCTCTGCTTGC
ATAAGGAGATCTAATAACAGTTTCTTTAGTAGATTGAATTGGTTGACCCACTTAAAATTCAAATACCCAG
CATTGAACGTGACTATGCCAAACAATGAAAAATTTGACAAATTGTACATTTGGGGGGTTCACCACCCG
GGTACGGACAATGACCAAATCTTCCTGTATGCTCAAGCATCAGGAAGAATCACAGTCTCTACCAAAAG
AAGCCAACAAACTGTAATCCCGAATATCGGATCTAGACCCAGAGTAAGGAATATCCCCAGCAGAATAA
GCATCTATTGGACAATAGTAAAACCGGGAGACATACTTTTGATTAACAGCACAGGGAATCTAATTGCTC
CTAGGGGTTACTTCAAAATACGAAGTGGGAAAAGCTCAATAATGAGATCAGATGCACCCATTGGCAAA
TGCAATTCTGAATGCATCACTCCAAACGGAAGCATTCCCAATGACAAACCATTCCAAAATGTAAACAGG
ATCACATACGGGGCCTGTCCCAGATATGTTAAGCAAAACACTCTGAAATTGGCAACAGGGATGCGAAA
TGTACCAGAGAAACAAACTAGAGGCATATTTGGCGCAATCGCGGGTTTCATAGAAAATGGTTGGGAGG
GAATGGTGGATGGTTGGTATGGTTTCAGGCATCAAAATTCTGAGGGAATAGGACAAGCAGCAGATCTC
AAAAGCACTCAAGCAGCAATCGATCAAATCAATGGGAAGCTGAATAGGTTGATCGGGAAAACCAACGA
GAAATTCCATCAGATTGAAAAAGAGTTCTCAGAAGTCGAAGGGAGAATCCAGGACCTTGAGAAATATG
TTGAGGACACCAAAATAGATCTCTGGTCATACAACGCGGAGCTTCTTGTTGCCCTGGAGAACCAACAT
ACAATTGATCTAACTGACTCAGAAATGAACAAACTGTTTGAAAAAACAAAGAAGCAACTGAGGGAAAAT
GCTGAGGATATGGGCAATGGTTGTTTCAAAATATACCACAAATGTGACAATGCCTGCATAGGATCAATC
AGAAATGGAACTTATGACCACGATGTATACAGAGATGAAGCATTAAACAACCGGTTCCAGATCAAGGG
CGTTGAGCTGAAGTCAGGATACAAAGATTGGATACTATGGATTTCCTTTGCCATATCATGTTTTTTGCT
TTGTGTTGCTTTGTTGGGGTTCATCATGTGGGCCTGCCAAAAAGGCAACATTAGGTGCAACATTTGCA
TTTGAGAGCTC

Figure 36

SEQ. ID NO. 71

Construct 736, from PacI (upstream of the 35S promoter) to AscI (immediately downstream of the NOS terminator). Coding sequence of SpPDI-H3 A/Brisbane/10/2007 is underlined.

TTAATTAAGAATTCGAGCTCCACCGCGGAAACCTCCTCGGATTCCATTGCCCAGCTATCTGTCACTTTATTGAGAA
GATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGT
CTTCAAAGCAAGTGGATTGATGTGATATCTCCACTGACGTAAGGGATGACGCACAATCCCACTATCCTTCGCAAG
ACCCTTCCTCTATATAAGGAAGTTCATTTCATTTGGAGAGGTATTAAAATCTTAATAGGTTTTGATAAAAGCGAACG
TGGGGAAACCCGAACCAAACCTTCTTCTAAACTCTCTCTCATCTCTCTTAAAGCAAACTTCTCTCTTGTCTTTCTTG
CGTGAGCGATCTTCAACGTTGTCAGATCGTGCTTCGGCACCAGTACAACGTTTTCTTTCACTGAAGCGAAATCAAA
GATCTCTTTGTGGACACGTAGTGCGGCGCCATTAAATAACGTGTACTTGTCCTATTCTTGTCGGTGTGGTCTTGGG
AAAAGAAAGCTTGCTGGAGGCTGCTGTTCAGCCCCATACATTACTTGTTACGATTCTGCTGACTTTCGGCGGGTG
CAATATCTCTACTTCTGCTTGACGAGGTATTGTTGCCTGTACTTCTTTCTTCTTCTTCTTGCTGATTGGTTCTATAAG
AAATCTAGTATTTTCTTTGAAACAGAGTTTTCCCGTGGTTTTCGAACTTGGAGAAAGATTGTTAAGCTTCTGTATATT
CTGCCCAAATTTGTCGGGCCCATGGCGAAAAACGTTGCGATTTTCGGCTTATTGTTTTCTCTTCTTGTGTTGGTTC
CTTCTCAGATCTTCGCTCAAAAACTTCCCGGAAATGACAACAGCACGGCAACGCTGTGCCTTGGGCACCATGCAG
TACCAAACGGAACGATAGTGAAAACAATCACGAATGACCAAATTGAAGTTACTAATGCTACTGAGCTGGTTCAGAG
TTCCTCAACAGGTGAAATATGCGACAGTCCTCATCAGATCCTTGATGGAGAAAACTGCACACTAATAGATGCTCTA
TTGGGAGACCCTCAGTGTGATGGCTTCCAAAATAAGAAATGGGACCTTTTTGTTGAACGCAGCAAAGCCTACAGC
AACTGTTACCCTTATGATGTGCCGGATTATGCCTCCCTTAGGTCACTAGTTGCCTCATCCGGCACACTGGAGTTTA
ACAATGAAAGTTTCAATTGGACTGGAGTCACTCAAAACGGAACAAGCTCTGCTTGCATAAGGAGATCTAATAACAG
TTTCTTTAGTAGATTGAATTGGTTGACCCACTTAAAATTCAAATACCCAGCATTGAACGTGACTATGCCAAACAATG
AAAAATTTGACAAATTGTACATTTGGGGGGTTCACCACCCGGGTACGGACAATGACCAAATCTTCCTGTATGCTCA
AGCATCAGGAAGAATCACAGTCTCTACCAAAAGAAGCCAACAAACTGTAATCCCGAATATCGGATCTAGACCCAG
AGTAAGGAATATCCCCAGCAGAATAAGCATCTATTGGACAATAGTAAAACCGGGAGACATACTTTTGATTAACAGC
ACAGGGAATCTAATTGCTCCTAGGGGTTACTTCAAAATACGAAGTGGGAAAAGCTCAATAATGAGATCAGATGCAC
CCATTGGCAAATGCAATTCTGAATGCATCACTCCAAACGGAAGCATTCCCAATGACAAACCATTCCAAAATGTAAA
CAGGATCACATACGGGGCCTGTCCCAGATATGTTAAGCAAAACACTCTGAAATTGGCAACAGGGATGCGAAATGT
ACCAGAGAAACAAACTAGAGGCATATTTGGCGCAATCGCGGGTTTCATAGAAAATGGTTGGGAGGGAATGGTGG
ATGGTTGGTATGGTTTCAGGCATCAAAATTCTGAGGGAATAGGACAAGCAGCAGATCTCAAAAGCACTCAAGCAG
CAATCGATCAAATCAATGGGAAGCTGAATAGGTTGATCGGGAAAACCAACGAGAAATTCCATCAGATTGAAAAAGA
GTTCTCAGAAGTCGAAGGGAGAATCCAGGACCTTGAGAAATATGTTGAGGACACCAAAATAGATCTCTGGTCATA
CAACGCGGAGCTTCTTGTTGCCCTGGAGAACCAACATACAATTGATCTAACTGACTCAGAAATGAACAAACTGTTT
GAAAAAACAAAGAAGCAACTGAGGGAAAATGCTGAGGATATGGGCAATGGTTGTTTCAAAATATACCACAAATGTG
ACAATGCCTGCATAGGATCAATCAGAAATGGAACTTATGACCACGATGTATACAGAGATGAAGCATTAAACAACCG
GTTCCAGATCAAGGGCGTTGAGCTGAAGTCAGGATACAAAGATTGGATACTATGGATTTCCTTTGCCATATCATGT
TTTTTGCTTTGTGTTGCTTTGTTGGGGTTCATCATGTGGGCCTGCCAAAAAGGCAACATTAGGTGCAACATTTGCA
TTTGAAGGCCTATTTTCTTTAGTTTGAATTTACTGTTATTCGGTGTGCATTTCTATGTTTGGTGAGCGGTTTTCTGTG
CTCAGAGTGTGTTTATTTTATGTAATTTAATTTCTTTGTGAGCTCCTGTTTAGCAGGTCGTCCCTTCAGCAAGGACA
CAAAAAGATTTTAATTTTATTAAAAAAAAAAAAAAAAAAAGACCGGGAATTCGATATCAAGCTTATCGACCTGCAGAT
CGTTCAAACATTTGGCAATAAAGTTTCTTAAGATTGAATCCTGTTGCCGGTCTTGCGATGATTATCATATAATTTCT
GTTGAATTACGTTAAGCATGTAATAATTAACATGTAATGCATGACGTTATTTATGAGATGGGTTTTTATGATTAGAGT
CCCGCAATTATACATTTAATACGCGATAGAAAACAAAATATAGCGCGCAAACTAGGATAAATTATCGCGCGCGGTG
TCATCTATGTTACTAGATTCTAGAGTCTCAAGCTTCGGCGCGCC

Figure 37

SEQ. ID. NO. 72

Construct 737, from PacI (upstream of the 35S promoter) to AscI (immediately downstream of the NOS terminator). Coding sequence of chimeric HA is underlined.

TTAATTAAGAATTCGAGCTCCACCGCGGAAACCTCCTCGGATTCCATTGCCCAGCTATCTGTCACTTTATTGAGAAGA
TAGTGGAAAAGGAAGGTGGCTCCTACAAATGCCATCATTGCGATAAAGGAAAGGCCATCGTTGAAGATGCCTCTGC
CGACAGTGGTCCCAAAGATGGACCCCCACCCACGAGGAGCATCGTGGAAAAAGAAGACGTTCCAACCACGTCTTCA
AAGCAAGTGGATTGATGTGATATCTCCACTGACGTAAGGGATGACGCACAATCCCACTATCCTTCGCAAGACCCTTC
CTCTATATAAGGAAGTTCATTTCATTTGGAGAGGTATTAAAATCTTAATAGGTTTTGATAAAAGCGAACGTGGGGAAA
CCCGAACCAAACCTTCTTCTAAACTCTCTCTCATCTCTCTTAAAGCAAACTTCTCTCTTGTCTTTCTTGCGTGAGCGAT
CTTCAACGTTGTCAGATCGTGCTTCGGCACCAGTACAACGTTTTCTTTCACTGAAGCGAAATCAAAGATCTCTTTGTG
GACACGTAGTGCGGCGCCATTAAATAACGTGTACTTGTCCTATTCTTGTCGGTGTGGTCTTGGGAAAAGAAAGCTTG
CTGGAGGCTGCTGTTCAGCCCCATACATTACTTGTTACGATTCTGCTGACTTTCGGCGGGTGCAATATCTCTACTTCT
GCTTGACGAGGTATTGTTGCCTGTACTTCTTTCTTCTTCTTCTTGCTGATTGGTTCTATAAGAAATCTAGTATTTTCTTT
GAAACAGAGTTTTCCCGTGGTTTTCGAACTTGGAGAAAGATTGTTAAGCTTCTGTATATTCTGCCCAAATTTGTCGGG
CCCATGGCGAAAAACGTTGCGATTTTCGGCTTATTGTTTTCTCTTCTTGTGTTGGTTCCTTCTCAGATCTTCGCTCAA
AAACTTCCCGGAAATGACAACAGCACGGCAACGCTGTGCCTTGGGCACCATGCAGTACCAAACGGAACGATAGTGA
AAACAATCACGAATGACCAAATTGAAGTTACTAATGCTACTGAGCTGGTTCAGAGTTCCTCAACAGGTGAAATATGCG
ACAGTCCTCATCAGATCCTTGATGGAGAAAACTGCACACTAATAGATGCTCTATTGGGAGACCCTCAGTGTGATGGC
TTCCAAAATAAGAAATGGGACCTTTTTGTTGAACGCAGCAAAGCCTACAGCAACTGTTACCCTTATGATGTGCCGGAT
TATGCCTCCCTTAGGTCACTAGTTGCCTCATCCGGCACACTGGAGTTTAACAATGAAAGTTTCAATTGGACTGGAGT
CACTCAAAACGGAACAAGCTCTGCTTGCATAAGGAGATCTAATAACAGTTTCTTTAGTAGATTGAATTGGTTGACCCA
CTTAAAATTCAAATACCCAGCATTGAACGTGACTATGCCAAACAATGAAAAATTTGACAAATTGTACATTTGGGGGGT
TCACCACCCGGGTACGGACAATGACCAAATCTTCCTGTATGCTCAAGCATCAGGAAGAATCACAGTCTCTACCAAAA
GAAGCCAACAAACTGTAATCCCGAATATCGGATCTAGACCCAGAGTAAGGAATATCCCCAGCAGAATAAGCATCTAT
TGGACAATAGTAAAACCGGGAGACATACTTTTGATTAACAGCACAGGGAATCTAATTGCTCCTAGGGGTTACTTCAAA
ATACGAAGTGGGAAAAGCTCAATAATGAGATCAGATGCACCCATTGGCAAATGCAATTCTGAATGCATCACTCCAAA
CGGAAGCATTCCCAATGACAAACCATTCCAAAATGTAAACAGGATCACATACGGGGCCTGTCCCAGATATGTTAAGC
AAAACACTCTGAAATTGGCAACAGGGATGCGAAATGTACCAGAGAAACAAACTAGAGGCATATTTGGCGCAATCGCG
GGTTTCATAGAAAATGGTTGGGAGGGAATGGTGGATGGTTGGTATGGTTTCAGGCATCAAAATTCTGAGGGAATAG
GACAAGCAGCAGATCTCAAAAGCACTCAAGCAGCAATCGATCAAATCAATGGGAAGCTGAATAGGTTGATCGGGAA
AACCAACGAGAAATTCCATCAGATTGAAAAAGAGTTCTCAGAAGTCGAAGGGAGAATCCAGGACCTTGAGAAATATG
TTGAGGACACCAAAATAGATCTCTGGTCATACAACGCGGAGCTTCTTGTTGCCCTGGAGAACCAACATACAATTGAT
CTAACTGACTCAGAAATGAACAAACTGTTTGAAAAAACAAAGAAGCAACTGAGGGAAAATGCTGAGGATATGGGCAA
TGGTTGTTTCAAAATATACCACAAATGTGACAATGCCTGCATAGGATCAATCAGAAATGGAACTTATGACCACGATGT
ATACAGAGATGAAGCATTAAACAACCGGTTCCAGATCAAGGGCGTTGAGCTGAAGTCAATAGGAACTTACCAAATAC
TGTCAATTTATTCAACAGTGGCGAGTTCCCTAGCACTGGCAATCATGATGGCTGGTCTATCTTTATGGATGTGCTCCA
ATGGATCGTTACAATGCAGAATTTGCATTTAAAGGCCTATTTTCTTTAGTTTGAATTTACTGTTATTCGGTGTGCATTT
CTATGTTTGGTGAGCGGTTTTCTGTGCTCAGAGTGTGTTTATTTTATGTAATTTAATTTCTTTGTGAGCTCCTGTTTAG
CAGGTCGTCCCTTCAGCAAGGACACAAAAAGATTTTAATTTTATTAAAAAAAAAAAAAAAAAAAGACCGGGAATTCGAT
ATCAAGCTTATCGACCTGCAGATCGTTCAAACATTTGGCAATAAAGTTTCTTAAGATTGAATCCTGTTGCCGGTCTTG
CGATGATTATCATATAATTTCTGTTGAATTACGTTAAGCATGTAATAATTAACATGTAATGCATGACGTTATTTATGAGA
TGGGTTTTTATGATTAGAGTCCCGCAATTATACATTTAATACGCGATAGAAAACAAAATATAGCGCGCAAACTAGGAT
AAATTATCGCGCGCGGTGTCATCTATGTTACTAGATTCTAGAGTCTCAAGCTTCGGCGCGCC

Figure 38

SEQ. ID. NO. 73

Synthesized fragment DraIII-Plasto(-84+1)-HA B/Florida/4/06-SacI

CACTTTGTGAGTCTACACTTTGATTCCCTTCAAACACATACAAAGAGAAGAGACTAATTAATTAATTAA
TCATCTTGAGAGAAAATGAAGGCAATAATTGTACTACTCATGGTAGTAACATCCAATGCAGATCGAAT
CTGCACTGGAATAACATCTTCAAACTCACCTCATGTGGTCAAAACAGCCACTCAAGGGGAGGTCAAT
GTGACTGGTGTGATACCACTAACAACAACACCAACAAAATCTTATTTTGCAAATCTCAAAGGAACAAG
GACCAGAGGGAAACTATGCCCAGACTGTCTCAACTGCACAGATCTGGATGTGGCTTTGGGCAGACC
AATGTGTGTGGGGACCACACCTTCGGCGAAGGCTTCAATACTCCACGAAGTCAAACCTGTTACATCC
GGGTGCTTTCCTATAATGCACGACAGAACAAAAATCAGGCAACTACCCAATCTTCTCAGAGGATATGA
AAATATCAGGCTATCAACCCAAAACGTCATCGATGCGGAAAAGGCACCAGGAGGACCCTACAGACTT
GGAACCTCAGGATCTTGCCCTAACGCTACCAGTAAGAGCGGATTTTTCGCAACAATGGCTTGGGCTG
TCCCAAAGGACAACAACAAAAATGCAACGAACCCACTAACAGTAGAAGTACCATACATTTGTACAGAA
GGGGAAGACCAAATCACTGTTTGGGGGTTCCATTCAGATAACAAAACCCAAATGAAGAACCTCTATG
GAGACTCAAATCCTCAAAAGTTCACCTCATCTGCTAATGGAGTAACCACACACTATGTTTCTCAGATT
GGCAGCTTCCCAGATCAAACAGAAGACGGAGGACTACCACAAAGCGGCAGGATTGTTGTTGATTACA
TGATGCAAAAACCTGGGAAAACAGGAACAATTGTCTACCAAAGAGGTGTTTTGTTGCCTCAAAAGGTG
TGGTGCGCGAGTGGCAGGAGCAAAGTAATAAAAGGGTCCTTGCCTTTAATTGGTGAAGCAGATTGCC
TTCATGAAAAATACGGTGGATTAAACAAAAGCAAGCCTTACTACACAGGAGAACATGCAAAAGCCATA
GGAAATTGCCCAATATGGGTGAAAACACCTTTGAAGCTCGCCAATGGAACCAAATATAGACCTCCTG
CAAAACTATTAAAGGAAAGGGGTTTCTTCGGAGCTATTGCTGGTTTCCTAGAAGGAGGATGGGAAGG
AATGATTGCAGGCTGGCACGGATACACATCTCACGGAGCACATGGAGTGGCAGTGGCGGCGGACCT
TAAGAGTACGCAAGAAGCTATAAACAAGATAACAAAAAATCTCAATTCTTTGAGTGAGCTAGAAGTAAA
GAATCTTCAAAGACTAAGTGGTGCCATGGATGAACTCCACAACGAAATACTCGAGCTGGATGAGAAA
GTGGATGATCTCAGAGCTGACACTATAAGCTCGCAAATAGAACTTGCAGTCTTGCTTTCCAACGAAG
GAATAATAAACAGTGAAGATGAGCATCTATTGGCACTTGAGAGAAAACTAAAGAAAATGCTGGGTCCC
TCTGCTGTAGAGATAGGAAATGGATGCTTCGAAACCAAACACAAGTGCAACCAGACCTGCTTAGACA
GGATAGCTGCTGGCACCTTTAATGCAGGAGAATTTTCTCTCCCCACTTTTGATTCACTGAACATTACT
GCTGCATCTTTAAATGATGATGGATTGGATAACCATACTATACTGCTCTATTACTCAACTGCTGCTTCT
AGTTTGGCTGTAACATTGATGCTAGCTATTTTTATTGTTTATATGGTCTCCAGAGACAACGTTTCATGC
TCCATCTGTCTATAAGAGCTC

Figure 39

SEQ. ID. NO. 74

Construct 739, from PacI (upstream of the 35S promoter) to AscI (immediately downstream of the NOS terminator). Coding sequence of SpPDI-HA B/Florida/4/2006 is underlined.

TTAATTAAGAATTCGAGCTCCACCGCGGAAACCTCCTCGGATTCCATTGCCCAGCTATCTGTCACTTTATTGAGAA
GATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGT
CTTCAAAGCAAGTGGATTGATGTGATATCTCCACTGACGTAAGGGATGACGCACAATCCCACTATCCTTCGCAAG
ACCCTTCCTCTATATAAGGAAGTTCATTTCATTTGGAGAGGTATTAAAATCTTAATAGGTTTTGATAAAAGCGAACG
TGGGGAAACCCGAACCAAACCTTCTTCTAAACTCTCTCTCATCTCTCTTAAAGCAAACTTCTCTCTTGTCTTTCTTG
CGTGAGCGATCTTCAACGTTGTCAGATCGTGCTTCGGCACCAGTACAACGTTTTCTTTCACTGAAGCGAAATCAAA
GATCTCTTTGTGGACACGTAGTGCGGCGCCATTAAATAACGTGTACTTGTCCTATTCTTGTCGGTGTGGTCTTGGG
AAAAGAAAGCTTGCTGGAGGCTGCTGTTCAGCCCCATACATTACTTGTTACGATTCTGCTGACTTTCGGCGGGTG
CAATATCTCTACTTCTGCTTGACGAGGTATTGTTGCCTGTACTTCTTTCTTCTTCTTCTTGCTGATTGGTTCTATAAG
AAATCTAGTATTTTCTTTGAAACAGAGTTTTCCCGTGGTTTTCGAACTTGGAGAAAGATTGTTAAGCTTCTGTATATT
CTGCCCAAATTTGTCGGGCCCATGGCGAAAAACGTTGCGATTTTCGGCTTATTGTTTTCTCTTCTTGTGTTGGTTC
CTTCTCAGATCTTCGCTGATCGAATCTGCACTGGAATAACATCTTCAAACTCACCTCATGTGGTCAAAACAGCCAC
TCAAGGGGAGGTCAATGTGACTGGTGTGATACCACTAACAACAACACCAACAAAATCTTATTTTGCAAATCTCAAA
GGAACAAGGACCAGAGGGAAACTATGCCCAGACTGTCTCAACTGCACAGATCTGGATGTGGCTTTGGGCAGACC
AATGTGTGTGGGGACCACACCTTCGGCGAAGGCTTCAATACTCCACGAAGTCAAACCTGTTACATCCGGGTGCTT
TCCTATAATGCACGACAGAACAAAAATCAGGCAACTACCCAATCTTCTCAGAGGATATGAAAATATCAGGCTATCA
ACCCAAAACGTCATCGATGCGGAAAAGGCACCAGGAGGACCCTACAGACTTGGAACCTCAGGATCTTGCCCTAA
CGCTACCAGTAAGAGCGGATTTTTCGCAACAATGGCTTGGGCTGTCCCAAAGGACAACAACAAAAATGCAACGAA
CCCACTAACAGTAGAAGTACCATACATTTGTACAGAAGGGGAAGACCAAATCACTGTTTGGGGGTTCCATTCAGAT
AACAAAACCCAAATGAAGAACCTCTATGGAGACTCAAATCCTCAAAAGTTCACCTCATCTGCTAATGGAGTAACCA
CACACTATGTTTCTCAGATTGGCAGCTTCCCAGATCAAACAGAAGACGGAGGACTACCACAAAGCGGCAGGATTG
TTGTTGATTACATGATGCAAAAACCTGGGAAAACAGGAACAATTGTCTACCAAAGAGGTGTTTTGTTGCCTCAAAA
GGTGTGGTGCGCGAGTGGCAGGAGCAAAGTAATAAAAGGGTCCTTGCCTTTAATTGGTGAAGCAGATTGCCTTCA
TGAAAAATACGGTGGATTAAACAAAAGCAAGCCTTACTACACAGGAGAACATGCAAAAGCCATAGGAAATTGCCC
AATATGGGTGAAAACACCTTTGAAGCTCGCCAATGGAACCAAATATAGACCTCCTGCAAAACTATTAAAGGAAAGG
GGTTTCTTCGGAGCTATTGCTGGTTTCCTAGAAGGAGGATGGGAAGGAATGATTGCAGGCTGGCACGGATACAC
ATCTCACGGAGCACATGGAGTGGCAGTGGCGGCGGACCTTAAGAGTACGCAAGAAGCTATAAACAAGATAACAA
AAAATCTCAATTCTTTGAGTGAGCTAGAAGTAAAGAATCTTCAAAGACTAAGTGGTGCCATGGATGAACTCCACAA
CGAAATACTCGAGCTGGATGAGAAAGTGGATGATCTCAGAGCTGACACTATAAGCTCGCAAATAGAACTTGCAGT
CTTGCTTTCCAACGAAGGAATAATAAACAGTGAAGATGAGCATCTATTGGCACTTGAGAGAAAACTAAAGAAAATG
CTGGGTCCCTCTGCTGTAGAGATAGGAAATGGATGCTTCGAAACCAAACACAAGTGCAACCAGACCTGCTTAGAC
AGGATAGCTGCTGGCACCTTTAATGCAGGAGAATTTTCTCTCCCCACTTTTGATTCACTGAACATTACTGCTGCAT
CTTTAAATGATGATGGATTGGATAACCATACTATACTGCTCTATTACTCAACTGCTGCTTCTAGTTTGGCTGTAACA
TTGATGCTAGCTATTTTTATTGTTTATATGGTCTCCAGAGACAACGTTTCATGCTCCATCTGTCTATAAAGGCCTAT
TTTCTTTAGTTTGAATTTACTGTTATTCGGTGTGCATTTCTATGTTTGGTGAGCGGTTTTCTGTGCTCAGAGTGTGT
TTATTTTATGTAATTTAATTTCTTTGTGAGCTCCTGTTTAGCAGGTCGTCCCTTCAGCAAGGACACAAAAAGATTTTA
ATTTTATTAAAAAAAAAAAAAAAAAAGACCGGGAATTCGATATCAAGCTTATCGACCTGCAGATCGTTCAAACATTT
GGCAATAAAGTTTCTTAAGATTGAATCCTGTTGCCGGTCTTGCGATGATTATCATATAATTTCTGTTGAATTACGTT
AAGCATGTAATAATTAACATGTAATGCATGACGTTATTTATGAGATGGGTTTTTATGATTAGAGTCCCGCAATTATA
CATTTAATACGCGATAGAAAACAAAATATAGCGCGCAAACTAGGATAAATTATCGCGCGCGGTGTCATCTATGTTA
CTAGATTCTAGAGTCTCAAGCTTCGGCGCGCC

Figure 40

SEQ. ID. NO. 75

Construct 745, from PacI (upstream of the 35S promoter) to AscI (immediately downstream of the NOS terminator). Coding sequence of chimeric HA is underlined.

TTAATTAAGAATTCGAGCTCCACCGCGGAAACCTCCTCGGATTCCATTGCCCAGCTATCTGTCACTTTATTGAGAA
GATAGTGGAAAAGGAAGGTGGCTCCTACAAATGCCATCATTGCGATAAAGGAAAGGCCATCGTTGAAGATGCCTC
TGCCGACAGTGGTCCCAAAGATGGACCCCCACCCACGAGGAGCATCGTGGAAAAAGAAGACGTTCCAACCACGT
CTTCAAAGCAAGTGGATTGATGTGATATCTCCACTGACGTAAGGGATGACGCACAATCCCACTATCCTTCGCAAGA
CCCTTCCTCTATATAAGGAAGTTCATTTCATTTGGAGAGGTATTAAAATCTTAATAGGTTTTGATAAAAGCGAACGT
GGGGAAACCCGAACCAAACCTTCTTCTAAACTCTCTCTCATCTCTCTTAAAGCAAACTTCTCTCTTGTCTTTCTTGC
GTGAGCGATCTTCAACGTTGTCAGATCGTGCTTCGGCACCAGTACAACGTTTTCTTTCACTGAAGCGAAATCAAAG
ATCTCTTTGTGGACACGTAGTGCGGCGCCATTAAATAACGTGTACTTGTCCTATTCTTGTCGGTGTGGTCTTGGGA
AAAGAAAGCTTGCTGGAGGCTGCTGTTCAGCCCCATACATTACTTGTTACGATTCTGCTGACTTTCGGCGGGTGCA
ATATCTCTACTTCTGCTTGACGAGGTATTGTTGCCTGTACTTCTTTCTTCTTCTTCTTGCTGATTGGTTCTATAAGAA
ATCTAGTATTTTCTTTGAAACAGAGTTTTCCCGTGGTTTTCGAACTTGGAGAAAGATTGTTAAGCTTCTGTATATTCT
GCCCAAATTTGTCGGGCCCATGGCGAAAAACGTTGCGATTTTCGGCTTATTGTTTTCTCTTCTTGTGTTGGTTCCTT
CTCAGATCTTCGCTGATCGAATCTGCACTGGAATAACATCTTCAAACTCACCTCATGTGGTCAAAACAGCCACTCA
AGGGGAGGTCAATGTGACTGGTGTGATACCACTAACAACAACACCAACAAAATCTTATTTTGCAAATCTCAAAGGA
ACAAGGACCAGAGGGAAACTATGCCCAGACTGTCTCAACTGCACAGATCTGGATGTGGCTTTGGGCAGACCAATG
TGTGTGGGGACCACACCTTCGGCGAAGGCTTCAATACTCCACGAAGTCAAACCTGTTACATCCGGGTGCTTTCCT
ATAATGCACGACAGAACAAAAATCAGGCAACTACCCAATCTTCTCAGAGGATATGAAAATATCAGGCTATCAACCC
AAAACGTCATCGATGCGGAAAAGGCACCAGGAGGACCCTACAGACTTGGAACCTCAGGATCTTGCCCTAACGCTA
CCAGTAAGAGCGGATTTTTCGCAACAATGGCTTGGGCTGTCCCAAAGGACAACAACAAAAATGCAACGAACCCAC
TAACAGTAGAAGTACCATACATTTGTACAGAAGGGGAAGACCAAATCACTGTTTGGGGGTTCCATTCAGATAACAA
AACCCAAATGAAGAACCTCTATGGAGACTCAAATCCTCAAAAGTTCACCTCATCTGCTAATGGAGTAACCACACAC
TATGTTTCTCAGATTGGCAGCTTCCCAGATCAAACAGAAGACGGAGGACTACCACAAAGCGGCAGGATTGTTGTT
GATTACATGATGCAAAAACCTGGGAAAACAGGAACAATTGTCTACCAAAGAGGTGTTTTGTTGCCTCAAAAGGTGT
GGTGCGCGAGTGGCAGGAGCAAAGTAATAAAAGGGTCCTTGCCTTTAATTGGTGAAGCAGATTGCCTTCATGAAA
AATACGGTGGATTAAACAAAAGCAAGCCTTACTACACAGGAGAACATGCAAAAGCCATAGGAAATTGCCCAATATG
GGTGAAAACACCTTTGAAGCTCGCCAATGGAACCAAATATAGACCTCCTGCAAAACTATTAAAGGAAAGGGGTTTC
TTCGGAGCTATTGCTGGTTTCCTAGAAGGAGGATGGGAAGGAATGATTGCAGGCTGGCACGGATACACATCTCAC
GGAGCACATGGAGTGGCAGTGGCGGCGGACCTTAAGAGTACGCAAGAAGCTATAAACAAGATAACAAAAAATCTC
AATTCTTTGAGTGAGCTAGAAGTAAAGAATCTTCAAAGACTAAGTGGTGCCATGGATGAACTCCACAACGAAATAC
TCGAGCTGGATGAGAAAGTGGATGATCTCAGAGCTGACACTATAAGCTCGCAAATAGAACTTGCAGTCTTGCTTTC
CAACGAAGGAATAATAAACAGTGAAGATGAGCATCTATTGGCACTTGAGAGAAAACTAAAGAAAATGCTGGGTCCC
TCTGCTGTAGAGATAGGAAATGGATGCTTCGAAACCAAACACAAGTGCAACCAGACCTGCTTAGACAGGATAGCT
GCTGGCACCTTTAATGCAGGAGAATTTTCTCTCCCCACTTTTGATTCACTGAACATTACTGCTGCATCTTTAAATGA
TGATGGATTGGATAACTACCAAATACTGTCAATTTATTCAACAGTGGCGAGTTCCCTAGCACTGGCAATCATGATG
GCTGGTCTATCTTTATGGATGTGCTCCAATGGATCGTTACAATGCAGAATTTGCATTTAAAGGCCTATTTTCTTTAG
TTTGAATTTACTGTTATTCGGTGTGCATTTCTATGTTTGGTGAGCGGTTTTCTGTGCTCAGAGTGTGTTTATTTTATG
TAATTTAATTTCTTTGTGAGCTCCTGTTTAGCAGGTCGTCCCTTCAGCAAGGACACAAAAAGATTTTAATTTTATTAA
AAAAAAAAAAAAAAAAGACCGGGAATTCGATATCAAGCTTATCGACCTGCAGATCGTTCAAACATTTGGCAATAAAG
TTTCTTAAGATTGAATCCTGTTGCCGGTCTTGCGATGATTATCATATAATTTCTGTTGAATTACGTTAAGCATGTAAT
AATTAACATGTAATGCATGACGTTATTTATGAGATGGGTTTTTATGATTAGAGTCCCGCAATTATACATTTAATACGC
GATAGAAAACAAAATATAGCGCGCAAACTAGGATAAATTATCGCGCGCGGTGTCATCTATGTTACTAGATTCTAGA
GTCTCAAGCTTCGGCGCGCC

Figure 41

SEQ. ID. NO. 76

Msj1 coding sequence.

ATGTTTGGGCGCGGACCAACAAGGAAGAGTGATAACACCAAATATTACGATATTCTTGGTGTTTCAAA
AAGTGCTAGTGAAGATGAAATCAAGAAAGCCTATAGAAAGGCAGCGATGAAGAACCATCCAGATAAG
GGTGGGGATCCTGAGAAGTTCAAGGAGTTGGGCCAAGCATATGAAGTGTTGAGCGATCCTGAAAAG
AAAGAACTGTATGATCAATATGGTGAAGATGCCCTTAAAGAAGGAATGGGGGGAGGCGCAGGAAGC
TCATTTCATAATCCGTTTGATATTTTCGAATCATTTTTTGGTGCAGGCTTTGGTGGTGGTGGTCCTTCA
CGCGCAAGAAGACAGAAGCAAGGAGAAGATGTGGTGCATTCTATAAAGGTTTCCTTGGAGGATGTGT
ATAACGGCACTACAAAGAAGCTATCACTTTCTAGGAATGCACTGTGCTCAAAATGTAAAGGGAAAGGT
TCAAAAAGTGGAACTGCTGGAAGGTGTTTTGGATGCCAGGGCACAGGTATGAAGATTACCAGAAGG
CAAATTGGACTGGGCATGATTCAACAAATGCAACACGTCTGTCCTGACTGCAAAGGAACAGGCGAGG
TCATTAGTGAGAGAGATAGATGCCCTCAATGCAAGGGAAACAAGATTACTCAAGAAAAGAAGGTGCT
GGAGGTGCATGTGGAAAAGGGGATGCAGCAGGGTCACAAGATTGTATTCGAAGGACAAGCTGATGA
AGCTCCTGATACAATCACAGGAGACATAGTTTTTGTCTTGCAAGTAAAGGGACATCCGAAGTTTCGGA
GGGAGCGTGATGACCTCCACATTGAACACAATTTGAGCTTAACTGAGGCTCTCTGTGGCTTCCAGTT
TAATGTCACACATCTTGATGGAAGGCAACTATTGGTCAAATCGAACCCCGGCGAAGTCATCAAGCCA
GGTCAACATAAAGCTATAAATGATGAGGGAATGCCACAACATGGTAGGCCGTTCATGAAGGGACGCC
TATACATCAAGTTTAGTGTTGATTTCCCGGATTCGGGTTTTCTTTCCCCAAGCCAAAGCCTGGAATTA
GAAAAGATATTACCTCAAAAGACAAGCAAGAACTTGTCCCAAAAGGAGGTAGATGATTGTGAGGAGA
CCACCCTGCATGATGTCAATATTGCAGAGGAGATGAGTCGAAAGAAGCAACAATACCGTGAGGCATA
TGATGACGATGATGATGAAGATGATGAGCACTCGCAGCCTCGGGTGCAATGCGCTCAACAGTAG

Figure 42

SEQ. ID. NO. 77.

Construct number R850, from HindIII (in the multiple cloning site, upstream of the promoter) to EcoRI (immediately downstream of the NOS terminator). HSP40 coding sequence underlined AAGCTTGCATGCCTGCAGGTCGACTCTAGAGGATCCCCGGGCTGGTCTGTACATTCATCTTGCCGCCTTTGCATT
CACTTGGCCACAAAGAGTAGAGAGAAGGAAGAGAAGAGCCCAGACTTCAAGAAGCGACCTTGCAAGTGCACTCG
AGGGTCAGAAACTGTATATCATATCTATGTGAGAGAAAGGGGAACATTTGAGATGGAGTCCATTTACTTGAGGTAT
ACTTATTATTTTGATCAATAAATTTGTATACTTCTTATTTAGATCAATAAATTTGTCATTAAGCTATAATCCAAAATAA
ATTACGATCAAATATGCAAATGTTAGCCAGTACTTGTGTTAAACTTGATGGCATCTCTTGGTTTCTTTGGCAATCAC
ATGCCTAAGAAATAAATAGTATCATATGATTGTGTTTGGTCAGACTTCAGAGTCAGATGACTCTGTTTGGATAAAC
AGCTTAATTAAGCGCTTATAGAATATCATATGATTGTGTTTGGTCAGACTTCAGAGCATCTCTTGGTTTCTCTGGCA
ATCATATGCCTAAGAAATAAATAGTATCATATGATTGTGTTTGGTCAGACTTCAGAGTCAGATGACCCTGTTTGGG
TAAACAGCTTAATTAAGTGCTTATAGAATAAGCGCTTATCATATAAGTGCTTTTGTACAGTTATTTCTATGAAAGTA
GAAGAAATAGTCATATTGTTTTAATATAAGCTATCCTGGAGAGCTTGTGGAAATAACCAGAAAAGAACTTATGGAC
ACGTCATGAGCTGTTTACATAAGATCTCCCTAACAGTCTCAAAAGTGTTTATGCCAGTAGATAAATTCAAATAAGTC
AATCTAAACAGACCCTAAATCCATTATGGTACCTATCATTTTAGCTTATTCCATCTTTATTAAGAATGTCATGAGATA
ACATAATGATAACACATTATTTTGACACAAATGGGCAGATCTAGCAATTTAACTCTGGAGTCCTTCAAGACTGCTG
TTCTTACGAAGTTCACGTCCCTGAATCATGTTCCTGTATGGAAGCCTGAAAGACCTCAAATTCTAAAAGGTGGCGA
TAAATTGAAGGTTTACAAAATATACCCTGCGGGCTTGACACAGAGGCAAGCTCTTTATACCTTCCAGTTCAACGG
GGATGTTGATTTCAGAAGTCACTTGGAGAGCAATCCTTGTGCCAAGTTTGAAGTAATTTTTGTGTAGCATATGTTG
AGCTACCTACAATTTACATGATCACCTAGCATTAGCTCTTTCACTTAACTGAGAGAATGAAGTTTTAGGAATGAGTA
TGACCATGGAGTCGGCATGGCTTTGTAATGCCTACCCTACTTTGGCCAACTCATCGGGGATTTACATTCAGAAAA
TATACATGACTTCAACCATACTTAAACCCCTTTTTGTAAGATAACTGAATGTTCATATTTAATGTTGGGTTGTAGTG
TTTTTACTTGATTATATCCAGACAGTTACAAGTTGGACAACAAGATTGTGGGTCTGTACTGTTATTTATTTATTTTTT
TTTTAGCAGAAACACCTTATCTTTTGTTTCGTTTGAATGTAGAATGAAAATAAAAGAAAGAAAATATAACATCATCG
GCCGCGCTTGTCTAATTTCGGGCAGTTAGGATCCTCTCCGGTCACCGGAAAGTTTCAGTAGAAGAAACAAAACAC
CGTGACTAAAATGATACTATTATTTTATTTATTGTGTTTTTCTTTTTTCTACCGGAACTTTTTAGAACGGATCCCAAC
TCGTTCCGGGGCCGCTACAACTGAAACAAAAGAAGATATTTTCTCTCTCTTCAGAAATGTAAGTTTTCCTTTACAG
ATACCCATTCACCATTTGATTCAGATGTGGTGACTAGAGATAAAGCATACTAATTTGACTCTTGGAAACCCATAAA
GTTTATGTTATCCGTGTTCTGGACCAATCCACTTGGGGGCATAACCTGTGTCTATGTGTGGTTTGGTTTCCATTCT
GATTTATGCGGCGACTTGTAATTTAAAATCTAGGAGGGGCAGACATTGAACAATCCCAATATTTTAATAACTTATG
CAAGATTTTTTTTATTAATGAGATGATGTGTTTGTGACTGAGATTGAGTCATACATTTCACTAAGAAATGGTTCCAA
GTACCAAACTATCATGACCCAGTTGCAAACATGACGTTCGGGAGTGGTCACTTTGATAGTTCAATTTCATCTTGGC
TTCTTATTCCTTTTATAATTCTAATTCTTCTTGTGTAAACTATTTCATGTATTATTTTTCTTTAAAATTTACATGTCATT
TATTTTGCCTCACTAACTCAATTTTGCATATAACAATGATAAGTGATATTTTGACTCACAAAATTTACATCAAATTTC
GACATCGTTTATTATGTTCATTGGATGATTAACAAATATAACAAACTTTGCAACTAATTAACCACCAACTGAATATAA
TTAACTATAACTGTGAAAGTAGTTAACTCATTTTTATATTTCATAGATCAAATAAGAGAAATAACGGTATATTAATCC
CTCCAAAAAAAAAAAACGGTATATTTACTAAAAAATCTAAGCCACGTAGGAGGATAACAGGATCCCCGTAGGAGG
ATAACATCCAATCCAACCAATCACAACAATCCTGATGAGATAACCCACTTTAAGCCCACGCATCTGTGGCACATCT
ACATTATCTAAATCACACATTCTTCCACACATCTGAGCCACACAAAAACCAATCCACATCTTTATCACCCATTCTAT
AAAAAATCACACTTTGTGAGTCTACACTTTGATTCCCTTCAAACACATACAAAGAGAAGAGACTAATTAATTAATTA
ATCATCTTGAGAGAAAATGTTTGGGCGCGGACCAACAAGGAAGAGTGATAACACCAAATATTACGATATTCTTGG
TGTTTCAAAAAGTGCTAGTGAAGATGAAATCAAGAAAGCCTATAGAAAGGCAGCGATGAAGAACCATCCAGATAA
GGGTGGGGATCCTGAGAAGTTCAAGGAGTTGGGCCAAGCATATGAAGTGTTGAGCGATCCTGAAAAGAAAGAAC
TGTATGATCAATATGGTGAAGATGCCCTTAAAGAAGGAATGGGGGGAGGCGCAGGAAGCTCATTTCATAATCCGT
TTGATATTTTCGAATCATTTTTTGGTGCAGGCTTTGGTGGTGGTGGTCCTTCACGCGCAAGAAGACAGAAGCAAG
GAGAAGATGTGGTGCATTCTATAAAGGTTTCCTTGGAGGATGTGTATAACGGCACTACAAAGAAGCTATCACTTTC
TAGGAATGCACTGTGCTCAAAATGTAAAGGGAAAGGTTCAAAAAGTGGAACTGCTGGAAGGTGTTTTGGATGCCA
GGGCACAGGTATGAAGATTACCAGAAGGCAAATTGGACTGGGCATGATTCAACAAATGCAACACGTCTGTCCTGA
CTGCAAAGGAACAGGCGAGGTCATTAGTGAGAGAGATAGATGCCCTCAATGCAAGGGAAACAAGATTACTCAAG
AAAAGAAGGTGCTGGAGGTGCATGTGGAAAAGGGGATGCAGCAGGGTCACAAGATTGTATTCGAAGGACAAGCT
GATGAAGCTCCTGATACAATCACAGGAGACATAGTTTTTGTCTTGCAAGTAAAGGGACATCCGAAGTTTCGGAGG
GAGCGTGATGACCTCCACATTGAACACAATTTGAGCTTAACTGAGGCTCTCTGTGGCTTCCAGTTTAATGTCACA
CATCTTGATGGAAGGCAACTATTGGTCAAATCGAACCCCGGCGAAGTCATCAAGCCAGGTCAACATAAAGCTATA
AATGATGAGGGAATGCCACAACATGGTAGGCCGTTCATGAAGGGACGCCTATACATCAAGTTTAGTGTTGATTTC
CCGGATTCGGGTTTTCTTTCCCCAAGCCAAAGCCTGGAATTAGAAAAGATATTACCTCAAAAGACAAGCAAGAAC
TTGTCCCAAAAGGAGGTAGATGATTGTGAGGAGACCACCCTGCATGATGTCAATATTGCAGAGGAGATGAGTCG
AAAGAAGCAACAATACCGTGAGGCATATGATGACGATGATGATGAAGATGATGAGCACTCGCAGCCTCGGGTGC
AATGCGCTCAACAGTAGGAGCTCAGCTCGAATTTCCCCGATCGTTCAAACATTTGGCAATAAAGTTTCTTAAGATT
GAATCCTGTTGCCGGTCTTGCGATGATTATCATATAATTTCTGTTGAATTACGTTAAGCATGTAATAATTAACATGT
AATGCATGACGTTATTTATGAGATGGGTTTTTATGATTAGAGTCCCGCAATTATACATTTAATACGCGATAGAAAAC
AAAATATAGCGCGCAAACTAGGATAAATTATCGCGCGCGGTGTCATCTATGTTACTAGATCGAATTC

Figure 43

SEQ. ID. NO. 78

Construct number R860, from HindIII (in the multiple cloning site, upstream of the promoter) to EcoRI (immediately downstream of the NOS terminator). HSP70 coding sequence underlined

AAGCTTGCATGCCTGCAGGTCGACTCTAGAGGATCCCCGGGCTGGTCTGTACATTCATCTTGCCGCCTTTGCATTCACTTGGCCAC
AAAGAGTAGAGAGAAGGAAGAGAAGAGCCCAGACTTCAAGAAGCGACCTTGCAAGTGCACTCGAGGGTCAGAAACTGTATATCATA
TCTATGTGAGAGAAAGGGGAACATTTGAGATGGAGTCCATTTACTTGAGGTATACTTATTATTTTGATCAATAAATTTGTATACTTCTT
ATTTAGATCAATAAATTTGTCATTAAGCTATAATCCAAAATAAATTACGATCAAATATGCAAATGTTAGCCAGTACTTGTGTTAAACTTG
ATGGCATCTCTTGGTTTCTTTGGCAATCACATGCCTAAGAAATAAATAGTATCATATGATTGTGTTTGGTCAGACTTCAGAGTCAGAT
GACTCTGTTTGGATAAACAGCTTAATTAAGCGCTTATAGAATATCATATGATTGTGTTTGGTCAGACTTCAGAGCATCTCTTGGTTTCT
CTGGCAATCATATGCCTAAGAAATAAATAGTATCATATGATTGTGTTTGGTCAGACTTCAGAGTCAGATGACCCTGTTTGGGTAAACA
GCTTAATTAAGTGCTTATAGAATAAGCGCTTATCATATAAGTGCTTTTGTACAGTTATTTCTATGAAAGTAGAAGAAATAGTCATATTG
TTTTAATATAAGCTATCCTGGAGAGCTTGTGGAAATAACCAGAAAAGAACTTATGGACACGTCATGAGCTGTTTACATAAGATCTCCC
TAACAGTCTCAAAAGTGTTTATGCCAGTAGATAAATTCAAATAAGTCAATCTAAACAGACCCTAAATCCATTATGGTACCTATCATTTT
AGCTTATTCCATCTTTATTAAGAATGTCATGAGATAACATAATGATAACACATTATTTTGACACAAATGGGCAGATCTAGCAATTTAAC
TCTGGAGTCCTTCAAGACTGCTGTTCTTACGAAGTTCACGTCCCTGAATCATGTTCCTGTATGGAAGCCTGAAAGACCTCAAATTCTA
AAAGGTGGCGATAAATTGAAGGTTTACAAAATATACCCTGCGGGCTTGACACAGAGGCAAGCTCTTTATACCTTCCAGTTCAACGGG
GATGTTGATTTCAGAAGTCACTTGGAGAGCAATCCTTGTGCCAAGTTTGAAGTAATTTTTGTGTAGCATATGTTGAGCTACCTACAAT
TTACATGATCACCTAGCATTAGCTCTTTCACTTAACTGAGAGAATGAAGTTTTAGGAATGAGTATGACCATGGAGTCGGCATGGCTTT
GTAATGCCTACCCTACTTTGGCCAACTCATCGGGGATTTACATTCAGAAAATATACATGACTTCAACCATACTTAAACCCCTTTTTGTA
AGATAACTGAATGTTCATATTTAATGTTGGGTTGTAGTGTTTTTACTTGATTATATCCAGACAGTTACAAGTTGGACAACAAGATTGTG
GGTCTGTACTGTTATTTATTTATTTTTTTTTTAGCAGAAACACCTTATCTTTTGTTTCGTTTGAATGTAGAATGAAAATAAAAGAAAGAA
AATATAACATCATCGGCCGCGCTTGTCTAATTTCGGGCAGTTAGGATCCTCTCCGGTCACCGGAAAGTTTCAGTAGAAGAAACAAAA
CACCGTGACTAAAATGATACTATTATTTTATTTATTGTGTTTTTCTTTTTTCTACCGGAACTTTTTAGAACGGATCCCAACTCGTTCCG
GGGCCGCTACAACTGAAACAAAAGAAGATATTTTCTCTCTCTTCAGAAATGTAAGTTTTCCTTTACAGATACCCATTCACCATTTGATT
CAGATGTGGTGACTAGAGATAAAGCATACTAATTTGACTCTTGGAAACCCATAAAGTTTATGTTATCCGTGTTCTGGACCAATCCACT
TGGGGGCATAACCTGTGTCTATGTGTGGTTTGGTTTCCATTCTGATTTATGCGGCGACTTGTAATTTAAAATCTAGGAGGGGCAGAC
ATTGAACAATCCCAATATTTTAATAACTTATGCAAGATTTTTTTTATTAATGAGATGATGTGTTTGTGACTGAGATTGAGTCATACATTT
CACTAAGAAATGGTTCCAAGTACCAAACTATCATGACCCAGTTGCAAACATGACGTTCGGGAGTGGTCACTTTGATAGTTCAATTTC
ATCTTGGCTTCTTATTCCTTTTATAATTCTAATTCTTCTTGTGTAAACTATTTCATGTATTATTTTTCTTTAAAATTTACATGTCATTTATT
TTGCCTCACTAACTCAATTTTGCATATAACAATGATAAGTGATATTTTGACTCACAAAATTTACATCAAATTTCGACATCGTTTATTATG
TTCATTGGATGATTAACAAATATAACAAACTTTGCAACTAATTAACCACCAACTGAATATAATTAACTATAACTGTGAAAGTAGTTAAC
TCATTTTTATATTTCATAGATCAAATAAGAGAAATAACGGTATATTAATCCCTCCAAAAAAAAAAAAACGGTATATTTACTAAAAAATCTA
AGCCACGTAGGAGGATAACAGGATCCCCGTAGGAGGATAACATCCAATCCAACCAATCACAACAATCCTGATGAGATAACCCACTT
TAAGCCCACGCATCTGTGGCACATCTACATTATCTAAATCACACATTCTTCCACACATCTGAGCCACACAAAAACCAATCCACATCTT
TATCACCCATTCTATAAAAAATCACACTTTGTGAGTCTACACTTTGATTCCCTTCAAACACATACAAAGAGAAGAGACTAATTAATTAA
TTAATCATCTTGAGAGAAAATGTCGGGTAAAGGAGAAGGACCAGCTATCGGTATCGATCTTGGTACCACTTACTCTTGCGTCGGAGT
ATGGCAACACGACCGTGTTGAGATCATTGCTAATGATCAAGGAAACAGAACCACGCCATCTTACGTTGCTTTCACCGACTCCGAGA
GGTTGATCGGTGACGCAGCTAAGAATCAGGTCGCCATGAACCCCGTTAACACCGTTTTCGACGCTAAGAGGTTGATCGGTCGTCGT
TTCTCTGACAGCTCTGTTCAGAGTGACATGAAATTGTGGCCATTCAAGATTCAAGCCGGACCTGCCGATAAGCCAATGATCTACGTC
GAATACAAGGGTGAAGAGAAAGAGTTCGCAGCTGAGGAGATTTCTTCCATGGTTCTTATTAAGATGCGTGAGATTGCTGAGGCTTA
CCTTGGTGTCACAATCAAGAACGCCGTTGTTACCGTTCCAGCTTACTTCAACGACTCTCAGCGTCAGGCTACAAAGGATGCTGGTGT
CATCGCTGGTTTGAACGTTATGCGAATCATCAACGAGCCTACAGCCGCCGCTATTGCCTACGGTCTTGACAAAAAGGCTACCAGCG
TTGGAGAGAAGAATGTTCTTATCTTCGATCTTGGTGGTGGCACTTTTGATGTCTCTCTTCTTACCATTGAAGAGGGTATCTTTGAGGT
GAAGGCAACTGCTGGTGACACCCATCTTGGTGGGGAAGATTTTGACAACAGAATGGTTAACCACTTTGTCCAAGAGTTCAAGAGGA
AGAGTAAGAAGGATATCACCGGTAACCCAAGAGCTCTTAGGAGGTTGAGAACTTCCTGTGAGAGAGCGAAGAGGACTCTTTCTTCC
ACTGCTCAGACCACCATCGAGATTGACTCTCTATACGAGGGTATCGACTTCTACTCCACCATCACCCGTGCTAGATTTGAGGAGCTC
AACATGGATCTCTTCAGGAAGTGTATGGAGCCAGTTGAGAAGTGTCTTCGTGATGCTAAGATGGACAAGAGCACTGTTCATGATGTT
GTCCTTGTTGGTGGTTCTACCCGTATCCCTAAGGTTCAGCAATTGCTCCAGGACTTCTTCAACGGCAAAGAGCTTTGCAAGTCTATT
AACCCTGATGAGGCTGTTGCCTACGGTGCTGCTGTCCAGGGAGCTATTCTCAGCGGTGAAGGAAACGAGAAGGTTCAAGATCTTCT
ATTGCTCGATGTCACTCCTCTCTCCCTTGGTTTGGAAACTGCCGGTGGTGTCATGACCACTTTGATCCCAAGGAACACAACCATCCC
AACCAAGAAGGAACAAGTCTTCTCCACCTACTCAGACAACCAACCCGGTGTGTTGATCCAGGTGTACGAAGGAGAGAGAGCCAGAA
CCAAGGACAACAACCTTCTTGGTAAATTTGAGCTCTCCGGAATTCCTCCAGCTCCTCGTGGTGTCCCCCAGATCACAGTCTGCTTTG
ACATTGATGCCAATGGTATCCTCAATGTCTCTGCTGAGGACAAGACCACCGGACAGAAGAACAAGATCACCATCACCAATGACAAG
GGTCGTCTCTCCAAGGATGAGATTGAGAAGATGGTTCAAGAGGCTGAGAAGTACAAGTCCGAAGACGAGGAGCACAAGAAGAAGG
TTGAAGCCAAGAACGCTCTCGAGAACTACGCTTACAACATGAGGAACACCATCCAAGACGAGAAGATTGGTGAGAAGCTCCCGGCT
GCAGACAAGAAGAAGATCGAGGATTCTATTGAGCAGGCGATTCAATGGCTCGAGGGTAACCAGTTGGCTGAGGCTGATGAGTTCG
AAGACAAGATGAAGGAATTGGAGAGCATCTGCAACCCAATCATTGCCAAGATGTACCAAGGAGCTGGTGGTGAAGCCGGTGGTCC
AGGTGCCTCTGGTATGGACGATGATGCTCCCCCTGCTTCAGGCGGTGCTGGACCTAAGATCGAGGAGGTCGACTAAGAGCTCAGC
TCGAATTTCCCCGATCGTTCAAACATTTGGCAATAAAGTTTCTTAAGATTGAATCCTGTTGCCGGTCTTGCGATGATTATCATATAATT
TCTGTTGAATTACGTTAAGCATGTAATAATTAACATGTAATGCATGACGTTATTTATGAGATGGGTTTTTATGATTAGAGTCCCGCAAT
TATACATTTAATACGCGATAGAAAACAAAATATAGCGCGCAAACTAGGATAAATTATCGCGCGCGGTGTCATCTATGTTACTAGATCG
AATTC

Figure 44a

SEQ. ID. NO. 79

Construct number R870, from HindIII (in the multiple cloning site, upstream of the promoter) to EcoRI (immediately downstream of the NOS terminator). HSP40 coding sequence is in underlined italic and HSP70 coding sequence underlined

AAGCTTGCATGCCTGCAGGTCGACTCTAGAGGATCCCCGGGCTGGTCTGTACATTCATCTTGCCGCCTTTGCATTCACTTGGC
CACAAAGAGTAGAGAGAAGGAAGAGAAGAGCCCAGACTTCAAGAAGCGACCTTGCAAGTGCACTCGAGGGTCAGAAACTGT
ATATCATATCTATGTGAGAGAAAGGGGAACATTTGAGATGGAGTCCATTTACTTGAGGTATACTTATTATTTTGATCAATAAATT
TGTATACTTCTTATTTAGATCAATAAATTTGTCATTAAGCTATAATCCAAAATAAATTACGATCAAATATGCAAATGTTAGCCAGT
ACTTGTGTTAAACTTGATGGCATCTCTTGGTTTCTTTGGCAATCACATGCCTAAGAAATAAATAGTATCATATGATTGTGTTTGG
TCAGACTTCAGAGTCAGATGACTCTGTTTGGATAAACAGCTTAATTAAGCGCTTATAGAATATCATATGATTGTGTTTGGTCAG
ACTTCAGAGCATCTCTTGGTTTCTCTGGCAATCATATGCCTAAGAAATAAATAGTATCATATGATTGTGTTTGGTCAGACTTCAG
AGTCAGATGACCCTGTTTGGGTAAACAGCTTAATTAAGTGCTTATAGAATAAGCGCTTATCATATAAGTGCTTTTGTACAGTTAT
TTCTATGAAAGTAGAAGAAATAGTCATATTGTTTTAATATAAGCTATCCTGGAGAGCTTGTGGAAATAACCAGAAAAGAACTTAT
GGACACGTCATGAGCTGTTTACATAAGATCTCCCTAACAGTCTCAAAAGTGTTTATGCCAGTAGATAAATTCAAATAAGTCAAT
CTAAACAGACCCTAAATCCATTATGGTACCTATCATTTTAGCTTATTCCATCTTTATTAAGAATGTCATGAGATAACATAATGATA
ACACATTATTTTGACACAAATGGGCAGATCTAGCAATTTAACTCTGGAGTCCTTCAAGACTGCTGTTCTTACGAAGTTCACGTC
CCTGAATCATGTTCCTGTATGGAAGCCTGAAAGACCTCAAATTCTAAAAGGTGGCGATAAATTGAAGGTTTACAAAATATACCC
TGCGGGCTTGACACAGAGGCAAGCTCTTTATACCTTCCAGTTCAACGGGGATGTTGATTTCAGAAGTCACTTGGAGAGCAATC
CTTGTGCCAAGTTTGAAGTAATTTTTGTGTAGCATATGTTGAGCTACCTACAATTTACATGATCACCTAGCATTAGCTCTTTCAC
TTAACTGAGAGAATGAAGTTTTAGGAATGAGTATGACCATGGAGTCGGCATGGCTTTGTAATGCCTACCCTACTTTGGCCAAC
TCATCGGGGATTTACATTCAGAAAATATACATGACTTCAACCATACTTAAACCCCTTTTTGTAAGATAACTGAATGTTCATATTTA
ATGTTGGGTTGTAGTGTTTTTACTTGATTATATCCAGACAGTTACAAGTTGGACAACAAGATTGTGGGTCTGTACTGTTATTTAT
TTATTTTTTTTTTAGCAGAAACACCTTATCTTTTGTTTCGTTTGAATGTAGAATGAAAATAAAAGAAAGAAAATATAACATCATCG
GCCGCGCTTGTCTAATTTCGGGCAGTTAGGATCCTCTCCGGTCACCGGAAAGTTTCAGTAGAAGAAACAAAACACCGTGACTA
AAATGATACTATTATTTTATTTATTGTGTTTTTCTTTTTTCTACCGGAACTTTTTAGAACGGATCCCAACTCGTTCCGGGGCCGCT
ACAACTGAAACAAAAGAAGATATTTTCTCTCTCTTCAGAAATGTAAGTTTTCCTTTACAGATACCCATTCACCATTTGATTCAGAT
GTGGTGACTAGAGATAAAGCATACTAATTTGACTCTTGGAAACCCATAAAGTTTATGTTATCCGTGTTCTGGACCAATCCACTT
GGGGGCATAACCTGTGTCTATGTGTGGTTTGGTTTCCATTCTGATTTATGCGGCGACTTGTAATTTAAAATCTAGGAGGGGCA
GACATTGAACAATCCCAATATTTTAATAACTTATGCAAGATTTTTTTTATTAATGAGATGATGTGTTTGTGACTGAGATTGAGTCA
TACATTTCACTAAGAAATGGTTCCAAGTACCAAACTATCATGACCCAGTTGCAAACATGACGTTCGGGAGTGGTCACTTTGATA
GTTCAATTTCATCTTGGCTTCTTATTCCTTTTATAATTCTAATTCTTCTTGTGTAAACTATTTCATGTATTATTTTTCTTTAAAATTT
ACATGTCATTTATTTTGCCTCACTAACTCAATTTTGCATATAACAATGATAAGTGATATTTTGACTCACAAAATTTACATCAAATTT
CGACATCGTTTATTATGTTCATTGGATGATTAACAAATATAACAAACTTTGCAACTAATTAACCACCAACTGAATATAATTAACTA
TAACTGTGAAAGTAGTTAACTCATTTTTATATTTCATAGATCAAATAAGAGAAATAACGGTATATTAATCCCTCCAAAAAAAAAAA
ACGGTATATTTACTAAAAAATCTAAGCCACGTAGGAGGATAACAGGATCCCCGTAGGAGGATAACATCCAATCCAACCAATCA
CAACAATCCTGATGAGATAACCCACTTTAAGCCCACGCATCTGTGGCACATCTACATTATCTAAATCACACATTCTTCCACACA
TCTGAGCCACACAAAAACCAATCCACATCTTTATCACCCATTCTATAAAAAATCACACTTTGTGAGTCTACACTTTGATTCCCTT
CAAACACATACAAAGAGAAGAGACTAATTAATTAATTAATCATCTTGAGAGAAAATGTCGGGTAAAGGAGAAGGACCAGCTATC
GGTATCGATCTTGGTACCACTTACTCTTGCGTCGGAGTATGGCAACACGACCGTGTTGAGATCATTGCTAATGATCAAGGAAA
CAGAACCACGCCATCTTACGTTGCTTTCACCGACTCCGAGAGGTTGATCGGTGACGCAGCTAAGAATCAGGTCGCCATGAAC
CCCGTTAACACCGTTTTCGACGCTAAGAGGTTGATCGGTCGTCGTTTCTCTGACAGCTCTGTTCAGAGTGACATGAAATTGTG
GCCATTCAAGATTCAAGCCGGACCTGCCGATAAGCCAATGATCTACGTCGAATACAAGGGTGAAGAGAAAGAGTTCGCAGCT
GAGGAGATTTCTTCCATGGTTCTTATTAAGATGCGTGAGATTGCTGAGGCTTACCTTGGTGTCACAATCAAGAACGCCGTTGTT
ACCGTTCCAGCTTACTTCAACGACTCTCAGCGTCAGGCTACAAAGGATGCTGGTGTCATCGCTGGTTTGAACGTTATGCGAAT
CATCAACGAGCCTACAGCCGCCGCTATTGCCTACGGTCTTGACAAAAAGGCTACCAGCGTTGGAGAGAAGAATGTTCTTATCT
TCGATCTTGGTGGTGGCACTTTTGATGTCTCTCTTCTTACCATTGAAGAGGGTATCTTTGAGGTGAAGGCAACTGCTGGTGAC
ACCCATCTTGGTGGGGAAGATTTTGACAACAGAATGGTTAACCACTTTGTCCAAGAGTTCAAGAGGAAGAGTAAGAAGGATAT
CACCGGTAACCCAAGAGCTCTTAGGAGGTTGAGAACTTCCTGTGAGAGAGCGAAGAGGACTCTTTCTTCCACTGCTCAGACC
ACCATCGAGATTGACTCTCTATACGAGGGTATCGACTTCTACTCCACCATCACCCGTGCTAGATTTGAGGAGCTCAACATGGA
TCTCTTCAGGAAGTGTATGGAGCCAGTTGAGAAGTGTCTTCGTGATGCTAAGATGGACAAGAGCACTGTTCATGATGTTGTCC
TTGTTGGTGGTTCTACCCGTATCCCTAAGGTTCAGCAATTGCTCCAGGACTTCTTCAACGGCAAAGAGCTTTGCAAGTCTATTA
ACCCTGATGAGGCTGTTGCCTACGGTGCTGCTGTCCAGGGAGCTATTCTCAGCGGTGAAGGAAACGAGAAGGTTCAAGATCT
TCTATTGCTCGATGTCACTCCTCTCTCCCTTGGTTTGGAAACTGCCGGTGGTGTCATGACCACTTTGATCCCAAGGAACACAA
CCATCCCAACCAAGAAGGAACAAGTCTTCTCCACCTACTCAGACAACCAACCCGGTGTGTTGATCCAGGTGTACGAAGGAGA
GAGAGCCAGAACCAAGGACAACAACCTTCTTGGTAAATTTGAGCTCTCCGGAATTCCTCCAGCTCCTCGTGGTGTCCCCCAG
ATCACAGTCTGCTTTGACATTGATGCCAATGGTATCCTCAATGTCTCTGCTGAGGACAAGACCACCGGACAGAAGAACAAGAT
CACCATCACCAATGACAAGGGTCGTCTCTCCAAGGATGAGATTGAGAAGATGGTTCAAGAGGCTGAGAAGTACAAGTCCGAA
GACGAGGAGCACAAGAAGAAGGTTGAAGCCAAGAACGCTCTCGAGAACTACGCTTACAACATGAGGAACACCATCCAAGACG
AGAAGATTGGTGAGAAGCTCCCGGCTGCAGACAAGAAGAAGATCGAGGATTCTATTGAGCAGGCGATTCAATGGCTCGAGG
GTAACCAGTTGGCTGAGGCTGATGAGTTCGAAGACAAGATGAAGGAATTGGAGAGCATCTGCAACCCAATCATTGCCAAGAT
GTACCAAGGAGCTGGTGGTGAAGCCGGTGGTCCAGGTGCCTCTGGTATGGACGATGATGCTCCCCCTGCTTCAGGCGGTGC
TGGACCTAAGATCGAGGAGGTCGACTAAGAGCTCAGCTCGAATTTCCCCGATCGTTCAAACATTTGGCAATAAAGTTTCTTAA
GATTGAATCCTGTTGCCGGTCTTGCGATGATTATCATATAATTTCTGTTGAATTACGTTAAGCATGTAATAATTAACATGTAATG

Figure 44b

CATGACGTTATTTATGAGATGGGTTTTTATGATTAGAGTCCCGCAATTATACATTTAATACGCGATAGAAAACAAAATATAGCGCGCA
AACTAGGATAAATTATCGCGCGCGGTGTCATCTATGTTACTAGATCGAATTCGTAATCATGGTCATAGCTGTTTCCTGTGTGAAATTG
TTATCCGGGGCTGGTCTGTACATTCATCTTGCCGCCTTTGCATTCACTTGGCCACAAAGAGTAGAGAGAAGGAAGAGAAGAGCCCA
GACTTCAAGAAGCGACCTTGCAAGTGCACTCGAGGGTCAGAAACTGTATATCATATCTATGTGAGAGAAAGGGGAACATTTGAGATG
GAGTCCATTTACTTGAGGTATACTTATTATTTTGATCAATAAATTTGTATACTTCTTATTTAGATCAATAAATTTGTCATTAAGCTATAAT
CCAAAATAAATTACGATCAAATATGCAAATGTTAGCCAGTACTTGTGTTAAACTTGATGGCATCTCTTGGTTTCTTTGGCAATCACATG
CCTAAGAAATAAATAGTATCATATGATTGTGTTTGGTCAGACTTCAGAGTCAGATGACTCTGTTTGGATAAACAGCTTAATTAAGCGC
TTATAGAATATCATATGATTGTGTTTGGTCAGACTTCAGAGCATCTCTTGGTTTCTCTGGCAATCATATGCCTAAGAAATAAATAGTAT
CATATGATTGTGTTTGGTCAGACTTCAGAGTCAGATGACCCTGTTTGGGTAAACAGCTTAATTAAGTGCTTATAGAATAAGCGCTTAT
CATATAAGTGCTTTTGTACAGTTATTTCTATGAAAGTAGAAGAAATAGTCATATTGTTTTAATATAAGCTATCCTGGAGAGCTTGTGGA
AATAACCAGAAAAGAACTTATGGACACGTCATGAGCTGTTTACATAAGATCTCCCTAACAGTCTCAAAAGTGTTTATGCCAGTAGATA
AATTCAAATAAGTCAATCTAAACAGACCCTAAATCCATTATGGTACCTATCATTTTAGCTTATTCCATCTTTATTAAGAATGTCATGAGA
TAACATAATGATAACACATTATTTTGACACAAATGGGCAGATCTAGCAATTTAACTCTGGAGTCCTTCAAGACTGCTGTTCTTACGAA
GTTCACGTCCCTGAATCATGTTCCTGTATGGAAGCCTGAAAGACCTCAAATTCTAAAAGGTGGCGATAAATTGAAGGTTTACAAAATA
TACCCTGCGGGCTTGACACAGAGGCAAGCTCTTTATACCTTCCAGTTCAACGGGGATGTTGATTTCAGAAGTCACTTGGAGAGCAAT
CCTTGTGCCAAGTTTGAAGTAATTTTTGTGTAGCATATGTTGAGCTACCTACAATTTACATGATCACCTAGCATTAGCTCTTTCACTTA
ACTGAGAGAATGAAGTTTTAGGAATGAGTATGACCATGGAGTCGGCATGGCTTTGTAATGCCTACCCTACTTTGGCCAACTCATCGG
GGATTTACATTCAGAAAATATACATGACTTCAACCATACTTAAACCCCTTTTTGTAAGATAACTGAATGTTCATATTTAATGTTGGGTTG
TAGTGTTTTTACTTGATTATATCCAGACAGTTACAAGTTGGACAACAAGATTGTGGGTCTGTACTGTTATTTATTTATTTTTTTTTTTAGC
AGAAACACCTTATCTTTTGTTTCGTTTGAATGTAGAATGAAAATAAAAGAAAGAAAATATAACATCATCGGCCGCGCTTGTCTAATTTC
GGGCAGTTAGGATCCTCTCCGGTCACCGGAAAGTTTCAGTAGAAGAAACAAAACACCGTGACTAAAATGATACTATTATTTTATTTAT
TGTGTTTTTCTTTTTTCTACCGGAACTTTTTAGAACGGATCCCAACTCGTTCCGGGGCCGCTACAACTGAAACAAAAGAAGATATTTT
CTCTCTCTTCAGAAATGTAAGTTTTCCTTTACAGATACCCATTCACCATTTGATTCAGATGTGGTGACTAGAGATAAAGCATACTAATT
TGACTCTTGGAAACCCATAAAGTTTATGTTATCCGTGTTCTGGACCAATCCACTTGGGGGCATAACCTGTGTCTATGTGTGGTTTGGT
TTCCATTCTGATTTATGCGGCGACTTGTAATTTAAAATCTAGGAGGGGCAGACATTGAACAATCCCAATATTTTAATAACTTATGCAAG
ATTTTTTTTATTAATGAGATGATGTGTTTGTGACTGAGATTGAGTCATACATTTCACTAAGAAATGGTTCCAAGTACCAAACTATCATG
ACCCAGTTGCAAACATGACGTTCGGGAGTGGTCACTTTGATAGTTCAATTTCATCTTGGCTTCTTATTCCTTTTATAATTCTAATTCTT
CTTGTGTAAACTATTTCATGTATTATTTTTCTTTAAAATTTACATGTCATTTATTTTGCCTCACTAACTCAATTTTGCATATAACAATGAT
AAGTGATATTTTGACTCACAAAATTTACATCAAATTTCGACATCGTTTATTATGTTCATTGGATGATTAACAAATATAACAAACTTTGCA
ACTAATTAACCACCAACTGAATATAATTAACTATAACTGTGAAAGTAGTTAACTCATTTTTATATTTCATAGATCAAATAAGAGAAATAA
CGGTATATTAATCCCTCCAAAAAAAAAAAAACGGTATATTTACTAAAAAATCTAAGCCACGTAGGAGGATAACAGGATCCCCGTAGGA
GGATAACATCCAATCCAACCAATCACAACAATCCTGATGAGATAACCCACTTTAAGCCCACGCATCTGTGGCACATCTACATTATCTA
AATCACACATTCTTCCACACATCTGAGCCACACAAAAACCAATCCACATCTTTATCACCCATTCTATAAAAAATCACACTTTGTGAGTC
TACACTTTGATTCCCTTCAAACACATACAAAGAGAAGAGACTAATTAATTAATTAATCATCTTGAGAGAAA*ATGTTTGGGCGCGGACC*
*AACAAGGAAGAGTGATAACACCAAATATTACGATATTCTTGGTGTTTCAAAAAGTGCTAGTGAAGATGAAATCAAGAAAGCCTATAGA*
*AAGGCAGCGATGAAGAACCATCCAGATAAGGGTGGGGATCCTGAGAAGTTCAAGGAGTTGGGCCAAGCATATGAAGTGTTGAGCG*
*ATCCTGAAAAGAAAGAACTGTATGATCAATATGGTGAAGATGCCCTTAAAGAAGGAATGGGGGGAGGCGCAGGAAGCTCATTTCAT*
*AATCCGTTTGATATTTTCGAATCATTTTTTGGTGCAGGCTTTGGTGGTGGTGGTCCTTCACGCGCAAGAAGACAGAAGCAAGGAGAA*
*GATGTGGTGCATTCTATAAAGGTTTCCTTGGAGGATGTGTATAACGGCACTACAAAGAAGCTATCACTTTCTAGGAATGCACTGTGC*
*TCAAAATGTAAAGGGAAAGGTTCAAAAAGTGGAACTGCTGGAAGGTGTTTTGGATGCCAGGGCACAGGTATGAAGATTACCAGAAG*
*GCAAATTGGACTGGGCATGATTCAACAAATGCAACACGTCTGTCCTGACTGCAAAGGAACAGGCGAGGTCATTAGTGAGAGAGATA*
*GATGCCCTCAATGCAAGGGAAACAAGATTACTCAAGAAAAGAAGGTGCTGGAGGTGCATGTGGAAAAGGGGATGCAGCAGGGTCA*
*CAAGATTGTATTCGAAGGACAAGCTGATGAAGCTCCTGATACAATCACAGGAGACATAGTTTTTGTCTTGCAAGTAAAGGGACATCC*
*GAAGTTTCGGAGGGAGCGTGATGACCTCCACATTGAACACAATTTGAGCTTAACTGAGGCTCTCTGTGGCTTCCAGTTTAATGTCAC*
*ACATCTTGATGGAAGGCAACTATTGGTCAAATCGAACCCCGGCGAAGTCATCAAGCCAGGTCAACATAAAGCTATAAATGATGAGGG*
*AATGCCACAACATGGTAGGCCGTTCATGAAGGGACGCCTATACATCAAGTTTAGTGTTGATTTCCCGGATTCGGGTTTTCTTTCCCC*
*AAGCCAAAGCCTGGAATTAGAAAAGATATTACCTCAAAAGACAAGCAAGAACTTGTCCCAAAAGGAGGTAGATGATTGTGAGGAGAC*
*CACCCTGCATGATGTCAATATTGCAGAGGAGATGAGTCGAAAGAAGCAACAATACCGTGAGGCATATGATGACGATGATGATGAAG*
*ATGATGAGCACTCGCAGCCTCGGGTGCAATGCGCTCAACAGTAG*GAGCTCAGCTCGAATTTCCCCGATCGTTCAAACATTTGGCAA
TAAAGTTTCTTAAGATTGAATCCTGTTGCCGGTCTTGCGATGATTATCATATAATTTCTGTTGAATTACGTTAAGCATGTAATAATTAAC
ATGTAATGCATGACGTTATTTATGAGATGGGTTTTTATGATTAGAGTCCCGCAATTATACATTTAATACGCGATAGAAAACAAAATATA
GCGCGCAAACTAGGATAAATTATCGCGCGCGGTGTCATCTATGTTACTAGATCGAATTC

Figure 48

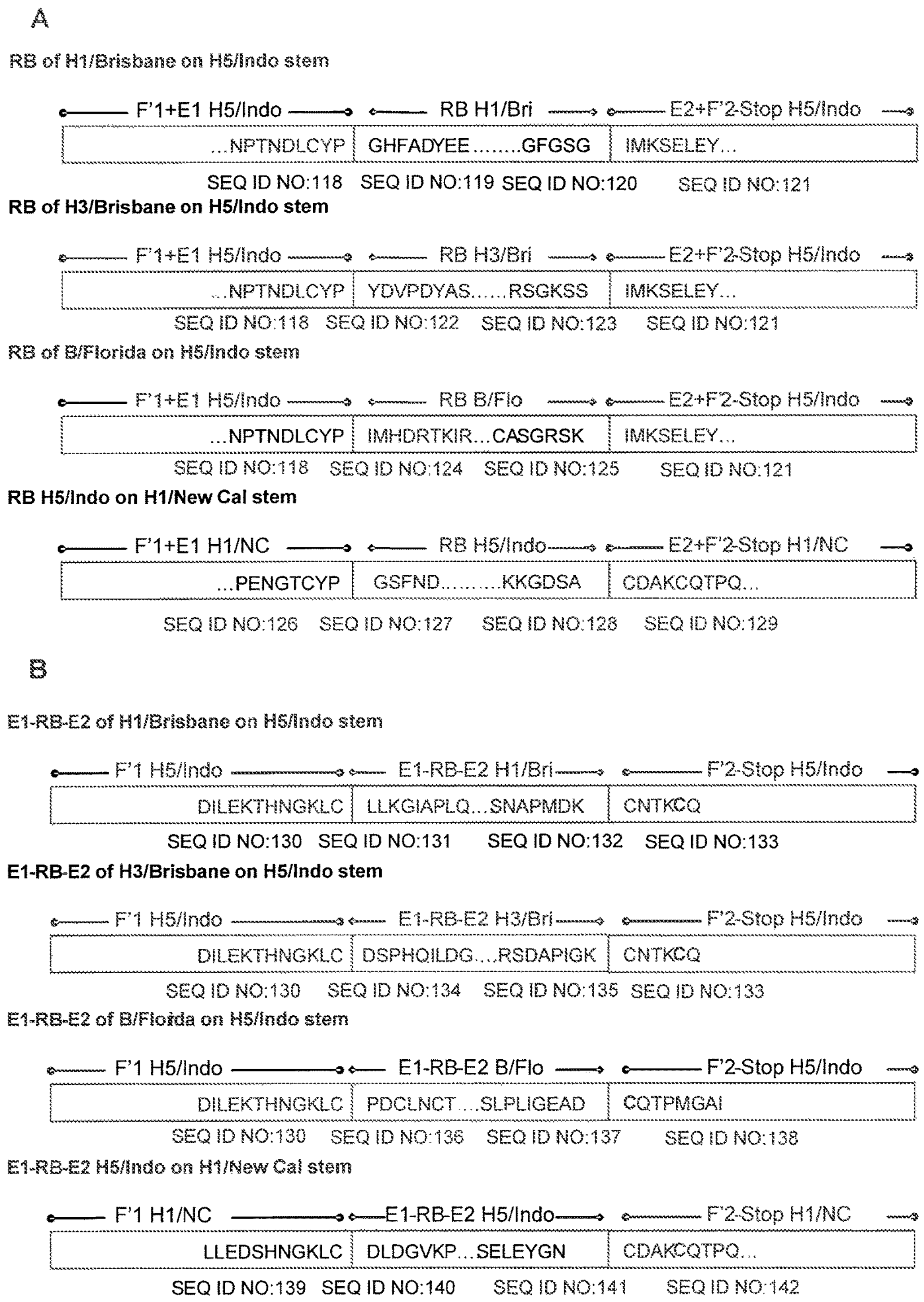

A

RB of H1/Brisbane on H5/Indo stem

⟵──── F'1+E1 H5/Indo ────⟶ ⟵──── RB H1/Bri ────⟶ ⟵──── E2+F'2-Stop H5/Indo ────⟶

| ...NPTNDLCYP | GHFADYEE........GFGSG | IMKSELEY... |
|---|---|---|
| SEQ ID NO:118 | SEQ ID NO:119  SEQ ID NO:120 | SEQ ID NO:121 |

RB of H3/Brisbane on H5/Indo stem

⟵──── F'1+E1 H5/Indo ────⟶ ⟵──── RB H3/Bri ────⟶ ⟵──── E2+F'2-Stop H5/Indo ────⟶

| ...NPTNDLCYP | YDVPDYAS......RSGKSS | IMKSELEY... |
|---|---|---|
| SEQ ID NO:118 | SEQ ID NO:122  SEQ ID NO:123 | SEQ ID NO:121 |

RB of B/Florida on H5/Indo stem

⟵──── F'1+E1 H5/Indo ────⟶ ⟵──── RB B/Flo ────⟶ ⟵──── E2+F'2-Stop H5/Indo ────⟶

| ...NPTNDLCYP | IMHDRTKIR...CASGRSK | IMKSELEY... |
|---|---|---|
| SEQ ID NO:118 | SEQ ID NO:124  SEQ ID NO:125 | SEQ ID NO:121 |

RB H5/Indo on H1/New Cal stem

⟵──── F'1+E1 H1/NC ────⟶ ⟵──── RB H5/Indo ────⟶ ⟵──── E2+F'2-Stop H1/NC ────⟶

| ...PENGTCYP | GSFND..........KKGDSA | CDAKCQTPQ... |
|---|---|---|
| SEQ ID NO:126 | SEQ ID NO:127  SEQ ID NO:128 | SEQ ID NO:129 |

B

E1-RB-E2 of H1/Brisbane on H5/Indo stem

⟵──── F'1 H5/Indo ────⟶ ⟵──── E1-RB-E2 H1/Bri ────⟶ ⟵──── F'2-Stop H5/Indo ────⟶

| DILEKTHNGKLC | LLKGIAPLQ...SNAPMDK | CNTKCQ |
|---|---|---|
| SEQ ID NO:130 | SEQ ID NO:131  SEQ ID NO:132 | SEQ ID NO:133 |

E1-RB-E2 of H3/Brisbane on H5/Indo stem

⟵──── F'1 H5/Indo ────⟶ ⟵──── E1-RB-E2 H3/Bri ────⟶ ⟵──── F'2-Stop H5/Indo ────⟶

| DILEKTHNGKLC | DSPHQILDG....RSDAPIGK | CNTKCQ |
|---|---|---|
| SEQ ID NO:130 | SEQ ID NO:134  SEQ ID NO:135 | SEQ ID NO:133 |

E1-RB-E2 of B/Florida on H5/Indo stem

⟵──── F'1 H5/Indo ────⟶ ⟵──── E1-RB-E2 B/Flo ────⟶ ⟵──── F'2-Stop H5/Indo ────⟶

| DILEKTHNGKLC | PDCLNCT....SLPLIGEAD | CQTPMGAI |
|---|---|---|
| SEQ ID NO:130 | SEQ ID NO:136  SEQ ID NO:137 | SEQ ID NO:138 |

E1-RB-E2 H5/Indo on H1/New Cal stem

⟵──── F'1 H1/NC ────⟶ ⟵──── E1-RB-E2 H5/Indo ────⟶ ⟵──── F'2-Stop H1/NC ────⟶

| LLEDSHNGKLC | DLDGVKP...SELEYGN | CDAKCQTPQ... |
|---|---|---|
| SEQ ID NO:139 | SEQ ID NO:140  SEQ ID NO:141 | SEQ ID NO:142 |

Figure 49A

SEQ ID NO:86

PDI sp - A/California/04/09

ATGGCGAAAAACGTTGCGATTTTCGGCTTATTGTTTTCTCTTCTTGTGTTGGTTCCT
CTCAGATCTTCGCTGACACATTATGTATAGGTTATCATGCGAACAATTCAACAGA
CACTGTAGACACAGTACTAGAAAAGAATGTAACAGTAACACACTCTGTTAACCTT
CTAGAAGACAAGCATAACGGGAAACTATGCAAACTAAGAGGGGTAGCCCCATTG
CATTTGGGTAAATGTAACATTGCTGGCTGGATCCTGGGAAATCCAGAGTGTGAAT
CACTCTCCACAGCAAGCTCATGGTCCTACATTGTGGAAACACCTAGTTCAGACAA
TGGAACGTGTTACCCAGGAGATTTCATCGATTATGAGGAGCTAAGAGAGCAATT
AAGCTCAGTGTCATCATTTGAAAGGTTTGAGATATTCCCCAAGACAAGTTCATGG
CCCAATCATGACTCGAACAAAGGTGTAACGGCAGCATGTCCTCATGCTGGAGCA
AAAAGCTTCTACAAAAATTTAATATGGCTAGTTAAAAAAGGAAATTCATACCCAA
AGCTCAGCAAATCCTACATTAATGATAAAGGGAAAGAAGTCCTCGTGCTATGGG
GCATTCACCATCCATCTACTAGTGCTGACCAACAAAGTCTCTATCAGAATGCAGA
TACATATGTTTTTGTGGGGTCATCAAGATACAGCAAGAAGTTCAAGCCGGAAATA
GCAATAAGACCCAAAGTGAGGGATCAAGAAGGGAGAATGAACTATTACTGGAC
ACTAGTAGAGCCGGGAGACAAAATAACATTCGAAGCAACTGGAAATCTAGTGGT
ACCGAGATATGCATTCGCAATGGAAAGAAATGCTGGATCTGGTATTATCATTTCA
GATACACCAGTCCACGATTGCAATACAACTTGTCAAACACCCAAGGGTGCTATA
AACACCAGCCTCCCATTTCAGAATATACATCCGATCACAATTGGAAAATGTCCAA
AATATGTAAAAAGCACAAAATTGAGACTGGCCACAGGATTGAGGAATATCCCGT
CTATTCAATCTAGAGGACTATTTGGGGCCATTGCCGGTTTCATTGAAGGGGGGTG
GACAGGGATGGTAGATGGATGGTACGGTTATCACCATCAAAATGAGCAGGGGTC
AGGATATGCAGCCGACCTGAAGAGCACACAGAATGCCATTGACGAGATTACTAA
CAAAGTAAATTCTGTTATTGAAAAGATGAATACACAGTTCACAGCAGTAGGTAAA
GAGTTCAACCACCTGGAAAAAAGAATAGAGAATTTAAATAAAAAAGTTGATGAT
GGTTTCCTGGACATTTGGACTTACAATGCCGAACTGTTGGTTCTATTGGAAAATG
AAAGAACTTTGGACTACCACGATTCAAATGTGAAGAACTTATATGAAAAGGTAAG
AAGCCAGCTAAAAAACAATGCCAAGGAAATTGGAAACGGCTGCTTTGAATTTTA
CCACAAATGCGATAACACGTGCATGGAAAGTGTCAAAAATGGGACTTATGACTA
CCCAAAATACTCAGAGGAAGCAAAATTAAACAGAGAAGAAATAGATGGGGTAAA
GCTGGAATCAACAAGGATTTACCAGATTTTGGCGATCTATTCAACTGTCGCCAGT
TCATTGGTACTGGTAGTCTCCCTGGGGGCAATCAGTTTCTGGATGTGCTCTAATG
GGTCTCTACAGTGTAGAATATGTATT

Figure 49B

SEQ ID NO:87

PDI sp - A/California/04/09

MAKNVAIFGLLFSLLVLVPSQIFADTLCIGYHANNSTDTVDTVLEKNVTVTHSVNLLEDKHNGKLCKLRG
VAPLHLGKCNIAGWILGNPECESLSTASSWSYIVETPSSDNGTCYPGDFIDYEELREQLSSVSSFERFEI
FPKTSSWPNHDSNKGVTAACPHAGAKSFYKNLIWLVKKGNSYPKLSKSYINDKGKEVLVLWGIHHPST
SADQQSLYQNADTYVFVGSSRYSKKFKPEIAIRPKVRDQEGRMNYYWTLVEPGDKITFEATGNLVVPR
YAFAMERNAGSGIIISDTPVHDCNTTCQTPKGAINTSLPFQNIHPITIGKCPKYVKSTKLRLATGLRNIPSI
QSRGLFGAIAGFIEGGWTGMVDGWYGYHHQNEQGSGYAADLKSTQNAIDEITNKVNSVIEKMNTQFT
AVGKEFNHLEKRIENLNKKVDDGFLDIWTYNAELLVLLENERTLDYHDSNVKNLYEKVRSQLKNNAKEI
GNGCFEFYHKCDNTCMESVKNGTYDYPKYSEEAKLNREEIDGVKLESTRIYQILAIYSTVASSLVLVVSL
GAISFWMCSNGSLQCRICI

SEQ ID NO:88

2X35S promoter sequence

GTCAACATGGTGGAGCACGACACACTTGTCTACTCCAAAAATATCAAA
GATACAGTCTCAGAAGACCAAAGGGCAATTGAGACTTTTCAACAAAGG
GTAATATCCGGAAACCTCCTCGGATTCCATTGCCCAGCTATCTGTCACT
TTATTGTGAAGATAGTGGAAAAGGAAGGTGGCTCCTACAAATGCCATC
ATTGCGATAAAGGAAAGGCCATCGTTGAAGATGCCTCTGCCGACAGTG
GTCCCAAAGATGGACCCCCACCCACGAGGAGCATCGTGGAAAAAGAA
GACGTTCCAACCACGTCTTCAAAGCAAGTGGATTGATGTGATAACATG
GTGGAGCACGACACACTTGTCTACTCCAAAAATATCAAAGATACAGTCT
CAGAAGACCAAAGGGCAATTGAGACTTTTCAACAAAGGGTAATATCCG
GAAACCTCCTCGGATTCCATTGCCCAGCTATCTGTCACTTTATTGTGAA
GATAGTGGAAAAGGAAGGTGGCTCCTACAAATGCCATCATTGCGATAA
AGGAAAGGCCATCGTTGAAGATGCCTCTGCCGACAGTGGTCCCAAAG
ATGGACCCCCACCCACGAGGAGCATCGTGGAAAAAGAAGACGTTCCA
ACCACGTCTTCAAAGCAAGTGGATTGATGTGATATCTCCACTGACGTAA
GGGATGACGCACAATCCCACTATCCTTCGCAAGACCCTTCCTCTATAT
AAGGAAGTTCATTTCATTTGGAGAGG

Figure 51A

SEQ ID NO:93

Construct 747, from PacI (upstream 35S promoter) to AscI (immediately downstream NOS terminator).
Coding sequence of chimeric HA is underlined. 2X35S promoter sequence is in italics.

TTAATTAAGTCGACAAGCTTGCATGCCTGCAG*GTCAACATGGTGGAGCACGACACACTTGTCTACTC*
*CAAAAATATCAAAGATACAGTCTCAGAAGACCAAAGGGCAATTGAGACTTTTCAACAAAGGGTAATATC*
*CGGAAACCTCCTCGGATTCCATTGCCCAGCTATCTGTCACTTTATTGTGAAGATAGTGGAAAAGGAAG*
*GTGGCTCCTACAAATGCCATCATTGCGATAAAGGAAAGGCCATCGTTGAAGATGCCTCTGCCGACAG*
*TGGTCCCAAAGATGGACCCCCACCCACGAGGAGCATCGTGGAAAAAGAAGACGTTCCAACCACGTCT*
*TCAAAGCAAGTGGATTGATGTGATAACATGGTGGAGCACGACACACTTGTCTACTCCAAAAATATCAA*
*AGATACAGTCTCAGAAGACCAAAGGGCAATTGAGACTTTTCAACAAAGGGTAATATCCGGAAACCTCC*
*TCGGATTCCATTGCCCAGCTATCTGTCACTTTATTGTGAAGATAGTGGAAAAGGAAGGTGGCTCCTAC*
*AAATGCCATCATTGCGATAAAGGAAAGGCCATCGTTGAAGATGCCTCTGCCGACAGTGGTCCCAAAG*
*ATGGACCCCCACCCACGAGGAGCATCGTGGAAAAAGAAGACGTTCCAACCACGTCTTCAAAGCAAGT*
*GGATTGATGTGATATCTCCACTGACGTAAGGGATGACGCACAATCCCACTATCCTTCGCAAGACCCTT*
*CCTCTATATAAGGAAGTTCATTTCATTTGGAGAGG*TATTAAAATCTTAATAGGTTTTGATAAAAGCGAAC
GTGGGGAAACCCGAACCAAACCTTCTTCTAAACTCTCTCTCATCTCTCTTAAAGCAAACTTCTCTCTTG
TCTTTCTTGCGTGAGCGATCTTCAACGTTGTCAGATCGTGCTTCGGCACCAGTACAACGTTTTCTTTC
ACTGAAGCGAAATCAAAGATCTCTTTGTGGACACGTAGTGCGGCGCCATTAAATAACGTGTACTTGTC
CTATTCTTGTCGGTGTGGTCTTGGGAAAAGAAAGCTTGCTGGAGGCTGCTGTTCAGCCCCATACATTA
CTTGTTACGATTCTGCTGACTTTCGGCGGGTGCAATATCTCTACTTCTGCTTGACGAGGTATTGTTGC
CTGTACTTCTTTCTTCTTCTTCTTGCTGATTGGTTCTATAAGAAATCTAGTATTTTCTTTGAAACAGAGT
TTTCCCGTGGTTTTCGAACTTGGAGAAAGATTGTTAAGCTTCTGTATATTCTGCCCAAATTTGTCGGGC
CCATGGCGAAAAACGTTGCGATTTTCGGCTTATTGTTTTCTCTTCTTGTGTTGGTTCCTTCTCAGATCT
TCGCTGATCGAATCTGCACTGGAATAACATCTTCAAACTCACCTCATGTGGTCAAAACAGCCACTCAA
GGGGAGGTCAATGTGACTGGTGTGATACCACTAACAACAACACCAACAAAATCTTATTTTGCAAATCT
CAAAGGAACAAGGACCAGAGGGAAACTATGCCCAGACTGTCTCAACTGCACAGATCTGGATGTGGCT
TTGGGCAGACCAATGTGTGTGGGGACCACACCTTCGGCGAAGGCTTCAATACTCCACGAAGTCAAAC
CTGTTACATCCGGGTGCTTTCCTATAATGCACGACAGAACAAAAATCAGGCAACTACCCAATCTTCTC
AGAGGATATGAAAATATCAGGCTATCAACCCAAAACGTCATCGATGCGGAAAAGGCACCAGGAGGAC
CCTACAGACTTGGAACCTCAGGATCTTGCCCTAACGCTACCAGTAAGAGCGGATTTTTCGCAACAATG
GCTTGGGCTGTCCCAAAGGACAACAACAAAAATGCAACGAACCCACTAACAGTAGAAGTACCATACAT
TTGTACAGAAGGGGAAGACCAAATCACTGTTTGGGGGTTCCATTCAGATAACAAAACCCAAATGAAGA
ACCTCTATGGAGACTCAAATCCTCAAAAGTTCACCTCATCTGCTAATGGAGTAACCACACACTATGTTT
CTCAGATTGGCAGCTTCCCAGATCAAACAGAAGACGGAGGACTACCACAAAGCGGCAGGATTGTTGT
TGATTACATGATGCAAAAACCTGGGAAAACAGGAACAATTGTCTACCAAAGAGGTGTTTTGTTGCCTC
AAAAGGTGTGGTGCGCGAGTGGCAGGAGCAAAGTAATAAAAGGGTCCTTGCCTTTAATTGGTGAAGC
AGATTGCCTTCATGAAAAATACGGTGGATTAAACAAAAGCAAGCCTTACTACACAGGAGAACATGCAA
AAGCCATAGGAAATTGCCCAATATGGGTGAAAACACCTTTGAAGCTCGCCAATGGAACCAAATATAGA
CCTCCTGCAAAACTATTAAAGGAAAGGGGTTTCTTCGGAGCTATTGCTGGTTTCCTAGAAGGAGGATG
GGAAGGAATGATTGCAGGCTGGCACGGATACACATCTCACGGAGCACATGGAGTGGCAGTGGCGGC
GGACCTTAAGAGTACGCAAGAAGCTATAAACAAGATAACAAAAAATCTCAATTCTTTGAGTGAGCTAGA
AGTAAAGAATCTTCAAAGACTAAGTGGTGCCATGGATGAACTCCACAACGAAATACTCGAGCTGGATG
AGAAAGTGGATGATCTCAGAGCTGACACTATAAGCTCGCAAATAGAACTTGCAGTCTTGCTTTCCAAC
GAAGGAATAATAAACAGTGAAGATGAGCATCTATTGGCACTTGAGAGAAAACTAAAGAAAATGCTGGG
TCCCTCTGCTGTAGAGATAGGAAATGGATGCTTCGAAACCAAACACAAGTGCAACCAGACCTGCTTAG
ACAGGATAGCTGCTGGCACCTTTAATGCAGGAGAATTTTCTCTCCCCACTTTTGATTCACTGAACATTA
CTGCTGCATCTTTAAATGATGATGGATTGGATAACTACCAAATACTGTCAATTTATTCAACAGTGGCGA
GTTCCCTAGCACTGGCAATCATGATGGCTGGTCTATCTTTATGGATGTGCTCCAATGGATCGTTACAA
TGCAGAATTTGCATTTAAAGGCCTATTTTCTTTAGTTTGAATTTACTGTTATTCGGTGTGCATTTCTATG
TTTGGTGAGCGGTTTTCTGTGCTCAGAGTGTGTTTATTTTATGTAATTTAATTTCTTTGTGAGCTCCTGT
TTAGCAGGTCGTCCCTTCAGCAAGGACACAAAAAGATTTTAATTTTATTAAAAAAAAAAAAAAAAAAGA
CCGGGAATTCGATATCAAGCTTATCGACCTGCAGATCGTTCAAACATTTGGCAATAAAGTTTCTTAAGA
TTGAATCCTGTTGCCGGTCTTGCGATGATTATCATATAATTTCTGTTGAATTACGTTAAGCATGTAATAA
TTAACATGTAATGCATGACGTTATTTATGAGATGGGTTTTTATGATTAGAGTCCCGCAATTATACATTTA
ATACGCGATAGAAAACAAAATATAGCGCGCAAACTAGGATAAATTATCGCGCGCGGTGTCATCTATGT
TACTAGATTCTAGAGTCTCAAGCTTCGGCGCGCC

Figure 51B

CHIMERIC INFLUENZA VIRUS-LIKE PARTICLES COMPRISING HEMAGGLUTININ

This application claims priority from U.S. Provisional Application No. 61/220,161 filed Jun. 24, 2009.

REFERENCE TO SEQUENCE LISTING SUBMITTED ELECTRONICALLY

The content of the electronically submitted substitute sequence listing, file name 3043_0020001_SequenceListing.ascii, size 256,991 bytes; and date of creation Aug. 20, 2013, filed herewith, is incorporated herein by reference in its entirety.

FIELD OF INVENTION

The present invention relates to virus-like particles. More specifically, the present invention is directed to virus-like particles comprising chimeric influenza hemagglutinin, and methods of producing chimeric influenza virus-like particles.

BACKGROUND OF THE INVENTION

Influenza is the leading cause of death in humans due to a respiratory virus, and during "flu season", it is estimated that 10-20% of the population worldwide may be infected, leading to 250-500,000 deaths annually.

The current method of combating influenza in humans is by annual vaccination. The vaccine is usually a combination of several strains that are predicted to be the dominant strains for the coming flu-season, however the number of vaccine doses produced annually is not sufficient to vaccinate the world's population. For example, Canada and the United-States obtain enough vaccine doses to immunize about one third of their population, and in Europe, only about 17% can be vaccinated given current production—in the face of a worldwide flu pandemic, this production would be insufficient. Even if the necessary annual production could somehow be met in a given year, the dominant strains change from year to year, thus stockpiling at low-need times in the year is not practical. Economical, large scale production of an effective influenza vaccine is of significant interest to government and private industry alike.

Influenza haemagglutinin (HA) surface glycoprotein is both a receptor-binding and membrane fusion protein. It is a trimer of identical subunits, each containing two disulphide-linked polypeptides, HA1 and HA2, that are derived by proteolytic cleavage of a precursor, HA0, that has a signal peptide sequence at its N-terminus and a membrane anchor sequence at its C-terminus. Cleavage to form HA1 and HA2 generates the N-terminus of the smaller polypeptide, HA2, which has the membrane anchor sequence at its C-terminus. Cleavage is required for membrane fusion activity but not for immunogenicity. The HA2 N-terminal sequence is called the 'fusion peptide' because cleavage at similar hydrophobic sequences is also required for the activity of other virus fusion proteins, and because 20-residue synthetic peptide analogues of the sequence fuse membranes in vitro.

Generally, the surface of the globular 'head' comprises several flexible loops with well-characterized and variable antigenic regions designated as sites A, B, C, D and E (reviewed in Wiley et al., 1987. Annu. Rev Biochem 56:365-394). Insertion or replacement of short peptide sequences at some sites (e.g. B and E) for immunity studies have been described (Garcia-Sastré et al. 1995. Biologicals 23:171-178). Epidermal growth factor (EGF), single chain antibody (scFV) and the Fc domain of an IgG, ranging in size from 53 to 246 amino acids, have been inserted at the N-terminal end of a H7 and chimeras has been successfully expressed (Hatziioannou et al., 1999. Human Gene Therapy 10:1533-1544). More recently, 90 and 140 amino acid domains of *Bacillus anthracis* protective antigen have been fused to the amino terminus of a H3 (Li et al., 2005. J. Virol 79:10003-1002). Copeland (Copeland et al., 2005. J. Virol 79:6459-6471) describes the expression of the gp120 Env HIV surface glycoprotein on a H3 stalk, where the gp120 domain replaced the whole globular head of HA.

Several recombinant products have been developed as recombinant influenza vaccine candidates. These approaches have focused on the expression, production, and purification of influenza type A HA and NA proteins, including expression of these proteins using baculovirus infected insect cells (Crawford et al, 1999 Vaccine 17:2265-74; Johansson, 1999 Vaccine 17:2073-80), viral vectors, and DNA vaccine constructs (Olsen et al., 1997 Vaccine 15:1149-56).

Production of a non-infectious influenza virus strain for vaccine purposes is one way to avoid inadvertent infection. Alternatively, virus-like particles (VLPs) as substitutes for the cultured virus have been investigated. VLPs mimic the structure of the viral capsid, but lack a genome, and thus cannot replicate or provide a means for a secondary infection. Current influenza VLP production technologies rely on the co-expression of multiple viral proteins, and this dependence represents a drawback of these technologies since in case of a pandemic and of yearly epidemics, response time is crucial for vaccination. A simpler VLP production system, for example, one that relies on the expression of only one or a few viral proteins without requiring expression of non-structural viral proteins is desirable to accelerate the development of vaccines.

Enveloped viruses may obtain their lipid envelope when 'budding' out of the infected cell and obtain the membrane from the plasma membrane, or from that of an internal organelle. In mammalian or baculovirus cell systems, for example, influenza buds from the plasma membrane (Quan et al 2007 J. Virol 81:3514-3524). Only a few enveloped viruses are known to infect plants (for example, members of the Tospoviruses and Rhabdoviruses). Of the known plant enveloped viruses, they are characterized by budding from internal membranes of the host cell, and not from the plasma membrane. Although a small number of recombinant VLPs have been produced in plant hosts, none were derived from the plasma membrane, raising the question whether plasma membrane-derived VLPs, including influenza VLPs can be produced in plants.

Formation of VLPs, in any system, places considerable demands on the structure of the proteins—altering short stretches of sequence that correspond to selected surface loops of a globular structure may not have much of an effect on expression of the polypeptide itself, however structural studies are lacking to demonstrate the effect of such alterations on the formation of VLPs. The cooperation of the various regions and structures of HA (e.g. the membrane anchor sequences, the stalk or stem regions of the trimer that separate the globular head from the membranes) has evolved with the virus and may not be amendable to similar alterations without loss of HA trimer integrity and VLP formation.

The production of influenza HA VLPs has been previously described by the inventors in WO 2009/009876.

SUMMARY OF THE INVENTION

The present invention relates to virus-like particles. More specifically, the present invention is directed to virus-like particles comprising chimeric influenza hemagglutinin, and methods of producing chimeric influenza hemagglutinin virus-like particles.

It is an object of the invention to provide an improved chimeric influenza virus-like particle (VLP).

The present invention provides a polypeptide comprising a chimeric influenza HA comprising a stem domain cluster (SDC), a head domain cluster (HDC) and a transmembrane domain cluster (TDC) wherein: the SDC comprises an F'1, F'2 and F subdomain; the HDC comprises an RB, E1 and E2 subdomain; the TDC comprises a TmD and Ctail subdomain; and wherein at least one subdomain is of a first influenza HA and the other subdomains are of one or more second influenza HA. The first and second influenza HA may independently be selected from the group comprising H1, H3, H5 and B. Furthermore, the polypeptide may comprise a signal peptide.

The present invention also provides a nucleic acid encoding the polypeptide comprising a chimeric influenza HA comprising a stem domain cluster (SDC), a head domain cluster (HDC) and a transmembrane domain cluster (TDC) wherein: the SDC comprises an F'1, F'2 and F subdomain; the HDC comprises an RB, E1 and E2 subdomain; the TDC comprises a TmD and Ctail subdomain; and wherein at least one subdomain is of a first influenza HA, and the other subdomains are of one or more second influenza HA. The nucleic acid may also encode the polypeptide that comprises a signal peptide in addition to the SDC, HDC and TDC as defined.

A method of producing chimeric influenza virus like particles (VLPs) in a plant is also provided, the method comprising:

a) introducing a nucleic acid encoding a chimeric influenza HA comprising a signal peptide, a stem domain cluster (SDC), a head domain cluster (HDC) and a transmembrane domain cluster (TDC) wherein: the SDC comprises an F'1, F'2 and F subdomain; the HDC comprises an RB, E1 and E2 subdomain; the TDC comprises a TmD and Ctail subdomain; and wherein at least one subdomain is of a first influenza HA, and the other subdomains are of one or more second influenza HA into the plant, or portion thereof, and b) incubating the plant, or portion thereof, under conditions that permit the expression of the nucleic acid, thereby producing the VLPs.

The present invention includes the method described above wherein in the step of introducing (step a), the nucleic acid is introduced in the plant in a transient manner. Alternatively, in the step of introducing (step a), the nucleic acid is introduced in the plant and is stably integrated. The method may further comprise a step of c) harvesting the host and purifying the VLPs.

The present invention provides a plant, or portion thereof, comprising a chimeric influenza HA, or a nucleotide sequence encoding the chimeric influenza HA, the chimeric influenza HA comprising a stem domain cluster (SDC), a head domain cluster (HDC) and a transmembrane domain cluster (TDC) wherein: the SDC comprises an F'1, F'2 and F subdomain; the HDC comprises an RB, E1 and E2 subdomain; the TDC comprises a TmD and Ctail subdomain; and wherein at least one subdomain is of a first influenza HA and the other subdomains are of one or more second influenza HA.

The plant, or portion thereof, may further comprise a nucleic acid comprising a nucleotide sequence encoding one or more than one chaperone protein operatively linked to a regulatory region active in a plant. The one or more than one chaperon proteins may be selected from the group comprising Hsp40 and Hsp70.

The present invention pertains to a virus like particle (VLP) comprising a chimeric influenza HA, the chimeric influenza HA comprising a stem domain cluster (SDC), a head domain cluster (HDC) and a transmembrane domain cluster (TDC) wherein: the SDC comprises an F'1, F'2 and F subdomain; the HDC comprises an RB, E1 and E2 subdomain; the TDC comprises a TmD and Ctail subdomain; and wherein at least one subdomain is of a first influenza HA and the other subdomains are of one or more second influenza HA. The VLP may further comprise plant-specific N-glycans, or modified N-glycans.

A composition comprising an effective dose of the VLP as just described and a pharmaceutically acceptable carrier is also provided.

In an alternate aspect of the present invention there is provided a method of inducing immunity to an influenza virus infection in a subject, comprising administering the VLP to the subject. The VLP may administered to a subject orally, intradermally, intranasally, intramuscularly, intraperitoneally, intravenously, or subcutaneously.

Regulatory regions that may be operatively linked to a sequence encoding a chimeric HA protein include those that are operative in a plant cell, an insect cell or a yeast cell. Such regulatory regions may include a plastocyanin regulatory region, a regulatory region of Ribulose 1,5-bisphosphate carboxylase/oxygenase (RuBisCO), chlorophyll a/b binding protein (CAB) or ST-LS1. Other regulatory regions include a 5' UTR, 3' UTR or terminator sequences. The plastocyanin regulatory region may be an alfalfa plastocyanin regulatory region; the 5' UTR, 3'UTR or terminator sequences may also be alfalfa sequences.

The present invention provides a chimeric influenza HA polypeptide comprised of a first influenza and a second influenza, the first influenza and the second influenza may be independently selected from the group comprising B, H1, H2, H3, H4, H5, H6, H7, H8, H9, H10, H11, H12, H13, H14, H15 and H16; with the proviso that the first influenza and the second influenza are not the same influenza type, subtype, or of the same origin.

In accordance with some aspects of the invention, the chimeric influenza HA polypeptide comprises a signal peptide sequence, the signal peptide sequence may be selected from the group comprising a native signal peptide sequence, an alfalfa PDI signal peptide sequence, an influenza H5 signal peptide sequence and an influenza H1 signal peptide sequence The present invention provides a method for producing a VLP containing chimeric influenza hemagglutinin (HA) within a host capable of producing a VLP, including a plant, insect, or yeast comprising, introducing a nucleic acid encoding a chimeric influenza HA comprising a stem domain cluster (SDC), a head domain cluster (HDC) and a transmembrane domain cluster (TDC) wherein: the SDC comprises an F'1, F'2 and F subdomain; the HDC comprises an RB, E1 and E2 subdomain; the TDC comprises a TmD and Ctail subdomain; and wherein at least one subdomain is of a first influenza HA and the other subdomains are of one or more second influenza HA, into the host, and incubating the host under conditions that permit the expression of the nucleic acid, thereby producing the VLPs.

The production of VLPs in plants presents several advantages over the production of these particles in insect cell culture. Plant lipids can stimulate specific immune cells and enhance the immune response induced. Plant membranes are made of lipids, phosphatidylcholine (PC) and phosphatidylethanolamine (PE), and also contain glycosphingolipids that are unique to plants and some bacteria and protozoa. Sphingolipids are unusual in that they are not esters of glycerol like PC or PE but rather consist of a long chain amino alcohol that forms an amide linkage to a fatty acid chain containing more than 18 carbons. PC and PE as well as glycosphingolipids can bind to CD1 molecules expressed by mammalian immune cells such as antigen-presenting cells (APCs) like dentritic cells and macrophages and other cells including B and T lymphocytes in the thymus and liver. Furthermore, in addition to the potential adjuvant effect of the presence of plant lipids, the ability of plant N-glycans to facilitate the capture of glycoprotein antigens by antigen presenting cells, may be advantageous of the production of chimeric VLPs in plants. Without wishing to be bound by theory, it is anticipated that plant-made chimeric VLPs induce a stronger immune reaction than chimeric VLPs made in other manufacturing systems and that the immune reaction induced by these plant-made chimeric VLPs is stronger when compared to the immune reaction induced by live or attenuated whole virus vaccines.

Contrary to vaccines made of whole viruses, chimeric VLPs provide the advantage as they are non-infectious, thus restrictive biological containment is not as significant an issue as it would be working with a whole, infectious virus, and is not required for production. Plant-made chimeric VLPs provide a further advantage again by allowing the expression system to be grown in a greenhouse or field, thus being significantly more economical and suitable for scale-up.

Additionally, plants do not comprise the enzymes involved in synthesizing and adding sialic acid residues to proteins. VLPs may be produced in the absence of neuraminidase (NA), and there is no need to co-express NA, or to treat the producing cells or extract with sialidase (neuraminidase), to ensure VLP production in plants This summary of the invention does not necessarily describe all features of the invention of the invention.

BRIEF DESCRIPTION OF THE DRAWINGS

These and other features of the invention will become more apparent from the following description in which reference is made to the appended drawings wherein:

FIG. 12 shows amino acid sequence of the chimeric H5/H3 hemagglutinin (SEQ. ID. NO. 83; construct 737) comprising a PDI signal peptide, an ectodomain of H3 A/Brisbane/10/2007 and a TMD/CT of H5 A/Indonesia/5/2005.

FIG. 13 shows the amino acid sequence of the chimeric H5/B hemagglutinin (SEQ. ID. NO. 84) comprising an ectodomain of B/Florida/4/2006 and a TMD/CT of H5 A/Indonesia/5/2005 encoded by the open reading frame in construct number 745.

FIG. 17 shows the nucleic acid sequence (SEQ ID NO: 52) of the synthesized fragment comprising the complete H5 (A/Indonesia/5/05 (H5N1)) coding region (including the signal peptide and the stop codon) flanked, in 5' by a HindIII site and, in 3', by a SacI site.

FIG. 18 shows the nucleic acid sequence (SEQ ID NO: 53) of construct 660, an HA expression cassette comprising an alfalfa plastocyanin promoter and 5' UTR, hemagglutinin coding sequence of H5 form A/Indonesia/5/05 (H5N1), alfalfa plastocyanin 3' UTR and terminator sequences.

FIG. 19 shows the nucleic acid sequence (SEQ ID NO: 54) of the wild-type H1 (A/New Caledonia/20/99 (H1N1) (GenBank acc. no. AY289929) coding sequence without a TmD and Ctail.

FIG. 20 shows the nucleic acid sequence (SEQ ID NO: 55) of a synthesized fragment comprising H1 (A/New Caledonia/20/99 (H1N1) coding sequence lacking TmD and Ctail. In the 5' region, the last nucleotides originate from PDI SP and include a BglII restriction site and in 3', a dual SacI/StuI site is found immediately downstream of the stop codon.

FIG. 21 shows the nucleic acid sequence (SEQ ID NO: 56) of the synthesized fragment comprising the C-ter H1 (A/New Caledonia/20/99 (H1N1) coding sequence including the TmD and Ctail from the KpnI site to the stop codon (flanked in 3' by a dual SacI/StuI site).

FIG. 22 shows the nucleotide sequence for *Medicago sativa* mRNA for protein disulfide isomerase. GenBank Accession No. Z11499 (SEQ ID NO: 57). Nucleotides 32-109 encode the PDI signal peptide.

FIG. 23 shows the nucleotide sequence for PromPlasto-PDISP-Plasto 3'UTR plasmid. FIG. 23A shows the nucleotide sequence for PromPlasto-PDISP (SEQ ID NO:58). FIG. 23B shows the nucleotide sequence from Plasto 3'UTR (SEQ ID NO:85). Protein disulfide isomerase (PDI) signal peptide is underlined. BglII (AGATCT) and SacI (GAGCTC) restriction sites used for cloning are shown in bold.

FIG. 24 shows the nucleic acid sequence (SEQ ID NO: 59; construct 540) of the an HA expression cassette comprising alfalfa plastocyanin promoter and 5' UTR, coding sequence of the signal peptide from PDI and of H1 form A/New Caledonia/20/99 (H1N1), alfalfa plastocyanin 3'

Figure 1A:
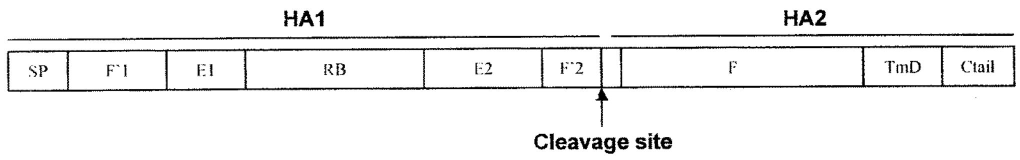
FIG. 1A shows a schematic diagram of HA subdomains. SP: signal peptide, F'1, F'2, and F: fusion subdomains; RB: receptor-binding subdomain, E1 and E2: esterase subdomains, TMD/CT: transmembrane and cytoplasmic tail subdomains.
Figure 1B:
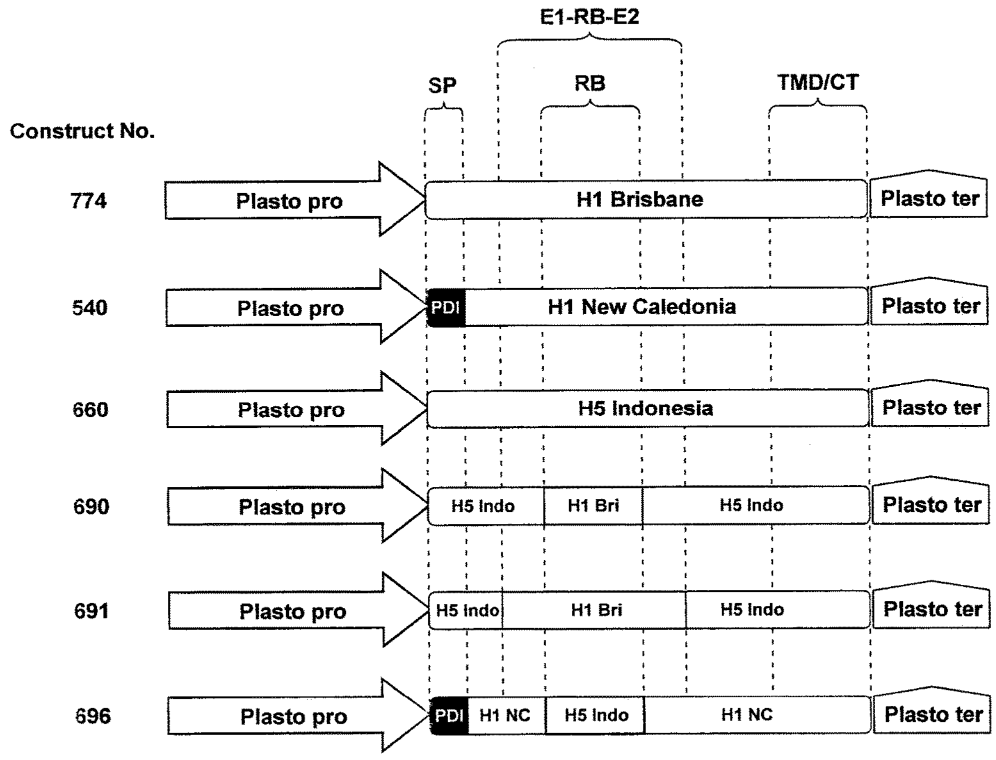
FIG. 1B shows schematic representations of plastocyanin-based expression cassettes (construct numbers: 774, 540, 660, 690, 691, 696) for the expression of hemagglutinin H1 A/Brisbane/59/2007 (H1/Bri), hemagglutinin H1 A/New Caledonia/20/99 (H1/NC) and hemagglutinin H5 A/Indonesia/5/05 (H5/Indo) in native and chimeric forms. Plasto pro: alfalfa plastocyanin promoter, Plasto ter: alfalfa plastocyanin terminator, SP: signal peptide, RB: receptor-binding subdomain, E1-RB-E2: esterase and receptor-binding subdomains, TMD/CT: transmembrane and cytoplasmic tail subdomains, PDI: alfalfa protein disulfide isomerase.

UTR and terminator sequences. H1 from A/New Caledonia/20/1999 coding sequence is underlined.

FIG. 25 shows the nucleic acid sequence (SEQ ID NO: 60) of the synthesized fragment comprising the complete H1 (A/Brisbane/59/07 (H1N1)) coding region (including the signal peptide and the stop codon) flanked, in 5' by alfalfa plastocyanin gene sequences corresponding to the first 84 nucleotides upstream of the initial ATG, starting with a DraIII site and, in 3', by a SacI site.

FIG. 26 shows the nucleic acid sequence (SEQ ID NO: 61; construct 774) of the an HA expression cassette comprising alfalfa plastocyanin promoter and 5' UTR, hemagglutinin coding sequence of H1 form A/Brisbane/59/07 (H1N1), alfalfa plastocyanin 3' UTR and terminator sequences.

FIG. 27 shows the nucleic acid sequence of expression cassette number 828 (SEQ ID NO: 62), from PacI (upstream of the promoter) to AscI (immediately downstream of the NOS terminator). CPMV HT 3' UTR sequencer underlined with mutated ATG in bold. ApaI restriction site underlined and italic.

FIG. 28 shows the nucleic acid sequence (SEQ ID NO: 63; construct 690) of a chimeric H5/H1 expression cassette comprising alfalfa plastocyanin promoter and 5' UTR, chimeric hemagglutinin coding sequence, alfalfa plastocyanin 3' UTR and terminator sequences. Chimeric HA coding sequence is underlined.

FIG. 29 shows the nucleic acid sequence (SEQ ID NO: 64; construct 691) of a chimeric H5/H1 expression cassette comprising alfalfa plastocyanin promoter and 5' UTR, chimeric hemagglutinin coding sequence, alfalfa plastocyanin 3' UTR and terminator sequences. Chimeric HA coding sequence is underlined.

FIG. 30 shows the nucleic acid sequence (SEQ ID NO: 65; construct 696) of a chimeric H1/H5 expression cassette comprising alfalfa plastocyanin promoter and 5' UTR, chimeric hemagglutinin coding sequence, alfalfa plastocyanin 3' UTR and terminator sequences. Chimeric HA coding sequence is underlined.

FIG. 31 shows the nucleic acid sequence (SEQ ID NO: 66; construct 732) of the an HA expression cassette comprising the CaMV 35S promoter, CPMV-HT 5' UTR, hemagglutinin coding sequence of H1 form A/Brisbane/59/07 (H1N1), CPMV-HT 3' UTR and NOS terminator sequences. Coding sequence of H1/Bri is underlined.

FIG. 32 shows the nucleic acid sequence (SEQ ID NO: 67) of the coding sequence, from ATG to stop, of intermediate construct number 787.

FIG. 33 shows the nucleic acid sequence (SEQ ID NO: 68; construct no. 733) of SpPDI H1/Bri expression cassette comprising the CaMV 35S promoter, CPMV-HT 5' UTR, coding sequence of the signal peptide from PDI, hemagglutinin coding sequence of H1 form A/Brisbane/59/07 (H1N1), CPMV-HT 3' UTR and NOS terminator sequences. Coding sequence of SpPDI H1/Bri is underlined.

FIG. 34 shows the nucleic acid sequence (SEQ ID NO: 69; construct 734) of a chimeric H5/H1 expression cassette comprising the CaMV 35S promoter, CPMV-HT 5' UTR, chimeric hemagglutinin coding sequence, CPMV-HT 3' UTR and NOS terminator sequences. Coding sequence of chimeric HA is underlined.

FIG. 35 shows the nucleic acid sequence (SEQ ID NO: 70) of the synthesized fragment comprising the complete H3 (A/Brisbane/10/07 (H3N2)) coding region (including the signal peptide and the stop codon) flanked, in 5' by alfalfa plastocyanin gene sequences corresponding to the first 84 nucleotides upstream of the initial ATG, starting with a DraIII site and, in 3', by a SacI site.

FIG. 36 shows the nucleic acid sequence (SEQ ID NO: 71; construct 736) of the an HA expression cassette comprising the CaMV 35S promoter, CPMV-HT 5' UTR, coding sequence of the signal peptide from PDI, hemagglutinin coding sequence of H3 form A/Brisbane/10/07 (H2N3), CPMV-HT 3' UTR and NOS terminator sequences. Coding sequence of Sp PDI H3/Bris is underlined.

FIG. 37 shows the nucleic acid sequence (SEQ ID NO: 72; construct no. 737) of a chimeric H5/H3 expression cassette comprising the CaMV 35S promoter, CPMV-HT 5' UTR, chimeric hemagglutinin coding sequence, CPMV-HT 3' UTR and NOS terminator sequences. Coding sequence of chimeric HA is underlined.

FIG. 38 shows the nucleic acid sequence (SEQ ID NO: 73) of the synthesized fragment comprising the complete HA (B/Florida/4/06) coding region (including the signal peptide and the stop codon) flanked, in 5' by alfalfa plastocyanin gene sequences corresponding to the first 84 nucleotides upstream of the initial ATG, starting with a DraIII site and, in 3', by a SacI site.

FIG. 39 shows the nucleic acid sequence (SEQ ID NO: 74; construct 739) of the an HA expression cassette comprising the CaMV 35S promoter, CPMV-HT 5' UTR, coding sequence of the signal peptide from PDI, hemagglutinin coding sequence of HA form B/Florida/4/06, CPMV-HT 3' UTR and NOS terminator sequences. Coding sequence of Sp PDI B/Flo is underlined.

FIG. 40 shows the nucleic acid sequence (SEQ ID NO: 75; construct 745) of a chimeric H5/B expression cassette comprising the CaMV 35S promoter, CPMV-HT 5' UTR, chimeric hemagglutinin coding sequence, CPMV-HT 3' UTR and NOS terminator sequences. Coding sequence of chimeric HA is underlined.

FIG. 41 shows the nucleic acid sequence encoding Msj1 (SEQ ID NO: 76).

FIG. 42 shows the nucleic acid sequence (SEQ ID NO: 77) of a portion of construct number R850, from HindIII (in the multiple cloning site, upstream of the promoter) to EcoRI (immediately downstream of the NOS terminator). HSP40 coding sequence is underlined.

FIG. 43 shows the nucleic acid sequence (SEQ ID NO: 78) of a portion of construct number R860, from HindIII (in the multiple cloning site, upstream of the promoter) to EcoRI (immediately downstream of the NOS terminator). The HSP70 coding sequence is underlined.

FIG. 44 shows the nucleic acid sequence (SEQ ID NO: 79) of a portion of construct number R870, from HindIII (in the multiple cloning site, 5 upstream of the promoter) to EcoRI (immediately downstream of the NOS terminator). The HSP40 coding sequence is in underlined italic and the HSP70 coding sequence is underlined. A) nucleotides 1-4946; B) nucleotides 4947-9493.

Figure 45:
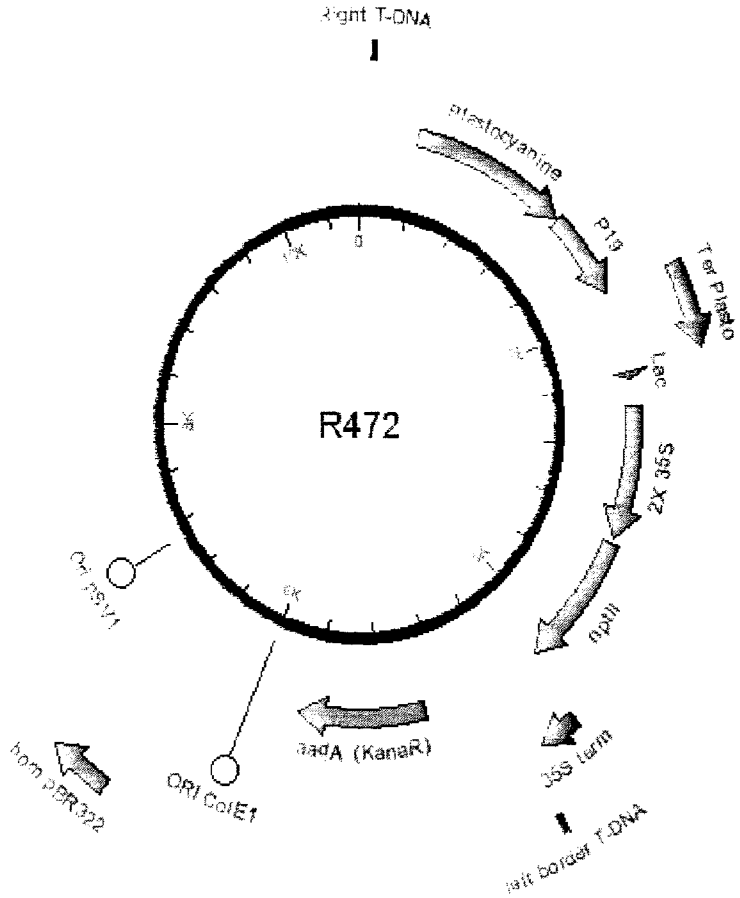

FIG. 45 shows a schematic representation of construct number R472.

Figure 46:
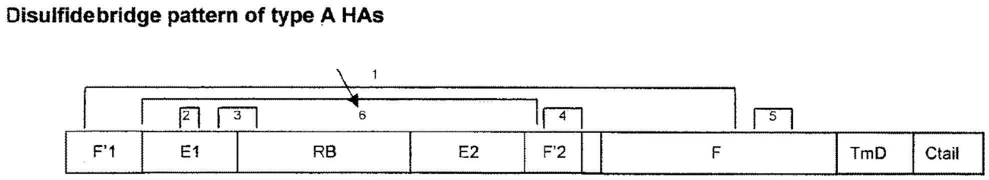

FIG. 46 shows the disulfide bridge pattern of influenza type A. Bridge numbering: 1) Cys4HA1-Cys137HA2, 2) Cys60HA1-Cys72HA1, 3) Cys94HA1-Cys143HA1, 4) Cys292HA1-Cys318HA1 5) Cys144HA2-Cys148HA2 and 6) Cys52HA1-Cys277HA1. The disulfide bridges that differ between A and B (FIG. 47) subtypes are indicated with arrows. The numbering from mature H3 protein was used.

Figure 47:
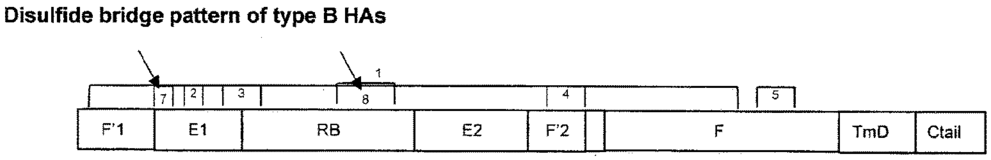

FIG. 47 shows the disulfide bridge pattern of influenza type B HA. Bridge numbering: 1) Cys4HA1-Cys137HA2, 2) Cys60HA1-Cys72HA1, 3) Cys94HA1-Cys143HA1, 4) Cys292HA1-Cys318HA1 5) Cys144HA2-Cys148HA2, 6)

Cys52HA1-Cys277HA1, 7) Cys54HA1-Cys57HA1 and 8) Cys178HA1-Cys272HA1. The disulfide bridges that differ between A (FIG. 46) and B subtypes are indicated with arrows. The numbering from mature H3 protein was used.

FIG. 48 shows a schematic diagram of domain swap fusion junctions. FIG. 48A shows the fusion of RB subdomain from H1/Bri, H3/Bri, and B/Flo with H5/Indo SDC's, and the RB subdomain of H5/Indo with H1/NC stem domain. FIG. 48B shows the fusion of E1-RB-E2 subdomains (HDC) from H1/Bri, H3/Bri or B/Flo with H5/Indo SDC, and of H5/Indo HDC within H1/NC SDC.

FIG. 49A shows the nucleotide sequence SEQ ID NO: 86) of H1 A/California/04/09. Alfalfa protein disulfide isomerase signal peptide coding sequence is underlined and mature H1 coding sequence is highlighted in bold. FIG. 49B shows the amino acid sequence (SEQ ID NO: 87) of the H1 A/California/04/09. Alfalfa protein disulfide isomerase signal peptide is underlined.

Figure 50:
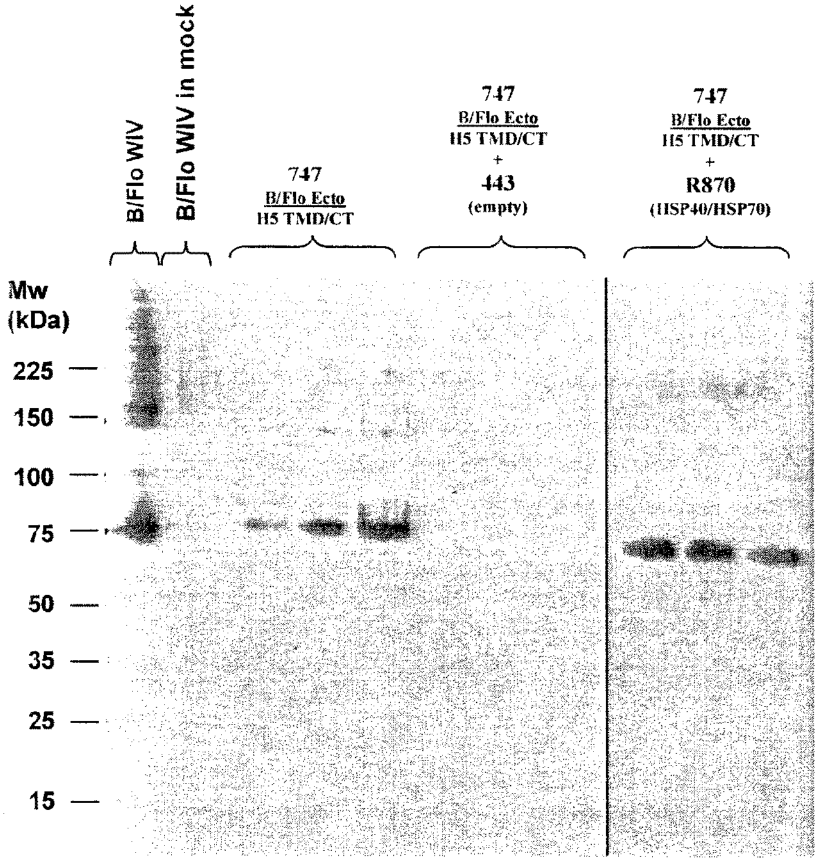

FIG. 50 shows an immunoblot analysis of expression of H5/B chimeric hemagglutinin (construct number 747; comprising B/Flo HDC and SDC fused with an H5/Indo TDC) after infiltration of AGL1/747 undiluted, co-infiltrated with AGL1/443 (empty vector) and co-infiltrated with AGL1/R870 (HSP40/HSP70). For each construct, total protein extracts from 3 separate plants were analyzed. Twenty micrograms of proteins were loaded for each plant analyzed. The Western blot was revealed with anti-B Florida polyclonal antibodies (NIBSC).

FIG. 51A shows the nucleotide sequence for the 2X35S promoter sequence (SEQ ID NO:88). FIG. 51B shows the nucleotide sequence for construct 747 (SEQ ID NO:93) from PacI (upstream 35S promoter) to AscI (immediately downstream NOS terminator). Coding sequence of chimeric HA is underlined. 2X35S promoter sequence is indicated in italics.

DETAILED DESCRIPTION

The present invention relates to virus-like particles. More specifically, the present to invention is directed to virus-like particles comprising chimeric influenza hemagglutinin, and methods of producing chimeric influenza virus-like particles.

The following description is of a preferred embodiment.

The present invention provides a nucleic acid comprising a nucleotide sequence encoding a chimeric influenza hemagglutinin (HA) operatively linked to a regulatory region active in a plant.

Furthermore, the present invention provides a method of producing virus like particles (VLPs) in a plant. The method involves introducing a nucleic acid encoding a chimeric influenza HA operatively linked to a regulatory region active in the plant, into the plant, or portion of the plant, and incubating the plant or a portion of the plant under conditions that permit the expression of the nucleic acid, thereby producing the VLPs.

The present invention further provides for a VLP comprising a chimeric influenza HA. The VLP may be produced by the method as provided by the present invention.

By "chimeric protein" or "chimeric polypeptide", it is meant a protein or polypeptide that comprises amino acid sequences from two or more than two sources, for example but not limited to, two or more influenza types or subtypes, or influenza's of a different origin, that are fused as a single polypeptide. The chimeric protein or polypeptide may include a signal peptide that is the same as, or heterologous with, the remainder of the polypeptide or protein. The chimeric protein or chimeric polypeptide may be produced as a transcript from a chimeric nucleotide sequence, and the chimeric protein or chimeric polypeptide cleaved following synthesis, and as required, associated to form a multimeric protein. Therefore, a chimeric protein or a chimeric polypeptide also includes a protein or polypeptide comprising subunits that are associated via disulphide bridges (i.e. a multimeric protein). For example, a chimeric polypeptide comprising amino acid sequences from two or more than two sources may be processed into subunits, and the subunits associated via disulphide bridges to produce a chimeric protein or chimeric polypeptide (see FIGS. 46 and 47). The polypeptide may be hemagglutinin (HA), and each of the two or more than two amino acid sequences that make up the polypeptide may be obtained from different HA's to produce a chimeric HA, or chimeric influenza HA. A chimeric HA may also include an amino acid sequence comprising heterologous signal peptide (a chimeric HA preprotein) that is cleaved after or during protein synthesis. Preferably, the chimeric polypeptide, or chimeric influenza HA is not naturally occurring. A nucleic acid encoding a chimeric polypeptide may be described as a "chimeric nucleic acid", or a "chimeric nucleotide sequence". A virus-like particle comprised of chimeric HA may be described as a "chimeric VLP".

The chimeric influenza HA according to various embodiments of the present invention may comprise a stem domain complex (SDC) a head domain complex (HDC) and a transmembrane domain complex (TDC), where one or more than one subdomain of either the SDC, HDC or TDC is of a first influenza HA type, subtype or from one origin, and one or more than one subdomain of either the SDC, HDC or TDC is from a second influenza HA type, subtype, or from a second or different origin. As described herein, the "SDC" comprises an F'1, F'2 and F subdomain, the "HDC" comprises an RB, E1 and E2 subdomain, the "TDC" comprises a TmD and Ctail subdomain (TMD/CT; see FIGS. 1A, 46 and 47).

The term "virus like particle" (VLP), or "virus-like particles" or "VLPs" refers to structures that self-assemble and comprise structural proteins such as influenza HA protein, or chimeric influenza HA protein. VLPs and chimeric VLPs are generally morphologically and antigenically similar to virions produced in an infection, but lack genetic information sufficient to replicate and thus are non-infectious. VLPs and chimeric VLPs may be produced in suitable host cells including plant host cells. Following extraction from the host cell and upon isolation and further purification under suitable conditions, VLPs and chimeric VLPs may be purified as intact structures.

Chimeric VLPs, or VLPs, produced from influenza derived proteins, in accordance with the present invention do not comprise M1 protein. The M1 protein is known to bind RNA (Wakefield and Brownlee, 1989) which is a contaminant of VLP preparation. The presence of RNA is undesired when obtaining regulatory approval for the chimeric VLP product, therefore a chimeric VLP preparation lacking RNA may be advantageous.

The chimeric VLPs of the present invention may be produced in a host cell that is characterized by lacking the ability to sialylate proteins, for example a plant cell, an insect cell, fungi, and other organisms including sponge, coelenterara, annelida, arthoropoda, mollusca, nemathelminthea, trochelmintes, plathelminthes, chaetognatha, tentaculate, chlamydia, spirochetes, gram-positive bacteria, cyanobacteria, archaebacteria, or the like. See, for example Gupta et al., 1999. Nucleic Acids Research 27:370-372;

Toukach et al., 2007. Nucleic Acids Research 35:D280-D286; Nakahara et al., 2008. Nucleic Acids Research 36:D368-D371. The chimeric VLPs produced as described herein do not typically comprise neuraminidase (NA). However, NA may be co-expressed with HA should VLPs comprising HA and NA be desired.

The invention also provides VLPs comprising chimeric HA that obtain a lipid envelope from the plasma membrane of the cell in which the chimeric HA are expressed. For example, if the chimeric HA is expressed in a plant-based system, the resulting VLP may obtain a lipid envelope from the plasma membrane of the plant cell.

Generally, the term “lipid” refers to a fat-soluble (lipophilic), naturally-occurring molecules. A chimeric VLP produced in a plant according to some aspects of the invention may be complexed with plant-derived lipids. The plant-derived lipids may be in the form of a lipid bilayer, and may further comprise an envelope surrounding the VLP. The plant derived lipids may comprise lipid components of the plasma membrane of the plant where the VLP is produced, including phospholipids, tri-, di- and monoglycerides, as well as fat-soluble sterol or metabolites comprising sterols. Examples include phosphatidylcholine (PC), phosphatidylethanolamine (PE), phosphatidylinositol, phosphatidylserine, glycosphingolipids, phytosterols or a combination thereof. A plant-derived lipid may alternately be referred to as a ‘plant lipid’. Examples of phytosterols include campesterol, stigmasterol, ergosterol, brassicasterol, delta-7-stigmasterol, delta-7-avenasterol, daunosterol, sitosterol, 24-methylcholesterol, cholesterol or beta-sitosterol—see, for example, Mongrand et al., 2004. As one of skill in the art would understand, the lipid composition of the plasma membrane of a cell may vary with the culture or growth conditions of the cell or organism, or species, from which the cell is obtained. Generally, beta-sitosterol is the most abundant phytosterol.

Cell membranes generally comprise lipid bilayers, as well as proteins for various functions. Localized concentrations of particular lipids may be found in the lipid bilayer, referred to as ‘lipid rafts’. These lipid raft microdomains may be enriched in sphingolipids and sterols. Without wishing to be bound by theory, lipid rafts may have significant roles in endo and exocytosis, entry or egress of viruses or other infectious agents, inter-cell signal transduction, interaction with other structural components of the cell or organism, such as intracellular and extracellular matrices.

The invention includes VLPs comprising chimeric HA, of which the subdomains may be obtained from any type, subtype of influenza virus which may infect humans, including, for example, B, H1, H2, H3, H4, H5, H6, H7, H8, H9, H10, H11, H12, H13, H14, H15 and H16 types or subtypes. In some embodiments, the influenza virus may be of an H1, H3, H5 or B types or subtypes. Non limiting examples of H1, H3, H15 or B types or subtypes include the A/New Caledonia/20/99 subtype (H1N1) (“H1/NC”; SEQ ID NO:56), the H1 A/California 04/09 subtype (H1N1) (“H1/Cal”; SEQ ID NO:86), the A/Indonesia/5/05 sub-type (H5N1) (“H5/Indo”), A/Brisbane/59/2007 (“H1/Bri”), and B/Florida/4/2006 (“B/Flo”) and H3 A/Brisbane/10/2007 (“H3/Bri”). Furthermore, the chimeric HA may comprise one or more subdomains of a hemagglutinin that is isolated from one or more emerging or newly-identified influenza viruses.

The present invention also pertains to influenza viruses which infect other mammals or host animals, for example humans, primates, horses, pigs, birds, avian water fowl, migratory birds, quail, duck, geese, poultry, chicken, camel, canine, dogs, feline, cats, tiger, leopard, civet, mink, stone marten, ferrets, house pets, livestock, mice, rats, seal, whale and the like. Some influenza viruses may infect more than one host animal.

With reference to influenza virus, the term “hemagglutinin” or “HA” as used herein refers to a structural glycoprotein of influenza viral particles. The structure of influenza hemagglutinin is well-studied and demonstrates a high degree of conservation in secondary, tertiary and quaternary structure. This structural conservation is observed even though the amino acid sequence may vary (see, for example, Skehel and Wiley, 2000 Ann Rev Biochem 69:531-69; Vaccaro et al 2005; which is incorporated herein by reference). Nucleotide sequences encoding HA are well known, and are available for example, from the BioDefense and Public Health Database (for example at URL: biohealthbase.org/GSearch/home.do?decorator=Influenza) or the databases maintained by the National Center for Biotechnology Information (NCBI; for example at URL: ncbi.nlm.nih.gov/sites/entrez?db=nuccore&cmd=search&term=influenza) both of which are incorporated herein by reference.

The HA monomer may be subdivided in three functional domains—a stem domain, or stem domain cluster (SDC), a globular head domain, or head domain cluster (HDC) and a transmembrane domain cluster (TDC). The SDC comprises four subdomains, a fusion peptide F, F'1 and F'2 (this subdomain may be generally referred to as a ‘backbone’). The TDC comprises two subdomains, the transmembrane (TmD) and a C terminal tail (CT). The HDC comprises three subdomains, vestigial esterase domains E1' and E2, and a receptor binding domain RB. The SDC and HDC may be collectively referred to as the ‘ectodomain’. A publication by Ha et al. 2002 (EMBO J. 21:865-875; which is incorporated herein by reference) illustrates the relative orientation of the various subdomains of the SDC and HDC in several influenza subtypes, based on Xray crystallographic structures. A schematic diagram of the subdomains relative to N and C termini of the HA1 and HA2 polypeptides is shown in FIG. 1A. An annotated structural alignment of various influenza subtypes is provided in FIG. 1C.

Amino acid variation is tolerated in hemagglutinins of influenza viruses. This variation provides for new strains that are continually being identified. Infectivity between the new strains may vary. However, formation of hemagglutinin trimers, which subsequently form VLPs is maintained. The present invention, therefore, provides for a hemagglutinin amino acid sequence comprising chimeric HA, or a nucleic acid encoding a chimeric hemagglutinin amino acid sequence, that forms VLPs in a plant, and includes known sequences and variant HA sequences that may develop. The present invention also pertains to the use of a chimeric HA polypeptide comprising a TDC, SDC and HDC. For example the chimeric HA protein may be HA0, or a cleaved chimeric HA comprising subdomains of HA1 and HA2 from two or more influenza types. The chimeric HA protein may be used in the production or formation of VLPs using a plant, or plant cell, expression system.

HA0 may be expressed and folded to form a trimer, which may subsequently assemble into VLPs. Cleavage of HA0 yields HA1 and HA2 polypeptides linked by a disulfide bridge (see FIGS. 1C, 46 and 47 for illustration of disulfide bridge patterns). For an infectious virus particle, cleavage of precursor HA0 is required to trigger the conformational change of HA2 that release the fusion peptide (at the N terminus of the HA2 polypeptide) and make it available for fusion of the cell and viral membranes. However, VLPs are not infectious, and cleavage of the HA into HA1 and HA2 is not required, for example, for vaccine production. Uncleaved HA0 precursor also assembles in trimers and bud from plasma membrane to form VLP nanoparticles.

Figures 1, 1C:
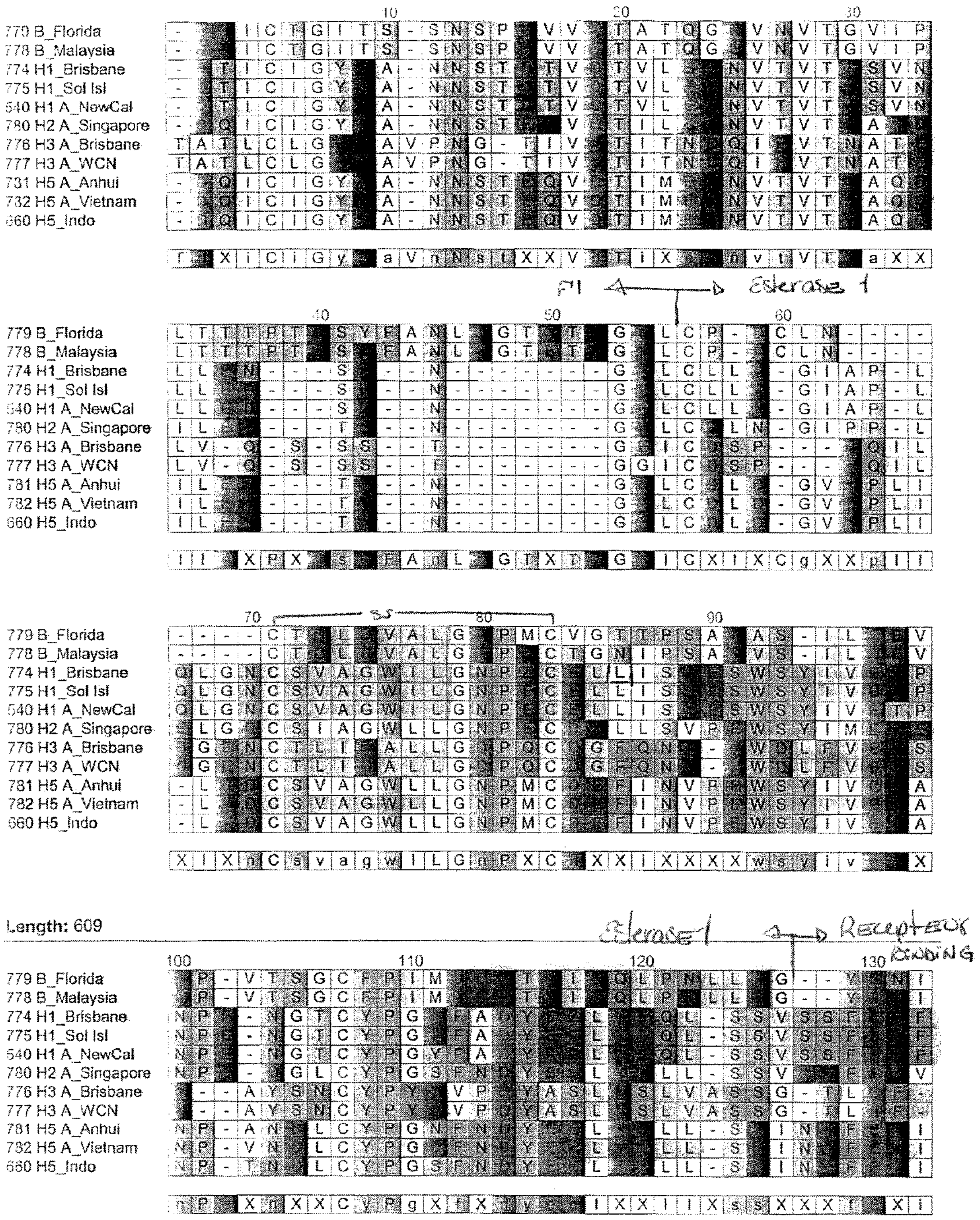
FIG. 1C shows the amino acid sequence alignment superimposed with a structural alignment for several influenza HAs (B/Florida/4/2006 (BFlorida), SEQ ID NO:94 (GenBank Accession No. ACA33493.1; B/Malaysia/2506/2004 (B-Malaysia), SEQ ID NO:95 (GenBank Accession No. ABU99194.1; H1/Bri (A-Brisbane), SEQ ID NO:96 (GenBank Accession No. ADE28750.1; H1 A/Solomon Islands/3/2006 (A-Sol.Isl), SEQ ID NO:97 (GenBank Accession No. ABU99109.1); H1/NC (A-NewCal). SEQ ID NO:98 (GenBank Accession No. AAP34324.1; H2 A/Singapore/1/1957 (A-Singapore), SEQ ID NO:99 (GenBank Accession No. AAA64366.1); H3 A/Brisbane/10/2007 (A-Brisbane), SEQ ID NO:100 (GenBank Accession No. ACI26318.1); H3 A/Wisconsin/67/2005 (A-WCN), SEQ ID NO:101 (GenBank Accession No. ABO37599.1); H5 A/Anhui/1/2005 (A-Anhui), SEQ ID NO:102 (GenBank Accession No. ABD28180.1); H5 A/Vietnam/1194/2004(A-Vietnam), SEQ ID NO:103 (GenBank Accession No. ACR48874.1); H5-Indo, SEQ ID NO:104 (GenBank Accession No. ABW06108.1. The boundaries between the F'1, Esterase 1, Receptor binding, Esterase 2, F'2, Peptide fusion, TMD/CT subdomains, and di-sulfide bridges are indicated.
Figures 1, 1C, 2:
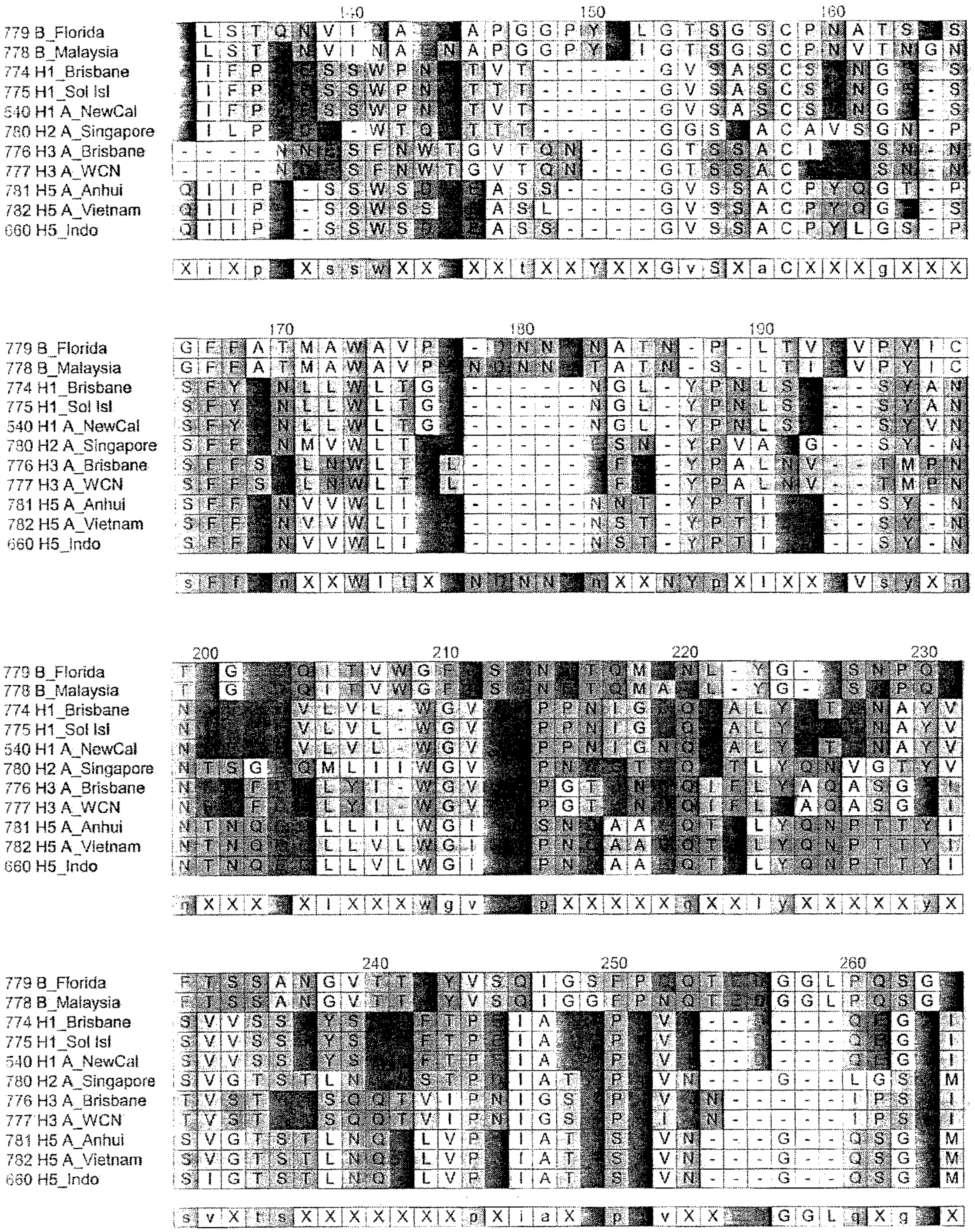
FIG. 2 shows the amino acid sequence of the indicated subdomains of chimeric HA expressed with, upper panel, constructs 690, 734 (SEQ ID NO: 11), 696 (SEQ ID NO: 112), and lower panel, 691 (SEQ ID NO: 113. Amino acids 1-92 of SEQ ID NO: 111 is the F'1+E1 domain of H5/Indo; amino acids 93-263 is an RB head domain of H1/Brisbane and amino acids 264-552 is an E2+F'2 domain of H5/Indo. Amino acids 1-92 of SEQ ID NO: 112 is the F'1+E1 domain of H5/NC; amino acids 93-301 is an RB head domain of H5/Indo and amino acids 302-586 is an E2+F'2 domain of H1/NC. Amino acids 1-42 of SEQ ID NO: 113 is the F'1 domain of H5/Indo; amino acids 43-273 is an E1-RB-E2 head domain of H1/Brisbane and amino acids 274-552 is an F'2 domain of H5/Indo.

The HA0 polypeptide comprises several domains. The RB subdomain of the HDC comprises several loops in antigenic regions designated as site A-E. Antibodies that may neutralize infectious influenza virus are frequently targeted to one or more of these sites. The vestigial esterase subdomains (E1 and E2) may have a role in fusion, and may bind Ca++. The F, F'1 and F'2 domains interact and cooperate to form a stem, raising the head of the HA trimer above the membrane. A TmD and CT may be involved in anchoring of the folded HA to a membrane. The TmD may have a role in affinity of HA for lipid rafts, while the CT may have a role in secretion of HA, while some of the cysteine residues found in the CT subdomain may be palmitoylated. A signal peptide (SP) may also be found at the N terminus of the HA0 polypeptide. FIG. 2, and Tables 4 and 5 provide examples of the amino acid sequences of SP, F'1, F'2, E1, RB, E2 and F domains of some influenza virus subtypes.

Processing of an N-terminal signal peptide (SP) sequence during expression and/or secretion of influenza hemagglutinins may have a role in the folding of the HA. The term "signal peptide" refers generally to a short (about 5-30 amino acids) sequence of amino acids, found generally at the N-terminus of a hemagglutinin polypeptide that may direct translocation of the newly-translated polypeptide to a particular organelle, or aid in positioning of specific domains of the polypeptide chain relative to others. The signal peptide of hemagglutinins target the translocation of the protein into the endoplasmic reticulum and have been proposed to aid in positioning of the N-terminus proximal domain relative to a membrane-anchor domain of the nascent hemagglutinin polypeptide to aid in cleavage and folding of the mature hemagglutinin.

Insertion of HA within the endoplasmic reticulum (ER) membrane of the host cell, signal peptide cleavage and protein glycosylation are co-translational events. Correct folding of HA requires glycosylation of the protein and formation of at least 6 intra-chain disulfide bonds (see FIGS. 46 and 47). In FIG. 46, the HA from subtype A is shown to have 6 conserved disulfide bridges per monomer. By comparison, the monomer of B HA (FIG. 47) has seven disulfide bridges, and five of these disulfide bridges have a counterpart in A (reviewed in Skehel and Wiley, 2000. Ann Rev Biochem. 69:531-569; examples of structures illustrating intra- and intermolecular disulfide bridges and other conserved amino acids and their relative positions are described in, for example, Gamblin et al 2004, Science 303:1838-1842; both of which are incorporated herein by reference). As one of skill in the art would realize, it is important to ensure a similar arrangement of disulfide bridges is obtained when preparing chimeric HAs.

A signal peptide may be native to the hemagglutinin, or a signal peptide may be heterologous with respect to the primary sequence of hemagglutinin being expressed. A chimeric HA may comprise a signal peptide from a first influenza type, subtype or strain with the balance of the HA from one or more than one different influenza type, subtype or strain. For example the native SP of HA subtypes B H1, H2, H3, H5, H6, H7, H9 or influenza type B may be used to express the HA in a plant system. In some embodiments of the invention, the SP may be of an influenza type B, H1, H3 or H5; or of the subtype H1/Bri, H1/NC, H5/Indo, H3/Bri or B/Flo.

A SP may also be non-native, for example, from a structural protein or hemagglutinin of a virus other than influenza, or from a plant, animal or bacterial polypeptide. A non limiting example of a signal peptide that may be used is that of alfalfa protein disulfide isomerase (PDI SP; nucleotides 32-109 of Accession No. Z11499; SEQ ID NO: 57; FIG. 22) encoding the amino acid sequence:

```
                    (SEQ ID NO: 134)
MAKNVAIFGLLFSLLLLVPSQIFAEE
```

The present invention therefore provides for a chimeric influenza hemagglutinin comprising a native, or a non-native signal peptide, and nucleic acids encoding such chimeric hemagglutinins.

Correct folding of the hemagglutinins may be important for stability of the protein, formation of multimers, formation of VLPs and function of the HA (ability to hemagglutinate), among other characteristics of influenza hemagglutinins. Folding of a protein may be influenced by one or more factors, including, but not limited to, the sequence of the protein, the relative abundance of the protein, the degree of intracellular crowding, the availability of cofactors that may bind or be transiently associated with the folded, partially folded or unfolded protein, the presence of one or more chaperone proteins, or the like.

Heat shock proteins (Hsp) or stress proteins are examples of chaperone proteins, which may participate in various cellular processes including protein synthesis, intracellular trafficking, prevention of misfolding, prevention of protein aggregation, assembly and disassembly of protein complexes, protein folding, and protein disaggregation. Examples of such chaperone proteins include, but are not limited to, Hsp60, Hsp65, Hsp 70, Hsp90, Hsp100, Hsp20-30, Hsp10, Hsp100-200, Hsp100, Hsp90, Lon, TF55, FKBPs, cyclophilins, ClpP, GrpE, ubiquitin, calnexin, and protein disulfide isomerases (see, for example, Macario, A. J. L., *Cold Spring Harbor Laboratory Res.* 25:59-70. 1995; Parsell, D. A. & Lindquist, S. *Ann. Rev. Genet.* 27:437-496 (1993); U.S. Pat. No. 5,232,833). As described herein, chaperone proteins, for example but not limited to Hsp40 and Hsp70 may be used to ensure folding of a chimeric HA.

Examples of Hsp70 include Hsp72 and Hsc73 from mammalian cells, DnaK from bacteria, particularly mycobacteria such as *Mycobacterium leprae, Mycobacterium tuberculosis*, and *Mycobacterium bovis* (such as Bacille-Calmette Guerin: referred to herein as Hsp71). DnaK from *Escherichia coli*, yeast and other prokaryotes, and BiP and Grp78 from eukaryotes, such as *A. thaliana* (Lin et al. 2001 (Cell Stress and Chaperones 6:201-208). A particular example of an Hsp70 is *A. thaliana* Hsp70 (encoded by Genbank ref: AY120747.1). Hsp70 is capable of specifically binding ATP as well as unfolded polypeptides and peptides, thereby participating in protein folding and unfolding as well as in the assembly and disassembly of protein complexes.

Examples of Hsp40 include DnaJ from prokaryotes such as *E. coli* and mycobacteria and HSJ1, HDJ1 and Hsp40 from eukaryotes, such as alfalfa (Frugis et al., 1999. Plant Molecular Biology 40:397-408). A particular example of an Hsp40 is *M. sativa* MsJ1 (AJ000995.1 or SEQ ID NO: 76). Hsp40 plays a role as a molecular chaperone in protein folding, thermotolerance and DNA replication, among other cellular activities. FIG. 41 shows the nucleic acid sequence encoding Msj1 (SEQ ID NO: 76).

Among Hsps, Hsp70 and its co-chaperone, Hsp40, are involved in the stabilization of translating and newly synthesized polypeptides before the synthesis is complete. Without wishing to be bound by theory, Hsp40 binds to the hydrophobic patches of unfolded (nascent or newly transferred) polypeptides, thus facilitating the interaction of Hsp70-ATP complex with the polypeptide. ATP hydrolysis leads to the formation of a stable complex between the polypeptide, Hsp70 and ADP, and release of Hsp40. The association of Hsp70-ADP complex with the hydrophobic patches of the polypeptide prevents their interaction with other hydrophobic patches, preventing the incorrect folding and the formation of aggregates with other proteins (reviewed in Hartl, F U. 1996. Nature 381:571-579).

Native chaperone proteins may be able to facilitate correct folding of low levels of recombinant protein, but as the expression levels increase, the abundance of native chaperones may become a limiting factor. High levels of expression of hemagglutinin in the agroinfiltrated leaves may lead to the accumulation of hemagglutinin polypeptides in the cytosol, and co-expression of one or more than one chaperone proteins such as Hsp70, Hsp40 or both Hsp70 and Hsp40 may reduce the level of misfolded or aggregated hemagglutinin polypeptides, and increase the number of polypeptides exhibiting tertiary and quaternary structural characteristics that allow for hemagglutination and/or formation of virus-like particles. SEQ ID NO: 77 is a nucleic acid sequence of a portion of construct number R850, from HindIII (in the multiple cloning site, upstream of the promoter) to EcoRI (immediately downstream of the NOS terminator), encoding HSP40 (underlined). SEQ ID NO: 78 is a nucleic acid sequence of a portion of construct number R860, from HindIII (in the multiple cloning site, upstream of the promoter) to EcoRI (immediately downstream of the NOS terminator), encoding HSP70 (underlined). SEQ ID NO: 79 is a nucleic acid sequence of a portion of construct number R870, from HindIII (in the multiple cloning site, 5 upstream of the promoter) to EcoRI (immediately downstream of the NOS terminator) encoding HSP40 (underlined italic) and HSP70 (underlined).

Therefore, the present invention also provides for a method of producing chimeric influenza VLPs in a plant, wherein a first nucleic acid encoding a chimeric influenza HA is co-expressed with a second nucleic acid encoding a chaperone. The first and second nucleic acids may be introduced to the plant in the same step, or may be introduced to the plant sequentially.

VLPs may be assessed for structure and size by, for example, hemagglutination assay, electron microscopy, or by size exclusion chromatography.

For size exclusion chromatography, total soluble proteins may be extracted from plant tissue by homogenizing (Polytron) sample of frozen-crushed plant material in extraction buffer, and insoluble material removed by centrifugation. Precipitation with PEG may also be of benefit. The soluble protein is quantified, and the extract passed through a Sephacryl™ column. Blue Dextran 2000 may be used as a calibration standard. Following chromatography, fractions may be further analyzed by immunoblot to determine the protein complement of the fraction.

The present invention also provides for a plant comprising a nucleic acid encoding one, or more than one chimeric influenza hemagglutinin and a nucleic acid encoding one or more than one chaperones.

The present invention includes nucleotide sequences:

SEQ ID NO: 63 (construct 690; a chimeric H5/H1 expression cassette comprising alfalfa plastocyanin promoter and 5' UTR, chimeric hemagglutinin coding sequence, alfalfa plastocyanin 3' UTR and terminator sequences) and the underlined portion of SEQ ID NO:63 encoding SP, F1, E1 of H5/Indo-RB of H1/Bri-E2, F2, F, TMD/CT of H5/Indo;

SEQ ID NO: 64 (construct 691; a chimeric H5/H1 expression cassette comprising alfalfa plastocyanin promoter and 5' UTR, chimeric hemagglutinin coding sequence, alfalfa plastocyanin 3' UTR and terminator sequences), and the underlined portion of SEQ ID NO:64, encoding SP, F'1, of H5/Indo-E1, RB. E2 of H1/Bri-F'2, F, TMD/CT of H5/Indo;

SEQ ID NO: 65 (construct 696; a chimeric H1/H5 expression cassette comprising alfalfa plastocyanin promoter and 5' UTR, chimeric hemagglutinin coding sequence, alfalfa plastocyanin 3' UTR and terminator sequences) and the underlined portion of SEQ ID NO:65 encoding PDI SP-F'1, E1 of H1/NC-RB of H5/Indo-E2, F'2, F, TMD/CT of H1/NC;

SEQ ID NO: 68 (construct 733; the SpPDI H1/Bri expression cassette comprising the CaMV 35S promoter, CPMV-HT 5' UTR, coding sequence of the signal peptide from PDI, hemagglutinin coding sequence of H1 form A/Brisbane/59/07 (H1N1), CPMV-HT 3' UTR and NOS terminator sequences), and the underlined portion of SEQ ID NO:68, encoding PDI SP-F'1, E1, RB, E2, F'2, F, TMD/CT of H1/BRI;

SEQ ID NO: 69 (construct 734; a chimeric H5/H1 expression cassette comprising the CaMV 35S promoter, CPMV-HT 5' UTR, chimeric hemagglutinin coding sequence, CPMV-HT 3' UTR and NOS terminator sequences). The coding sequence of chimeric HA is underlined, encoding the same chimeric HA as SEQ ID NO:63;

SEQ ID NO: 71 (construct 736; an HA expression cassette comprising the CaMV 35S promoter, CPMV-HT 5' UTR, coding sequence of the signal peptide from PDI, hemagglutinin coding sequence of H3 form A/Brisbane/10/07 (H2N3), CPMV-HT 3' UTR and NOS terminator sequences), and the underlined portion of SEQ ID NO: 71 encoding PDI SP-F'1, E1, RB, E2, F2, F, TMD/CT of H3/Bri;

SEQ ID NO: 72 (construct 737; a chimeric H5/H3 expression cassette comprising the CaMV 35S promoter, CPMV-HT 5' UTR, chimeric hemagglutinin coding sequence, CPMV-HT 3' UTR and NOS terminator sequences), and the underlined portion of SEQ ID NO:72 encoding PDI SP-F'1, E1, RB, E2, F'2, F, TMD/CT of H5/Indo;

SEQ ID NO: 74 (construct 739; an HA expression cassette comprising the CaMV 35S promoter, CPMV-HT 5' UTR, coding sequence of the signal peptide from PDI, hemagglutinin coding sequence of HA form B/Florida/4/06, CPMV-HT 3' UTR and NOS terminator sequences), and the underlined portion of SEQ ID NO:74 encoding PDI SP-F'1, E1, RB, E2, F'2, F, TMD/CT of B/Flo;

SEQ ID NO: 75 (construct 734; a chimeric H5/B expression cassette comprising the CaMV 35S promoter, CPMV-HT 5' UTR, chimeric hemagglutinin coding sequence, CPMV-HT 3' UTR and NOS terminator sequences), and the underlined portion of SEQ ID NO:75 encoding PDI SP-F'1, E1, RB, E2, F'2, F of B/Flo-TND/CT of H5/Indo.

The present invention also includes a nucleotide sequence that hybridizes under stringent hybridisation conditions to the underlined portions of any one of SEQ ID NOs:63-65, 68, 69, and 71-75. The present invention also includes a nucleotide sequence that hybridizes under stringent hybridisation conditions to a complement of the underlined portions of any one of SEQ ID NOs:63-65, 68, 69, and 71-75. These nucleotide sequences that hybridize to the underlined portions of SEQ ID NOs:63-65, 68, 69, and 71-75, or a complement of the underlined portions of SEQ ID NOs:63-65, 68, 69, and 71-75, encode a chimeric hemagglutinin protein that, when expressed forms a chimeric VLP, and the chimeric VLP induces production of an antibody when administered to a subject. For example, expression of the nucleotide sequence within a plant cell forms a chimeric VLP, and the chimeric VLP may be used to produce an antibody that is capable of binding HA, including mature HA, HA0, HA1 or HA2 of one or more influenza types or subtypes. The chimeric VLP, when administered to a subject, induces an immune response.

Hybridization under stringent hybridization conditions is known in the art (see for example Current Protocols in Molecular Biology, Ausubel et al., eds. 1995 and supplements; Maniatis et al., in Molecular Cloning (A Laboratory Manual), Cold Spring Harbor Laboratory, 1982; Sambrook and Russell, in Molecular Cloning: A Laboratory Manual, $3^{rd}$ edition 2001; each of which is incorporated herein by reference). An example of one such stringent hybridization conditions may be about 16-20 hours hybridization in 4×SSC at 65° C., followed by washing in 0.1×SSC at 65° C. for an hour, or 2 washes in 0.1×SSC at 65° C. each for 20 or 30 minutes. Alternatively, an exemplary stringent hybridization condition could be overnight (16-20 hours) in 50% formamide, 4×SSC at 42° C., followed by washing in 0.1×SSC at 65° C. for an hour, or 2 washes in 0.1×SSC at 65° C. each for 20 or 30 minutes, or overnight (16-20 hours), or hybridization in Church aqueous phosphate buffer (7% SDS; 0.5M $NaPO_4$ buffer pH 7.2; 10 mM EDTA) at 65° C., with 2 washes either at 50° C. in 0.1×SSC, 0.1% SDS for 20 or 30 minutes each, or 2 washes at 65° C. in 2×SSC, 0.1% SDS for 20 or 30 minutes each.

Additionally, the present invention includes nucleotide sequences that are characterized as having about 70, 75, 80, 85, 87, 90, 91, 92, 93 94, 95, 96, 97, 98, 99, 100% or any amount therebetween, sequence identity, or sequence similarity, with the nucleotide sequence encoding chimeric HA according to the underlined portions of any one of SEQ ID NO: 63, SEQ ID NO: 64, SEQ ID NO: 65, SEQ ID NO: 68, SEQ ID NO: 69, SEQ ID NO: 71, SEQ ID NO: 72, SEQ ID NO: 74, SEQ ID NO: 75, wherein the nucleotide sequence encodes a hemagglutinin protein that when expressed forms a chimeric VLP, and that the chimeric VLP induces the production of an antibody. For example, expression of the nucleotide sequence within a plant cell forms a chimeric VLP, and the chimeric VLP may be used to produce an antibody that is capable of binding HA, including mature HA, HA0, HA1, or HA2. The VLP, when administered to a subject, induces an immune response.

An "immune response" generally refers to a response of the adaptive immune system. The adaptive immune system generally comprises a humoral response, and a cell-mediated response. The humoral response is the aspect of immunity that is mediated by secreted antibodies, produced in the cells of the B lymphocyte lineage (B cell). Secreted antibodies bind to antigens on the surfaces of invading microbes (such as viruses or bacteria), which flags them for destruction. Humoral immunity is used generally to refer to antibody production and the processes that accompany it, as well as the effector functions of antibodies, including Th2 cell activation and cytokine production, memory cell generation, opsonin promotion of phagocytosis, pathogen elimination and the like. The terms "modulate" or "modulation" or the like refer to an increase or decrease in a particular response or parameter, as determined by any of several assays generally known or used, some of which are exemplified herein.

A cell-mediated response is an immune response that does not involve antibodies but rather involves the activation of macrophages, natural killer cells (NK), antigen-specific cytotoxic T-lymphocytes, and the release of various cytokines in response to an antigen. Cell-mediated immunity is used generally to refer to some Th cell activation, Tc cell activation and T-cell mediated responses. Cell mediated immunity is of particular importance in responding to viral infections.

For example, the induction of antigen specific CD8 positive T lymphocytes may be measured using an ELISPOT assay; stimulation of CD4 positive T-lymphocytes may be measured using a proliferation assay. Anti-influenza antibody titres may be quantified using an ELISA assay; isotypes of antigen-specific or cross reactive antibodies may also be measured using anti-isotype antibodies (e.g. anti-IgG, IgA, IgE or IgM). Methods and techniques for performing such assays are well-known in the art.

A hemagglutination inhibition (HI, or HAI) assay may also be used to demonstrate the efficacy of antibodies induced by a vaccine, or vaccine composition comprising chimeric HA or chimeric VLP can inhibit the agglutination of red blood cells (RBC) by recombinant HA. Hemagglutination inhibitory antibody titers of serum samples may be evaluated by microtiter HAI (Aymard et al 1973). Erythrocytes from any of several species may be used—e.g. horse, turkey, chicken or the like. This assay gives indirect information on assembly of the HA trimer on the surface of VLP, confirming the proper presentation of antigenic sites on HAs.

Cross-reactivity HAI titres may also be used to demonstrate the efficacy of an immune response to other strains of virus related to the vaccine subtype. For example, serum from a subject immunized with a vaccine composition comprising a chimeric hemagglutinin comprising an HDC of a first influenza type or subtype may be used in an HAI assay with a second strain of whole virus or virus particles, and the HAI titer determined.

Without wishing to be bound by theory, the capacity of HA to bind to RBC from different animals is driven by the affinity of HA for sialic acids bound with α2,3 or α2,6 linkages and the presence of these sialic acids on the surface of RBC. Equine and avian HA from influenza viruses agglutinate erythrocytes from all several species, including turkeys, chickens, ducks, guinea pigs, humans, sheep, horses and cows; whereas human HAs will bind to erythrocytes of turkey, chickens, ducks, guinea pigs, humans and sheep (Ito T. et al, 1997, Virology, 227:493-499; Medeiros R et al, 2001. Virology 289:74-85).

Cytokine presence or levels may also be quantified. For example a T-helper cell response (Th1/Th2) will be characterized by the measurement of IFN-γ and IL-4 secreting cells using by ELISA (e.g. BD Biosciences OptEIA kits). Peripheral blood mononuclear cells (PBMC) or splenocytes obtained from a subject may be cultured, and the supernatant analyzed. T lymphocytes may also be quantified by fluorescence-activated cell sorting (FACS), using marker specific fluorescent labels and methods as are known in the art.

A microneutralization assay may also be conducted to characterize an immune response in a subject, see for example the methods of Rowe et al., 1973. Virus neutralization titers may be obtained several ways, including: 1) enumeration of lysis plaques (plaque assay) following crystal violet fixation/coloration of cells; 2) microscopic observation of cell lysis in culture; 3) ELISA and spectrophotometric detection of NP virus protein (correlate with virus infection of host cells)

Sequence identity or sequence similarity may be determined using a sequence comparison program, such as that provided within DNASIS (for example, using, but not limited to, the following parameters: GAP penalty 5, #of top diagonals 5, fixed GAP penalty 10, k-tuple 2, floating gap 10, and window size 5). However, other methods of alignment of sequences for comparison are well-known in the art for example the algorithms of Smith & Waterman (1981, Adv. Appl. Math. 2:482), Needleman & Wunsch (J. Mol. Biol. 48:443, 1970), Pearson & Lipman (1988, Proc. Nat'l. Acad. Sci. USA 85:2444), and by computerized implementations of these algorithms (e.g. GAP, BESTFIT, FASTA, and BLAST (Altschul et al., 1990. J. Mol Biol 215:403-410), or by manual alignment and visual inspection. Nucleic acid or amino acid sequences may be compared or aligned and consensus sequences may be determined using any of several software packages known in the art, for example MULTALIN (Corpet F., 1988, Nucl. Acids Res., 16 (22), 10881-10890), BLAST, CLUSTAL or the like; alternately sequences may be aligned manually and similarities and differences between the sequences determined.

A fragment or portion of a protein, fusion protein or polypeptide includes a peptide or polypeptide comprising a subset of the amino acid complement of a particular protein or polypeptide, provided that the fragment can form a chimeric VLP when expressed. The fragment may, for example, comprise an antigenic region, a stress-response-inducing region, or a region comprising a functional domain of the protein or polypeptide. The fragment may also comprise a region or domain common to proteins of the same general family, or the fragment may include sufficient amino acid sequence to specifically identify the full-length protein from which it is derived.

For example, a fragment or portion may comprise from about 60% to about 100%, of the length of the full length of the protein, or any amount therebetween, provided that the fragment can form a chimeric VLP when expressed. For example, from about 60% to about 100%, from about 70% to about 100%, from about 80% to about 100%, from about 90% to about 100%, from about 95% to about 100%, of the length of the full length of the protein, or any amount therebetween. Alternately, a fragment or portion may be from about 150 to about 500 amino acids, or any amount therebetween, depending upon the chimeric HA, and provided that the fragment can form a chimeric VLP when expressed. For example, a fragment may be from 150 to about 500 amino acids, or any amount therebetween, from about 200 to about 500 amino acids, or any amount therebetween, from about 250 to about 500 amino acids, or any amount therebetween, from about 300 to about 500 or any amount therebetween, from about 350 to about 500 amino acids, or any amount therebetween, from about 400 to about 500 or any amount therebetween, from about 450 to about 500 or any amount therebetween, depending upon the chimeric HA, and provided that the fragment can form a chimeric VLP when expressed. For example, about 5, 10, 20, 30, 40 or 50 amino acids, or any amount therebetween may be removed from the C terminus, the N terminus or both the N and C terminus of a chimeric HA protein, provided that the fragment can form a chimeric VLP when expressed.

Numbering of amino acids in any given sequence are relative to the particular sequence, however one of skill can readily determine the 'equivalency' of a particular amino acid in a sequence based on structure and/or sequence. For example, if 6 N terminal amino acids were removed, this would change the specific numerical identity of the amino acid (e.g. relative to the full length of the protein), but would not alter the relative position of the amino acid in the structure.

The present invention describes, but is not limited to, expression of a nucleic acid encoding a chimeric HA in a plant portion of a plant, or a plant cell, and the production of chimeric influenza VLPs from the plant, suitable for vaccine production. Examples of such nucleic acids include, for example, but are not limited to, SEQ ID NO: 63, SEQ ID NO: 64, SEQ ID NO: 65, SEQ ID NO: 68, SEQ ID NO: 69, SEQ ID NO: 71, SEQ ID NO: 72, SEQ ID NO: 74, SEQ ID NO: 75.

The present invention further provides expression of a nucleic acid encoding a chimeric HA, for example but not limited to SEQ ID NO: 63, SEQ ID NO: 64, SEQ ID NO: 65, SEQ ID NO: 68, SEQ ID NO: 69, SEQ ID NO: 71, SEQ ID NO: 72, SEQ ID NO: 74, SEQ ID NO: 75 in a plant, a portion of a plant, or a plant cell, and production of influenza vaccine candidates or reagents comprised of recombinant influenza structural proteins that self-assemble into functional and immunogenic homotypic macromolecular protein structures, including subviral influenza particles and chimeric influenza VLP, in transformed plant cells.

Therefore, the invention provides for chimeric VLPs, and a method for producing chimeric VLPs in a plant expression system, from the expression of a single chimeric envelope protein.

The nucleic acid encoding the chimeric HA of influenza subtypes, for example SEQ ID NO: 63, SEQ ID NO: 64, SEQ ID NO: 65, SEQ ID NO: 68, SEQ ID NO: 69, SEQ ID NO: 71, SEQ ID NO: 72, SEQ ID NO: 74, SEQ ID NO: 75 may be synthesized by reverse transcription and polymerase chain reaction (PCR) using HA RNA. As an example, the RNA may be isolated from H1/NC, H1/Bri, H3/Bri, B/Flo or H5/Indo, or from cells infected with these or other influenza virus types or subtypes. For reverse transcription and PCR, oligonucleotide primers specific for the HA RNA may be used. Additionally, a nucleic acid encoding a chimeric HA may be chemically synthesized using methods as would be known to one of skill in the art.

The present invention is further directed to a gene construct comprising a nucleic acid encoding a chimeric HA, as described above, operatively linked to a regulatory element that is operative in a plant. Examples of regulatory elements operative in a plant cell and that may be used in accordance with the present invention include but are not limited to a plastocyanin regulatory region (U.S. Pat. No. 7,125,978; which is incorporated herein by reference), or a regulatory region of Ribulose 1,5-bisphosphate carboxylase/oxygenase (RuBisCO; U.S. Pat. No. 4,962,028; which is incorporated herein by reference), chlorophyll a/b binding protein (CAB; Leutwiler et al; 1986; which is incorporated herein by reference), ST-LS1 (associated with the oxygen-evolving complex of photosystem II and described by Stockhaus et al. 1987, 1989; which is incorporated herein by reference).

The gene construct of the present invention may also comprise a constitutive promoter that directs the expression of a gene that is operatively linked to the promoter throughout the various parts of a plant and continuously throughout plant development. A non-limiting example of a constitutive promoter is that associated with the CaMV 35S transcript (e.g. Odell et al., 1985, *Nature,* 313: 810-812, which is incorporated by reference).

An example of a sequence comprising a plastocyanin regulatory region is the sequence 5' to the underlined sequenced encoding a PDI signal peptide of SEQ ID NO: 58. A regulatory element or regulatory region may enhance translation of a nucleotide sequence to which is it operatively linked, where the nucleotide sequence may encode a protein or polypeptide. Another example of a regulatory region, is that derived from the untranslated regions of the Cowpea Mosaic Virus (CPMV), which may be used to preferentially translate the nucleotide sequence to which it is operatively linked. This CPMV regulatory region is exploited in a hyper-translatable CMPV system (CPMV-HT; see, for example, Sainsbury et al, 2008, Plant Physiology 148: 1212-1218; Sainsbury et al., 2008 Plant Biotechnology Journal 6:82-92; both of which are incorporated herein by reference).

Therefore, an aspect of the invention provides for a nucleic acid comprising a regulatory region operatively linked to a sequence encoding a chimeric influenza HA. The regulatory region may be a plastocyanin regulatory element, and the chimeric influenza HA may comprise subdomains from H5/Indo, H1/Bri, H3/Bri, H1/NC, B/Flo influenza types, subtypes or strains. Nucleic acid sequences comprising a plastocyanin regulatory element and a chimeric influenza HA are exemplified herein by SEQ ID NOs: 63 and 64. Nucleic acid sequences comprising a 35S regulatory element and a chimeric influenza HA are exemplified herein by SEQ ID NOs: 68, 69 and 71-75.

In another aspect, the invention provides for a nucleic acid comprising a CPMV regulatory region and a chimeric influenza HA, comprising subdomains from H5/Indo, H1/Bri, H3/Bri, H1/NC, B/Flo influenza types, subtypes or strains. Nucleic acid sequences comprising a CPMP regulatory element and a chimeric HA are exemplified herein by SEQ ID NOs: 66-69 and 71-75.

Plant-produced chimeric influenza VLPs bud from the plasma membrane and the lipid composition of the chimeric VLPs reflects that of the plant cell or plant tissue type from which they are produced. The VLPs produced according to the present invention comprise chimeric HA of two or more than two types or subtypes of influenza, complexed with plant derived lipids. Plant lipids can stimulate specific immune cells and enhance the immune response induced.

Plant lipids such as PC (phosphatidyl choline) and PE (phosphatidyl ethanolamine), as well as glycosphingolipids can bind to CD1 molecules expressed by mammalian immune cells such as antigen-presenting cells (APCs) like dendritic cells and macrophages and other cells including B and T lymphocytes in the thymus and liver (reviewed in Tsuji M, 2006 Cell Mol Life Sci 63:1889-98). CD1 molecules are structurally similar to major histocompatibility complex (MHC) molecules of class I and their role is to present glycolipid antigens to NKT cells (Natural Killer T cells). Upon activation, NKT cells activate innate immune cells such as NK cells and dendritic cells and also activate adaptive immune cells like the antibody-producing B cells and T-cells.

The phytosterols present in an influenza VLP complexed with a lipid bilayer, such as an plasma-membrane derived envelope may provide for an advantageous vaccine composition. Without wishing to be bound by theory, plant-made VLPs, including those comprising chimeric HA, complexed with a lipid bilayer, such as a plasma-membrane derived envelope, may induce a stronger immune reaction than VLPs made in other expression systems, and may be similar to the immune reaction induced by live or attenuated whole virus vaccines.

Therefore, in some embodiments, the invention provides for a VLP comprising a chimeric HA, complexed with a plant-derived lipid bilayer. In some embodiments the plant-derived lipid bilayer may comprise the envelope of the VLP.

The VLP produced within a plant may include a chimeric HA comprising plant-specific N-glycans. Therefore, this invention also provides for a VLP comprising a chimeric HA having plant specific N-glycans.

Furthermore, modification of N-glycan in plants is known (see for example WO 2008/151440; which is incorporated herein by reference) and chimeric HA having modified N-glycans may be produced. A chimeric HA comprising a modified glycosylation pattern, for example with reduced fucosylated, xylosylated, or both, fucosylated and xylosylated, N-glycans may be obtained, or chimeric HA having a modified glycosylation pattern may be obtained, wherein the protein lacks fucosylation, xylosylation, or both, and comprises increased galactosylation. Furthermore, modulation of post-translational modifications, for example, the addition of terminal galactose may result in a reduction of fucosylation and xylosylation of the expressed chimeric HA when compared to a wild-type plant expressing chimeric HA.

For example, which is not to be considered limiting, the synthesis of chimeric HA having a modified glycosylation pattern may be achieved by co-expressing the protein of interest along with a nucleotide sequence encoding beta-1, 4galactosyltransferase (GalT), for example, but not limited to mammalian GalT, or human GalT however GalT from another sources may also be used. The catalytic domain of GalT may also be fused to a CTS domain (i.e. the cytoplasmic tail, transmembrane domain, stem region) of N-acetylglucosaminyl transferase (GNT1), to produce a GNT1-GalT hybrid enzyme, and the hybrid enzyme may be co-expressed with HA. The HA may also be co-expressed along with a nucleotide sequence encoding N-acetylglucosaminyltransferase III (GnT-III), for example but not limited to mammalian GnT-III or human GnT-III, GnT-III from other sources may also be used. Additionally, a GNT1-GnT-III hybrid enzyme, comprising the CTS of GNT1 fused to GnT-III may also be used.

Therefore the present invention also includes VLP's comprising chimeric HA having modified N-glycans.

Without wishing to be bound by theory, the presence of plant N-glycans on a chimeric HA may stimulate the immune response by promoting the binding of HA by antigen presenting cells. Stimulation of the immune response using plant N glycan has been proposed by Saint-Jore-Dupas et al. (Trends Biotechnol 25: 317-23, 2007). Furthermore, the conformation of the VLP may be advantageous for the presentation of the antigen, and enhance the adjuvant effect of VLP when complexed with a plant derived lipid layer.

By "regulatory region", "regulatory element" or "promoter" it is meant a portion of nucleic acid typically, but not always, upstream of the protein coding region of a gene, which may be comprised of either DNA or RNA, or both DNA and RNA. When a regulatory region is active, and in operative association, or operatively linked, with a gene of interest, this may result in expression of the gene of interest. A regulatory element may be capable of mediating organ specificity, or controlling developmental or temporal gene activation. A "regulatory region" includes promoter elements, core promoter elements exhibiting a basal promoter activity, elements that are inducible in response to an external stimulus, elements that mediate promoter activity such as negative regulatory elements or transcriptional enhancers. "Regulatory region", as used herein, also includes elements that are active following transcription, for example, regulatory elements that modulate gene expression such as translational and transcriptional enhancers, translational and transcriptional repressors, upstream activating sequences, and mRNA instability determinants. Several of these latter elements may be located proximal to the coding region.

In the context of this disclosure, the term "regulatory element" or "regulatory region" typically refers to a sequence of DNA, usually, but not always, upstream (5') to the coding sequence of a structural gene, which controls the expression of the coding region by providing the recognition for RNA polymerase and/or other factors required for transcription to start at a particular site. However, it is to be understood that other nucleotide sequences, located within introns, or 3' of the sequence may also contribute to the regulation of expression of a coding region of interest. An example of a regulatory element that provides for the recognition for RNA polymerase or other transcriptional factors to ensure initiation at a particular site is a promoter element. Most, but not all, eukaryotic promoter elements contain a TATA box, a conserved nucleic acid sequence comprised of adenosine and thymidine nucleotide base pairs usually situated approximately 25 base pairs upstream of a transcriptional start site. A promoter element comprises a basal promoter element, responsible for the initiation of transcription, as well as other regulatory elements (as listed above) that modify gene expression.

There are several types of regulatory regions, including those that are developmentally regulated, inducible or constitutive. A regulatory region that is developmentally regulated, or controls the differential expression of a gene under its control, is activated within certain organs or tissues of an organ at specific times during the development of that organ or tissue. However, some regulatory regions that are developmentally regulated may preferentially be active within certain organs or tissues at specific developmental stages, they may also be active in a developmentally regulated manner, or at a basal level in other organs or tissues within the plant as well. Examples of tissue-specific regulatory regions, for example see-specific a regulatory region, include the napin promoter, and the cruciferin promoter (Rask et al., 1998, J. Plant Physiol. 152: 595-599; Bilodeau et al., 1994, Plant Cell 14: 125-130). An example of a leaf-specific promoter includes the plastocyanin promoter (see, for example SEQ ID NO: 58); U.S. Pat. No. 7,125,978, which is incorporated herein by reference).

An inducible regulatory region is one that is capable of directly or indirectly activating transcription of one or more DNA sequences or genes in response to an inducer. In the absence of an inducer the DNA sequences or genes will not be transcribed. Typically the protein factor that binds specifically to an inducible regulatory region to activate transcription may be present in an inactive form, which is then directly or indirectly converted to the active form by the inducer. However, the protein factor may also be absent. The inducer can be a chemical agent such as a protein, metabolite, growth regulator, herbicide or phenolic compound or a physiological stress imposed directly by heat, cold, salt, or toxic elements or indirectly through the action of a pathogen or disease agent such as a virus. A plant cell containing an inducible regulatory region may be exposed to an inducer by externally applying the inducer to the cell or plant such as by spraying, watering, heating or similar methods. Inducible regulatory elements may be derived from either plant or non-plant genes (e.g. Gatz, C. and Lenk, I. R. P., 1998, Trends Plant Sci. 3, 352-358; which is incorporated by reference). Examples, of potential inducible promoters include, but not limited to, tetracycline-inducible promoter (Gatz, C., 1997, Ann. Rev. Plant Physiol. Plant Mol. Biol. 48, 89-108; which is incorporated by reference), steroid inducible promoter (Aoyama, T. and Chua, N. H., 1997, Plant J. 2, 397-404; which is incorporated by reference) and ethanol-inducible promoter (Salter, M. G., et al, 1998, Plant Journal 16, 127-132; Caddick, M. X., et al, 1998, Nature Biotech. 16, 177-180, which are incorporated by reference) cytokinin inducible IB6 and CKI1 genes (Brandstatter, I. and Kieber, J. J., 1998, Plant Cell 10, 1009-1019; Kakimoto, T., 1996, Science 274, 982-985; which are incorporated by reference) and the auxin inducible element, DR5 (Ulmasov, T., et al., 1997, Plant Cell 9, 1963-1971; which is incorporated by reference).

A constitutive regulatory region directs the expression of a gene throughout the various parts of a plant and continuously throughout plant development. Examples of known constitutive regulatory elements include promoters associated with the CaMV 35S transcript. (Odell et al., 1985, Nature, 313: 810-812), the rice actin 1 (Zhang et al, 1991, Plant Cell, 3: 1155-1165), actin 2 (An et al., 1996, *Plant J.*, 10: 107-121), or tms 2 (U.S. Pat. No. 5,428,147, which is incorporated herein by reference), and triosephosphate isomerase 1 (Xu et. al., 1994, Plant Physiol. 106: 459-467) genes, the maize ubiquitin 1 gene (Cornejo et al, 1993, Plant Mol. Biol. 29: 637-646), the *Arabidopsis* ubiquitin 1 and 6 genes (Holtorf et al, 1995, Plant Mol. Biol. 29: 637-646), and the tobacco translational initiation factor 4A gene (Mandel et al, 1995 Plant Mol. Biol. 29: 995-1004). The term "constitutive" as used herein does not necessarily indicate that a gene under control of the constitutive regulatory region is expressed at the same level in all cell types, but that the gene is expressed in a wide range of cell types even though variation in abundance is often observed. Constitutive regulatory elements may be coupled with other sequences to further enhance the transcription and/or translation of the nucleotide sequence to which they are operatively linked. For example, the CPMV-HT system is derived from the untranslated regions of the Cowpea mosaic virus (CPMV) and demonstrates enhanced translation of the associated coding sequence.

By "native" it is meant that the nucleic acid or amino acid sequence is naturally occurring, or "wild type".

By "operatively linked" it is meant that the particular sequences, for example a regulatory element and a coding region of interest, interact either directly or indirectly to carry out an intended function, such as mediation or modulation of gene expression. The interaction of operatively linked sequences may, for example, be mediated by proteins that interact with the operatively linked sequences.

The one or more than one nucleotide sequence of the present invention may be expressed in any suitable plant host that is transformed by the nucleotide sequence, or constructs, or vectors of the present invention. Examples of suitable hosts include, but are not limited to, agricultural crops including alfalfa, canola, *Brassica* spp., maize, *Nicotiana* spp., alfalfa, potato, ginseng, pea, oat, rice, soybean, wheat, barley, sunflower, cotton and the like.

The one or more chimeric genetic constructs of the present invention can further comprise a 3' untranslated region. A 3' untranslated region refers to that portion of a gene comprising a DNA segment that contains a polyadenylation signal and any other regulatory signals capable of effecting mRNA processing or gene expression. The polyadenylation signal is usually characterized by effecting the addition of polyadenylic acid tracks to the 3' end of the mRNA precursor. Polyadenylation signals are commonly recognized by the presence of homology to the canonical form 5' AATAAA-3' although variations are not uncommon.

Non-limiting examples of suitable 3' regions are the 3' transcribed non-translated regions containing a polyadenylation signal of *Agrobacterium* tumor inducing (Ti) plasmid genes, such as the nopaline synthase (NOS) gene, plant genes such as the soybean storage protein genes, the small subunit of the ribulose-1,5-bisphosphate carboxylase gene (ssRUBISCO; U.S. Pat. No. 4,962,028; which is incorporated herein by reference), the promoter used in regulating plastocyanin expression, described in U.S. Pat. No. 7,125,978 (which is incorporated herein by reference).

One or more of the chimeric genetic constructs of the present invention may also include further enhancers, either translation or transcription enhancers, as may be required. Enhancers may be located 5' or 3' to the sequence being transcribed. Enhancer regions are well known to persons skilled in the art, and may include an ATG initiation codon, adjacent sequences or the like. The initiation codon, if present, may be in phase with the reading frame ("in frame") of the coding sequence to provide for correct translation of the transcribed sequence.

To aid in identification of transformed plant cells, the constructs of this invention may be further manipulated to include plant selectable markers. Useful selectable markers include enzymes that provide for resistance to chemicals such as an antibiotic for example, gentamycin, hygromycin, kanamycin, or herbicides such as phosphinothrycin, glyphosate, chlorosulfuron, and the like. Similarly, enzymes providing for production of a compound identifiable by colour change such as GUS (beta-glucuronidase), or luminescence, such as luciferase or GFP, may be used.

Also considered part of this invention are transgenic plants, plant cells or seeds containing the chimeric gene construct of the present invention. Methods of regenerating whole plants from plant cells are also known in the art. In general, transformed plant cells are cultured in an appropriate medium, which may contain selective agents such as antibiotics, where selectable markers are used to facilitate identification of transformed plant cells. Once callus forms, shoot formation can be encouraged by employing the appropriate plant hormones in accordance with known methods and the shoots transferred to rooting medium for regeneration of plants. The plants may then be used to establish repetitive generations, either from seeds or using vegetative propagation techniques. Transgenic plants can also be generated without using tissue cultures.

Also considered part of this invention are transgenic plants, trees, yeast, bacteria, fungi, insect and animal cells containing the chimeric gene construct comprising a nucleic acid encoding recombinant, chimeric HA or HA0 for VLP production, in accordance with the present invention.

The regulatory elements of the present invention may also be combined with coding region of interest for expression within a range of host organisms that are amenable to transformation, or transient expression. Such organisms include, but are not limited to plants, both monocots and dicots, for example but not limited to corn, cereal plants, wheat, barley, oat, *Nicotiana* spp, *Brassica* spp, soybean, bean, pea, alfalfa, potato, tomato, ginseng, and *Arabidopsis*.

Methods for stable transformation, and regeneration of these organisms are established in the art and known to one of skill in the art. The method of obtaining transformed and regenerated plants is not critical to the present invention.

By "transformation" it is meant the interspecific transfer of genetic information (nucleotide sequence) that is manifested genotypically, phenotypically or both. The interspecific transfer of genetic information from a chimeric construct to a host may be heritable and the transfer of genetic information considered stable, or the transfer may be transient and the transfer of genetic information is not inheritable.

By the term "plant matter", it is meant any material derived from a plant. Plant matter may comprise an entire plant, tissue, cells, or any fraction thereof. Further, plant matter may comprise intracellular plant components, extracellular plant components, liquid or solid extracts of plants, or a combination thereof. Further, plant matter may comprise plants, plant cells, tissue, a liquid extract, or a combination thereof, from plant leaves, stems, fruit, roots or a combination thereof. Plant matter may comprise a plant or portion thereof which has not been subjected to any processing steps. A portion of a plant may comprise plant matter. However, it is also contemplated that the plant material may be subjected to minimal processing steps as defined below, or more rigorous processing, including partial or substantial protein purification using techniques commonly known within the art including, but not limited to chromatography, electrophoresis and the like.

By the term "minimal processing" it is meant plant matter, for example, a plant or portion thereof comprising a protein of interest which is partially purified to yield a plant extract, homogenate, fraction of plant homogenate or the like (i.e. minimally processed). Partial purification may comprise, but is not limited to disrupting plant cellular structures thereby creating a composition comprising soluble plant components, and insoluble plant components which may be separated for example, but not limited to, by centrifugation, filtration or a combination thereof. In this regard, proteins secreted within the extracellular space of leaf or other tissues could be readily obtained using vacuum or centrifugal extraction, or tissues could be extracted under pressure by passage through rollers or grinding or the like to squeeze or liberate the protein free from within the extracellular space. Minimal processing could also involve preparation of crude extracts of soluble proteins, since these preparations would have negligible contamination from secondary plant products. Further, minimal processing may involve aqueous extraction of soluble protein from leaves, followed by precipitation with any suitable salt. Other methods may include large scale maceration and juice extraction in order to permit the direct use of the extract.

The plant matter, in the form of plant material or tissue may be orally delivered to a subject. The plant matter may be administered as part of a dietary supplement, along with other foods, or encapsulated. The plant matter or tissue may also be concentrated to improve or increase palatability, or provided along with other materials, ingredients, or pharmaceutical excipients, as required.

Examples of a subject or target organism that the VLPs of the present invention may be administered to include, but are not limited to, humans, primates, birds, water fowl, migratory birds, quail, duck, geese, poultry, chicken, swine, sheep, equine, horse, camel, canine, dogs, feline, cats, tiger, leopard, civet, mink, stone marten, ferrets, house pets, livestock, rabbits, mice, rats, guinea pigs or other rodents, seal, whale and the like. Such target organisms are exemplary, and are not to be considered limiting to the applications and uses of the present invention.

It is contemplated that a plant comprising the chimeric HA according to some embodiments of the invention, or expressing the VLP comprising the chimeric HA according to some embodiments of the invention, may be administered to a subject or target organism, in a variety of ways depending upon the need and the situation. For example, the chimeric HA obtained from the plant may be extracted prior to its use in either a crude, partially purified, or purified form. If the chimeric HA is to be at least partially purified, then it may be produced in either edible or non-edible plants. Furthermore, if the chimeric HA is orally administered, the plant tissue may be harvested and directly feed to the subject, or the harvested tissue may be dried prior to feeding, or an animal may be permitted to graze on the plant with no prior harvest taking place. It is also considered within the scope of this invention for the harvested plant tissues to be provided as a food supplement within animal feed. If the plant tissue is being feed to an animal with little or not further processing it is preferred that the plant tissue being administered is edible.

Post-transcriptional gene silencing (PTGS) may be involved in limiting expression of transgenes in plants, and co-expression of a suppressor of silencing from the potato virus Y (HcPro) may be used to counteract the specific degradation of transgene mRNAs (Brigneti et al., 1998). Alternate suppressors of silencing are well known in the art and may be used as described herein (Chiba et al., 2006, Virology 346:7-14; which is incorporated herein by reference), for example but not limited to, TEV-p1/HC-Pro (Tobacco etch virus-p1/HC-Pro), BYV-p21, p19 of Tomato bushy stunt virus (TBSV p19), capsid protein of Tomato crinkle virus (TCV-CP), 2b of Cucumber mosaic virus; CMV-2b), p25 of Potato virus X (PVX-p25), p11 of Potato virus M (PVM-p11), p11 of Potato virus S (PVS-p11), p16 of Blueberry scorch virus, (BScV-p16), p23 of Citrus tristeza virus (CTV-p23), p24 of Grapevine leafroll-associated virus-2, (GLRaV-2 p24), p10 of Grapevine virus A, (GVA-p10), p14 of Grapevine virus B (GVB-p14), p10 of Heracleum latent virus (HLV-p10), or p16 of Garlic common latent virus (GCLV-p16). Therefore, a suppressor of silencing, for example, but not limited to, HcPro, TEV-p1/HC-Pro, BYV-p21, TBSV p19, TCV-CP, CMV-2b, PVX-p25, PVM-p11, PVS-p11, BScV-p16, CTV-p23, GLRaV-2 p24, GBV-p14, HLV-p10, GCLV-p16 or GVA-p10, may be co-expressed along with the nucleic acid sequence encoding the protein of interest to further ensure high levels of protein production within a plant.

Furthermore, VLPs produced as described herein do not comprise neuraminidase (NA). However, NA may be co-expressed with HA should VLPs comprising HA and NA be desired.

Therefore, the present invention further includes a suitable vector comprising the chimeric HA sequence suitable for use with either stable or transient expression systems. The genetic information may be also provided within one or more than one construct. For example, a nucleotide sequence encoding a protein of interest may be introduced in one construct, and a second nucleotide sequence encoding a protein that modifies glycosylation of the protein of interest may be introduced using a separate construct. These nucleotide sequences may then be co-expressed within a plant. However, a construct comprising a nucleotide sequence encoding both the protein of interest and the protein that modifies glycosylation profile of the protein of interest may also be used. In this case the nucleotide sequence would comprise a first sequence comprising a first nucleic acid sequence encoding the protein of interest operatively linked to a promoter or regulatory region, and a second sequence comprising a second nucleic acid sequence encoding the protein that modifies the glycosylation profile of the protein of interest, the second sequence operatively linked to a promoter or regulatory region.

By "co-expressed" it is meant that two, or more than two, nucleotide sequences are expressed at about the same time within the plant, and within the same tissue of the plant. However, the nucleotide sequences need not be expressed at exactly the same time. Rather, the two or more nucleotide sequences are expressed in a manner such that the encoded products have a chance to interact. For example, the protein that modifies glycosylation of the protein of interest may be expressed either before or during the period when the protein of interest is expressed so that modification of the glycosylation of the protein of interest takes place. The two or more than two nucleotide sequences can be co-expressed using a transient expression system, where the two or more sequences are introduced within the plant at about the same time under conditions that both sequences are expressed. Alternatively, a platform plant comprising one of the nucleotide sequences, for example the sequence encoding the protein that modifies the glycosylation profile of the protein of interest, may be transformed, either transiently or in a stable manner, with an additional sequence encoding the protein of interest. In this case, the sequence encoding the protein that modifies the glycosylation profile of the protein of interest may be expressed within a desired tissue, during a desired stage of development, or its expression may be induced using an inducible promoter, and the additional sequence encoding the protein of interest may be expressed under similar conditions and in the same tissue, to ensure that the nucleotide sequences are co-expressed.

The constructs of the present invention can be introduced into plant cells using Ti plasmids, Ri plasmids, plant virus vectors, direct DNA transformation, micro-injection, electroporation, infiltration, and the like. For reviews of such techniques see for example Weissbach and Weissbach, *Methods for Plant Molecular Biology*, Academy Press, New York VIII, pp. 421-463 (1988); Geierson and Corey, *Plant Molecular Biology,* 2d Ed. (1988); and Miki and Iyer, Fundamentals of Gene Transfer in Plants. In *Plant Metabolism,* 2d Ed. D T. Dennis, D H Turpin, D D Lefebrve, D B Layzell (eds), Addison-Wesley, Langmans Ltd. London, pp. 561-579 (1997). Other methods include direct DNA uptake, the use of liposomes, electroporation, for example using protoplasts, micro-injection, microprojectiles or whiskers, and vacuum infiltration. See, for example, Bilang, et al. (Gene 100: 247-250 (1991), Scheid et al. (Mol. Gen. Genet. 228: 104-112, 1991), Guerche et al. (Plant Science 52: 111-116, 1987), Neuhause et al. (Theor. Appl Genet. 75: 30-36, 1987), Klein et al., Nature 327: 70-73 (1987); Howell et al. (Science 208: 1265, 1980), Horsch et al. (Science 227: 1229-1231, 1985), DeBlock et al., Plant Physiology 91: 694-701, 1989), Liu and Lomonossoff (J. Virol Meth, 105: 343-348, 2002), U.S. Pat. Nos. 4,945,050; 5,036,006; 5,100,792; 6,403,865; 5,625,136, (all of which are hereby incorporated by reference).

Transient expression methods may be used to express the constructs of the present invention (see Liu and Lomonossoff, 2002, Journal of Virological Methods, 105:343-348; which is incorporated herein by reference). Alternatively, a vacuum-based transient expression method, as described by Kapila et al. 1997 Plant Science 122:101-108 (incorporated herein by reference) may be used. These methods may include, for example, but are not limited to, a method of Agro-inoculation or Agro-infiltration, however, other transient methods may also be used as noted above. With either Agro-inoculation or Agro-infiltration, a mixture of *Agrobacteria* comprising the desired nucleic acid enter the intercellular spaces of a tissue, for example the leaves, aerial portion of the plant (including stem, leaves and flower), other portion of the plant (stem, root, flower), or the whole plant. After crossing the epidermis the *Agrobacterium* infect and transfer t-DNA copies into the cells. The t-DNA is episomally transcribed and the mRNA translated, leading to the production of the protein of interest in infected cells, however, the passage of t-DNA inside the nucleus is transient.

The VLPs comprising chimeric HA provided by the present invention may be used in conjunction with an existing influenza vaccine, to supplement the vaccine, render it more efficacious, or to reduce the administration dosages necessary. As would be known to a person of skill in the art, the vaccine may be directed against one or more than one influenza virus. Examples of suitable vaccines include, but are not limited to, those commercially available from Sanofi-Pasteur, ID Biomedical, Merial, Sinovac, Chiron, Roche, MedImmune, GlaxoSmithKline, Novartis, Sanofi-Aventis, Serono, Shire Pharmaceuticals and the like.

If desired, the VLPs of the present invention may be admixed with a suitable adjuvant as would be known to one of skill in the art. Furthermore, the VLP may be used in a vaccine composition comprising an effective dose of the VLP for the treatment of a target organism, as defined above. Furthermore, the VLP produced according to the present invention may be combined with VLPs obtained using different influenza proteins, for example, neuraminidase (NA).

Therefore, the present invention provides a method for inducing immunity to influenza virus infection in an animal or target organism comprising administering an effective dose of a vaccine comprising one or more than one VLP. The vaccine may be administered orally, intradermally, intranasally, intramuscularly, intraperitoneally, intravenously, or subcutaneously.

Compositions according to various embodiments of the invention may comprise VLPs of two or more influenza strains or subtypes. "Two or more" refers to two, three, four, five, six, seven, eight, nine, 10 or more strains or subtypes. The strains or subtypes represented may be of a single subtype (e.g. all H1N1, or all H5N1), or may be a combination of subtypes. Exemplary subtype and strains include H5/Indo, H1/Bri, H1/NC, H3/Bri, B/Flo. The choice of combination of strains and subtypes may depend on the geographical area of the subjects likely to be exposed to influenza, proximity of animal species to a human population to be immunized (e.g. species of waterfowl, agricultural animals such as swine, etc) and the strains they carry, are exposed to or are likely to be exposed to, predictions of antigenic drift within subtypes or strains, or combinations of these factors. Examples of combinations used in past years are available in the databases maintained by the World Health Organization (WHO) (see URL: who.int/csr/dieease/influenza/vaccine recommendations1/en).

The two or more VLPs may be expressed individually, and the purified or semi-purified VLPs subsequently combined. Alternately, the VLPs may be co-expressed in the same host, for example a plant, portion of plant, or plant cell. The VLPs may be combined or produced in a desired ratio, for example about equivalent ratios, or may be combined in such a manner that one subtype or strain comprises the majority of the VLPs in the composition.

Therefore, the invention provides for compositions comprising VLPs of two or more strains or subtypes.

Also provided is an article of manufacture, comprising packaging material and a composition comprising a VLP comprising a chimeric HA. The composition includes a physiologically or pharmaceutically acceptable excipient, and the packaging material may include a label which indicates the active ingredients of the composition (e.g. the VLP).

A kit comprising a composition comprising a nucleic acid encoding a chimeric HA as provided herein, along with instructions for use of the nucleic acid for production of chimeric HA, or VLPs comprising the chimeric HA is also provided. The kit may be useful for production of VLPs comprising the chimeric HA, and the instructions may include, for example, information on expressing the nucleic acid in a plant or a plant cell, instructions for harvesting and obtaining the VLPs from the plant or plant tissue.

In another embodiment, a kit for the preparation of a medicament, comprising a VLP comprising a chimeric HA, along with instructions for its use is provided. The instructions may comprise a series of steps for the preparation of the medicament, the medicament being useful for inducing a therapeutic or prophylactic immune response in a subject to whom it is administered. The kit may further comprise instructions addressing dose concentrations, dose intervals, preferred administration methods or the like.

The present invention will be further illustrated in the following examples. However it is to be understood that these examples are for illustrative purposes only, and should not be used to limit the scope of the present invention in any manner.

The sequences described herein are summarized below.

| SEQ ID NO: | Description |
|---|---|
| 1 | primer XmaI-pPlas.c |
| 2 | primer SacI-ATG-pPlas.r |
| 3 | primer SacI-PlasTer.c |
| 4 | primer EcoRI-PlasTer.r |
| 5 | primer Plasto-443c |
| 6 | primer SpHA(Ind)-Plasto.r |
| 7 | primer Plasto-SpHA |
| 8 | primer HA(Ind)-Sac.r |
| 9 | primer pBinPlus.2613c |
| 10 | primer Mut-ATG115.r |
| 11 | primer Mut-ATG161.c |
| 12 | primer LC-C5-1.110r |
| 13 | primer E1 H1B-E1 H5I.r |
| 14 | primer E1 H5N-E1 H1B.c |
| 15 | primer E2 H5I-RB H1B.r |
| 16 | primer RB H1B-E2 H5I.c |
| 17 | primer E1 H1B-F'1 H5I.r |
| 18 | primer F'1 H5N-E1 H1B.c |
| 19 | primer F'2 H5I-E2 H1B.r |
| 20 | primer E2 H1B-F'2 H5I.c |
| 21 | primer E1 H5I-E1 H1NC.r |
| 22 | primer E1 H1NC-E1 H5I.c |
| 23 | primer E2 H1NC-RB H5I.r |
| 24 | primer RB H5I-E2 H1NC.c |
| 25 | primer HA-SacI.r |
| 26 | primer ApaI-H1B.c |
| 27 | primer StuI-H1B.r |
| 28 | primer SpPDI-H1B.c |
| 29 | primer SacI-H1B.r |
| 30 | primer ApaI-SpPDI.c |
| 31 | primer ApaI-H5 (A-Indo).1c |
| 32 | primer H5 (A-Indo)-StuI.1707r |
| 33 | primer H3B-SpPDI.r |
| 34 | primer SpPDI-H3B.c |
| 35 | primer StuI-H3B.r |
| 36 | primer TmD H5I-H3B.r |
| 37 | primer H3B-TmD H5I.c |
| 38 | primer HBF-SpPDI.r |
| 39 | primer SpPDI-HBF.c |
| 40 | primer StuI-HBF.r |
| 41 | primer TmD H5I-B Flo.r |
| 42 | primer B Flo-TmD H5I.c |
| 43 | primer Hsp40Luz.1c |
| 44 | primer Hsp40Luz-SacI.1272r |
| 45 | primer Hsp40Luz-Plasto.r |
| 46 | primer Hsp70Ara.1c |
| 47 | primer Hsp70Ara-SacI.1956r |

-continued

| SEQ ID NO: | Description |
|---|---|
| 48 | primer Hsp70Ara-Plasto.r |
| 49 | primer supP19-plasto.r |
| 50 | primer supP19-1c |
| 51 | primer SupP19-SacI.r |
| 52 | nucleic acid sequence of complete H5 (A/Indonesia/5/05 (H5N1)) coding region (including the signal peptide and the stop codon) flanked, in 5' by a HindIII site and, in 3', by a SacI site |
| 53 | nucleic acid seq of construct 660 - an HA expression cassette comprising an alfalfa plastocyanin promoter and 5' UTR, hemagglutinin coding sequence of H5 form A/Indonesia/5/05 (H5N1), alfalfa plastocyanin 3' UTR and terminator sequences |
| 54 | nucleic acid seq of native H1/NC (lacking TMD/CT) |
| 55 | nucleic acid seq of synthetic BglII - PDI SP-H1/NC-SacI/StuI (lacking TMD/CT) |
| 56 | nucleic acid seq of KpnI - H1/NC TmD/CT-SacI/StuI comprising the C-ter H1 (A/New Caledonia/20/99 (H1N1) coding sequence including the TmD and Ctail from the KpnI site to the stop codon (flanked in 3' by a dual SacI/StuI site |
| 57 | nucleic acid seq of protein disulphide isomerase Nucleotides 32-109 encode the PDI signal peptide |
| 58 | nucleic acid seq of plasto promoter-PDI SP-BglI |
| 59 | nucleic acid seq of construct 540 comprising alfalfa plastocyanin promoter and 5' UTR, coding sequence of the signal peptide from PDI and of H1 form A/New Caledonia/20/99 (H1N1), alfalfa plastocyanin 3' UTR and terminator sequences. H1 from A/New Caledonia/20/1999 coding sequence is underlined. |
| 60 | nucleic acid seq of DraI - Plasto promoter-H1/Bri-SacI comprising the complete H1 (A/Brisbane/59/07 (H1N1)) coding region (including the signal peptide and the stop codon) flanked, in 5' by alfalfa plastocyanin gene sequences corresponding to the first 84 nucleotides upstream of the initial ATG, |
| 61 | nucleic acid seq of construct 774 comprising alfalfa plastocyanin promoter and 5' UTR, hemagglutinin coding sequence of H1 form A/Brisbane/59/07 (H1N1), alfalfa plastocyanin 3' UTR and terminator sequences |
| 62 | nucleic acid seq of construct 828, from PacI (upstream of the promoter) to AscI (immediately downstream of the NOS terminator). CPMV HT 3' UTR sequencer underlined with mutated ATG in bold. |
| 63 | nucleic acid seq of construct 690 |
| 64 | nucleic acid seq of construct 691 |
| 65 | nucleic acid seq of construct 696 |
| 66 | nucleic acid seq of construct 732 comprising the CaMV 35S promoter, CPMV-HT 5' UTR, hemagglutinin coding sequence of H1 form A/Brisbane/59/07 (H1N1), CPMV-HT 3' UTR and NOS terminator sequences. Coding sequence of H1/Bri is underlined. |
| 67 | nucleic acid seq of intermediate construct 787 |
| 68 | nucleic acid seq of construct 733 |
| 69 | nucleic acid seq of construct 734 |
| 70 | nucleic acid seq of DraIII-plasto promoter-H3/Bri-SacI comprising the complete H3 (A/Brisbane/10/07 (H3N2)) coding region (including the signal peptide and the stop codon) flanked, in 5' by alfalfa plastocyanin gene sequences corresponding to the first 84 nucleotides upstream of the initial ATG |
| 71 | nucleic acid seq of construct 736 |
| 72 | nucleic acid seq of construct 737 |
| 73 | nucleic acid seq of DraIII-plasto promoter-B/Flo-SacI |
| 74 | nucleic acid seq of construct 739 |
| 75 | nucleic acid seq of construct 745 |
| 76 | nucleic acid seq of Msj1 |
| 77 | nucleic acid seq of construct 850 |
| 78 | nucleic acid seq of construct 860 |
| 79 | nucleic acid seq of construct 870 |
| 80 | Amino acid sequence comprising an RB subdomain of H1/Bri, an H5/Indo signal peptide, and a stem domain complex (SDC) comprising an H5/Indo F'1, E1, E2, F'2 and F subdomains |
| 81 | amino acid sequence comprising H1/Bri head domain complex (HDC) comprsing E1, RB, E2, an H5/Indo signal peptide, and H5/Indo stem domain complex (SDC) comprising H5/Indo F'1, F'2 and F subdomains |
| 82 | amino acid sequence of comprising an RB subdomain of H5/Indo, a PDI signal peptide, and H1/NC stem domain complex comprising F'1, E1, E2 and F'2 |
| 83 | amino acid sequence of comprising a PDI signal peptide, an ectodomain of H3 A/Brisbane/10/2007 and a TMD/CT of H5 A/Indonesia/5/2005 |
| 84 | amino acid sequence comprising an ectodomain of B/Florida/4/2006 and a TMD/CT of H5 A/Indonesia/5/2005 encoded by the open reading frame in construct number 745 |
| 85 | nucleic acid seq of SacI - plastocyanin 3'UTR |
| 86 | nucleotide seq of PDI SP-H1 A/California/04/09 Alfalfa protein disulfide isomerase signal peptide coding sequence is underlined and mature H1 coding sequence is highlighted in bold. |
| 87 | amino acid sequence of PDI SP-H1 A/California/04/09 Alfalfa protein disulfide isomerase signal peptide is underlined |
| 88 | 2X35S promoter. |
| 89 | primer PacI-MCS-2X35S.c |
| 90 | primer CPMV 5'UTR-2X35S.r |
| 91 | primer 2X35S-CPMV 5'UTR.c |
| 92 | primer ApaI-M prot.r |
| 93 | nucleic acid sequence of construct 747. Coding sequence of chimeric HA is underlined. 2X35S promoter sequence is indicated in italics |
| 94 | amino acid sequence of B-Florida |
| 95 | amino acid sequence of B-Malaysia |

-continued

| SEQ ID NO: | Description |
|---|---|
| 96 | amino acid sequence of H1-Brisbane |
| 97 | amino acid sequence of H1-Sol. Isl. |
| 98 | amino acid sequence of H1-New Cal. |
| 99 | amino acid sequence of H2-Singapore |
| 100 | amino acid sequence of H3-Brisbane |
| 101 | amino acid sequence of H3A-WCN |
| 102 | amino acid sequence of H5A-Anhui |
| 103 | amino acid sequence of H5A-Vietnam |
| 104 | amino acid sequence of H5-Indo |

Methods and Materials

1. Assembly of HA Expression Cassettes

A—pCAMBIAPlasto

All manipulations were done using the general molecular biology protocols of Sambrook and Russell (2001; which is incorporated herein by reference). Table 1 presents oligonucleotide primers used for expression cassettes assembly. The first cloning step consisted in assembling a receptor plasmid containing upstream and downstream regulatory elements of the alfalfa plastocyanin gene. The plastocyanin promoter and 5'UTR sequences were amplified from alfalfa genomic DNA using oligonucleotide primers XmaI-pPlas.c (SEQ ID NO:1) and SacI-ATG-pPlas.r (SEQ ID NO:2). The resulting amplification product was digested with XmaI and SacI and ligated into pCAMBIA2300 (Cambia, Canberra, Australia), previously digested with the same enzymes, to create pCAMBIApromoPlasto. Similarly, the 3'UTR sequences and terminator of the plastocyanin gene was amplified from alfalfa genomic DNA using the following primers: SacI-PlasTer.c (SEQ ID NO:3) and EcoRI-PlasTer.r (SEQ ID NO:4), and the product was digested with SacI and EcoRI before being inserted into the same sites of pCAMBIApromoPlasto to create pCAMBIAPlasto.

B—Plasto-Native SP-H5 A/Indonesia/5/05 (Construct Number 660)

A fragment encoding hemagglutinin from influenza strain A/Indonesia/5/05 (H5N1; Acc. No. LANL ISDN125873) was synthesized by Epoch Biolabs (Sugar Land, Tex., USA). The fragment produced, containing the complete H5 coding region including the native signal peptide flanked by a HindIII site immediately upstream of the initial ATG, and a SacI site immediately downstream of the stop (TAA) codon, is presented in (SEQ ID NO:52; FIG. 17). The H5 coding region was cloned into a plastocyanin-based expression cassette by the PCR-based ligation method presented in Darveau et al. (1995). Briefly, a first PCR amplification was obtained using primers Plasto-443c (SEQ ID NO:5) and SpHA(Ind)-Plasto.r (SEQ ID NO:6) and pCAMBIApromoPlasto as template. In parallel, a second amplification was performed with primers Plasto-SpHA (SEQ ID NO:7) and HA(Ind)-Sac.r (SEQ ID NO:8) with H5 coding fragment (SEQ ID NO:52; FIG. 17) as template. The amplification obtained from both reactions were mixed together and the mixture served as template for a third reaction (assembling reaction) using Plasto-443c (SEQ ID NO:5) and HA(Ind)-Sac.r (SEQ ID NO:8) as primers. The resulting fragment was digested with BamHI (in the plastocyanin promoter) and SacI (at the 3'end of the fragment) and cloned into pCAMBIAPlasto previously digested with the same enzymes. The resulting plasmid, named 660, is presented in FIG. 18 (SEQ ID NO:53).

C—Plasto-PDI SP-H1 A/New Caledonia/20/99 (Construct Number 540)

The open reading frame from the H1 gene of influenza strain A/New Caledonia/20/99 (H1N1) was synthesized in two fragments (Plant Biotechnology Institute, National Research Council, Saskatoon, Canada). A first fragment synthesized corresponds to the wild-type H1 coding sequence (GenBank acc. No. AY289929; SEQ ID NO: 54; FIG. 19) lacking the signal peptide coding sequence at the 5' end and the transmembrane domain coding sequence at the 3' end. The 5' end of the fragment is composed of the last nucleotides encoding PDISP (including a BglII restriction site) and a dual SacI/StuI site was added immediately downstream of the stop codon at the 3' terminal end of the fragment, to yield SEQ ID NO: 55 (FIG. 20). A second fragment encoding the C-terminal end of the H1 protein (comprising a transmembrane domain and cytoplasmic tail) from the KpnI site to the stop codon, and flanked in 3' by SacI and StuI restriction sites was also synthesized (SEQ ID NO. 56; FIG. 21).

The first H1 fragment was digested with BglII and SacI and cloned into the same sites of a binary vector (pCAMBIAPlasto) containing the plastocyanin promoter and 5' UTR fused to the signal peptide of alfalfa protein disulfide isomerase (PDI) gene (nucleotides 32-109; Accession No. Z11499; SEQ ID NO: 57; FIG. 22) resulting in a PDI-H1 chimeric gene downstream of the plastocyanin regulatory elements. The sequence of the plastocyanin-based cassette, containing the promoter and PDI signal peptide up to the BglII restriction site and the plastocyanin terminator downstream of a SacI site, is presented in SEQ ID NO. 58 (FIG. 23). The addition of the C-terminal end of the H1 coding region (encoding the transmembrane domain and the cytoplasmic tail) was obtained by inserting the synthesized fragment (SEQ ID NO. 56; FIG. 21) previously digested with KpnI and SacI, into the H1 expression plasmid. The resulting construct, named 540, is presented in SEQ ID NO. 59 (FIG. 24).

D—Plasto-Native SP-H1 A/Brisbane/59/07 (Construct Number 774)

Expression cassette number 774, driving the expression of H1 from A/Brisbane/59/07, was assembled as follows. A synthetic fragment was synthesized comprising the complete hemagglutinin coding sequence (from ATG to stop) flanked in 3' by alfalfa plastocyanin gene sequences corresponding to the first 84 nucleotides upstream of the plastocyanin ATG starting with a DraIII restriction site. The synthetic fragments also comprised a SacI site immediately downstream of the stop codon.

The synthetic fragment was synthesized by Top Gene Technologies (Montreal, QC, Canada). The fragment synthesized is presented in SEQ ID NO. 60 (FIG. 25). For the assembly of the complete expression cassette, the synthetic fragment was digested with DraIII and SacI and cloned into pCAMBIAPlasto previously digested with the same enzymes to give construct 774 (SEQ ID NO. 61; FIG. 26).

E—CPMV HT-LC CM (Construct Number 828)

CPMV-HT expression cassettes use the 35S promoter to control the expression of an mRNA comprising a coding sequence of interest flanked, in 5', by nucleotides 1-512 from the Cowpea mosaic virus (CPMV) RNA2 with mutated ATG at positions 115 and 161, and in 3', by nucleotides 3330-3481 from the CPMV RNA2 (corresponding to the 3' UTR) followed by the NOS terminator. Plasmid pBD-C5-1LC, (Sainsbury et al. 2008; Plant Biotechnology Journal 6: 82-92 and PCT Publication WO 2007/135480), was used for the assembly of CPMV-HT-based hemagglutinin expression cassettes. The mutation of ATGs at position 115 and 161 of the CPMV RNA2 was done using a PCR-based ligation method presented in Darveau et al. (Methods in Neuroscience 26: 77-85 (1995)). Two separate PCRs were performed using pBD-C5-1LC as template. The primers for the first amplification were pBinPlus.2613c (SEQ ID NO: 9) and Mut-ATG115.r (SEQ ID NO: 10). The primers for the second amplification were Mut-ATG161.c (SEQ ID NO: 11) and LC-C5-1.110r (SEQ ID NO: 12). The two fragments obtained were mixed and used as template for a third amplification using pBinPlus.2613c (SEQ ID NO: 9) and LC-C5-1.110r (SEQ ID NO: 12) as primers. The resulting fragment was digested with PacI and ApaI and cloned into pBD-C5-1LC digested with the same enzymes. The construct generated, named 828, is presented in FIG. 27 (SEQ ID NO: 62).

F—H1 A/Brisbane/59/07 Receptor-Binding (RB) Domain in H5 A/Indonesia/5/05 Backbone (Construct Number 690)

A chimeric HA was made by replacing the RB domain in the H5 A/Indonesia/5/05 with that of H1 A/Brisbane/59/07 using the PCR-based ligation method presented in Darveau et al. (Methods in Neuroscience 26: 77-85(1995)). In a first round of PCR, a segment of the plastocyanin promoter fused to the natural signal peptide, the F'1 and E1 domains of the H5 A/Indonesia/5/05 was amplified using primers Plasto-443c (SEQ ID NO: 5) and E1 H1B-E1 H5I.r (SEQ ID NO:13) with construct number 660 (SEQ ID NO:53, FIG. 18) as template. A second fragment, comprising the H1 A/Brisbane/59/07 RB domain coding sequence, was amplified with primers E1 H5N-E1 H1B.c (SEQ ID NO:14) and E2 H5I-RB H1B.r (SEQ ID NO:15) using construct number 774 (SEQ ID NO:61; FIG. 26) as template. A third fragment comprising E2, F'2, F, transmembrane and cytoplasmic domains from H5 A/Indonesia/5/05 was amplified using primers RB H1B-E2 H5I.c (SEQ ID NO:16) and HA(Ind)-SacI.r (SEQ ID NO:8) with construct number 660 (SEQ ID NO: 53; FIG. 18) as template. Amplification products were then mixed and used as template for a second round of amplification (assembling reaction) with primers Plasto-443c (SEQ ID NO:5) and HA(Ind)-SacI.r (SEQ ID NO:8). The resulting fragment was digested with BamHI (in the plastocyanin promoter) and SacI (after the stop codon) and cloned into construct number 660 (SEQ ID NO: 53; FIG. 18), previously digested with the same restriction enzymes to give construct number 690 (SEQ ID NO: 63). The construct is presented in FIG. 28.

G—H1 A/Brisbane/59/07 Esterase and Receptor-Binding Domains (E1-RB-E2) in H5 A/Indonesia/5/05 Backbone (Construct Number 691)

A chimeric HA was assembled by replacing the E1-RB-E2 domains in H5 A/Indonesia/5/05 with those of H1 A/Brisbane/59/07 using the PCR-based ligation method presented in Darveau et al. (Methods in Neuroscience 26: 77-85(1995)). In a first round of PCR, a segment of the plastocyanin promoter fused to the natural signal peptide and the F'1 domain of H5 A/Indonesia/5/05 was amplified using primers Plasto-443c (SEQ ID NO:5) and E1 H1B-F'1 H5I.r (SEQ ID NO: 17) with construct number 660 (SEQ ID NO: 53; FIG. 18) as template. In parallel, two other fragments were amplified. The second fragment, containing the H1 A/Brisbane/59/07 E1-RB-E2 domains coding sequence, was amplified with primers F'1 H5N-E1 H1B.c (SEQ ID NO: 18) and F'2 H5I-E2 H1B.r (SEQ ID NO: 19) using construct number 774 (SEQ ID NO:61; FIG. 26) as template. For the third fragment, F'2, F, transmembrane and cytoplasmic domains from H5 A/Indonesia/5/05 were amplified using primers E2 H1B-F'2 H5I.c (SEQ ID NO: 20) and HA(Ind)-SacI.r (SEQ ID NO: 8) with construct number 660 (SEQ ID NO: 53; FIG. 18) as template. Amplification products were then mixed and used as template for a second round of amplification (assembling reaction) with primers Plasto-443c (SEQ ID NO:5) and HA(Ind)-SacI.r (SEQ ID NO: 8). The resulting fragment was digested with BamHI (in the plastocyanin promoter) and SacI (after the stop codon) and cloned into construct number 660 (SEQ ID NO: 53; FIG. 18), previously digested with the same restriction enzymes to give construct number 691 (SEQ ID NO: 64). The construct is presented in FIG. 29.

H—H5 A/Indonesia/5/05 Receptor-Binding (RB) Domain in H1 A/New Caledonia/20/99 Backbone (Construct Number 696)

A chimeric HA was made by replacing the RB domain in the H1 A/New Caledonia/20/99 with that of H5 A/Indonesia/5/05 using the PCR-based ligation method presented in Darveau et al. (Methods in Neuroscience 26: 77-85(1995)). In a first round of PCR, a segment, of the plastocyanin promoter fused to the signal peptide of alfalfa protein disulfide isomerase (PDISP; Accession No. Z11499; nucleotides 32-109 of SEQ ID NO: 57; FIG. 22), the F'1 and E1 domains of H1 A/New Caledonia/20/99 were amplified using primers Plasto-443c (SEQ ID NO: 5) and E1 H5I-E1 H1NC.r (SEQ ID NO: 21) with construct number 540 (SEQ ID NO: 59; FIG. 24) as template. A second fragment, comprising the H5 A/Indonesia/5/05 RB domain coding sequence, was amplified with primers E1 H1NC-E1 H5I.c (SEQ ID NO: 22) and E2 H1NC-RB H5I.r (SEQ ID NO: 23) using construct number 660 (SEQ ID NO: 53; FIG. 18) as template. A third fragment comprising E2, F'2, F, transmembrane and cytoplasmic domains from H1 A/New Caledonia/20/99 was amplified using primers RB H5I-E2 H1NC.c (SEQ ID NO: 24) and HA-SacI.r (SEQ ID NO: 25) with construct number 540 (SEQ ID NO: 59; FIG. 24) as template. Amplification products were then mixed and used as template for a second round of amplification (assembling reaction) with primers Plasto-443c (SEQ ID NO: 5) and HA-SacI.r (SEQ ID NO: 25). The resulting fragment was digested with BglII and SacI and cloned into construct number 540 (SEQ ID NO: 59; FIG. 24) previously digested with the same restriction enzymes to give construct number 696 (SEQ ID NO: 65). The construct is presented in FIG. 30.

I—Assembly of H1 A/Brisbane/59/2007 in CPMV-HT Expression Cassette (Construct Number 732).

The coding sequence of HA from H1 A/Brisbane/59/2007 was cloned into CPMV-HT as follows. Restriction sites ApaI (immediately upstream of ATG) and StuI (immediately downstream of the stop codon) were added to the hemagglutinin coding sequence by performing a PCR amplification with primers ApaI-H1B.c (SEQ ID NO: 26) and StuI-H1B.r (SEQ ID NO: 27) using construct number 774 (SEQ ID NO: 61; FIG. 26) as template. The resulting fragment was digested with ApaI and StuI restriction enzymes and cloned into construct number 828 (SEQ ID NO: 62; FIG. 27) digested with the same enzymes. Resulting cassette was named construct number 732 (SEQ ID NO: 66; FIG. 31).

J—Assembly of SpPDI-H1 A/Brisbane/59/2007 in CPMV-HT Expression Cassette (Construct Number 733).

A sequence encoding the signal peptide of alfalfa protein disulfide isomerase (PDISP; nucleotides 32-109 of SEQ ID NO: 57 FIG. 22; Accession No. Z11499) was fused to the HA0 coding sequence of H1 from A/Brisbane/59/2007, and the resulting fragment was cloned into CPMV-HT as follows. The H1 coding sequence was amplified with primers SpPDI-H1B.c (SEQ ID NO: 28) and SacI-H1B.r (SEQ ID NO: 29) using construct 774 (SEQ ID NO: 61; FIG. 26) as template. The resulting fragment consisted in the H1 coding sequence flanked, in 5', by the last nucleotides encoding PDISP (including a BglII restriction site) and, in 3', by a SacI restriction site. The fragment was digested with BglII and SacI and cloned into construct number 540 (SEQ ID NO: 59; FIG. 24) previously digested with the same restriction enzymes. The coding sequence of intermediate cassette, named construct number 787 (SEQ ID NO: 67), is presented in FIG. 32. Restriction sites ApaI (immediately upstream ATG) and StuI (immediately downstream stop codon) were added to the hemagglutinin coding sequence by performing a PCR amplification with primers ApaI-SpPDI.c (SEQ ID NO: 30) and StuI-H1B.r (SEQ ID NO: 27) using construct number 787 (SEQ ID NO: 67; FIG. 32) as template. Resulting fragment was digested with ApaI and StuI restriction enzymes and cloned into construct number 828 (SEQ ID NO: 62; FIG. 27) digested with the same enzymes. Resulting cassette was named construct number 733 (SEQ ID NO: 68; FIG. 33).

K—Assembly of H1 A/Brisbane/59/07 Receptor-Binding (RB) Domain in H5 A/Indonesia/5/05 Backbone in CPMV-HT Expression Cassette (Construct Number 734).

The coding sequence of chimeric HA consisting in RB domain from H1 A/Brisbane/59/07 in H5 A/Indonesia/5/05 backbone was cloned into CPMV-HT as follows. Restriction sites ApaI (immediately upstream of ATG) and StuI (immediately downstream of the stop codon) were added to the chimeric hemagglutinin coding sequence by performing a PCR amplification with primers ApaI-H5 (A-Indo).1c (SEQ ID NO: 31) and H5 (A-Indo)-StuI.1707r (SEQ ID NO: 32) using construct number 690 (SEQ ID NO: 63; FIG. 28) as template. Resulting fragment was digested with ApaI and StuI restriction enzymes and cloned into construct number 828 (SEQ ID NO: 62; FIG. 27) digested with the same enzymes. Resulting cassette was named construct number 734 (SEQ ID NO: 69; FIG. 34).

L—Assembly of SpPDI-H3 A/Brisbane/10/2007 in CPMV-HT Expression Cassette (Construct Number 736).

A sequence encoding alfalfa PDI signal peptide fused to HA0 from H3 A/Brisbane/10/2007 was cloned into CPMV-HT as follows. First, a synthetic fragment was synthesized comprising the complete hemagglutinin coding sequence (from ATG to stop) flanked in 3' by alfalfa plastocyanin gene sequence corresponding to the first 84 nucleotides (starting with a DraIII restriction site) upstream of the plastocyanin ATG. The synthetic fragment also comprised a SacI site immediately after the stop codon. Synthetic fragment was synthesized by Top Gene Technologies (Montreal, QC, Canada). The fragment synthesized is presented in SEQ ID NO: 70 (FIG. 35) and was used as template for further PCR-based ligation.

Second, the signal peptide of alfalfa protein disulfide isomerase (PDISP) (nucleotides 32-109; Accession No Z11499; SEQ ID NO: 57; FIG. 22) was linked to the HA0 coding sequence of H3 from A/Brisbane/10/2007 along with ApaI restriction site immediately upstream of ATG and StuI restriction site downstream of the stop codon as follows. PDISP was linked to the H3 coding sequence by the PCR-based ligation method presented in Darveau et al. (Methods in Neuroscience 26: 77-85(1995)). In a first round of PCR, PDISP signal peptide was amplified using primers ApaI-SpPDI.c (SEQ ID NO: 30) and H3B-SpPDI.r (SEQ ID NO: 33) with construct number 540 (SEQ ID NO: 59; FIG. 24) as template. In parallel, another fragment containing a portion of the coding sequence of H3 A/Brisbane/10/2007 (from codon 17 to the stop codon) was amplified with primers SpPDI-H3B.c (SEQ ID NO: 34) and StuI-H3B.r (SEQ ID NO: 35) using previously synthesized fragment (SEQ ID NO. 70; FIG. 35) as template. Amplification products were then mixed and used as template for a second round of amplification (assembling reaction) with primers ApaI-SpPDI.c (SEQ ID NO: 30) and StuI-H3B.r (SEQ ID NO: 35). The resulting fragment was digested with ApaI and StuI restriction enzymes and cloned into construct number 828 (SEQ ID NO: 62; FIG. 27) digested with the same enzymes. Resulting cassette was named construct number 736 (SEQ ID NO: 71; FIG. 36).

M—Assembly of Chimeric SpPDI-H3 A/Brisbane/10/2007 (Ectodomain)+H5 A/Indonesia/5/2005 (TmD+Cyto Tail) in CPMV-HT Expression Cassette (Construct Number 737).

A sequence encoding alfalfa PDI signal peptide fused to the ectodomain of H3 A/Brisbane/10/2007 and to the transmembrane and cytoplasmic domains of H5 A/Indonesia/5/2005 was cloned into CPMV-HT as follows. PDISP-H3 coding sequence was fused to the H5 transmembrane domain by the PCR-based ligation method presented in Darveau et al. (Methods in Neuroscience 26: 77-85(1995)). In a first round of PCR, a fragment comprising PDISP signal peptide and ectodomain from H3 Brisbane was generated by amplification (with ApaI restriction site upstream of the PDISP initial ATG) using primers ApaI-SpPDI.c (SEQ ID NO: 30) and TmD H5I-H3B.r (SEQ ID NO: 36) with construct number 736 (SEQ ID NO: 71; FIG. 36) as template. In parallel, another fragment containing transmembrane and cytoplasmic domains of H5 Indonesia was amplified with primers H3B-TmD H5I.c (SEQ ID NO: 37) and H5 (A-Indo)-StuI.1707r (SEQ ID NO: 32) using construct number 660 (SEQ ID NO. 53; FIG. 18) as template. Amplification products were then mixed and used as template for a second round of amplification (assembling reaction) with primers ApaI-SpPDI.c (SEQ ID NO: 30) and H5 (A-Indo)-StuI.1707r (SEQ ID NO: 32). The resulting fragment was digested with ApaI and StuI restriction enzymes and cloned into construct number 828 (SEQ ID NO: 62; FIG. 27) digested with the same enzymes. Resulting cassette was named construct number 737 (SEQ ID NO: 72; FIG. 37).

N—Assembly of SpPDI-HA B/Florida/4/2006 in CPMV-HT Expression Cassette (Construct Number 739).

A sequence encoding alfalfa PDI signal peptide fused to HA0 from HA B/Florida/4/2006 was cloned into CPMV-HT as follows. First, a synthetic fragment was synthesized comprising the complete hemagglutinin coding sequence (from ATG to stop) flanked in 3' by alfalfa plastocyanin gene sequence corresponding to the first 84 nucleotides (starting with a DraIII restriction site) upstream of the plastocyanin ATG. The synthetic fragment also comprised a SacI restriction site immediately after the stop codon. The synthetic fragment was synthesized by Epoch Biolabs (Sugar Land, Tex., USA). The fragment synthesized is presented in SEQ ID NO: 73 (FIG. 38) and was used as template for further PCR-based ligation.

Second, the signal peptide of alfalfa protein disulfide isomerase (PDISP) (nucleotides 32-109 of SEQ ID NO: 57; FIG. 22; Accession No Z11499) was linked to the HA0 coding sequence of HA from B/Florida/4/2006 along with ApaI restriction site immediately upstream ATG and StuI restriction site downstream stop codon as follows. PDISP was linked to the HA coding sequence by the PCR-based ligation method presented in Darveau et al. (Methods in Neuroscience 26: 77-85(1995)). In a first round of PCR, PDISP signal peptide was amplified using primers ApaI-SpPDI.c (SEQ ID NO: 30) and HBF-SpPDI.r (SEQ ID NO: 38) with construct number 540 (SEQ ID NO: 59; FIG. 24) as template. In parallel, another fragment containing a portion of the coding sequence of HA from B/Florida/4/2006 (from codon 16 to the stop codon) was amplified with primers SpPDI-HBF.c (SEQ ID NO: 39) and StuI-HBF.r (SEQ ID NO: 40) using previously synthesized fragment (SEQ ID NO. 73; FIG. 38) as template. Amplification products were then mixed and used as template for a second round of amplification (assembling reaction) with primers ApaI-SpPDI.c, (SEQ ID NO: 30) and StuI-HBF.r (SEQ ID NO: 40). The resulting fragment was digested with ApaI and StuI restriction enzymes and cloned into construct number 828 (SEQ ID NO: 62; FIG. 27) digested with the same enzymes. Resulting cassette was named construct number 739 (SEQ ID NO: 74; FIG. 39).

O—Assembly of Chimeric SpPDI-HA B/Florida/4/2006 (Ectodomain)+H5 A/Indonesia/5/2005 (TmD+Cyto Tail) in CPMV-HT Expression Cassette (Construct Number 745).

A sequence encoding alfalfa PDI signal peptide fused to the ectodomain from HA B/Florida/4/2006 and to the transmembrane and cytoplasmic domains of H5 A/Indonesia/5/2005 was cloned into CPMV-HT as follows. PDISP-B/Florida/4/2006 ectodomain coding sequence was fused to the H5 transmembrane and cytoplasmic domains by the PCR-based ligation method presented in Darveau et al. (Methods in Neuroscience 26: 77-85(1995)). In a first round of PCR, a fragment comprising PDISP signal peptide fused to the ectodomain from HA B/Florida/4/2006 was generated by amplification using primers ApaI-SpPDI.c (SEQ ID NO: 30) and TmD H5I-B Flo.r (SEQ ID NO: 41) with construct number 739 (SEQ ID NO: 74; FIG. 39) as template. In parallel, another fragment containing H5 Indonesia transmembrane and cytoplasmic domains was amplified with primers B Flo-TmD H5I.c (SEQ ID NO: 42) and H5 (A-Indo)-StuI.1707r (SEQ ID NO: 32) using construct number 660 (SEQ ID NO. 53; FIG. 18) as template. Amplification products were then mixed and used as template for a second round of amplification (assembling reaction) with primers ApaI-SpPDI.c (SEQ ID NO: 30) and H5 (A-Indo)-StuI.1707r (SEQ ID NO: 32). The resulting fragment was digested with ApaI and StuI restriction enzymes and cloned into construct number 828 (SEQ ID NO: 62; FIG. 27) digested with the same enzymes. Resulting cassette was named construct number 745 (SEQ ID NO: 75; FIG. 40).

P—Assembly of Chimeric SpPDI-HA B/Florida/4/2006+H5 A/Indonesia/5/2005 (TmD+Cyto Tail) in 2X35S-CPMV-HT Expression Cassette (Construct Number 747).

A sequence encoding alfalfa PDI signal peptide fused to HA0 from HA B/Florida/4/2006 and to the transmembrane and cytoplasmic domain of H5 A/Indonesia/5/2005 was cloned into 2X35S-CPMV-HT as follows. The promoter switch was performed using the PCR-based ligation method presented in Darveau et al. (Methods in Neuroscience 26: 77-85 (1995)). A first fragment containing 2X35S promoter (SEQ ID NO: 88; FIG. 50A) was amplified by PCR with primers PacI-MCS-2X35S.c (SEQ ID NO: 89) and CPMV 5'UTR-2X35S.r (SEQ ID NO: 90):

```
PacI-MCS-2X35S.c
                                        (SEQ ID NO: 89)
AATTGTTAATTAAGTCGACAAGCTTGCATGCCTGCAGGTCAAC

CPMV 5'UTR-2X35S.r
                                        (SEQ ID NO: 90)
TCAAAACCTATTAAGATTTTAATACCTCTCCAAATGAAATGAACTTCC
```

using a plasmid containing the 2X35S promoter as template. In parallel, a second PCR was performed using primers 2X35S-CPMV 5'UTR.c (SEQ ID NO: 91) and ApaI-M prot.r (SEQ ID NO: 92):

```
2X35S-CPMV 5'UTR.c
                                        (SEQ ID NO: 91)
TTGGAGAGGTATTAAAATCTTAATAGGTTTTGATAAAAGCGAACGTGGG

ApaI-M prot.r
                                        (SEQ ID NO: 92)
TCTCCATGGGCCCGACAAATTTGGGCAGAATATACAGAAGCTTA
```

using construct 745 (SEQ ID NO 75; FIG. 40) as template. The two fragments obtained were then mixed and used as template for a second round of PCR (assembling reaction) with PacI-MCS-2X35S.c (SEQ ID NO:89 and ApaI-M prot.r (SEQ ID NO:92) as primers. Resulting fragment was the digested with PacI and ApaI and cloned into construct 745 (SEQ ID NO 75; FIG. 40) digested with the same restriction enzymes. The sequence of the expression cassette, named construct 747 (SEQ ID NO:93), is presented in FIG. 50B.

2. Assembly of Chaperone Expression Cassettes

Two heat shock protein (Hsp) expression cassettes were assembled. In a first cassette, expression of the *Arabidopsis thaliana* (ecotype Columbia) cytosolic HSP70 (Athsp70-1 in Lin et al. (2001) Cell Stress and Chaperones 6: 201-208) is controlled by a chimeric promoter combining elements of the alfalfa Nitrite reductase (Nir) and alfalfa Plastocyanin promoters (Nir/Plasto). A second cassette comprising the coding region of the alfalfa cytosolic HSP40 (MsJ1; Frugis et al. (1999) Plant Molecular Biology 40: 397-408) under the control of the chimeric Nir/Plasto promoter was also assembled.

An acceptor plasmid containing the alfalfa Nitrite reductase promoter (Nir), the GUS reporter gene and NOS terminator in plant binary vector was first assembled. Plasmid pNir3K51 (previously described in U.S. Pat. No. 6,420,548) was digested with HindIII and EcoRI. The resulting fragment was cloned into pCAMBIA2300 (Cambia, Canberra, Australia) digested by the same restriction enzyme to give pCAMBIA-Nir3K51.

Coding sequences for Hsp70 and Hsp40 were cloned separately in the acceptor plasmid pCAMBIANir3K51 by the PCR-based ligation method presented in Darveau et al. (Methods in Neuroscience 26:77-85 (1995)).

For Hsp40, Msj1 coding sequence (SEQ ID NO: 76; FIG. 41) was amplified by RT-PCR from alfalfa (ecotype Rangelander) leaf total RNA using primers Hsp40Luz.1c (SEQ ID NO: 43) and Hsp40Luz-SacI.1272r (SEQ ID NO: 44). A second amplification was performed with primers Plasto-443c (SEQ ID NO: 5) and Hsp40Luz-Plasto.r (SEQ ID NO: 45) with construct 660 (SEQ ID NO: 53; FIG. 18) as template. PCR products were then mixed and used as template for a third amplification (assembling reaction) with primers Plasto-443c (SEQ ID NO: 5) and Hsp40Luz-SacI.1272r (SEQ ID NO: 44). The resulting fragment was digested with HpaI (in the plastocyanin promoter) and cloned into pCAMBIANir3K51, previously digested with HpaI (in the Nir promoter) and SacI, and filed with T4 DNA polymerase to generate blunt ends. Clones obtained were screened for correct orientation and sequenced for sequence integrity. The resulting plasmid, named R850, is presented in FIG. 42 (SEQ ID NO: 77). The coding region of the Athsp70-1 was amplified by RT-PCR from *Arabidopsis* leaf RNA using primers Hsp70Ara.1c (SEQ ID NO: 46) and Hsp70Ara-SacI.1956r (SEQ ID NO: 47). A second amplification was performed with primers Plato-443c (SEQ ID NO: 5) and Hsp70Ara-Plasto.r (SEQ ID NO: 48) with construct 660 (SEQ ID NO: 53; FIG. 18) as template. PCR products were then mixed and used as template for a third amplification (assembling reaction) with primers Plasto-443c (SEQ ID NO: 5) and Hsp70ARA-SacI.1956r (SEQ ID NO: 47). The resulting fragment was digested with HpaI (in the plastocyanin promoter) and cloned into pCAMBIANir3K51 digested with HpaI (in the Nir promoter) and SacI and filed with T4 DNA polymerase to generate blunt ends. Clones obtained were screened for correct orientation and sequenced for sequence integrity. The resulting plasmid, named R860, is presented in FIG. 43 (SEQ ID NO: 78).

A dual Hsp expression plasmid was assembled as follows. R860 (SEQ ID NO: 78; FIG. 43) was digested with BsrBI (downstream the NOS terminator), treated with T4 DNA polymerase to generate a blunt end, and digested with SbfI (upstream the chimeric NIR/Plasto promoter). The resulting fragment (Chimeric Nir/Plasto promoter-HSP70 coding sequence-Nos terminator) was cloned into R850 (SEQ ID NO: 77; FIG. 42) previously digested with SbfI and SmaI (both located in the multiple cloning site upstream chimeric Nir/Plasto promoter). The resulting plasmid, named R870, is presented in FIG. 44 (SEQ ID NO: 79).

3. Assembly of Other Expression Cassettes

HcPro Expression Cassette

An HcPro construct (35HcPro) was prepared as described in Hamilton et al. (2002). All clones were sequenced to confirm the integrity of the constructs. The plasmids were used to transform *Agrobacteium tumefaciens* (AGL1; ATCC, Manassas, Va. 20108, USA) by electroporation (Mattanovich et al., 1989). The integrity of all *A. tumefaciens* strains were confirmed by restriction mapping.

P19 Expression Cassette

The coding sequence of p19 protein of tomato bushy stunt virus (TBSV) was linked to the alfalfa plastocyanin expression cassette by the PCR-based ligation method presented in Darveau et al. (Methods in Neuroscience 26: 77-85(1995)). In a first round of PCR, a segment of the plastocyanin promoter was amplified using primers Plasto-443c (SEQ ID NO: 5) and supP19-plasto.r (SEQ ID NO: 49) with construct 660 (SEQ ID NO: 53) as template. In parallel, another fragment containing the coding sequence of p19 was amplified with primers supP19-1c (SEQ ID NO: 50) and SupP19-SacI.r (SEQ ID NO: 51) using construct 35S:p19 as described in Voinnet et al. (The Plant Journal 33: 949-956 (2003)) as template. Amplification products were then mixed and used as template for a second round of amplification (assembling reaction) with primers Plasto-443c (SEQ ID NO: 5) and SupP19-SacI.r (SEQ ID NO: 51). The resulting fragment was digested with BamHI (in the plastocyanin promoter) and SacI (at the end of the p19 coding sequence) and cloned into construct number 660 (SEQ ID NO: 53; FIG. 18), previously digested with the same restriction enzymes to give construct number R472. Plasmid R472 is presented in FIG. 45.

Construct Number 443

Construct number 443 corresponds to pCAMBIA2300 (empty vector).

TABLE 1

Oligonucleotide primers used for assembly of expression cassettes.

| SEQ ID | Title | Oligonucleotide sequence (5'---3') |
|---|---|---|
| 1 | XmaI-pPlas.c | AGTTCCCCGGGCTGGTATATTTATATGTTGTC |
| 2 | SacI-ATG-pPlas.r | AATAGAGCTCCATTTTCTCTCAAGATGATTAATTAATTAATTAGTC |
| 3 | SacI-PlasTer.c | AATAGAGCTCGTTAAAATGCTTCTTCGTCTCCTATTTATAATATGG |
| 4 | EcoRI-PlasTer.r | TTACGAATTCTCCTTCCTAATTGGTGTACTATCATTTATCAAAGGGGA |
| 5 | Plasto-443c | GTATTAGTAATTAGAATTTGGTGTC |
| 6 | SpHA(Ind)-Plasto.r | GCAAGAAGAAGCACTATTTTCTCCATTTTCTCTCAAGATGATTA |
| 7 | Plasto-SpHA.c | TTAATCATCTTGAGAGAAAATGGAGAAAATAGTGCTTCTTCTTGC |
| 8 | HA(Ind)-Sac.r | ACTTTGAGCTCTTAAATGCAAATTCTGCATTGTAACGA |
| 9 | pBinPlus.2613c | AGGAAGGGAAGAAAGCGAAAGGAG |
| 10 | Mut-ATG115.r | GTGCCGAAGCACGATCTGACAACGTTGAAGATCGCTCACGCAAGAAAGACAAGAGA |
| 11 | Mut-ATG161.c | GTTGTCAGATCGTGCITCGGCACCAGTACAACGTTTTCTTTCACTGAAGCGA |
| 12 | LC-C5-1.110r | TCTCCTGGAGTCACAGACAGGGTGG |
| 13 | E1 H1B-E1 H5I.r | TCATAGTCAGCGAAATGCCCTGGGTAACAGAGGTCATTGGTTGGATTGGCCT |
| 14 | E1 HSN-E1 H1B.c | ATGACCTCTGTTACCCAGGGCATTTCGCTGACTATGAGGAACTGAGGG |
| 15 | E2 H5I-RB H1B.r | CCAATTCACTTTTCATAATTCCTGATCCAAAGCCTCTACTCAGTGCGA |
| 16 | RB H1B-E2 H5I.c | GGCTTTGGATCAGGAATTATGAAAAGTGAATTGGAATATGGTAACTGCAAC |
| 17 | E1 H1B-F'1 H5I.r | GGCTATTCCTTTTAATAGGCAGAGCTTCCCGTTGTGTGTCTTTTCCAG |

TABLE 1-continued

Oligonucleotide primers used for assembly of expression cassettes.

| SEQ ID | Title | Oligonucleotide sequence (5'---3') |
|---|---|---|
| 18 | F'1 H5N-E1 H1B.c | AACGGGAAGCTCTGCCTATTAAAAGGAATAGCCCCACTACAATTGGG T |
| 19 | F'2 H5I-E2 H1B.r | GGAGTTTGACACTTGGTGTTGCATTTATCCATTGGTGCATTTGAGTTG |
| 20 | E2 H1B-F'2 H5I.c | AATGCACCAATGGATAAATGCAACACCAAGTGTCAAACTCCAATGGG G |
| 21 | E1 H5I-E1 H1NC.r | TCTTCATAGTCGTTGAAACTCCCTGGGTAACATGTTCCATTCTCAGGA |
| 22 | E1 H1NC-E1 H5I.c | CTGAGAATGGAACATGTTACCCAGGGAGTTTCAACGACTATGAAGAA C |
| 23 | E2 H1NC-RB H5I.r | ATTTGAGGTGATGATTGCTGAGTCCCCTTTCTTGACAATTTTGTATGC ATA |
| 24 | RB H5I-E2 H1NC.c | GTCAAGAAAGGGGACTCAGCAATCATCACCTCAAATGCACCAATGGA T |
| 25 | HA-SacI.r | TTAACTTAGAGCTCTTAGATGCATATTCTACACTGCAAAGACC |
| 26 | ApaI-H1B.c | TGTCGGGCCCATGAAAGTAAAACTACTGGTCCTGTTATGCACATT |
| 27 | StuI-H1B.r | AAATAGGCCTTTAGATGCATATTCTACACTGTAAAGACCCATTGGA |
| 28 | SpPDI-H1B.c | TTCTCAGATCTTCGCTGACACAATATGTATAGGCTACCATGCTAACA AC |
| 29 | SacI-H1B.r | CTTAGAGCTCTTAGATGCATATTCTACACTGTAAAGACCCATTGGAA |
| 30 | ApaI-SpPDI.c | TTGTCGGGCCCATGGCGAAAAACGTTGCGATTTTCGGCTTATTGT |
| 31 | Apal-H5 (A-Indo).1c | TGTCGGGCCCATGGAGAAAATAGTGCTTCTTCTTGCAAT |
| 32 | H5 (A-Indo)-StuI.1 707r | AAATAGGCCTTTAAATGCAAATTCTGCATTGTAACGA |
| 33 | H3B-SpPDI.r | TGTCATTTCCGGGAAGTTTTTGAGCGAAGATCTGAGAAGGAACCA |
| 34 | SpPDI-H3B.c | TCTCAGATCTTCGCTCAAAAACTTCCCGGAAATGACAACAGCACG |
| 35 | StuI-H3B.r | AAAATAGGCCTTCAAATGCAAATGTTGCACCTAATGTTGCCTTT |
| 36 | TmD H5I-H3B.r | ATTTGGTAAGTTCCTATTGACTTCAGCTCAACGCCCTTGATCTGG |
| 37 | H3B-TmD H5I.c | TGAGCTGAAGTCAATAGGAACTTACCAAATACTGTCAATTTATTCAA C |
| 38 | HBF-SpPDI.r | GTTATTCCAGTGCAGATTCGATCAGCGAAGATCTGAGAAGGAACCAA CAC |
| 39 | SpPDI-HBF.c | CAGATCTTCGCTGATCGAATCTGCACTGGAATAACATCTTCAAACTC ACC |
| 40 | StuI-HBF.r | AAAATAGGCCTTTATAGACAGATGGAGCATGAAACGTTGTCTCTGG |
| 41 | TmD H5I-B Flo.r | TGACAGTATTTGGTAGTTATCCAATCCATCATCATTTAAAGATGC |
| 42 | B Flo-TmD H5I.c | GGATTGGATAACTACCAAATACTGTCAATTTATTCAACAGTGGCGAG TTC |
| 43 | Hsp-40Luz.1c | ATGTTTGGGCGCGGACCAAC |
| 44 | Hsp40Luz-SacI.1272r | AGCTGAGCTCCTACTGTTGAGCGCATTGCAC |
| 45 | Hsp40Luz-Plasto.r | GTTGGTCCGCGCCCAAACATTTTCTCTCAAGATGAT |
| 46 | Hsp70Ara.1c | ATGTCGGGTAAAGGAGAAGGA |
| 47 | Hsp70Ara-SacI.1956r | AGCTGAGCTCTTAGTCGACCTCCTCGATCTTAG |

TABLE 1-continued

| Oligonucleotide primers used for assembly of expression cassettes. | | |
|---|---|---|
| SEQ ID | Title | Oligonucleotide sequence (5'---3') |
| 48 | Hsp70Ara-Plasto.r | TCCTTCTCCTTTACCCGACATTTTCTCTCAAGATGAT |
| 49 | supP19-plasto.r | CCTTGTATAGCTCGTTCCATTTTCTCTCAAGATG |
| 50 | supP19-1c | ATGGAACGAGCTATACAAGG |
| 51 | SupP19-SacI.r | AGTCGAGCTCTTACTCGCTTTCTTTTTCGAAG |
| 89 | PacI-MCS-2X35S.c | AATTG**TTAATTAA**GTCGACAAGCTTGCATGCCTGCAGGTCAAC |
| 90 | CPMV 5'UTR-2X35S.r | TCAAAACCTATTAAGATTTTAATA**CCTCTCCAAATGAAATGAACTTCC** |
| 91 | 2X35S-CPMV 5'UTR.c | **TTGGAGAGG**TATTAAAATCTTAATAGGTTTTGATAAAAGCGAACGTG(G |
| 92 | ApaI-M prot.r | TCTCCAT**GGGCCC**GACAAATTTGGGCAGAATATACAGAAGCTTA |

TABLE 2

| *Agrobacterium* strains used for expression of influenza hemagglutinins with native or PDI signal peptides | | | |
|---|---|---|---|
| Agro strain | HA expressed | Signal Peptide | Expression Cassette |
| AGL1/540 | H1 (A/New Caledonia/20/99) | PDI | Plastocyanin |
| AGL1/774 | H1 (A/Brisbane/59/2007) | native | Plastocyanin |
| AGL1/787 | H1 (A/Brisbane/59/2007) | PDI | Plastocyanin |
| AGL1/732 | H1 (A/Brisbane/59/2007) | native | 35S/CPMV-HT |
| AGL1/736 | H3 (A/Brisbane/10/2007) | PDI | 35S/CPMV-HT |
| AGL1/660 | H5 (A/Indonesia/5/2005) | native | Plastocyanin |
| AGL1/739 | B (B/Florida/4/2006) | PDI | 35S/CPMV-HT |
| AGLI/828 | CPMV HT-LC C51 | C51LC | 35S/CPMV-HT |
| AGLI/690 | H1/Bris RB + H5/Indo SDC | native | Plasto |
| AGLI/691 | H1/Bri E1-RB-E2 + H5 SDC | native | Plasto |
| AGLI/696 | H5/Indo RB + H1/NC SDC | PDI | Plasto |
| AGLI/733 | H1/Bri | PDI | 35S/CPMV-HT |
| AGLI/734 | H1/Bri RB + H5/Indo SDC | native | 35S/CPMV-HT |
| AGLI/737 | H3/Bri Ectodomain + H5/Indo TDC | PDI | 35S/CPMV-HT |
| AGLI/745 | B/Flo ectodomain_H5/Indo TDC | PDI | 35S/CPMV-HT |
| AGL1/747 | B/Flo ectodomain_H5/Indo TDC | PDI | 2X35S/CPMV-HT |

4. Preparation of Plant Biomass, Inoculum, Agroinfiltration, and Harvesting

*Nicotiana benthamiana* plants were grown from seeds in flats filled with a commercial peat moss substrate. The plants were allowed to grow in the greenhouse under a 16/8 photoperiod and a temperature regime of 25° C. day/20° C. night. Three weeks after seeding, individual plantlets were picked out, transplanted in pots and left to grow in the greenhouse for three additional weeks under the same environmental conditions. Prior to transformation, apical and axillary buds were removed at various times as indicated below, either by pinching the buds from the plant, or by chemically treating the plant

*Agrobacteria* transfected with each construct were grown in a YEB medium supplemented with 10 mM 2-[N-morpholino]ethanesulfonic acid (MES), 20 μM acetosyringone, 50 μg/ml kanamycin and 25 μg/ml of carbenicillin pH5.6 until they reached an $OD_{600}$ between 0.6 and 1.6. *Agrobacterium* suspensions were centrifuged before use and resuspended in infiltration medium (10 mM $MgCl_2$ and 10 mM MES pH 5.6). Syringe-infiltration was performed as described by Liu and Lomonossoff (2002, Journal *of Virological Methods,* 105:343-348). For vacuum-infiltration, *A. tumefaciens* suspensions were centrifuged, resuspended in the infiltration medium and stored overnight at 4° C. On the day of infiltration, culture batches were diluted in 2.5 culture volumes and allowed to warm before use. Whole plants of *N. benthamiana* or *N. tabacum* were placed upside down in the bacterial suspension in an air-tight stainless steel tank under a vacuum of 20-40 Torr for 2-min. Following syringe or vacuum infiltration, plants were returned to the greenhouse for a 4-5 day incubation period until harvest. Unless otherwise specified, all infiltrations were performed as co-infiltration with AGL1/35S-HcPro in a 1:1 ratio, except for CPMV-HT cassette-bearing strains which were co-infiltrated with strain AGL1/R472 in a 1:1 ratio.

5. Leaf Sampling and Total Protein Extraction

Following incubation, the aerial part of plants was harvested, frozen at −80° C., crushed into pieces. Total soluble proteins were extracted by homogenizing (Polytron) each sample of frozen-crushed plant material in 3 volumes of cold 50 mM Tris pH 8, 0.15 M NaCl, 0.04% sodium metabisulfite and 1 mM phenylmethanesulfonyl fluoride. After homogenization, the slurries were centrifuged at 20,000 g for 20 min at 4° C. and these clarified crude extracts (supernatant) kept for analyses. The total protein content of clarified crude extracts was determined by the Bradford assay (Bio-Rad, Hercules, Calif.) using bovine serum albumin as the reference standard.

6. Protein Analysis and Immunoblotting

Protein concentrations were determined by the BCA protein assay (Pierce Biochemicals, Rockport Ill.). Proteins were separated by SDS-PAGE under reducing conditions and stained with Coomassie Blue. Stained gels were scanned and densitometry analysis performed using ImageJ Software (NIH).

Proteins from elution fraction from SEC were precipitated with acetone (Bollag et al., 1996), resuspended in ⅕ volume in equilibration/elution buffer and separated by SDS-PAGE under reducing conditions and electrotransferred onto polyvinylene difluoride (PVDF) membranes (Roche Diagnostics Corporation, Indianapolis, Ind.) for immunodetection. Prior to immunoblotting, the membranes were blocked with 5% skim milk and 0.1% Tween-20 in Tris-buffered saline (TBS-T) for 16-18 h at 4° C.

Immunoblotting was performed by incubation with a suitable antibody (Table 6), in 2 μg/ml in 2% skim milk in TBS-Tween 20 0.1%. Secondary antibodies used for chemiluminescence detection were as indicated in Table 4, diluted as indicated in 2% skim milk in TBS-Tween 20 0.1%. Immunoreactive complexes were detected by chemiluminescence using luminol as the substrate (Roche Diagnostics Corporation). Horseradish peroxidase-enzyme conjugation of human IgG antibody was carried out by using the EZ-Link Plus® Activated Peroxidase conjugation kit (Pierce, Rockford, Ill.). Whole inactivated virus (WIV), used as controls of detection for H1, H3 and B subtypes, were purchased from National Institute for Biological Standards and Control (NIBSC).

TABLE 3

Electrophoresis conditions, antibodies, and dilutions for immunoblotting of expressed proteins.

| HA subtype | Influenza strain | Electrophoresis condition | Primary antibody | Dilution | Secondary antibody | Dilution |
|---|---|---|---|---|---|---|
| H1 | A/Brisbane/59/2007 (H1N1) | Reducing | FII 10-I50 | 4 μg/ml | Goat anti-mouse (JIR 115-035-146) | 1:10 000 |
| H1 | A/New Caledonia/20/99 (H1N1) | Reducing | FII 10-I50 | 4 μg/ml | Goat anti-mouse (JIR 115-035-146) | 1:10 000 |
| H3 | A/Brisbane/10/2007 (H3N2) | Non-Reducing | NIBSC 08/124 | 1:4000 | Rabbit anti-sheep (JIR 313-035-045) | 1:10 000 |
| H5 | A/Indonesia/5/2005 (H5N1) | Reducing | ITC IT-003-005V | 1:4000 | Goat anti-rabbit (JIR 111-035-144) | 1:10 000 |
| B | B/Florida/4/2006 | Non-Reducing | NIBSC 07/356 | 1:2000 | Rabbit anti-sheep (JIR 313-035-045) | 1:10 000 |

FII: Fitzgerald Industries International, Concord, MA, USA;
NIBSC: National Institute for Biological Standards and Control;
JIR: Jackson ImmunoResearch, West Grove, PA, USA;
ITC: Immune Technology Corporation, Woodside, NY, USA;

7. Clarification and Concentration Prior to SEC

To improve resolution and increase signal in elution fractions, extracts to be loaded on size exclusion chromatography, crude protein extracts were clarified and concentrated using the following method. Extracts were centrifuged at 70 000 g, 4° C. for 20 min and the pellet was washed twice by resuspension in 1 volume (compared to the initial extract volume) of extraction buffer (50 mM Tris pH 8, 0.15 M NaCl) and centrifugation at 70 000 g, 4° C. for 20 min. The resulting pellet was resuspended in ⅓ volume (compared to the initial extract volume) and proteins (including VLPs) were precipitated by the addition of 20% (w/v) PEG 3350 followed by incubation on ice for 1 h. Precipitated proteins were recovered by centrifugation at 10 000 g, 4° C., 20 min, and resuspended in 1/15 volume (compared to the initial extract volume) of extraction buffer. After complete resuspension of proteins, a final centrifugation at 20 000 g, 4° C., 5 min was performed to pellet insolubles and the clear supernatant was recovered.

8. Size Exclusion Chromatography of Protein Extract

Size exclusion chromatography (SEC) columns of 32 ml Sephacryl™ S-500 high resolution beads (S-500 HR: GE Healthcare, Uppsala, Sweden, Cat. No. 17-0613-10) were packed and equilibrated with equilibration/elution buffer (50 mM Tris pH8, 150 mM NaCl). One and a half milliliter of crude protein extract was loaded onto the column followed by an elution step with 45 mL of equilibration/elution buffer. The elution was collected in fractions of 1.5 mL relative protein content of eluted fractions was monitored by mixing 10 μL of the fraction with 200 μL of diluted Bio-Rad protein dye reagent (Bio-Rad, Hercules, Calif. The column was washed with 2 column volumes of 0.2N NaOH followed by 10 column volumes of 50 mM Tris pH8, 150 mM NaCl, 20% ethanol. Each separation was followed by a calibration of the column with Blue Dextran 2000 (GE Healthcare Bio-Science Corp., Piscataway, N.J., USA). Elution profiles of Blue Dextran 2000 and host soluble proteins were compared between each separation to ensure uniformity of the elution profiles between the columns used.

Figure 15:
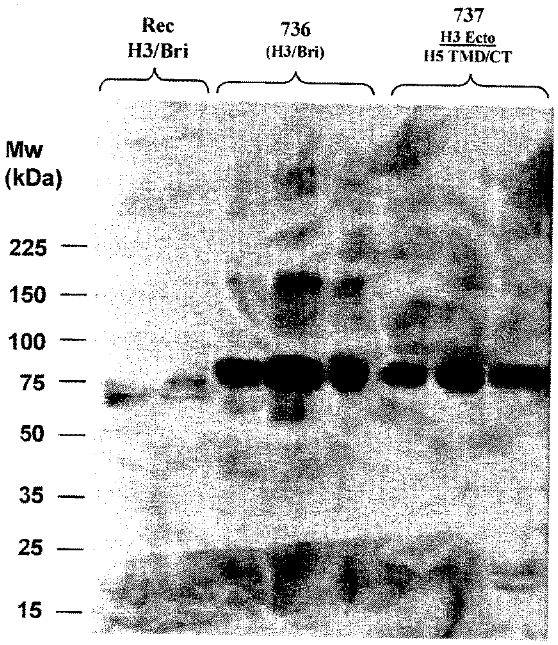
FIG. 15 shows immunoblot analysis of expression of H3/Bri in native form, construct 736 (comprising PDI sp-H3/Bri), or with construct 737 (H3/Bri HDC and SCD fused with an H5/Indo TDC). For each construct, total protein extracts from 3 separate plants were analyzed. Twenty micrograms of protein were loaded for each plant analyzed. The Western blot was revealed with anti-H3 Brisbane polyclonal antibodies (NIBSC 08/124).

Example 1: Domain Swapping Strategy for RB and/or Esterase Domains on Influenza Subtype Stems The RB subdomain of H5/Indo may be replaced by an RB subdomain of H1, H3 or B HA. The resulting chimeric HA provides an SDC H5/Indo to form VLPs and present the RB subdomain comprising immunogenic sites of H1, H3 or B. The H5/Indo RB subdomain may be inserted on an H1 stem (H1/NC). FIGS. 15A and 15B illustrate the amino acid sequences at the fusions of the indicated subdomains, and the amino acid sequences of the respective subdomains is provide in FIG. 2 (constructs 690, 734, 696 and 691) and Tables 4 (constructs 900 and 745) and 5 (constructs 910, 920 and 930). Amino acid sequences illustrated in FIG. 2, and Tables 4 and 5 do not include signal peptide sequences.

TABLE 4

Subdomains and chimeric influenza HA. Chimeric influenza HA comprising heterologous RB subdomain.

| Const No | N-terminal Stem: -F'1 + E1 | RB head | C-terminal stem: E2 + F'2-Stop |
|---|---|---|---|
| 900 (SEQ ID NO: 105) | H5/Indo DQICIGYHANNSTEQ VDTIMEKNVTVTHA QDILEKTHNGKLCDL DGVKPLILRDCSVAG WLLGNPMCDEFINV PEWSYIVEKANPTND LCYP | H3/Brisbane YDVPDYASLRSLVASSGTLEFN NESFNWTGVTQNGTSSACIRRS NNSFFSRLNWLTHLKFKYPALN VTMPNNEKFDKLYIWGVHHPG TDNDQIFLYAQASGRITVSTKRS QQTVIPNIGSRPRVRNIPSRISIY WTIVKPGDILLINSTGNLIAPRGY FKIRSGKSS | H5/Indo IMKSELEYGNCNTKCQTPMGAINSSMPFHNIHPLTIGECPKY VKSNRLVLATGLRNSPQRESRRKKRGLFGAIAGFIEGGWQG MVDGWYGYHHSNEQGSGYAADKESTQKAIDGVTNKVNSII DKMNTQFEAVGREFNNLERRIENLNKKMEDGELDVWTYNA ELLVLMENERTLDFHDSNVKNLYDKVRLQLRDNAKELGNG CFEFYHKCDNECMESIRNGTYNYPQYSEEARLKREEISGVKLE SIGTYQILSIYSTVASSLALAIMMAGLSLWMCSNGSLQCRICI |
| 745 (SEQ ID NO: 106 | H5/Indo DQICIGYHANNSTEQ VDTIMEKNVTVTHA QDILEKTHNGKLCDL DGVKPLILRDCSVAG WLLGNPMCDEFINV PEWSYIVEKANPTND LCYP | B/Florida IMHDRTKIRQLPNLLRGYENIRL STQNVIDAEKAPGGPYRLGTSG SCPNATSKSGFFATMAWAVPK DNNKNATNPLTVEVPYICTEGE DQITVWGFHSDNKTQMKNLYG DSNPQKFTSSANGVTTHYVSQI GSFPDQTEDGGLPQSGRIVVDY MMQKPGKTGTIVYQRGVLLPQ KVWCASGRSK | H5/Indo IMKSELEYGNCNTKCQTPMGAINSSMPFHNIHPLTIGECPKYV KSNRLVLATGLRNSPQRESRRKKRGLFGAIAGFIEGGWQGMV DGWYGYHHSNEQGSGYAADKESTQKAIDGVTNKVNSIIDKM NTQFEAVGREFNNLERRIENLNKKMEDGFLDVWTYNAELLV LMENERTLDFHDSNVKNLYDKVRLQLRDNAKELGNGCFEFY HKCDNECMESIRNGTYNYPQYSEEARLKREEISGVKLESIGTY QILSIYSTVASSLALAIMMAGLSLWMCSNGSLQCRICI |

Amino acids 1-92 of SEQ ID NO: 105 are an F'1+E1 domain of H5/Indo; amino acids 93-259 are the RB head domain of H3/Brisbane; amino acids 260-548 are the E2+F'2 domain of H5/Indo.

Amino acids 1-92 of SEQ ID NO: 106 are an F'1+E1 domain of H5/Indo; amino acids 93-276 are the RB head domain of B/Florida; amino acids 277-565 are the E2+F'2 domain of H5/Indo.

TABLE 5

Subdomains and chimeric influenza HA. Chimeric influenza HA comprising heterologous RB subdomain.

| Construct No. | N-terminal Stem: F'1 | E1-RB-E2 head | C-terminal stem: F'2- Stop |
|---|---|---|---|
| 910 (SEQ ID NO: 107) | H5/Indo DQICIGYHANNSTE QVDTIMEKNVTVT HAQDILEKTHNGK LC | H3/Brisbane DSPHQILDGENCTLIDALLGDPQCDG FQNKKWDLFVERSKAYSNCYPYDV PDYASLRSLVASSGTLEFNNESFNWT GVTQNGTSSACIRRSNNSFFSRLNWL THLKFKYPALNVTMPNNEKFDKLYI WGVHHPGTDNDQIFLYAQASGRITV STKRSQQTVIPNIGSRPRVRNIPSRISI YWTIVKPGDILLINSTGNLIAPRGYFK IRSGKSSIMRSDAPIGK | H5/Indo CNTKCQTPMGAINSSMPFHNIHPLTIGECPKYVKSNRLV LATGLRNSPQRESRRKKRGLFGAIAGFIEGGWQGMVD GWYGYHHSNEQGSGYAADKESTQKAIDGVTNKVNSII DKMNTQFEAVGREFNNLERRIENLNKKMEDGFLDVW TYNAELLVLMENERTLDFHDSNVKNLYDKVRLQLRDN AKELGNGCFEFYHKCDNECMESIRNGTYNYPQYSEEA RLKREEISGVKLESIGTYQILSIYSTVASSLALAIMMAGL SLWMCSNGSLQCRICI |
| 920 (SEQ ID NO: 108 | H5/Indo DQICIGYHANNSTE QVDTIMEKNVTVT HAQDILEKTHNGK LC | B/Florida PDCLNCTDLDVALGRPMCVGTTPSA KASILHEVKPVTSGCFPIMHDRTKIR QLPNLLRGYENIRLSTQNVIDAEKAP GGPYRLGTSGSCPNATSKSGFFATM AWAVPKDNNKNATNPLTVEVPYICT EGEDQITVWGFHSDNKTQMKNLYG DSNPQKFTSSANGVTTHYVSQIGSFP DQTEDGGLPQSGRIVVDYMMQKPG KTGTIVYQRGVLLPQKVWCASGRSK VIKGSLPLIGEAD | H5/Indo CQTPMGAINSSMPFHNIHPLTIGECPKYVKSNRLVLATG LRNSPQRESRRKKRGLFGAIAGFIEGGWQGMVDGWYG YHHSNEQGSGYAADKESTQKAIDGVTNKVNSIIDKMN TQFEAVGREFNNLERRIENLNKKMEDGFLDVWTYNAE LLVLMENERTLDFHDSNVKNLYDKVRLQLRDNAKELG NGCFEFYHKCDNECMESIRNGTYNYPQYSEEARLKREE ISGVKLESIGTYQILSIYSTVASSLALAIMMAGLSLWMC SNGSLQCRICI |
| 930 (SEQ ID NO: 109) | H1/NC DTICIGYHANNSTD TVDTVLEKNVTVT HSVNLLEDSHNGK LC | H5/Indo DLDGVKPLILRDCSVAGWLLGNPMC DEFINVPEWSYIVEKANPTNDLCYPG SFNDYEELKHLLSRINHFEKIQIIPKSS WSDHEASSGVSSACPYLGSPSFFRN VVWLIKKNSTYPTIKKSYNNTNQED LLVLWGIHHPNDAAEQTRLYQNPTT YISIGTSTLNQRLVPKIATRSKVNGQS GRMEFFWTILKPNDAINFESNGNFIA PEYAYKIVKKGDSAIMKSELEYGN | H1/NC CDAKCQTPQGAINSSLPFQNVHPVTIGECPKYVRSAKL RMVTGLRNIPSIQSRGLFGAIAGFIEGGWTGMVDGWYG YHHQNEQGSGYAADQKSTQNAINGITNKVNSVIEKMN TQFTAVGKEFNKLERRMENLNKKVDDGFLDIWTYNAE LLVLLENERTLDFHDSNVKNLYEKVKSQLKNNAKEIGN GCFEFYHKCNNECMESVKNGTYDYPKYSEESKLNREK IDGVKLESMGVYQILAIYSTVASSLVLLVSLGAISFWMC SNGSLQCRICI |

Amino acids 1-42 of SEQ ID NO: 107 are an N terminal F'1 domain of H5/Indo; amino acids 43-228 are the E1-RB-E2 head domain of H3/Brisbane; amino acids 229-507 are the F'2 domain of H5/Indo.

Amino acids 1-42 of SEQ ID NO: 108 are an N terminal F'1 domain of H5/Indo; amino acids 43-281 are the E1-RB-E2 head domain of B/Florida; amino acids 282-556 are the F'2 domain of H5/Indo.

Amino acids 1-42 of SEQ ID NO: 109 are an N terminal F'1 domain of H1/NC; amino acids 43-273 are the E1-RB-E2 head domain of H5/Indo; amino acids 274-548 are the F'2 domain of H1/NC.

The fusion points for the various chimeras were selected so as to be as close to (but not necessarily directly at) the N and C termini of the various subdomains—without wishing to be bound by theory, these fusions were selected so as to maximize the stability of the chimeric HA. For example, structure and sequence conservation is observed at the N-terminus of the RB subdomain (Ha et al. 2002, EMBO J. 21:865-875; which is incorporated herein by reference). A less variable region in the primary sequence is found at the C-F/Y-P triad located at approximately 15 amino acids before, in the E1 subdomain. This cysteine is involved in disulfide bridge #3, which is conserved among HAs (see FIGS. 46 and 47). A junction at this Cys may provide for suitable, or superior, stability to the chimeric HA relative to the native sequence. The C-terminus end of the RB provides conserved features: for example, a conserved Ser residue at position −1 and the E2 subdomain starts with a beta-sheet observed in all HA on the alignment (Ha et al. 2002, EMBO J. 21:865-875; which is incorporated herein by reference). Therefore, the C-terminus of this RB may be fused to the initiating amino acid of this beta sheet structure of the E2 subdomain. Further, the disulfide bridge pattern is not changed, or is not substantively changed, for the chimeras comprising RB subdomains of H1/NC, H1Bri, H3/Bri, or B/Flo on an H5/Indo SDC, and for H5/Indo RB subdomain on H1 SDC (total of 6), but a disulfide bridge will be added (bridge #8) on the hybrid HA of B RB on H5 stem. This addition of disulfide bridge should not interfere with the folding of the HA (because it is located within the RB domain and the Cys are adjacent on the sequence), and may be produce a even more stable hybrid HA.

The E1-RB-E2 subdomains of a first influenza type were replaced by E1-RB-E2 subdomains of a second influenza type. Such an arrangement may present a greater number of amino acids of the second type at the surface of the H5-VLP. In this example, the HDC of H1, H3 or B was placed on an H5/Indo SDC, and an HDC of H5/Indo on an H1/NC SDC (Table 5).

The junction of the HDC was defined with a conserved cysteine residue (comprising disulfide bridge #6 of HA type A and #7 in HA type B). The junction of the HDC at the C-terminus of the E2 subdomain was defined with another conserved cysteine residue comprising disulfide bridge #6 (the second amino acid of the F'2 subdomain) of influenza type H1 or H3 on an SDC of H5/Indo or for influenza type H5 on an SDC of H1. For the influenza B chimera, the junction was established the connection at the first Cysteine comprising of disulfide bridge #4 (located 4 amino acids away on the F'2 subdomain, and conserved among the HAs). The resulting chimeras do not exhibit any alteration in disulfide bridge patterns—the H1/H3/H5 hybrid HAs will contain 6 disulfide bridges and the B hybrid will have 7 of them.

Example 2: Replacement of Receptor B Binding (RB) or Receptor Binding and Esterase (E1-RB-E2) Subdomains of H5 A/Indonesia/5/05 with that of H1 A/Brisbane/59/2007: Comparison of Expression for Chimeric and Native Forms To combine the high accumulation level of VLPs from H5 A/Indonesia/5/05 with the antigenicity characteristics of H1 A/Brisbane/59/2007, chimeric hemagglutinins were designed comprising domains from H1 A/Brisbane/59/2007 fused to an H5 A/Indonesia/5/05 stem domain cluster. Expression cassettes for the expression of the H5/H1 hemagglutinin fusions are represented in FIG. 1 and amino acid sequences of the mature fusion proteins produced illustrated in FIG. 2.

Figures 1, 1C, 2, 3:
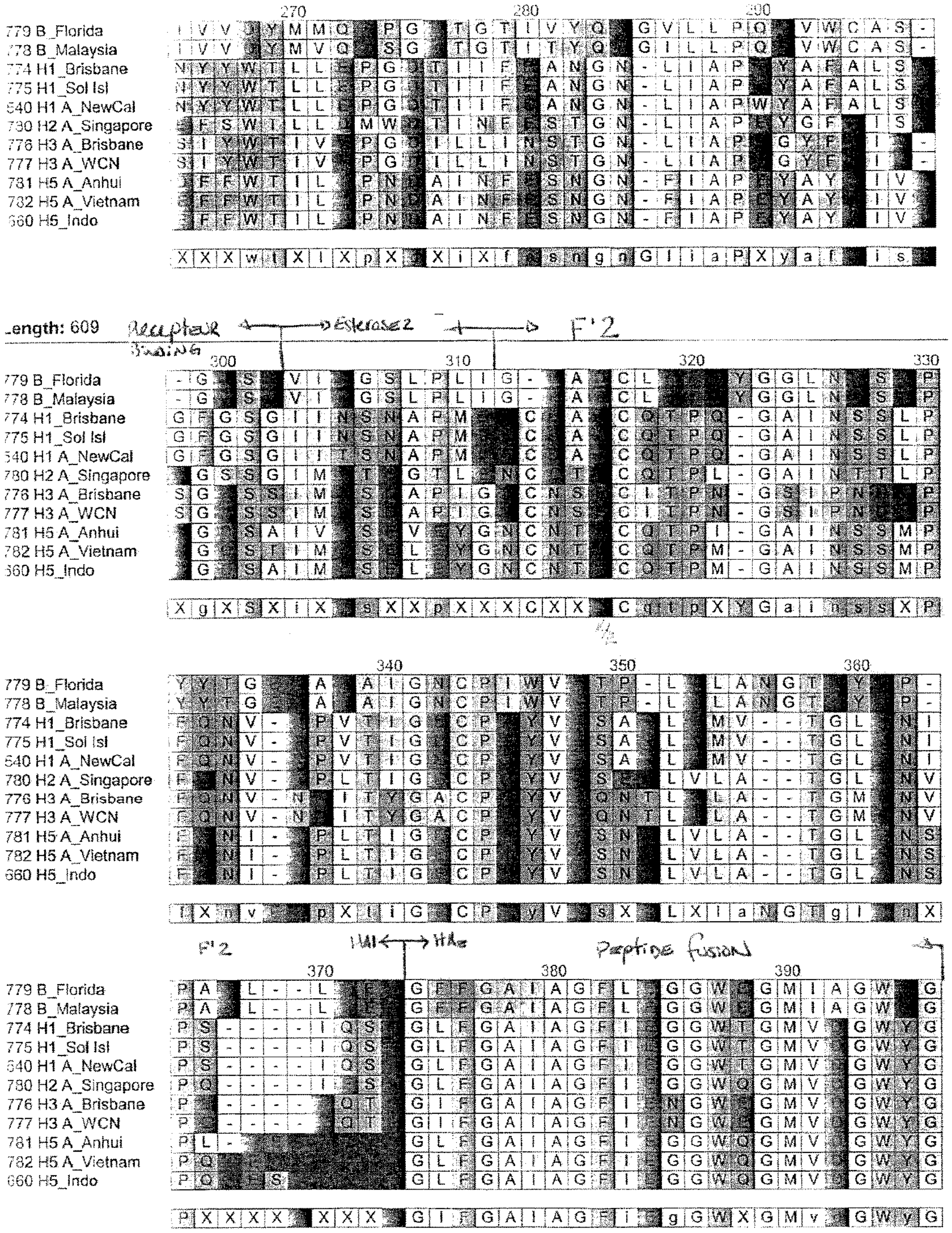
FIG. 3 shows the amino acid sequence of the coding region of constructs 690 and 734 (SEQ. ID. NO. 80) comprising an RB subdomain of H1/Bri, an H5/Indo signal peptide, and a stem domain complex (SDC) comprising an H5/Indo F'1, E1, E2, F'2 and F subdomains.
Figures 1, 1C, 2, 3, 4:
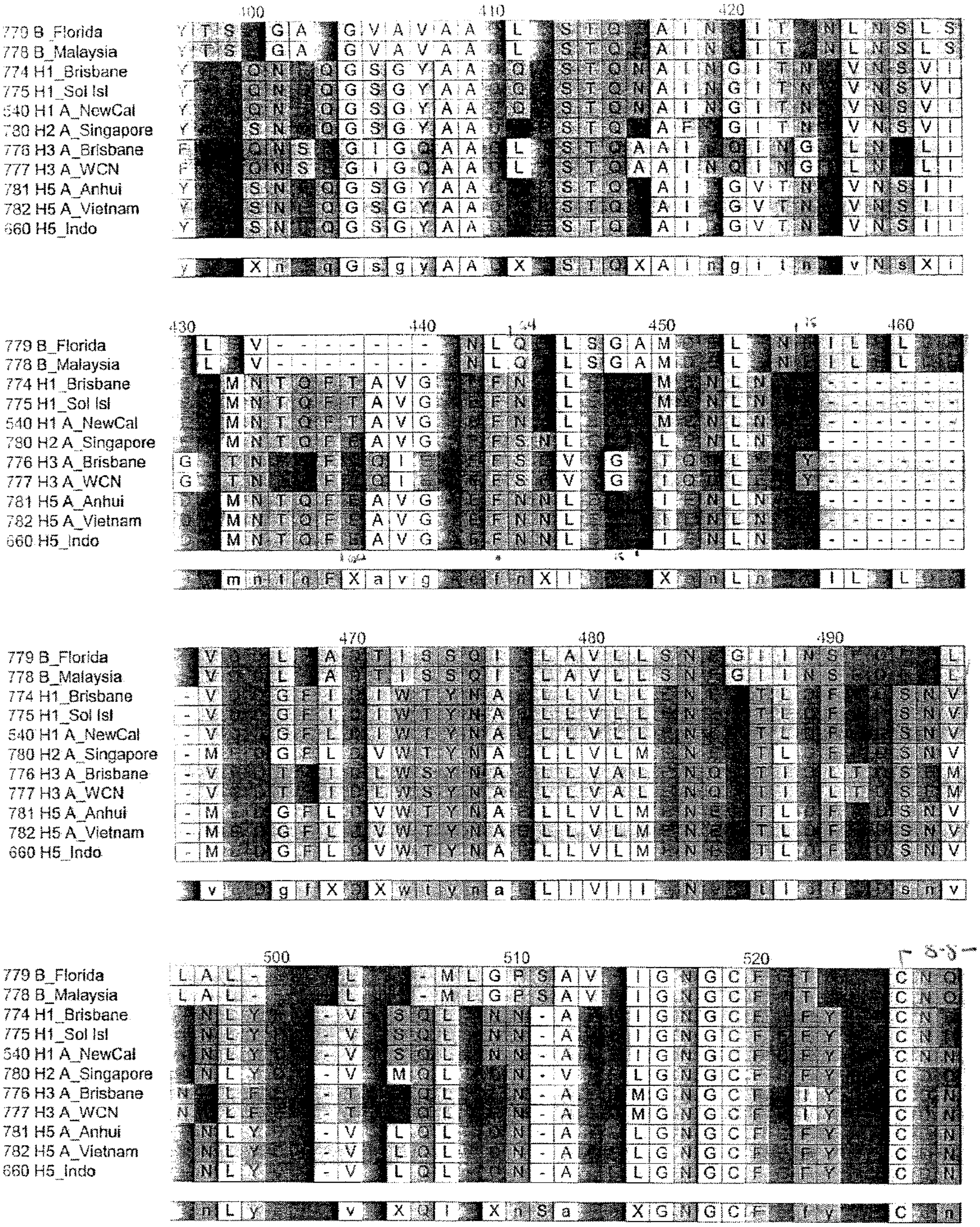
FIG. 4 shows the amino acid sequence of the coding region of construct 691 (SEQ. ID. NO. 81) comprising H1/Bri head domain complex (HDC) comprising E1, RB, E2, an H5/Indo signal peptide, and H5/Indo stem domain complex (SDC) comprising H5/Indo F'1, F'2 and F subdomains.
Figures 1, 1C, 2, 3, 4, 5:
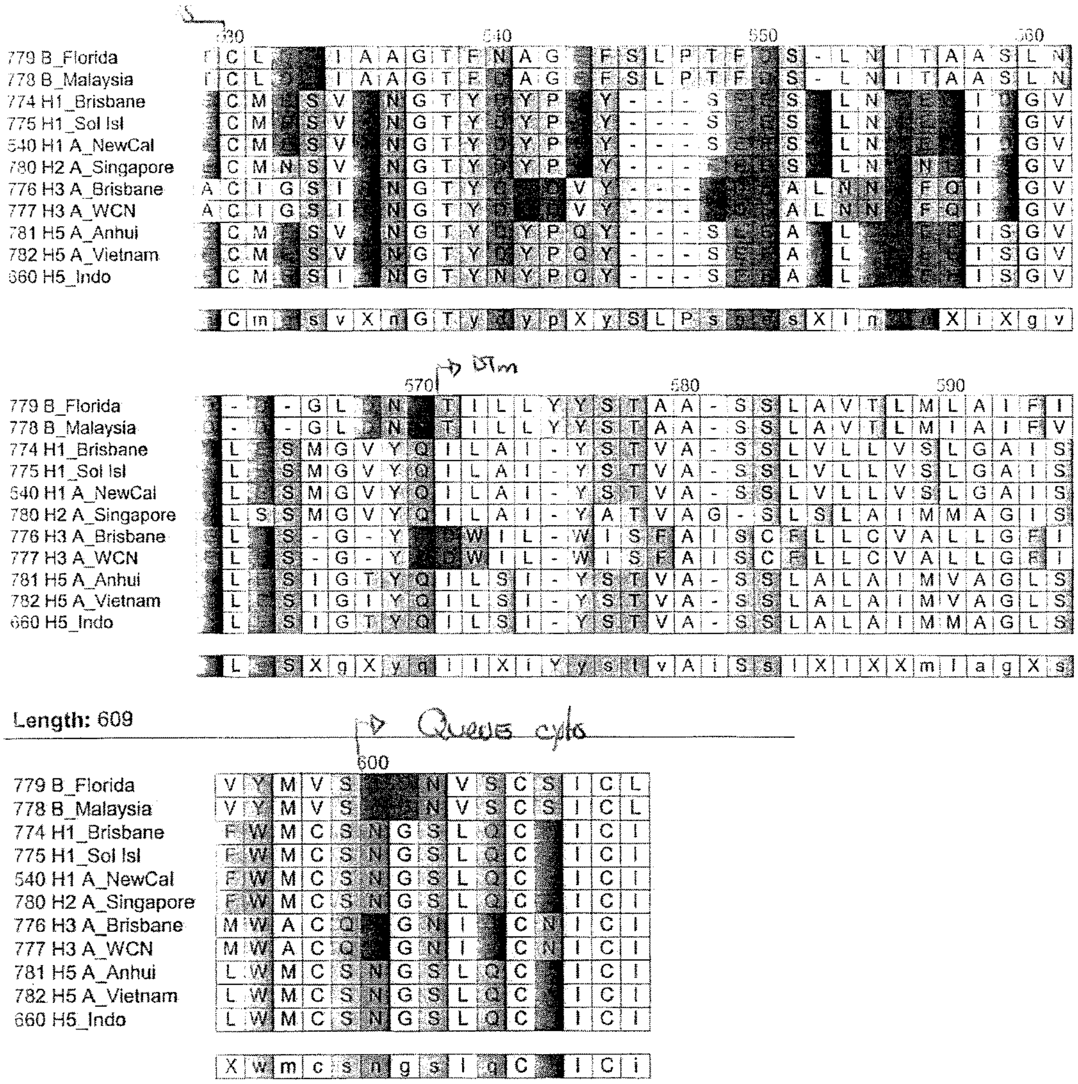
FIG. 5 shows the amino acid sequence of the coding region of construct 696 (SEQ. ID. NO. 82) comprising an RB subdomain of H5/Indo, a PDI signal peptide, and H1/NC stem domain complex comprising F'1, E1, E2 and F'2.

To compare the accumulation level of H5/H1 chimeric hemagglutinins with that of their native forms, *Nicotiana benthamiana* plants were infiltrated with AGL1/774, AGL1/691 and AGL1/690, and the leaves were harvested after a six-day incubation period. To determine the accumulation level of each HA form in the agroinfiltrated leaves, proteins were extracted from infiltrated leaf tissue and analyzed by Western blotting using anti-HA monoclonal antibodies. A unique band of approximately 75 kDa (FIG. 3), corresponding in size to the uncleaved HA0 form of influenza hemagglutinin, was detected in extracts from leaves infiltrated with AGL1/690 but not in AGL1/774 or AGL1/691, indicating that the chimeric hemagglutinin comprising the receptor-binding region of H1 A/Brisbane/59/2007 fused to the H5 A/Indonesia/5/05 backbone accumulated to higher level than both the native form of H1 A/Brisbane/59/2007 (AGL1/774) and the chimeric hemagglutinin combining the esterase and receptor-binding regions of H1 A/Brisbane/59/2007 with the H5 A/Indonesia/5/05 backbone. The whole inactivated virus (WIV) (H1 A/Brisbane/59/2007) used as a positive control was detected as multiple bands with a major band at approximately 80 kDa, corresponding to the molecular weight of the precursor HA0 of H1 A/Brisbane/59/2007. These results demonstrated that the replacement of the receptor-binding region from H5 A/Indonesia/5/05 with that of H1 A/Brisbane/59/2007 generated a chimeric hemagglutinin which presented the antigenic region of H1 and which accumulated at higher level than the native H1 A/Brisbane/59/2007 in plants. However, the chimeric hemagglutinin in which the esterase and receptor-binding regions from H5 A/Indonesia/5/05 were replaced by those of H1 A/Brisbane/59/2007 did not accumulate to a detectable level in the plants.

Figure 8:
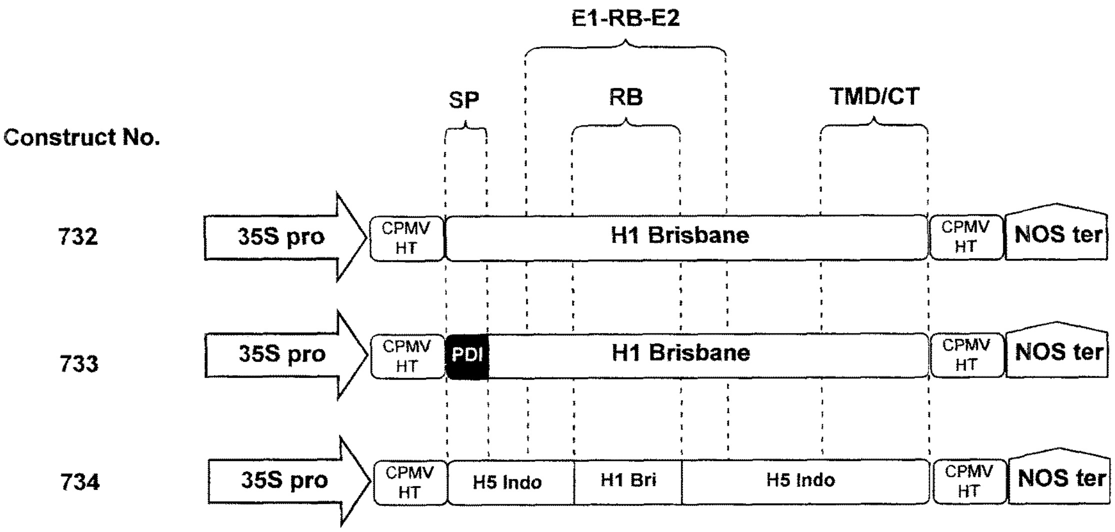
FIG. 8 shows a schematic representation of 35SCPMV/HT-based expression cassettes for the expression of H1/Bri in native (construct 732) and chimeric (constructs 733 and 734) forms. Construct 733, comprising PDI signal peptide and HDC, SDC and transmembrane domain complex (TDC) of H1/Bri, and construct 734 comprising an H5/Indo signal peptide, E1, E2, F'2, F, and an RB from H1/Bri. 35S pro: CaMV 35S promoter, NOS ter: nopaline synthase terminator, SP: signal peptide, RB: receptor-binding subdomain, E1-RB-E2: esterase and receptor-binding subdomains, TMD/CT: transmembrane and cytoplasmic tail subdomains, PDI: alfalfa protein disulfide isomerase; CPMV-HT: 5' and 3' elements of the hyper translatable Cowpea Mosaic Virus expression system.
Figure 9:
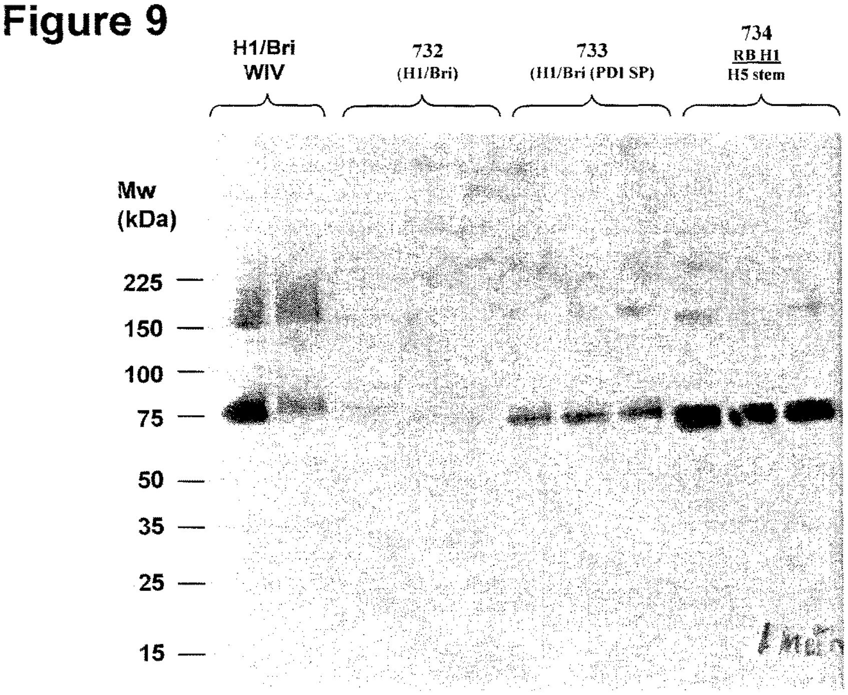
FIG. 9 shows immunoblot analysis of expression of H1/Bri in native form, construct 732 (comprising H1/Bri under the control of the 35SCPMV/HT-based expression cassette), construct 733 (comprising a PDI signal peptide fused with H1/Bri; under the control of the 35SCPMV/HT-based expression cassette), or construct 734 comprising an H1/Bri RB subdomain fused with an H5/Indo SDC, E1 and E2 subdomains; under the control of the 35SCPMV/HT-based expression cassette). For each construct, total protein extracts from 3 separate plants were analyzed. Five micrograms of protein were loaded for each plant analyzed. The Western blot was revealed with anti-HA monoclonal antibodies (FII 10-I50).

The fusion of the receptor-binding region from H1 A/Brisbane/59/2007 to the H5 A/Indonesia/5/05 backbone as a method of increasing accumulation of H1 antigen-presenting VLPs in plants was re-evaluated under the control of a strong CPMV-HT-based expression cassette. This fusion strategy was also compared to signal peptide replacement as mean of increasing accumulation level. Expression cassettes for the expression of the H5/H1 hemagglutinin fusions under CPMV-HT are represented in FIG. 8 and amino acid sequence of the mature fusion protein produced is presented in FIG. 2.

Figure 6:
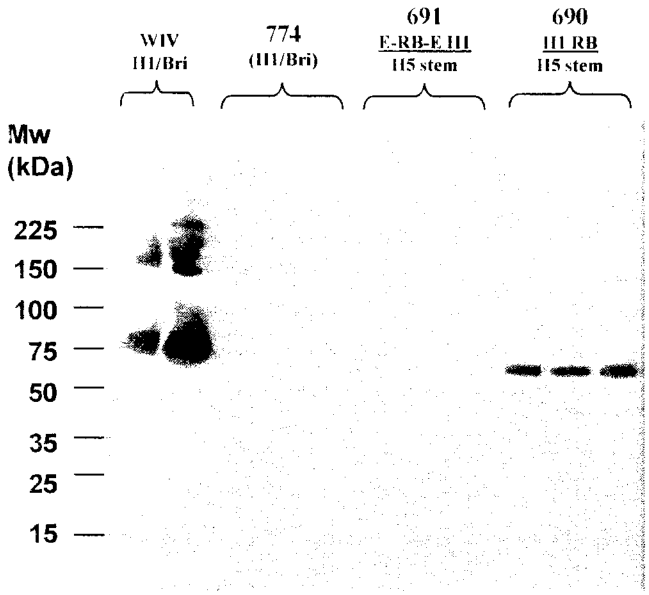
FIG. 6 shows an immunoblot analysis of expression of H1/Bri in native form, construct 774 (comprising H1/Bri), construct 692 (comprising the head domain complex (HDC) of H1/Bri), and construct 690 (comprising the RB sub domain of H1/Bri fused with H5/Indo stem domain complex (SDC) in plants. For each construct, total protein extracts from 3 separate plants were analyzed. Twenty micrograms of protein were loaded for each plant analyzed. The Western blot was revealed with anti-HA monoclonal antibodies (anti H1-Brisbane; FII 10-I50). Construct 774 expresses H1/Bri with the native signal peptide of H1/Bri; constructs 690, 691 express the HA with the native signal peptide of H5/Indo.

*Nicotiana benthamiana* plants were infiltrated with AGL1/732, AGL1/733 or AGL1/734, and the leaves were harvested after a six-day incubation period. To determine the accumulation level of each HA form in the agroinfiltrated leaves, protein were first extracted from infiltrated leaf tissue and analyzed by Western blotting using anti-H1 (Brisbane) polyclonal antibodies. A unique band of approximately 75 kDa (FIG. 6), corresponding in size to the uncleaved HA0 form of influenza hemagglutinin, was detected in extracts from leaves infiltrated with AGL1/732, AGL1/733 and AGL1/734. However, although hemagglutinin was detected in all extracts analyzed, important differences in accumulation could be noticed. While H1 A/Brisbane/59/2007 expression was barely detectable under these conditions when using its natural signal peptide (732), replacement of signal peptide with that of PDI resulted in higher accumulation of mature H1 A/Brisbane/59/2007 (733), and the chimeric H5/H1 hemagglutinin (734) accumulated to the highest level. Taken together, these results show that the fusion of the receptor-binding domain from H1 on a H5 backbone leads to high accumulation of H1 antigens-presenting hemagglutinin and that the accumulation level obtained for such fusion in plants is higher than that obtained with the native form with or without replacement of the signal peptide.

Example 3: Replacement of Receptor Binding (RB) Subdomain of H1 A/New Caledonia/20/99 with that of H5 A/Indonesia/5/05. Comparison of Expression for Chimeric and Native Forms Use of an H1 backbone (from A/New Caledonia/20/99) for the presentation of H5 antigenic region was also evaluated. Expression cassettes for the expression of the H1/H5 hemagglutinin fusion are represented in FIG. 1 and amino acid sequence of the mature fusion protein produced is presented in FIG. 2.

Figure 7:
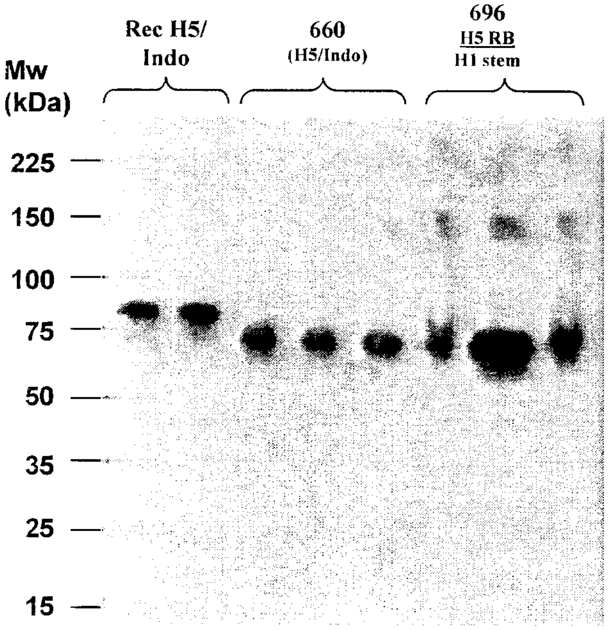
FIG. 7 shows an immunoblot analysis of expression of H5/Indo in native form, construct 660 (comprising H5/Indo, or construct 696 (comprising H1/Indo RB subdomain fused with H1/NC SDC, E1 and E2 subdomains). For each construct, total protein extracts from 3 separate plants were analyzed. Twenty micrograms of proteins were loaded for each plant analyzed. The Western blot was revealed with anti-H5 Indonesia polyclonal antibodies (ITC IT-003-005V). Construct 660 expresses H5/Indo with its native signal peptide; construct 696 expresses the chimeric HA with a PDI signal peptide.

To compare the accumulation level of H1/H5 chimeric hemagglutinin with that of its native form, *Nicotiana benthamiana* plants were infiltrated with AGL1/660 and AGL1/696, and the leaves were harvested after a six-day incubation period. To determine the accumulation level of each HA form in the agroinfiltrated leaves, proteins were extracted from infiltrated leaf tissue and analyzed by Western blotting using anti-H5 (Indonesia) polyclonal antibodies. A unique band of approximately 75 kDa (FIG. 7), corresponding in size to the uncleaved HA0 form of influenza hemagglutinin, was detected in extracts from leaves infiltrated with AGL1/660 and AGL1/696, indicating that both the native H5 A/Indonesia/5/05 and the H1/H5 chimeric hemagglutinin accumulate at high level in plants.

Figure 10:
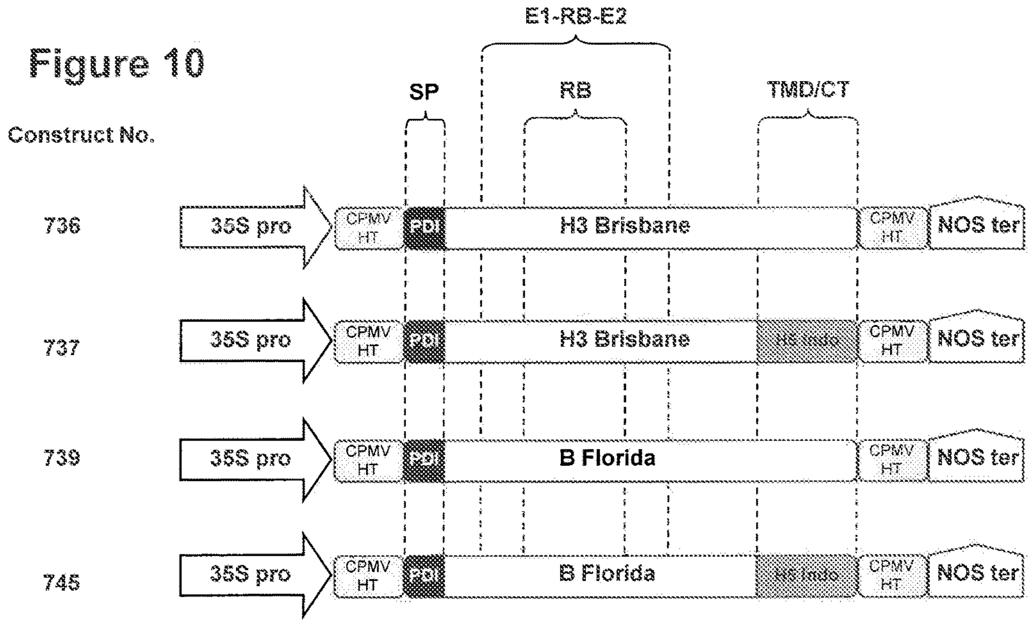
FIG. 10 shows schematic representation of 35SCPMV/HT-based expression cassettes for the expression of H3 A/Brisbane/10/2007 HA (H3/Bri) and B/Florida/4/2006 HA (B/Flo) hemagglutinins. Construct 736 comprises H3/Bri fused to a PDI signal peptide. Construct 737 comprises the H3/Bri fused to a PDI signal peptide and an H5/Indo TMD/CT. Construct 739 comprises B/Flo fused to a PDI signal peptide. Contract 745 comprises the B/Flo fused to a PDI signal peptide and an H5/Indo TMD/CT. 35S pro: CaMV 35S promoter, NOS ter: nopaline synthase terminator, SP: signal peptide, RB: receptor-binding subdomain, E1-RB-E2: esterase and receptor-binding subdomains, TMD/CT: transmembrane and cytoplasmic tail subdomains, PDI: alfalfa protein disulfide isomerase; CPMV-HT: 5' and 3' elements of the hyper translatable Cowpea Mosaic Virus expression system.
Figure 11:
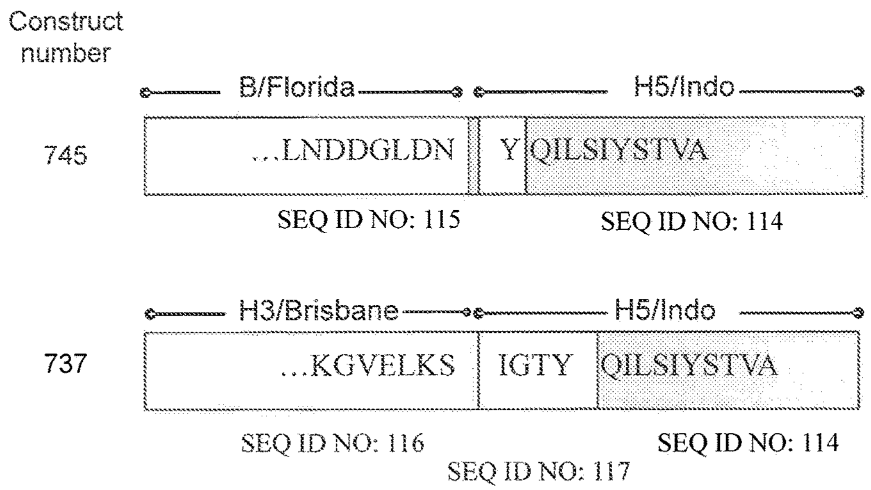
FIG. 11 shows the fusion border in constructs number 745 and 737. Origin of HA sequence is indicated by bullet-ended arrows. Amino acids of the transmembrane domain are QILSIYSTVA (SEQ ID NO:114), and are preceded by amino acids that are part of the ectodomain (LNDDGLDN (SEQ ID NO:115), KGVELKS (SEQ ID NO:116) and IGTY (SEQ ID NO:117)).

Example 4: Replacement of the Ectodomain of H5 A/Indonesia/5/05 with that of H3 or B. Comparison of Expression for Chimeric and Native Forms The fusion of the ectodamain from H3 A/Brisbane/10/2007 or B Florida/4/2006 to the transmembrane and cytoplasmic subdomains from H5 A/Indonesia/5/05 was evaluated as a strategy to present hemagglutinin antigenic regions from H3 and B strains while increasing their accumulation level in plants. Expression cassettes for the expression of the H5/H3 and H5/B hemagglutinin fusions are represented in FIG. 10 and amino acids at the border of the fusions are presented in FIG. 11.

Figure 14:
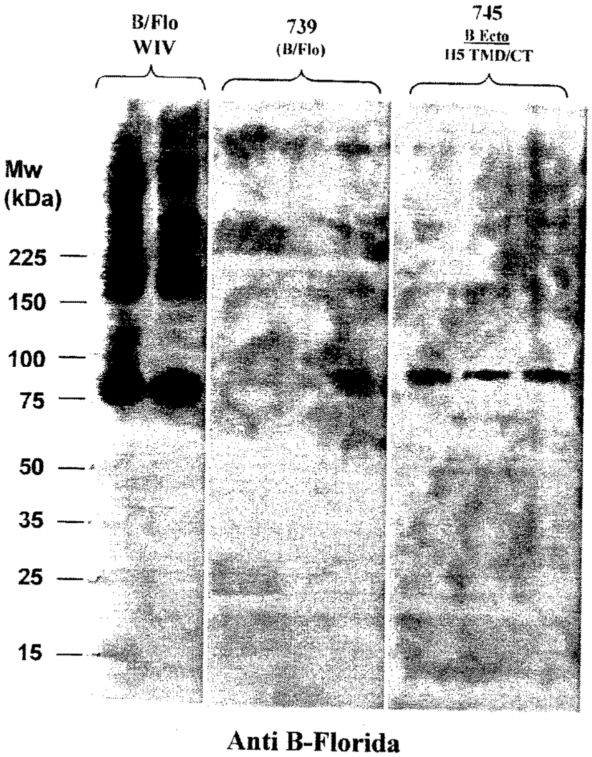
FIG. 14 shows immunoblot analysis of expression of B/Flo in native form, construct 739 (comprising PDI-B/Flo), or with construct 745 (comprising B/Flo HDC and SDC fused with an H5/Indo TDC). For each construct, total protein extracts from 3 separate plants were analyzed. Twenty micrograms of protein were loaded for each plant analyzed. The Western blot was revealed with anti-HA B/Florida polyclonal antibodies (NIBSC 07/356).

Accumulation level of H5/B chimeric hemagglutinin (745) was compared with that of native HA B (739) in *Nicotiana benthamiana* plants. Plants were infiltrated with AGL1/739 and AGL1/745, and the leaves were harvested after a six-day incubation period. To determine the accumulation level of each HA form in the agroinfiltrated leaves, proteins were first extracted from infiltrated leaf tissue and analyzed by Western blotting using anti-B (Florida) polyclonal antibodies. A unique band of approximately 75 kDa (FIG. 14), corresponding in size to the uncleaved HA0 form of influenza hemagglutinin, was detected in extracts from leaves of one plant infiltrated with AGL1/739 while the 3 plants infiltrated with AGL1/745 showed positive signal corresponding to hemagglutinin, indicating that the H5/B chimeric form of hemagglutinin accumulated more regularly at high level than the native form of B hemagglutinin.

Similarly, accumulation level of H5/H3 chimeric hemagglutinin (737) was compared with that of its native form (736) in *Nicotiana benthamiana* plants. Plants were infiltrated with AGL1/736 and AGL1/737, and the leaves were harvested after a six-day incubation period. To determine the accumulation level of each HA form in the agroinfiltrated leaves, proteins were extracted from infiltrated leaf tissue and analyzed by Western blotting using anti-H3 (Brisbane) polyclonal antibodies. A unique band of approximately 75 kDa (FIG. 15), corresponding in size to the uncleaved HA0 form of influenza hemagglutinin, was detected in extracts from leaves infiltrated with AGL1/736 and AGL1/737. This result indicates that the fusion of transmembrane and cytoplasmic subdomains from H5 A/Indonesia/5/05 to the ectodomain of H3 A/Brisbane/10/2007 creates a chimeric hemagglutinin that accumulates to a similar level as the native H3 A/Brisbane/10/2007.

Figure 16:
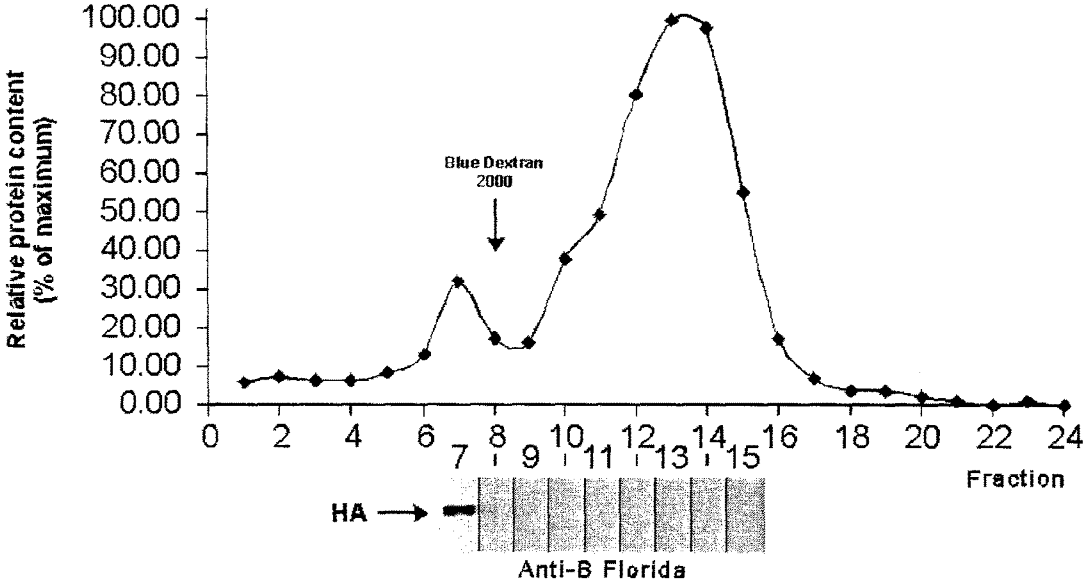
FIG. 16 shows size exclusion chromatography of leaf protein extracts from plants infiltrated with construct number 745. Relative protein content of elution fractions is presented for each fraction. Immunodetection (Western blot) of hemagglutinin using anti-HA B/Florida polyclonal antibodies (NIBSC 07/356) in fractions 7 to 15 is presented under the graph. The elution peak of Blue Dextran 2000 is indicated by the arrow (fraction 8).

The production of VLPs from expression of the H5/B chimeric hemagglutinin (construct no. 745) was evaluated using size exclusion chromatography. Concentrated protein extracts from AGL1/745-infiltrated plants (1.5 mL) were fractionated by size exclusion chromatography (SEC) on Sephacryl™ S-500 HR columns (GE Healthcare Bio-Science Corp., Piscataway, N.J., USA). As shown in FIG. 16, Blue Dextran (2 MDa) elution peaked early in fraction 8. When proteins from 200 μL of each SEC elution fraction were concentrated (5-fold) by acetone-precipitation and analyzed by Western blotting using anti-B (Florida) polyclonal antibodies (FIG. 16), chimeric hemagglutinin was primarily found in fraction 7, indicating the incorporation of HA into high molecular weight structures. Without wishing to be bound by theory, this suggests that the chimeric HA protein had either assembled into a large superstructure or that it has attached to a high molecular weight structure. The results obtained indicate that the chimeric HA consisting in the ectodomain from HA B/Florida/4/2006 fused to the transmembrane and cytosolic subdomains from H5 A/Indonesia/5/05 assembles into high molecular weight particles and that the elution profile of these high molecular weight particles is indistinguishable to that of influenza VLPs.

Example 5: Co-Expression of H5/B Chimeric Hemagglutinin (Construct Number 747; Comprising B/Flo HDC and SDC Fused with an H5/Indo TDC) with Hsp70 and Hsp40 in Combination with Signal Peptide Modification Expression of Hsp40 and Hsp70 in plants and co-expression with influenza hemagglutinins is described in co-pending application PCT/CA2009/000032. Cytosolic Hsp70 and Hsp40 (construct number R870) of plant origin may also be co-expressed with chimeric hemagglutinins, to increase their accumulation level in plants. The co-expression may be performed by agroinfiltration of *N. benthamiana* plants with a bacterial suspension containing a mixture (1:1:1 ratio) of AGL1 bearing the cassette for the expression of the desired chimeric HA with AGL1/R870 and AGL1/35SHcPro.

Accumulation level of H5/B chimeric hemagglutinin (B/Flo HDC and SDC fused with an H5/Indo TDC) was evaluated in co-expression with HSP40 and HSP70 in *Nicotiana benthamiana* plants. Plants were infiltrated with AGL1/747, AGL1/747+AGL1/443 (empty vector) or AGL1/747+AGL1/R870 (HSP40/HSP70), and the leaves were harvested after a six-day incubation period. To determine the accumulation level of H5/B chimeric HA in the agroinfiltrated leaves, proteins were first extracted from infiltrated leaf tissue and analyzed by Western blotting using anti-B (Florida) polyclonal antibodies. A unique band of approximately 75 kDa (FIG. 50), corresponding in size to the uncleaved HA0 form of influenza hemagglutinin, was detected in extracts from leaves from 3 plants infiltrated with AGL1/747+AGL1/R870 while the 3 plants infiltrated with AGL1/747+ control vector (443) showed no signal (under the exposure condition used) indicating that the H5/B chimeric form of hemagglutinin accumulated at high level when co-expressed with the HSP40 and HSP 70 chaperones.

All citations are herein incorporated by reference, as if each individual publication was specifically and individually indicated to be incorporated by reference herein and as though it were fully set forth herein. Citation of references herein is not to be construed nor considered as an admission that such references are prior art to the present invention.

In the description a number of terms are used extensively and definitions are provided to facilitate understanding of various aspects of the invention. Use of examples in the specification, including examples of terms, is for illustrative purposes only and is not intended to limit the scope and meaning of the embodiments of the invention herein. Numeric ranges are inclusive of the numbers defining the range. In the specification, the word "comprising" is used as an open-ended term, substantially equivalent to the phrase "including, but not limited to," and the word "comprises" has a corresponding meaning.

One or more currently preferred embodiments of the invention have been described by way of example. The invention includes all embodiments, modifications and variations substantially as hereinbefore described and with reference to the examples and figures. It will be apparent to persons skilled in the art that a number of variations and modifications can be made without departing from the scope of the invention as defined in the claims. Examples of such modifications include the substitution of known equivalents for any aspect of the invention in order to achieve the same result in substantially the same way.

What is claimed is:

1. A nucleic acid comprising one or more regulatory regions comprising a promoter, the promoter recognized by RNA polymerase 2 and operatively linked to a sequence encoding a chimeric influenza hemagglutinin (HA) polypeptide comprising a stem domain cluster (SDC), a head domain cluster (HDC) and a transmembrane domain cluster (TDC), the one or more regulatory regions further including a 5'UTR and 3'UTR, and wherein a) the SDC comprises an F'1, F'2 and F subdomain;

b) the HDC comprises receptor binding (RB) subdomain, vestigial esterase subdomain E1 (E1) and vestigial esterase subdomain E2 (E2);

c) the TDC comprises a transmembrane (TmD) and C terminal tail (CT) subdomain; and wherein the RB subdomain is of a first influenza HA polypeptide, the SDC, the E1, the E2, and the TDC subdomains are from a second influenza HA polypeptide, and wherein the first influenza HA polypeptide is from influenza H1 or H5, and the second influenza HA polypeptide is from influenza H1 or H5, and the second influenza HA is derived from a different influenza strain than the first influenza polypeptide, wherein the F'1 subdomain is fused to a native or plant derived signal peptide, and the 3'UTR and 5'UTR is heterologous to the first, and the second, influenza HA.

2. The nucleic acid of claim 1, wherein the sequence encoding a chimeric influenza HA polypeptide further comprises a signal peptide sequence selected from the group consisting of an HA native signal peptide sequence, and an alfalfa PDI signal peptide sequence.

3. The nucleic acid of claim 1, wherein the 5'UTR and 3'UTR are obtained from a plastocyanin UTR or Cowpea Mosaic Virus (CPMV) UTR.

4. The nucleic acid of claim 1, wherein the regulatory region is obtained from a plastocyanin regulatory region, a Ribulose 1,5-bisphosphate carboxylase/oxygenase (RuBisCO) regulatory region, a chlorophyll a/b binding protein (CAB) regulatory region, a CaMV 35S regulatory region, an actin regulatory region, a ubiquitin regulatory region, a triosephosphate isomerase 1 regulatory region, a translational initiation factor 4A regulatory region, or an ST-LSI regulatory region.

5. A method of producing chimeric influenza HA protein in a plant comprising:

a) introducing the nucleic acid of claim 1 into the plant, or portion thereof b) incubating the plant, or portion thereof, under conditions that permit the expression of the nucleic acid, thereby producing the chimeric influenza HA protein; and c) harvesting the plant and obtaining the chimeric influenza HA protein.

6. A polypeptide encoded by the nucleic acid of claim 1.

7. The polypeptide of claim 6 further comprising plant-specific N-glycans or modified N-glycans.

8. A composition comprising an effective dose of the polypeptide of claim 7 and a pharmaceutically acceptable carrier.

9. A plant cell, comprising a polypeptide encoded by the nucleic acid of claim 1.

10. A method of producing chimeric influenza virus like particles (VLPs) in a plant comprising:

a) introducing the nucleic acid of claim 3 into the plant, or portion thereof using agroinfiltration;

b) incubating the plant, or portion thereof, under conditions that permit the expression of the nucleic acid, thereby producing the chimeric VLPs; and c) harvesting the plant and obtaining the chimeric VLPs.

11. A nucleic acid comprising one or more regulatory regions comprising a promoter, the promoter recognized by RNA polymerase 2 and operatively linked to a sequence encoding a chimeric influenza hemagglutinin (HA) polypeptide, the chimeric influenza HA polypeptide comprising a stem domain cluster (SDC), a head domain cluster (HDC) and a transmembrane domain cluster (TDC), the one or more regulatory regions further including a 5'UTR and 3'UTR, wherein a) the SDC comprises an F'1, F'2 and F subdomain;

b) the HDC comprises a receptor binding (RB) subdomain, vestigial esterase subdomain E1 (E1) and vestigial esterase subdomain E2 (E2);

c) the TDC comprises a transmembrane (TmD) and C terminal tail (CT) subdomain; and wherein the HDC and SDC subdomain is obtained from influenza H3, H6 or B, and the TDC is obtained from influenza H1 or H5 wherein the F'1 subdomain is fused to a native or plant derived signal peptide, and the 3'UTR and 5'UTR is heterologous to the sequence encoding the influenza H1, H3, H5, H6 or B HA.

12. A method of producing chimeric influenza HA protein in a plant comprising:

a) introducing the nucleic acid of claim 11 into the plant, or portion thereof b) incubating the plant, or portion thereof, under conditions that permit the expression of the nucleic acid, thereby producing the chimeric influenza HA protein; and c) harvesting the plant and obtaining the chimeric influenza HA protein.

13. The nucleic acid of claim 2 wherein the HA native signal peptide sequence is selected from an influenza H5 signal peptide sequence and an influenza H1 signal peptide sequence.

14. A polypeptide encoded by the nucleic acid of claim 11.

15. A plant cell comprising a polypeptide encoded by the nucleic acid of claim 11.

16. The nucleic acid of claim 11, wherein the 5'UTR and 3'UTR are obtained from a plastocyanin UTR or Cowpea Mosaic Virus (CPMV) UTR.

17. A method of producing chimeric influenza virus like particles (VLPs) in a plant comprising:

a) introducing the nucleic acid of claim 16 into the plant, or portion thereof using agroinfiltration;

b) incubating the plant, or portion thereof, under conditions that permit the expression of the nucleic acid, thereby producing the chimeric VLPs; and c) harvesting the plant and obtaining the chimeric VLPs.

* * * * *

SEQUENCE LISTING

```
<160> NUMBER OF SEQ ID NOS: 143

<210> SEQ ID NO 1
<211> LENGTH: 32
<212> TYPE: DNA
<213> ORGANISM: Artificial sequence
<220> FEATURE:
<223> OTHER INFORMATION: Synthesized XmaI-pPlas.c

<400> SEQUENCE: 1

agttccccgg gctggtatat ttatatgttg tc                                    32


<210> SEQ ID NO 2
<211> LENGTH: 46
<212> TYPE: DNA
<213> ORGANISM: Artificial Sequence
<220> FEATURE:
<223> OTHER INFORMATION: Synthesized SacI-ATG-pPlas.r

<400> SEQUENCE: 2

aatagagctc cattttctct caagatgatt aattaattaa ttagtc                     46


<210> SEQ ID NO 3
<211> LENGTH: 46
<212> TYPE: DNA
<213> ORGANISM: Artificial sequence
<220> FEATURE:
<223> OTHER INFORMATION: Synthesized SacI-PlasTer.c

<400> SEQUENCE: 3

aatagagctc gttaaaatgc ttcttcgtct cctatttata atatgg                     46


<210> SEQ ID NO 4
<211> LENGTH: 48
<212> TYPE: DNA
<213> ORGANISM: Artificial sequence
<220> FEATURE:
<223> OTHER INFORMATION: Synthesized EcoRI-PlasTer.r

<400> SEQUENCE: 4

ttacgaattc tccttcctaa ttggtgtact atcatttatc aaagggga                   48
```

<210> SEQ ID NO 5
<211> LENGTH: 25
<212> TYPE: DNA
<213> ORGANISM: Artificial sequence
<220> FEATURE:
<223> OTHER INFORMATION: Synthesized Plasto-443C

<400> SEQUENCE: 5
gtattagtaa ttagaatttg gtgtc 25

<210> SEQ ID NO 6
<211> LENGTH: 44
<212> TYPE: DNA
<213> ORGANISM: Artificial Sequence
<220> FEATURE:
<223> OTHER INFORMATION: SpHa(Ind)-Plasto-r

<400> SEQUENCE: 6
gcaagaagaa gcactatttt ctccattttc tctcaagatg atta 44

<210> SEQ ID NO 7
<211> LENGTH: 45
<212> TYPE: DNA
<213> ORGANISM: Artificial sequence
<220> FEATURE:
<223> OTHER INFORMATION: Plasto-SpHa.c

<400> SEQUENCE: 7
ttaatcatct tgagagaaaa tggagaaaat agtgcttctt cttgc 45

<210> SEQ ID NO 8
<211> LENGTH: 38
<212> TYPE: DNA
<213> ORGANISM: Artificial sequence
<220> FEATURE:
<223> OTHER INFORMATION: HA(Ind)-Sac.r

<400> SEQUENCE: 8
actttgagct cttaaatgca aattctgcat tgtaacga 38

<210> SEQ ID NO 9
<211> LENGTH: 24
<212> TYPE: DNA
<213> ORGANISM: Artificial sequence
<220> FEATURE:
<223> OTHER INFORMATION: Synthesized pBinPlus.2613c

<400> SEQUENCE: 9
aggaagggaa gaaagcgaaa ggag 24

<210> SEQ ID NO 10
<211> LENGTH: 56
<212> TYPE: DNA
<213> ORGANISM: Artificial sequence
<220> FEATURE:
<223> OTHER INFORMATION: Synthesized Mut-ATG115.r

<400> SEQUENCE: 10
gtgccgaagc acgatctgac aacgttgaag atcgctcacg caagaaagac aagaga 56

<210> SEQ ID NO 11
<211> LENGTH: 52
<212> TYPE: DNA
<213> ORGANISM: Artificial Sequence
<220> FEATURE:
<223> OTHER INFORMATION: Synthesized Mut-ATG161.c

<400> SEQUENCE: 11
gttgtcagat cgtgcttcgg caccagtaca acgttttctt tcactgaagc ga 52

<210> SEQ ID NO 12
<211> LENGTH: 25
<212> TYPE: DNA
<213> ORGANISM: Artificial sequence
<220> FEATURE:
<223> OTHER INFORMATION: Synthesized LC-C5-1.110r

<400> SEQUENCE: 12
tctcctggag tcacagacag ggtgg 25

<210> SEQ ID NO 13
<211> LENGTH: 52
<212> TYPE: DNA
<213> ORGANISM: Artificial Sequence
<220> FEATURE:
<223> OTHER INFORMATION: Synthesized E1 H1B-E1 H5I.r

<400> SEQUENCE: 13
tcatagtcag cgaaatgccc tgggtaacag aggtcattgg ttggattggc ct 52

<210> SEQ ID NO 14
<211> LENGTH: 48
<212> TYPE: DNA
<213> ORGANISM: Artificial Sequence
<220> FEATURE:
<223> OTHER INFORMATION: Synthesized E1 H5N-E1 H1B.c

<400> SEQUENCE: 14
atgacctctg ttacccaggg catttcgctg actatgagga actgaggg 48

<210> SEQ ID NO 15
<211> LENGTH: 48
<212> TYPE: DNA
<213> ORGANISM: Artificial Sequence
<220> FEATURE:
<223> OTHER INFORMATION: Synthesized E2 H5I-RB H1B.r

<400> SEQUENCE: 15
ccaattcact tttcataatt cctgatccaa agcctctact cagtgcga 48

<210> SEQ ID NO 16
<211> LENGTH: 51
<212> TYPE: DNA
<213> ORGANISM: Artificial Sequence
<220> FEATURE:
<223> OTHER INFORMATION: Synthesized RB H1B-E2 H5I.c

<400> SEQUENCE: 16
ggctttggat caggaattat gaaaagtgaa ttggaatatg gtaactgcaa c 51

<210> SEQ ID NO 17
<211> LENGTH: 48
<212> TYPE: DNA
<213> ORGANISM: Artificial Sequence
<220> FEATURE:
<223> OTHER INFORMATION: Synthesized E1 H1B-F'1 H5I.r

<400> SEQUENCE: 17
ggctattcct tttaataggc agagcttccc gttgtgtgtc ttttccag 48

<210> SEQ ID NO 18
<211> LENGTH: 48

-continued

<212> TYPE: DNA
<213> ORGANISM: Artificial Sequence
<220> FEATURE:
<223> OTHER INFORMATION: Synthesized F'1 H5N-E1 H1B.c

<400> SEQUENCE: 18
aacgggaagc tctgcctatt aaaaggaata gccccactac aattgggt 48

<210> SEQ ID NO 19
<211> LENGTH: 48
<212> TYPE: DNA
<213> ORGANISM: Artificial Sequence
<220> FEATURE:
<223> OTHER INFORMATION: Synthesized F'2 H5I-E2 H1B.r

<400> SEQUENCE: 19
ggagtttgac acttggtgtt gcatttatcc attggtgcat ttgagttg 48

<210> SEQ ID NO 20
<211> LENGTH: 48
<212> TYPE: DNA
<213> ORGANISM: Artificial Sequence
<220> FEATURE:
<223> OTHER INFORMATION: Synthesized E2 H1B-F'2 H5I.c

<400> SEQUENCE: 20
aatgcaccaa tggataaatg caacaccaag tgtcaaactc caatgggg 48

<210> SEQ ID NO 21
<211> LENGTH: 48
<212> TYPE: DNA
<213> ORGANISM: Artificial Sequence
<220> FEATURE:
<223> OTHER INFORMATION: Synthesized E1 H5I-E1 H1NC.r

<400> SEQUENCE: 21
tcttcatagt cgttgaaact ccctgggtaa catgttccat tctcagga 48

<210> SEQ ID NO 22
<211> LENGTH: 48
<212> TYPE: DNA
<213> ORGANISM: Artificial Sequence
<220> FEATURE:
<223> OTHER INFORMATION: Synthesized E1 H1NC-E1 H5I.c

<400> SEQUENCE: 22
ctgagaatgg aacatgttac ccagggagtt tcaacgacta tgaagaac 48

<210> SEQ ID NO 23
<211> LENGTH: 51
<212> TYPE: DNA
<213> ORGANISM: Artificial Sequence
<220> FEATURE:
<223> OTHER INFORMATION: Synthesized E2 H1NC-RB H5I.r

<400> SEQUENCE: 23
atttgaggtg atgattgctg agtccccttt cttgacaatt ttgtatgcat a 51

<210> SEQ ID NO 24
<211> LENGTH: 48
<212> TYPE: DNA
<213> ORGANISM: Artificial Sequence
<220> FEATURE:
<223> OTHER INFORMATION: Synthesized RB H5I-E2 H1NC.c

<400> SEQUENCE: 24

-continued gtcaagaaag gggactcagc aatcatcacc tcaaatgcac caatggat 48

<210> SEQ ID NO 25
<211> LENGTH: 43
<212> TYPE: DNA
<213> ORGANISM: Artificial Sequence
<220> FEATURE:
<223> OTHER INFORMATION: Synthesized HA-SacI.r

<400> SEQUENCE: 25
ttaacttaga gctcttagat gcatattcta cactgcaaag acc 43

<210> SEQ ID NO 26
<211> LENGTH: 45
<212> TYPE: DNA
<213> ORGANISM: Artificial sequence
<220> FEATURE:
<223> OTHER INFORMATION: Synthesized ApaI-H1B.c

<400> SEQUENCE: 26
tgtcgggccc atgaaagtaa aactactggt cctgttatgc acatt 45

<210> SEQ ID NO 27
<211> LENGTH: 46
<212> TYPE: DNA
<213> ORGANISM: Artificial Sequence
<220> FEATURE:
<223> OTHER INFORMATION: Synthesized StuI-H1B.r

<400> SEQUENCE: 27
aaataggcct ttagatgcat attctacact gtaaagaccc attgga 46

<210> SEQ ID NO 28
<211> LENGTH: 49
<212> TYPE: DNA
<213> ORGANISM: Artificial Sequence
<220> FEATURE:
<223> OTHER INFORMATION: Synthesized SpPDI-H1B.c

<400> SEQUENCE: 28
ttctcagatc ttcgctgaca caatatgtat aggctaccat gctaacaac 49

<210> SEQ ID NO 29
<211> LENGTH: 47
<212> TYPE: DNA
<213> ORGANISM: Artificial Sequence
<220> FEATURE:
<223> OTHER INFORMATION: Synthesized SacI-H1B.r

<400> SEQUENCE: 29
cttagagctc ttagatgcat attctacact gtaaagaccc attggaa 47

<210> SEQ ID NO 30
<211> LENGTH: 45
<212> TYPE: DNA
<213> ORGANISM: Artificial sequence
<220> FEATURE:
<223> OTHER INFORMATION: Synthesized ApaI-SpPDI.c

<400> SEQUENCE: 30
ttgtcgggcc catggcgaaa aacgttgcga ttttcggctt attgt 45

<210> SEQ ID NO 31
<211> LENGTH: 39
<212> TYPE: DNA
<213> ORGANISM: Artificial Sequence
<220> FEATURE:
<223> OTHER INFORMATION: Synthesized ApaI-H5 (A-Indo).1c

<400> SEQUENCE: 31
tgtcgggccc atggagaaaa tagtgcttct tcttgcaat 39

<210> SEQ ID NO 32
<211> LENGTH: 37
<212> TYPE: DNA
<213> ORGANISM: Artificial Sequence
<220> FEATURE:
<223> OTHER INFORMATION: Synthesized H5 (A-Indo)-StuI.1707r

<400> SEQUENCE: 32
aaataggcct ttaaatgcaa attctgcatt gtaacga 37

<210> SEQ ID NO 33
<211> LENGTH: 45
<212> TYPE: DNA
<213> ORGANISM: Artificial Sequence
<220> FEATURE:
<223> OTHER INFORMATION: Synthesized H3B-SpPDI.r

<400> SEQUENCE: 33
tgtcatttcc gggaagtttt tgagcgaaga tctgagaagg aacca 45

<210> SEQ ID NO 34
<211> LENGTH: 45
<212> TYPE: DNA
<213> ORGANISM: Artificial Sequence
<220> FEATURE:
<223> OTHER INFORMATION: Synthesized SpPDI-H3B.c

<400> SEQUENCE: 34
tctcagatct tcgctcaaaa acttcccgga aatgacaaca gcacg 45

<210> SEQ ID NO 35
<211> LENGTH: 44
<212> TYPE: DNA
<213> ORGANISM: Artificial Sequence
<220> FEATURE:
<223> OTHER INFORMATION: Synthesized StuI-H3B.r

<400> SEQUENCE: 35
aaaataggcc ttcaaatgca aatgttgcac ctaatgttgc cttt 44

<210> SEQ ID NO 36
<211> LENGTH: 45
<212> TYPE: DNA
<213> ORGANISM: Artificial Sequence
<220> FEATURE:
<223> OTHER INFORMATION: Synthesized TmD H5I-H3B.r

<400> SEQUENCE: 36
atttggtaag ttcctattga cttcagctca acgcccttga tctgg 45

<210> SEQ ID NO 37
<211> LENGTH: 48
<212> TYPE: DNA
<213> ORGANISM: Artificial Sequence
<220> FEATURE:
<223> OTHER INFORMATION: Synthesized H3B-TmD H5I.c

<400> SEQUENCE: 37
tgagctgaag tcaataggaa cttaccaaat actgtcaatt tattcaac 48

-continued

<210> SEQ ID NO 38
<211> LENGTH: 50
<212> TYPE: DNA
<213> ORGANISM: Artificial sequence
<220> FEATURE:
<223> OTHER INFORMATION: Synthesized HBF-SpPDI.r

<400> SEQUENCE: 38
gttattccag tgcagattcg atcagcgaag atctgagaag gaaccaacac 50

<210> SEQ ID NO 39
<211> LENGTH: 50
<212> TYPE: DNA
<213> ORGANISM: Artificial Sequence
<220> FEATURE:
<223> OTHER INFORMATION: Synthesized SpPDI-HBF.c

<400> SEQUENCE: 39
cagatcttcg ctgatcgaat ctgcactgga ataacatctt caaactcacc 50

<210> SEQ ID NO 40
<211> LENGTH: 46
<212> TYPE: DNA
<213> ORGANISM: Artificial Sequence
<220> FEATURE:
<223> OTHER INFORMATION: Synthesized StuI-HBF.r

<400> SEQUENCE: 40
aaaataggcc tttatagaca gatggagcat gaaacgttgt ctctgg 46

<210> SEQ ID NO 41
<211> LENGTH: 45
<212> TYPE: DNA
<213> ORGANISM: Artificial sequence
<220> FEATURE:
<223> OTHER INFORMATION: Synthesized TmD H5I-B Flo.r

<400> SEQUENCE: 41
tgacagtatt tggtagttat ccaatccatc atcatttaaa gatgc 45

<210> SEQ ID NO 42
<211> LENGTH: 50
<212> TYPE: DNA
<213> ORGANISM: Artificial Sequence
<220> FEATURE:
<223> OTHER INFORMATION: Synthesized B Flo-TmD H5I.c

<400> SEQUENCE: 42
ggattggata actaccaaat actgtcaatt tattcaacag tggcgagttc 50

<210> SEQ ID NO 43
<211> LENGTH: 20
<212> TYPE: DNA
<213> ORGANISM: Artificial Sequence
<220> FEATURE:
<223> OTHER INFORMATION: Synthesized Hsp-40Luz.1c

<400> SEQUENCE: 43
atgtttgggc gcggaccaac 20

<210> SEQ ID NO 44
<211> LENGTH: 31
<212> TYPE: DNA
<213> ORGANISM: Artificial Sequence
<220> FEATURE:
<223> OTHER INFORMATION: Synthesized Hsp40Luz-SacI.1272r

<400> SEQUENCE: 44
agctgagctc ctactgttga gcgcattgca c 31

<210> SEQ ID NO 45
<211> LENGTH: 36
<212> TYPE: DNA
<213> ORGANISM: Artificial Sequence
<220> FEATURE:
<223> OTHER INFORMATION: Synthesized Hsp40Luz-Plasto.r

<400> SEQUENCE: 45
gttggtccgc gcccaaacat tttctctcaa gatgat 36

<210> SEQ ID NO 46
<211> LENGTH: 21
<212> TYPE: DNA
<213> ORGANISM: Artificial Sequence
<220> FEATURE:
<223> OTHER INFORMATION: Synthesized Hsp70Ara.1c

<400> SEQUENCE: 46
atgtcgggta aaggagaagg a 21

<210> SEQ ID NO 47
<211> LENGTH: 33
<212> TYPE: DNA
<213> ORGANISM: Artificial Sequence
<220> FEATURE:
<223> OTHER INFORMATION: Synthesized Hsp70Ara-SacI.1956r

<400> SEQUENCE: 47
agctgagctc ttagtcgacc tcctcgatct tag 33

<210> SEQ ID NO 48
<211> LENGTH: 37
<212> TYPE: DNA
<213> ORGANISM: Artificial Sequence
<220> FEATURE:
<223> OTHER INFORMATION: Synthesized Hsp70Ara-Plasto.r

<400> SEQUENCE: 48
tccttctcct ttacccgaca ttttctctca agatgat 37

<210> SEQ ID NO 49
<211> LENGTH: 34
<212> TYPE: DNA
<213> ORGANISM: Artificial Sequence
<220> FEATURE:
<223> OTHER INFORMATION: Synthesized supP19-plasto.r

<400> SEQUENCE: 49
ccttgtatag ctcgttccat tttctctcaa gatg 34

<210> SEQ ID NO 50
<211> LENGTH: 20
<212> TYPE: DNA
<213> ORGANISM: Artificial Sequence
<220> FEATURE:
<223> OTHER INFORMATION: Synthesized supP19-1c

<400> SEQUENCE: 50
atggaacgag ctatacaagg 20

<210> SEQ ID NO 51

<211> LENGTH: 32
<212> TYPE: DNA
<213> ORGANISM: Artificial Sequence
<220> FEATURE:
<223> OTHER INFORMATION: Synthesized SupP19-SacI.r

<400> SEQUENCE: 51
agtcgagctc ttactcgctt tctttttcga ag 32

<210> SEQ ID NO 52
<211> LENGTH: 1719
<212> TYPE: DNA
<213> ORGANISM: Artificial Sequence
<220> FEATURE:
<223> OTHER INFORMATION: Synthesized B-Plasto-Native SP-H5
A/Indonesia/5/05

<400> SEQUENCE: 52
aagcttatgg agaaaatagt gcttcttctt gcaatagtca gtcttgttaa aagtgatcag 60
atttgcattg gttaccatgc aaacaattca acagagcagg ttgacacaat catggaaaag 120
aacgttactg ttacacatgc ccaagacata ctggaaaaga cacacaacgg gaagctctgc 180
gatctagatg gagtgaagcc tctaatttta agagattgta gtgtagctgg atggctcctc 240
gggaacccaa tgtgtgacga attcatcaat gtaccggaat ggtcttacat agtggagaag 300
gccaatccaa ccaatgacct ctgttaccca gggagtttca acgactatga agaactgaaa 360
cacctattga gcagaataaa ccattttgag aaaattcaaa tcatccccaa aagttcttgg 420
tccgatcatg aagcctcatc aggagttagc tcagcatgtc catacctggg aagtccctcc 480
ttttttagaa atgtggtatg gcttatcaaa aagaacagta catacccaac aataaagaaa 540
agctacaata ataccaacca agaggatctt ttggtactgt ggggaattca ccatcctaat 600
gatgcggcag agcagacaag gctatatcaa aacccaacca cctatatttc cattgggaca 660
tcaacactaa accagagatt ggtaccaaaa atagctacta gatccaaagt aaacgggcaa 720
agtggaagga tggagttctt ctggacaatt ttaaaaccta atgatgcaat caacttcgag 780
agtaatggaa atttcattgc tccagaatat gcatacaaaa ttgtcaagaa aggggactca 840
gcaattatga aaagtgaatt ggaatatggt aactgcaaca ccaagtgtca aactccaatg 900
ggggcgataa actctagtat gccattccac aacatacacc ctctcaccat cggggaatgc 960
cccaaatatg tgaaatcaaa cagattagtc cttgcaacag ggctcagaaa tagccctcaa 1020
agagagagca gaagaaaaaa gagaggacta tttggagcta tagcaggttt tatagaggga 1080
ggatggcagg gaatggtaga tggttggtat gggtaccacc atagcaatga gcaggggagt 1140
gggtacgctg cagacaaaga atccactcaa aaggcaatag atggagtcac caataaggtc 1200
aactcaatca ttgacaaaat gaacactcag tttgaggccg ttggaaggga atttaataac 1260
ttagaaagga gaatagagaa tttaaacaag aagatggaag acgggtttct agatgtctgg 1320
acttataatg ccgaacttct ggttctcatg gaaaatgaga gaactctaga ctttcatgac 1380
tcaaatgtta agaacctcta cgacaaggtc cgactacagc ttagggataa tgcaaaggag 1440
ctgggtaacg gttgtttcga gttctatcac aaatgtgata atgaatgtat ggaaagtata 1500
agaaacggaa cgtacaacta tccgcagtat tcagaagaag caagattaaa aagagaggaa 1560
ataagtgggg taaaattgga atcaatagga acttaccaaa tactgtcaat ttattcaaca 1620
gtggcgagtt ccctagcact ggcaatcatg atggctggtc tatctttatg gatgtgctcc 1680
aatggatcgt tacaatgcag aatttgcatt taagagctc 1719

<210> SEQ ID NO 53
<211> LENGTH: 3194
<212> TYPE: DNA
<213> ORGANISM: Artificial Sequence
<220> FEATURE:
<223> OTHER INFORMATION: Synthesized 660 expression cassette from
HindIII to Eco-R1

<400> SEQUENCE: 53
aagcttgcta gcggcctcaa tggccctgca ggtcgactct agaggtaccc cgggctggta 60
tatttatatg ttgtcaaata actcaaaaac cataaaagtt taagttagca agtgtgtaca 120
tttttacttg aacaaaaata ttcacctact actgttataa atcattatta aacattagag 180
taaagaaata tggatgataa gaacaagagt agtgatattt tgacaacaat tttgttgcaa 240
catttgagaa aattttgttg ttctctcttt tcattggtca aaaacaatag agagagaaaa 300
aggaagaggg agaataaaaa cataatgtga gtatgagaga gaaagttgta caaaagttgt 360
accaaaatag ttgtacaaat atcattgagg aatttgacaa aagctacaca aataagggtt 420
aattgctgta aataaataag gatgacgcat tagagagatg taccattaga gaatttttgg 480
caagtcatta aaaagaaaga ataaattatt tttaaaatta aaagttgagt catttgatta 540
aacatgtgat tatttaatga attgatgaaa gagttggatt aaagttgtat tagtaattag 600
aatttggtgt caaatttaat ttgacatttg atcttttcct atatattgcc ccatagagtc 660
agttaactca tttttatatt tcatagatca aataagagaa ataacggtat attaatccct 720
ccaaaaaaaa aaaacggtat atttactaaa aaatctaagc cacgtaggag gataacagga 780
tccccgtagg aggataacat ccaatccaac caatcacaac aatcctgatg agataaccca 840
ctttaagccc acgcatctgt ggcacatcta cattatctaa atcacacatt cttccacaca 900
tctgagccac acaaaaacca atccacatct ttatcaccca ttctataaaa aatcacactt 960
tgtgagtcta cactttgatt cccttcaaac acatacaaag agaagagact aattaattaa 1020
ttaatcatct tgagagaaaa tggagaaaat agtgcttctt cttgcaatag tcagtcttgt 1080
taaaagtgat cagatttgca ttggttacca tgcaaacaat tcaacagagc aggttgacac 1140
aatcatggaa aagaacgtta ctgttacaca tgcccaagac atactggaaa agacacacaa 1200
cgggaagctc tgcgatctag atggagtgaa gcctctaatt ttaagagatt gtagtgtagc 1260
tggatggctc ctcgggaacc caatgtgtga cgaattcatc aatgtaccgg aatggtctta 1320
catagtggag aaggccaatc caaccaatga cctctgttac ccagggagtt tcaacgacta 1380
tgaagaactg aaacacctat tgagcagaat aaaccatttt gagaaaattc aaatcatccc 1440
caaaagttct tggtccgatc atgaagcctc atcaggagtt agctcagcat gtccatacct 1500
gggaagtccc tcctttttta gaaatgtggt atggcttatc aaaaagaaca gtacataccc 1560
aacaataaag aaaagctaca ataataccaa ccaagaggat cttttggtac tgtggggaat 1620
tcaccatcct aatgatgcgg cagagcagac aaggctatat caaaacccaa ccacctatat 1680
ttccattggg acatcaacac taaaccagag attggtacca aaaatagcta ctagatccaa 1740
agtaaacggg caaagtggaa ggatggagtt cttctggaca attttaaaac ctaatgatgc 1800
aatcaacttc gagagtaatg gaaatttcat tgctccagaa tatgcataca aaattgtcaa 1860
gaaaggggac tcagcaatta tgaaaagtga attggaatat ggtaactgca acaccaagtg 1920
tcaaactcca atgggggcga taaactctag tatgccattc cacaacatac accctctcac 1980
catcggggaa tgccccaaat atgtgaaatc aaacagatta gtccttgcaa cagggctcag 2040

-continued

```
aaatagccct caaagagaga gcagaagaaa aaagagagga ctatttggag ctatagcagg   2100

ttttatagag ggaggatggc agggaatggt agatggttgg tatgggtacc accatagcaa   2160

tgagcagggg agtgggtacg ctgcagacaa agaatccact caaaaggcaa tagatggagt   2220

caccaataag gtcaactcaa tcattgacaa aatgaacact cagtttgagg ccgttggaag   2280

ggaatttaat aacttagaaa ggagaataga gaatttaaac aagaagatgg aagacgggtt   2340

tctagatgtc tggacttata atgccgaact tctggttctc atggaaaatg agagaactct   2400

agactttcat gactcaaatg ttaagaacct ctacgacaag gtccgactac agcttaggga   2460

taatgcaaag gagctgggta acggttgttt cgagttctat cacaaatgtg ataatgaatg   2520

tatggaaagt ataagaaacg gaacgtacaa ctatccgcag tattcagaag aagcaagatt   2580

aaaaagagag gaaataagtg gggtaaaatt ggaatcaata ggaacttacc aaatactgtc   2640

aatttattca acagtggcga gttccctagc actggcaatc atgatggctg gtctatcttt   2700

atggatgtgc tccaatggat cgttacaatg cagaatttgc atttaagagc tctaagttaa   2760

aatgcttctt cgtctcctat ttataaatatg gtttgttatt gttaattttg ttcttgtaga   2820

agagcttaat taatcgttgt tgttatgaaa tactatttgt atgagatgaa ctggtgtaat   2880

gtaattcatt tacataagtg gagtcagaat cagaatgttt cctccataac taactagaca   2940

tgaagacctg ccgcgtacaa ttgtcttata tttgaacaac taaaattgaa catcttttgc   3000

cacaacttta taagtggtta atatagctca aatatatggt caagttcaat agattaataa   3060

tggaaatatc agttatcgaa attcattaac aatcaactta acgttattaa ctactaattt   3120

tatatcatcc cctttgataa atgatagtac accaattagg aaggagcatg ctcgaggcct   3180

ggctggccga attc                                                     3194
```

```
<210> SEQ ID NO 54
<211> LENGTH: 1711
<212> TYPE: DNA
<213> ORGANISM: Artificial Sequence
<220> FEATURE:
<223> OTHER INFORMATION: Synthesized Wild-type H1/NC coding sequence
      lacking TmD and Ctail

<400> SEQUENCE: 54

atgaaagcaa aactactggt cctgttatgt acatttacag ctacatatgc agacacaata     60

tgtataggct accatgccaa caactcaacc gacactgttg acacagtact tgagaagaat    120

gtgacagtga cacactctgt caacctactt gaggacagtc acaatggaaa actatgtcta    180

ctaaaaggaa tagccccact acaattgggt aattgcagcg ttgccggatg gatcttagga    240

aacccagaat gcgaattact gatttccaag gaatcatggt cctacattgt agaaacacca    300

aatcctgaga atggaacatg ttacccaggg tatttcgccg actatgagga actgagggag    360

caattgagtt cagtatcttc atttgagaga ttcgaaatat tccccaaaga aagctcatgg    420

cccaaccaca ccgtaaccgg agtatcagca tcatgctccc ataatgggaa aagcagtttt    480

tacagaaatt tgctatggct gacggggaag aatggtttgt acccaaacct gagcaagtcc    540

tatgtaaaca acaaagagaa agaagtcctt gtactatggg gtgttcatca cccgcctaac    600

atagggaacc aaagggccct ctatcataca gaaaatgctt atgtctctgt agtgtcttca    660

cattatagca gaagattcac cccagaaata gccaaaagac ccaaagtaag agatcaggaa    720

ggaagaatca actactactg gactctgctg gaacctgggg atacaataat atttgaggca    780

aatggaaatc taatagcgcc atggtatgct tttgcactga gtagaggctt tggatcagga    840
```

-continued

```
atcatcacct caaatgcacc aatggatgaa tgtgatgcga agtgtcaaac acctcaggga    900

gctataaaca gcagtcttcc tttccagaat gtacacccag tcacaatagg agagtgtcca    960

aagtatgtca ggagtgcaaa attaaggatg gttacaggac taaggaacat cccatccatt   1020

caatccagag gtttgtttgg agccattgcc ggtttcattg aaggggggtg gactggaatg   1080

gtagatgggt ggtatggtta tcatcatcag aatgagcaag gatctggcta tgctgcagat   1140

caaaaaagta cacaaaatgc cattaacggg attacaaaca aggtgaattc tgtaattgag   1200

aaaatgaaca ctcaattcac agctgtgggc aaagaattca acaaattgga aagaaggatg   1260

gaaaacttaa ataaaaaagt tgatgatggg tttctagaca tttggacata taatgcagaa   1320

ttgttggttc tactggaaaa tgaaaggact ttggatttcc atgactccaa tgtgaagaat   1380

ctgtatgaga aagtaaaaag ccaattaaag aataatgcca aagaaatagg aaacgggtgt   1440

tttgaattct atcacaagtg taacaatgaa tgcatggaga gtgtgaaaaa tggaacttat   1500

gactatccaa aatattccga agaatcaaag ttaaacaggg agaaaattga tggagtgaaa   1560

ttggaatcaa tgggagtcta tcagattctg gcgatctact caactgtcgc cagttccctg   1620

gttcttttgg tctccctggg ggcaatcagc ttctggatgt gttccaatgg gtctttgcag   1680

tgtagaatat gcatctgaga ccagaatttc a                                  1711
```

<210> SEQ ID NO 55
<211> LENGTH: 1556
<212> TYPE: DNA
<213> ORGANISM: Artificial Sequence
<220> FEATURE:
<223> OTHER INFORMATION: Synthesized BglII-H1
A/NewCaledonia/20/99-SacI/StuI.

<400> SEQUENCE: 55

```
agatcttcgc tgacacaata tgtataggct accatgccaa caactcaacc gacactgttg     60

acacagtact tgagaagaat gtgacagtga cacactctgt caacctactt gaggacagtc    120

acaatggaaa actatgtcta ctaaaaggaa tagccccact acaattgggt aattgcagcg    180

ttgccggatg gatcttagga aacccagaat gcgaattact gatttccaag gaatcatggt    240

cctacattgt agaaacacca aatcctgaga atggaacatg ttacccaggg tatttcgccg    300

actatgagga actgagggag caattgagtt cagtatcttc atttgagaga ttcgaaatat    360

tccccaaaga aagctcatgg cccaaccaca ccgtaaccgg agtatcagca tcatgctccc    420

ataatgggaa aagcagtttt tacagaaatt tgctatggct gacggggaag aatggtttgt    480

acccaaacct gagcaagtcc tatgtaaaca acaaagagaa agaagtcctt gtactatggg    540

gtgttcatca cccgcctaac atagggaacc aaagggcact ctatcataca gaaaatgctt    600

atgtctctgt agtgtcttca cattatagca gaagattcac cccagaaata gccaaaagac    660

ccaaagtaag agatcaggaa ggaagaatca actactactg gactctgctg gaacctgggg    720

atacaataat atttgaggca aatggaaatc taatagcgcc atggtatgct tttgcactga    780

gtagaggctt tggatcagga atcatcacct caaatgcacc aatggatgaa tgtgatgcga    840

agtgtcaaac acctcaggga gctataaaca gcagtcttcc tttccagaat gtacacccag    900

tcacaatagg agagtgtcca aagtatgtca ggagtgcaaa attaaggatg gttacaggac    960

taaggaacat cccatccatt caatccagag gtttgtttgg agccattgcc ggtttcattg   1020

aaggggggtg gactggaatg gtagatgggt ggtatggtta tcatcatcag aatgagcaag   1080

gatctggcta tgctgcagat caaaaaagta cacaaaatgc cattaacggg attacaaaca   1140
```

-continued aggtcaattc tgtaattgag aaaatgaaca ctcaattcac agctgtgggc aaagagttca 1200
acaaattgga aagaaggatg gaaaacttaa ataaaaaagt tgatgatggg tttctagaca 1260
tttggacata taatgcagaa ttgttggttc tactggaaaa tgaaaggact ttggatttcc 1320
atgactccaa tgtgaagaat ctgtatgaga aagtaaaaag ccaattaaag aataatgcca 1380
aagaaatagg aaacgggtgt tttgagttct atcacaagtg taacaatgaa tgcatggaga 1440
gtgtgaaaaa tggtacctat gactatccaa aatattccga agaatcaaag ttaaacaggg 1500
agaaaattga tggagtgaaa ttggaatcaa tgggagtata ctaagagctc aggcct 1556

<210> SEQ ID NO 56
<211> LENGTH: 219
<212> TYPE: DNA
<213> ORGANISM: Artificial Sequence
<220> FEATURE:
<223> OTHER INFORMATION: Synthesized KpnI-H1 A/NewCaledonia/20/99 TmD+Ctail-SacI/StuI.

<400> SEQUENCE: 56
ggtacctatg actatccaaa atattccgaa gaatcaaagt taaacaggga gaaaattgat 60
ggagtgaaat tggaatcaat gggagtatac cagattctgg cgatctactc aactgtcgcc 120
agttccctgg ttcttttggt ctccctgggg gcaatcagct tctggatgtg ttccaatggg 180
tctttgcagt gtagaatatg catctaagag ctcaggcct 219

<210> SEQ ID NO 57
<211> LENGTH: 1781
<212> TYPE: DNA
<213> ORGANISM: Artificial Sequence
<220> FEATURE:
<223> OTHER INFORMATION: Synthesized Signal peptide of alfalfa protein disulfide isomerase (PDI) gene

<400> SEQUENCE: 57
ccaaatcctt aacattcttt caacaccaac aatggcgaaa aacgttgcga ttttcggttt 60
attgttttct cttcttctgt tggttccttc tcagatcttc gctgaggaat catcaactga 120
cgctaaggaa tttgttctta cattggataa cactaatttc catgacactg ttaagaagca 180
cgatttcatc gtcgttgaat tctacgcacc ttggtgtgga cactgtaaga agctagcccc 240
agagtatgag aaggctgctt ctatcttgag cactcacgag ccaccagttg ttttggctaa 300
agttgatgcc aatgaggagc acaacaaaga cctcgcatcg gaaaatgatg ttaagggatt 360
cccaaccatt aagattttta ggaatggtgg aaagaacatt caagaataca aaggtccccg 420
tgaagctgaa ggtattgttg agtatttgaa aaaacaaagt ggccctgcat ccacagaaat 480
taaatctgct gatgatgcga ccgcttttgt tggtgacaac aaagttgtta ttgtcggagt 540
tttccctaaa ttttctggtg aggagtacga taacttcatt gcattagcag agaagttgcg 600
ttctgactat gactttgctc acactttgaa tgccaaacac cttccaaagg gagactcatc 660
agtgtctggg cctgtggtta ggttatttaa gccatttgac gagctctttg ttgactcaaa 720
ggatttcaat gtagaagctc tagagaaatt cattgaagaa tccagtaccc caattgtgac 780
tgtcttcaac aatgagccta gcaatcaccc ttttgttgtc aaattcttta actctcccaa 840
cgcaaaggct atgttgttca tcaactttac taccgaaggt gctgaatctt tcaaaacaaa 900
ataccatgaa gtggctgagc aatacaaaca acagggagtt agctttcttg ttggagatgt 960
tgagtctagt caaggtgcct tccagtattt tggactgaag gaagaacaag tacctctaat 1020
tattattcag cataatgatg gcaagaagtt tttcaaaccc aatttggaac ttgatcaact 1080

-continued

```
cccaacttgg ttgaaggcat acaaggatgg caaggttgaa ccatttgtca agtctgaacc   1140

tattcctgaa actaacaacg agcctgttaa agtggtggtt gggcaaactc ttgaggacgt   1200

tgttttcaag tctgggaaga atgttttgat agagttttat gctccttggt gtggtcactg   1260

caagcagttg gctccaatct tggatgaagt tgctgtctca ttccaaagcg atgctgatgt   1320

tgttattgca aaactggatg caactgccaa cgatatccca accgacacct ttgatgtcca   1380

aggctatcca accttgtact tcaggtcagc aagtggaaaa ctatcacaat acgacggtgg   1440

taggacaaag gaagacatca tagaattcat tgaaaagaac aaggataaaa ctggtgctgc   1500

tcatcaagaa gtagaacaac caaaagctgc tgctcagcca gaagcagaac aaccaaaaga   1560

tgagctttga aaagttccgc ttggaggata tcggcacaca gtcatctgcg ggctttacaa   1620

ctcttttgta tctcagaatc agaagttagg aaatcttagt gccaatctat ctatttttgc   1680

gtttcatttt atctttttgg tttactctaa tgtattactg aataatgtga gttttggcgg   1740

agtttagtac tggaactttt gtttctgtaa aaaaaaaaaa a                        1781
```

<210> SEQ ID NO 58
<211> LENGTH: 1457
<212> TYPE: DNA
<213> ORGANISM: Artificial Sequence
<220> FEATURE:
<223> OTHER INFORMATION: Synthesized PromPlasto-PDISP-Plasto 3'UTR plasmid sequence

<400> SEQUENCE: 58

```
ctggtatatt tatatgttgt caaataactc aaaaaccata aaagtttaag ttagcaagtg     60

tgtacatttt tacttgaaca aaaatattca cctactactg ttataaatca ttattaaaca    120

ttagagtaaa gaaatatgga tgataagaac aagagtagtg atattttgac aacaattttg    180

ttgcaacatt tgagaaaatt ttgttgttct ctcttttcat tggtcaaaaa caatagagag    240

agaaaaagga agagggagaa taaaaacata atgtgagtat gagagagaaa gttgtacaaa    300

agttgtacca aaatagttgt acaaatatca ttgaggaatt tgacaaaagc tacacaaata    360

agggttaatt gctgtaaata aataaggatg acgcattaga gagatgtacc attagagaat    420

ttttggcaag tcattaaaaa gaaagaataa attattttta aaattaaaag ttgagtcatt    480

tgattaaaca tgtgattatt taatgaattg atgaaagagt tggattaaag ttgtattagt    540

aattagaatt tggtgtcaaa tttaatttga catttgatct tttcctatat attgccccat    600

agagtcagtt aactcatttt tatatttcat agatcaaata agagaaataa cggtatatta    660

atccctccaa aaaaaaaaaa cggtatattt actaaaaaat ctaagccacg taggaggata    720

acaggatccc cgtaggagga taacatccaa tccaaccaat cacaacaatc ctgatgagat    780

aacccacttt aagcccacgc atctgtggca catctacatt atctaaatca cacattcttc    840

cacacatctg agccacacaa aaaccaatcc acatctttat cacccattct ataaaaaatc    900

acactttgtg agtctacact ttgattccct tcaaacacat acaaagagaa gagactaatt    960

aattaattaa tcatcttgag agaaaatggc gaaaaacgtt gcgattttcg gcttattgtt   1020

ttctcttctt gtgttggttc cttctcagat ctgagctcta agttaaaatg cttcttcgtc   1080

tcctatttat aatatggttt gttattgtta attttgttct tgtagaagag cttaattaat   1140

cgttgttgtt atgaaatact atttgtatga gatgaactgg tgtaatgtaa ttcatttaca   1200

taagtggagt cagaatcaga atgtttcctc cataactaac tagacatgaa gacctgccgc   1260

gtacaattgt cttatatttg aacaactaaa attgaacatc ttttgccaca actttataag   1320
```

-continued tggttaatat agctcaaata tatggtcaag ttcaatagat taataatgga aatatcagtt 1380
atcgaaattc attaacaatc aacttaacgt tattaactac taattttata tcatcccctt 1440
tgataaatga tagtaca 1457

<210> SEQ ID NO 59
<211> LENGTH: 3206
<212> TYPE: DNA
<213> ORGANISM: Artificial Sequence
<220> FEATURE:
<223> OTHER INFORMATION: Synthesized 540 expression cassette from HindIII

<400> SEQUENCE: 59
aagcttgcta gcggcctcaa tggccctgca ggtcgactct agaggtaccc cgggctggta 60
tatttatatg ttgtcaaata actcaaaaac cataaaagtt taagttagca agtgtgtaca 120
tttttacttg aacaaaaata ttcacctact actgttataa atcattatta aacattagag 180
taaagaaata tggatgataa gaacaagagt agtgatattt tgacaacaat tttgttgcaa 240
catttgagaa aattttgttg ttctctcttt tcattggtca aaaacaatag agagagaaaa 300
aggaagaggg agaataaaaa cataatgtga gtatgagaga gaaagttgta caaaagttgt 360
accaaaatag ttgtacaaat atcattgagg aatttgacaa aagctacaca aataagggtt 420
aattgctgta aataaataag gatgacgcat tagagagatg taccattaga gaatttttgg 480
caagtcatta aaaagaaaga ataaattatt tttaaaatta aaagttgagt catttgatta 540
aacatgtgat tatttaatga attgatgaaa gagttggatt aaagttgtat tagtaattag 600
aatttggtgt caaatttaat ttgacatttg atcttttcct atatattgcc ccatagagtc 660
agttaactca tttttatatt tcatagatca aataagagaa ataacggtat attaatccct 720
ccaaaaaaaa aaaacggtat atttactaaa aaatctaagc cacgtaggag gataacagga 780
tccccgtagg aggataacat ccaatccaac caatcacaac aatcctgatg agataaccca 840
ctttaagccc acgcatctgt ggcacatcta cattatctaa atcacacatt cttccacaca 900
tctgagccac acaaaaacca atccacatct ttatcaccca ttctataaaa aatcacactt 960
tgtgagtcta cactttgatt cccttcaaac acatacaaag agaagagact aattaattaa 1020
ttaatcatct tgagagaaaa tggcgaaaaa cgttgcgatt ttcggcttat tgttttctct 1080
tcttgtgttg gttccttctc agatcttcgc tgacacaata tgtataggct accatgccaa 1140
caactcaacc gacactgttg acacagtact tgagaagaat gtgacagtga cacactctgt 1200
caacctactt gaggacagtc acaatggaaa actatgtcta ctaaaaggaa tagccccact 1260
acaattgggt aattgcagcg ttgccggatg gatcttagga aacccagaat gcgaattact 1320
gatttccaag gaatcatggt cctacattgt agaaacacca aatcctgaga atggaacatg 1380
ttacccaggg tatttcgccg actatgagga actgagggag caattgagtt cagtatcttc 1440
atttgagaga ttcgaaatat tccccaaaga aagctcatgg cccaaccaca ccgtaaccgg 1500
agtatcagca tcatgctccc ataatgggaa aagcagtttt tacagaaatt tgctatggct 1560
gacggggaag aatggtttgt acccaaacct gagcaagtcc tatgtaaaca acaaagagaa 1620
agaagtcctt gtactatggg gtgttcatca cccgcctaac atagggaacc aaagggcact 1680
ctatcataca gaaaatgctt atgtctctgt agtgtcttca cattatagca gaagattcac 1740
cccagaaata gccaaaagac ccaaagtaag agatcaggaa ggaagaatca actactactg 1800
gactctgctg gaacctgggg atacaataat atttgaggca aatggaaatc taatagcgcc 1860

```
atggtatgct tttgcactga gtagaggctt tggatcagga atcatcacct caaatgcacc   1920
aatggatgaa tgtgatgcga agtgtcaaac acctcaggga gctataaaca gcagtcttcc   1980
tttccagaat gtacacccag tcacaatagg agagtgtcca aagtatgtca ggagtgcaaa   2040
attaaggatg gttacaggac taaggaacat cccatccatt caatccagag gtttgtttgg   2100
agccattgcc ggtttcattg aagggggtg gactggaatg gtagatgggt ggtatggtta   2160
tcatcatcag aatgagcaag gatctggcta tgctgcagat caaaaaagta cacaaaatgc   2220
cattaacggg attacaaaca aggtcaattc tgtaattgag aaaatgaaca ctcaattcac   2280
agctgtgggc aaagagttca acaaattgga aagaaggatg gaaaacttaa ataaaaaagt   2340
tgatgatggg tttctagaca tttggacata taatgcagaa ttgttggttc tactggaaaa   2400
tgaaaggact ttggatttcc atgactccaa tgtgaagaat ctgtatgaga aagtaaaaag   2460
ccaattaaag aataatgcca aagaaatagg aaacgggtgt tttgagttct atcacaagtg   2520
taacaatgaa tgcatggaga gtgtgaaaaa tggtacctat gactatccaa aatattccga   2580
agaatcaaag ttaaacaggg agaaaattga tggagtgaaa ttggaatcaa tgggagtata   2640
ccagattctg gcgatctact caactgtcgc cagttccctg gttcttttgg tctccctggg   2700
ggcaatcagc ttctggatgt gttccaatgg gtctttgcag tgtagaatat gcatctaaga   2760
gctctaagtt aaaatgcttc ttcgtctcct atttataata tggtttgtta ttgttaattt   2820
tgttcttgta gaagagctta attaatcgtt gttgttatga aatactattt gtatgagatg   2880
aactggtgta atgtaattca tttacataag tggagtcaga atcagaatgt ttcctccata   2940
actaactaga catgaagacc tgccgcgtac aattgtctta tatttgaaca actaaaattg   3000
aacatctttt gccacaactt tataagtggt taatatagct caaatatatg gtcaagttca   3060
atagattaat aatggaaata tcagttatcg aaattcatta acaatcaact taacgttatt   3120
aactactaat tttatatcat cccctttgat aaatgatagt acaccaatta ggaaggagca   3180
tgctcgaggc ctggctggcc gaattc                                        3206
```

```
<210> SEQ ID NO 60
<211> LENGTH: 1788
<212> TYPE: DNA
<213> ORGANISM: Artificial Sequence
<220> FEATURE:
<223> OTHER INFORMATION: Synthesized fragment DraIII-Plasto(-84+1)-H1
      A/Brisbane/59/07-SacI.

<400> SEQUENCE: 60

cactttgtga gtctacactt tgattccctt caaacacata caaagagaag agactaatta     60
attaattaat catcttgaga gaaaatgaaa gtaaaactac tggtcctgtt atgcacattt    120
acagctacat atgcagacac aatatgtata ggctaccatg ctaacaactc gaccgacact    180
gttgacacag tacttgaaaa gaatgtgaca gtgacacact ctgtcaacct gcttgagaac    240
agtcacaatg gaaaactatg tctattaaaa ggaatagccc cactacaatt gggtaattgc    300
agcgttgccg ggtggatctt aggaaaccca gaatgcgaat tactgatttc caaggagtca    360
tggtcctaca ttgtagaaaa accaaatcct gagaatggaa catgttaccc agggcatttc    420
gctgactatg aggaactgag ggagcaattg agttcagtat cttcatttga gaggttcgaa    480
atattcccca aagaaagctc atggcccaac cacaccgtaa ccggagtgtc agcatcatgc    540
tcccataatg gggaaagcag tttttacaga aatttgctat ggctgacggg gaagaatggt    600
ttgtacccaa acctgagcaa gtcctatgca aacaacaaag aaaaagaagt ccttgtacta    660
```

```
tggggtgttc atcacccgcc aaacataggt gaccaaaagg ccctctatca tacagaaaat    720
gcttatgtct ctgtagtgtc ttcacattat agcagaaaat tcaccccaga aatagccaaa    780
agacccaaag taagagatca agaaggaaga atcaattact actggactct gcttgaaccc    840
ggggatacaa taatatttga ggcaaatgga aatctaatag cgccaagata tgctttcgca    900
ctgagtagag gctttggatc aggaatcatc aactcaaatg caccaatgga taaatgtgat    960
gcgaagtgcc aaacacctca gggagctata aacagcagtc ttcctttcca gaacgtacac   1020
ccagtcacaa taggagagtg tccaaagtat gtcaggagtg caaaattaag gatggttaca   1080
ggactaagga acatcccatc cattcaatcc agaggtttgt ttggagccat tgccggtttc   1140
attgaagggg ggtggactgg aatggtagat ggttggtatg gttatcatca tcagaatgag   1200
caaggatctg gctatgctgc agatcaaaaa agcacacaaa atgccattaa tgggattaca   1260
aacaaggtca attctgtaat tgagaaaatg aacactcaat tcacagcagt gggcaaagag   1320
ttcaacaaat tggaaagaag gatggaaaac ttgaataaaa aagttgatga tgggtttata   1380
gacatttgga catataatgc agaactgttg gttctactgg aaaatgaaag gactttggat   1440
ttccatgact ccaatgtgaa gaatctgtat gagaaagtaa aaagccagtt aaagaataat   1500
gctaaagaaa taggaaatgg gtgttttgag ttctatcaca agtgtaacga tgaatgcatg   1560
gagagtgtaa agaatggaac ttatgactat ccaaaatatt ccgaagaatc aaagttaaac   1620
agggagaaaa ttgatggagt gaaattggaa tcaatgggag tctatcagat tctggcgatc   1680
tactcaacag tcgccagttc tctggttctt ttggtctccc tgggggcaat cagcttctgg   1740
atgtgttcca atgggtcttt acagtgtaga atatgcatct aagagctc                1788
```

```
<210> SEQ ID NO 61
<211> LENGTH: 3185
<212> TYPE: DNA
<213> ORGANISM: Artificial Sequence
<220> FEATURE:
<223> OTHER INFORMATION: Synthesized 774 expression cassette from
      HindIII

<400> SEQUENCE: 61
```

```
aagcttgcta gcggcctcaa tggccctgca ggtcgactct agaggtaccc cgggctggta     60
tatttatatg ttgtcaaata actcaaaaac cataaaagtt taagttagca agtgtgtaca    120
tttttacttg aacaaaaata ttcacctact actgttataa atcattatta aacattagag    180
taaagaaata tggatgataa gaacaagagt agtgatattt tgacaacaat tttgttgcaa    240
catttgagaa aattttgttg ttctctcttt tcattggtca aaaacaatag agagagaaaa    300
aggaagaggg agaataaaaa cataatgtga gtatgagaga gaaagttgta caaaagttgt    360
accaaaatag ttgtacaaat atcattgagg aatttgacaa aagctacaca aataagggtt    420
aattgctgta aataaataag gatgacgcat tagagagatg taccattaga gaatttttgg    480
caagtcatta aaaagaaaga ataaattatt tttaaaatta aaagttgagt catttgatta    540
aacatgtgat tatttaatga attgatgaaa gagttggatt aaagttgtat tagtaattag    600
aatttggtgt caaatttaat ttgacatttg atcttttcct atatattgcc ccatagagtc    660
agttaactca tttttatatt tcatagatca aataagagaa ataacggtat attaatccct    720
ccaaaaaaaa aaaacggtat atttactaaa aaatctaagc cacgtaggag gataacagga    780
tccccgtagg aggataacat ccaatccaac caatcacaac aatcctgatg agataaccca    840
ctttaagccc acgcatctgt ggcacatcta cattatctaa atcacacatt cttccacaca    900
```

-continued

```
tctgagccac acaaaaacca atccacatct ttatcaccca ttctataaaa aatcacactt    960
tgtgagtcta cactttgatt cccttcaaac acatacaaag agaagagact aattaattaa   1020
ttaatcatct tgagagaaaa tgaaagtaaa actactggtc ctgttatgca catttacagc   1080
tacatatgca gacacaatat gtataggcta ccatgctaac aactcgaccg acactgttga   1140
cacagtactt gaaaagaatg tgacagtgac acactctgtc aacctgcttg agaacagtca   1200
caatggaaaa ctatgtctat taaaaggaat agccccacta caattgggta attgcagcgt   1260
tgccgggtgg atcttaggaa acccagaatg cgaattactg atttccaagg agtcatggtc   1320
ctacattgta gaaaaaccaa atcctgagaa tggaacatgt tacccagggc atttcgctga   1380
ctatgaggaa ctgagggagc aattgagttc agtatcttca tttgagaggt tcgaaatatt   1440
ccccaaagaa agctcatggc ccaaccacac cgtaaccgga gtgtcagcat catgctccca   1500
taatggggaa agcagttttt acagaaattt gctatggctg acggggaaga atggtttgta   1560
cccaaacctg agcaagtcct atgcaaacaa caaagaaaaa gaagtccttg tactatgggg   1620
tgttcatcac ccgccaaaca taggtgacca aaaggccctc tatcatacag aaaatgctta   1680
tgtctctgta gtgtcttcac attatagcag aaaattcacc ccagaaatag ccaaaagacc   1740
caaagtaaga gatcaagaag gaagaatcaa ttactactgg actctgcttg aacccgggga   1800
tacaataata tttgaggcaa atggaaatct aatagcgcca agatatgctt tcgcactgag   1860
tagaggcttt ggatcaggaa tcatcaactc aaatgcacca atggataaat gtgatgcgaa   1920
gtgccaaaca cctcagggag ctataaacag cagtcttcct ttccagaacg tacacccagt   1980
cacaatagga gagtgtccaa agtatgtcag gagtgcaaaa ttaaggatgg ttacaggact   2040
aaggaacatc ccatccattc aatccagagg tttgtttgga gccattgccg gtttcattga   2100
agggggtgg actggaatgg tagatggttg gtatggttat catcatcaga atgagcaagg   2160
atctggctat gctgcagatc aaaaaagcac acaaaatgcc attaatggga ttacaaacaa   2220
ggtcaattct gtaattgaga aaatgaacac tcaattcaca gcagtgggca aagagttcaa   2280
caaattggaa agaaggatgg aaaacttgaa taaaaaagtt gatgatgggt ttatagacat   2340
ttggacatat aatgcagaac tgttggttct actggaaaat gaaaggactt tggatttcca   2400
tgactccaat gtgaagaatc tgtatgagaa agtaaaaagc cagttaaaga ataatgctaa   2460
agaaatagga aatgggtgtt ttgagttcta tcacaagtgt aacgatgaat gcatggagag   2520
tgtaaagaat ggaacttatg actatccaaa atattccgaa gaatcaaagt taaacaggga   2580
gaaaattgat ggagtgaaat tggaatcaat gggagtctat cagattctgg cgatctactc   2640
aacagtcgcc agttctctgg ttcttttggt ctccctgggg gcaatcagct tctggatgtg   2700
ttccaatggg tctttacagt gtagaatatg catctaagag ctctaagtta aaatgcttct   2760
tcgtctccta tttataatat ggtttgttat tgttaatttt gttcttgtag aagagcttaa   2820
ttaatcgttg ttgttatgaa atactatttg tatgagatga actggtgtaa tgtaattcat   2880
ttacataagt ggagtcagaa tcagaatgtt tcctccataa ctaactagac atgaagacct   2940
gccgcgtaca attgtcttat atttgaacaa ctaaaattga acatcttttg ccacaacttt   3000
ataagtggtt aatatagctc aaatatatgg tcaagttcaa tagattaata atggaaatat   3060
cagttatcga aattcattaa caatcaactt aacgttatta actactaatt ttatatcatc   3120
ccctttgata aatgatagta caccaattag gaaggagcat gctcgaggcc tggctggccg   3180
aattc                                                               3185
```

-continued

```
<210> SEQ ID NO 62
<211> LENGTH: 2065
<212> TYPE: DNA
<213> ORGANISM: Artificial Sequence
<220> FEATURE:
<223> OTHER INFORMATION: Synthesized Expression cassette number 828,
      from PacI to AscI

<400> SEQUENCE: 62

ttaattaaga attcgagctc caccgcggaa acctcctcgg attccattgc ccagctatct     60

gtcactttat tgagaagata gtggaaaagg aaggtggctc ctacaaatgc catcattgcg    120

ataaaggaaa ggccatcgtt gaagatgcct ctgccgacag tggtcccaaa gatggacccc    180

cacccacgag gagcatcgtg gaaaaagaag acgttccaac cacgtcttca aagcaagtgg    240

attgatgtga tatctccact gacgtaaggg atgacgcaca atcccactat ccttcgcaag    300

acccttcctc tatataagga agttcatttc atttggagag gtattaaaat cttaataggt    360

tttgataaaa gcgaacgtgg ggaaacccga accaaacctt cttctaaact ctctctcatc    420

tctcttaaag caaacttctc tcttgtcttt cttgcgtgag cgatcttcaa cgttgtcaga    480

tcgtgcttcg gcaccagtac aacgttttct ttcactgaag cgaaatcaaa gatctctttg    540

tggacacgta gtgcggcgcc attaaataac gtgtacttgt cctattcttg tcggtgtggt    600

cttgggaaaa gaaagcttgc tggaggctgc tgttcagccc catacattac ttgttacgat    660

tctgctgact ttcggcgggt gcaatatctc tacttctgct tgacgaggta ttgttgcctg    720

tacttctttc ttcttcttct tgctgattgg ttctataaga aatctagtat tttctttgaa    780

acagagtttt cccgtggttt tcgaacttgg agaaagattg ttaagcttct gtatattctg    840

cccaaatttg tcgggcccat ggttttcaca cctcagatac ttggacttat gctttttttgg    900

atttcagcct ccagaggtga tattgtgcta actcagtctc cagccaccct gtctgtgact    960

ccaggagata gtgtcagtct ttcctgcagg gccagccaaa gtattagcaa caacctacac   1020

tggtttcaac aaaaatcgca tgagtctcca aggcttctca tcaagtatgc ttcccagtcc   1080

atatctggga tcccctccag gttcagtggc agtggatctg ggacagattt cactctcagt   1140

atcaacagtg tgaagactga agattttgga atgtttttct gtcaacagag taacagctgg   1200

cctctcacgt tcggtgatgg gacaaagctg gagctgaaac gggctgatgc tgcaccaact   1260

gtatccatct tcccaccatc cagtgagcag ttaacatctg gaggtgcctc agtcgtgtgc   1320

ttcttgaaca acttctaccc caaagacatc aatgtcaagt ggaagattga tggcagtgaa   1380

cgacaaaatg gcgtcctgaa cagttggact gatcaggaca gcaaagacag cacctacagc   1440

atgagcagca ccctcacgtt gaccaaggac gagtatgaac gacataacag ctatacctgt   1500

gaggccactc acaagacatc aacttcaccc attgtcaaga gcttcaacag gaatgagtgt   1560

tagaggccta ttttctttag tttgaattta ctgttattcg gtgtgcattt ctatgtttgg   1620

tgagcggttt tctgtgctca gagtgtgttt attttatgta atttaatttc tttgtgagct   1680

cctgtttagc aggtcgtccc ttcagcaagg acacaaaaag attttaattt tattaaaaaa   1740

aaaaaaaaaa aagaccggga attcgatatc aagcttatcg acctgcagat cgttcaaaca   1800

tttggcaata aagtttctta agattgaatc ctgttgccgg tcttgcgatg attatcatat   1860

aatttctgtt gaattacgtt aagcatgtaa taattaacat gtaatgcatg acgttattta   1920

tgagatgggt ttttatgatt agagtcccgc aattatacat ttaatacgcg atagaaaaca   1980

aaatatagcg cgcaaactag gataaattat cgcgcgcggt gtcatctatg ttactagatt   2040
```

ctagagtctc aagcttcggc gcgcc 2065

<210> SEQ ID NO 63
<211> LENGTH: 3194
<212> TYPE: DNA
<213> ORGANISM: Artificial Sequence
<220> FEATURE:
<223> OTHER INFORMATION: Synthesized Construct number 690, from HindIII to EcoRI

<400> SEQUENCE: 63
aagcttgcta gcggcctcaa tggccctgca ggtcgactct agaggtaccc cgggctggta 60
tatttatatg ttgtcaaata actcaaaaac cataaaagtt taagttagca agtgtgtaca 120
tttttacttg aacaaaaata ttcacctact actgttataa atcattatta aacattagag 180
taaagaaata tggatgataa gaacaagagt agtgatattt tgacaacaat tttgttgcaa 240
catttgagaa aattttgttg ttctctcttt tcattggtca aaaacaatag agagagaaaa 300
aggaagaggg agaataaaaa cataatgtga gtatgagaga gaaagttgta caaaagttgt 360
accaaaatag ttgtacaaat atcattgagg aatttgacaa aagctacaca aataagggtt 420
aattgctgta aataaataag gatgacgcat tagagagatg taccattaga gaatttttgg 480
caagtcatta aaaagaaaga ataaattatt tttaaaatta aaagttgagt catttgatta 540
aacatgtgat tatttaatga attgatgaaa gagttggatt aaagttgtat tagtaattag 600
aatttggtgt caaatttaat ttgacatttg atcttttcct atatattgcc ccatagagtc 660
agttaactca tttttatatt tcatagatca aataagagaa ataacggtat attaatccct 720
ccaaaaaaaa aaaacggtat atttactaaa aaatctaagc cacgtaggag gataacagga 780
tccccgtagg aggataacat ccaatccaac caatcacaac aatcctgatg agataaccca 840
ctttaagccc acgcatctgt ggcacatcta cattatctaa atcacacatt cttccacaca 900
tctgagccac acaaaaacca atccacatct ttatcaccca ttctataaaa aatcacactt 960
tgtgagtcta cactttgatt cccttcaaac acatacaaag agaagagact aattaattaa 1020
ttaatcatct tgagagaaaa tggagaaaat agtgcttctt cttgcaatag tcagtcttgt 1080
taaaagtgat cagatttgca ttggttacca tgcaaacaat tcaacagagc aggttgacac 1140
aatcatggaa aagaacgtta ctgttacaca tgcccaagac atactggaaa agacacacaa 1200
cgggaagctc tgcgatctag atggagtgaa gcctctaatt ttaagagatt gtagtgtagc 1260
tggatggctc ctcgggaacc caatgtgtga cgaattcatc aatgtaccgg aatggtctta 1320
catagtggag aaggccaatc caaccaatga cctctgttac ccagggcatt tcgctgacta 1380
tgaggaactg agggagcaat tgagttcagt atcttcattt gagaggttcg aaatattccc 1440
caaagaaagc tcatggccca accacaccgt aaccggagtg tcagcatcat gctcccataa 1500
tggggaaagc agtttttaca gaaatttgct atggctgacg gggaagaatg gtttgtaccc 1560
aaacctgagc aagtcctatg caaacaacaa agaaaaagaa gtccttgtac tatggggtgt 1620
tcatcacccg ccaaacatag gtgaccaaaa ggccctctat catacagaaa atgcttatgt 1680
ctctgtagtg tcttcacatt atagcagaaa attcacccca gaaatagcca aaagacccaa 1740
agtaagagat caagaaggaa gaatcaatta ctactggact ctgcttgaac ccggggatac 1800
aataatattt gaggcaaatg gaaatctaat agcgccaaga tatgctttcg cactgagtag 1860
aggctttgga tcaggaatta tgaaaagtga attggaatat ggtaactgca acaccaagtg 1920
tcaaactcca atgggggcga taaactctag tatgccattc cacaacatac accctctcac 1980

```
catcggggaa tgccccaaat atgtgaaatc aaacagatta gtccttgcaa cagggctcag   2040

aaatagccct caaagagaga gcagaagaaa aaagagagga ctatttggag ctatagcagg   2100

ttttatagag ggaggatggc agggaatggt agatggttgg tatgggtacc accatagcaa   2160

tgagcagggg agtgggtacg ctgcagacaa agaatccact caaaaggcaa tagatggagt   2220

caccaataag gtcaactcaa tcattgacaa aatgaacact cagtttgagg ccgttggaag   2280

ggaatttaat aacttagaaa ggagaataga gaatttaaac aagaagatgg aagacgggtt   2340

tctagatgtc tggacttata atgccgaact tctggttctc atggaaaatg agagaactct   2400

agactttcat gactcaaatg ttaagaacct ctacgacaag gtccgactac agcttaggga   2460

taatgcaaag gagctgggta acggttgttt cgagttctat cacaaatgtg ataatgaatg   2520

tatggaaagt ataagaaacg gaacgtacaa ctatccgcag tattcagaag aagcaagatt   2580

aaaaagagag gaaataagtg gggtaaaatt ggaatcaata ggaacttacc aaatactgtc   2640

aatttattca acagtggcga gttccctagc actggcaatc atgatggctg gtctatcttt   2700

atggatgtgc tccaatggat cgttacaatg cagaatttgc atttaagagc tctaagttaa   2760

aatgcttctt cgtctcctat ttataatatg gtttgttatt gttaattttg ttcttgtaga   2820

agagcttaat taatcgttgt tgttatgaaa tactatttgt atgagatgaa ctggtgtaat   2880

gtaattcatt tacataagtg gagtcagaat cagaatgttt cctccataac taactagaca   2940

tgaagacctg ccgcgtacaa ttgtcttata tttgaacaac taaaattgaa catcttttgc   3000

cacaacttta taagtggtta atatagctca aatatatggt caagttcaat agattaataa   3060

tggaaatatc agttatcgaa attcattaac aatcaactta acgttattaa ctactaattt   3120

tatatcatcc cctttgataa atgatagtac accaattagg aaggagcatg ctcgaggcct   3180

ggctggccga attc                                                     3194
```

<210> SEQ ID NO 64
<211> LENGTH: 3194
<212> TYPE: DNA
<213> ORGANISM: Artificial Sequence
<220> FEATURE:
<223> OTHER INFORMATION: Synthesized Construct number 691, from HindIII to EcoRI

<400> SEQUENCE: 64

```
aagcttgcta gcggcctcaa tggccctgca ggtcgactct agaggtaccc cgggctggta     60

tatttatatg ttgtcaaata actcaaaaac cataaaagtt taagttagca agtgtgtaca    120

tttttacttg aacaaaaata ttcacctact actgttataa atcattatta aacattagag    180

taaagaaata tggatgataa gaacaagagt agtgatattt tgacaacaat tttgttgcaa    240

catttgagaa aattttgttg ttctctcttt tcattggtca aaaacaatag agagagaaaa    300

aggaagaggg agaataaaaa cataatgtga gtatgagaga gaaagttgta caaaagttgt    360

accaaaatag ttgtacaaat atcattgagg aatttgacaa aagctacaca aataagggtt    420

aattgctgta aataaataag gatgacgcat tagagagatg taccattaga gaatttttgg    480

caagtcatta aaaagaaaga ataaattatt tttaaaatta aaagttgagt catttgatta    540

aacatgtgat tatttaatga attgatgaaa gagttggatt aaagttgtat tagtaattag    600

aatttggtgt caaatttaat ttgacatttg atcttttcct atatattgcc ccatagagtc    660

agttaactca tttttatatt tcatagatca aataagagaa ataacggtat attaatccct    720

ccaaaaaaaa aaaacggtat atttactaaa aaatctaagc cacgtaggag gataacagga    780
```

-continued

```
tccccgtagg aggataacat ccaatccaac caatcacaac aatcctgatg agataaccca    840
ctttaagccc acgcatctgt ggcacatcta cattatctaa atcacacatt cttccacaca    900
tctgagccac acaaaaacca atccacatct ttatcaccca ttctataaaa aatcacactt    960
tgtgagtcta cactttgatt cccttcaaac acatacaaag agaagagact aattaattaa   1020
ttaatcatct tgagagaaaa tggagaaaat agtgcttctt cttgcaatag tcagtcttgt   1080
taaaagtgat cagatttgca ttggttacca tgcaaacaat tcaacagagc aggttgacac   1140
aatcatggaa aagaacgtta ctgttacaca tgcccaagac atactggaaa agacacacaa   1200
cgggaagctc tgcctattaa aaggaatagc cccactacaa ttgggtaatt gcagcgttgc   1260
cgggtggatc ttaggaaacc cagaatgcga attactgatt tccaaggagt catggtccta   1320
cattgtagaa aaaccaaatc ctgagaatgg aacatgttac ccagggcatt tcgctgacta   1380
tgaggaactg agggagcaat tgagttcagt atcttcattt gagaggttcg aaatattccc   1440
caaagaaagc tcatggccca accacaccgt aaccggagtg tcagcatcat gctcccataa   1500
tggggaaagc agtttttaca gaaatttgct atggctgacg gggaagaatg gtttgtaccc   1560
aaacctgagc aagtcctatg caaacaacaa agaaaaagaa gtccttgtac tatggggtgt   1620
tcatcacccg ccaaacatag gtgaccaaaa ggccctctat catacagaaa atgcttatgt   1680
ctctgtagtg tcttcacatt atagcagaaa attcacccca gaaatagcca aaagacccaa   1740
agtaagagat caagaaggaa gaatcaatta ctactggact ctgcttgaac ccggggatac   1800
aataatattt gaggcaaatg gaaatctaat agcgccaaga tatgctttcg cactgagtag   1860
aggctttgga tcaggaatca tcaactcaaa tgcaccaatg gataaatgca acaccaagtg   1920
tcaaactcca atgggggcga taaactctag tatgccattc cacaacatac accctctcac   1980
catcggggaa tgccccaaat atgtgaaatc aaacagatta gtccttgcaa cagggctcag   2040
aaatagccct caaagagaga gcagaagaaa aaagagagga ctatttggag ctatagcagg   2100
ttttatagag ggaggatggc agggaatggt agatggttgg tatgggtacc accatagcaa   2160
tgagcagggg agtgggtacg ctgcagacaa agaatccact caaaaggcaa tagatggagt   2220
caccaataag gtcaactcaa tcattgacaa aatgaacact cagtttgagg ccgttggaag   2280
ggaatttaat aacttagaaa ggagaatag a gaatttaaac aagaagatgg aagacgggtt   2340
tctagatgtc tggacttata atgccgaact tctggttctc atggaaaatg agagaactct   2400
agactttcat gactcaaatg ttaagaacct ctacgacaag gtccgactac agcttaggga   2460
taatgcaaag gagctgggta acggttgttt cgagttctat cacaaatgtg ataatgaatg   2520
tatggaaagt ataagaaacg gaacgtacaa ctatccgcag tattcagaag aagcaagatt   2580
aaaaagagag gaaataagtg gggtaaaatt ggaatcaata ggaacttacc aaatactgtc   2640
aatttattca acagtggcga gttccctagc actggcaatc atgatggctg gtctatcttt   2700
atggatgtgc tccaatggat cgttacaatg cagaatttgc atttaagagc tctaagttaa   2760
aatgcttctt cgtctcctat ttataatatg gtttgttatt gttaattttg ttcttgtaga   2820
agagcttaat taatcgttgt tgttatgaaa tactatttgt atgagatgaa ctggtgtaat   2880
gtaattcatt tacataagtg gagtcagaat cagaatgttt cctccataac taactagaca   2940
tgaagacctg ccgcgtacaa ttgtcttata tttgaacaac taaaattgaa catcttttgc   3000
cacaacttta taagtggtta atatagctca aatatatggt caagttcaat agattaataa   3060
tggaaatatc agttatcgaa attcattaac aatcaactta acgttattaa ctactaattt   3120
tatatcatcc cctttgataa atgatagtac accaattagg aaggagcatg ctcgaggcct   3180
```

ggctggccga attc 3194

<210> SEQ ID NO 65
<211> LENGTH: 3206
<212> TYPE: DNA
<213> ORGANISM: Artificial Sequence
<220> FEATURE:
<223> OTHER INFORMATION: Synthesized Construct number 696, from HindIII to EcoRI

<400> SEQUENCE: 65
aagcttgcta gcggcctcaa tggccctgca ggtcgactct agaggtaccc cgggctggta 60
tatttatatg ttgtcaaata actcaaaaac cataaaagtt taagttagca agtgtgtaca 120
tttttacttg aacaaaaata ttcacctact actgttataa atcattatta aacattagag 180
taaagaaata tggatgataa gaacaagagt agtgatattt tgacaacaat tttgttgcaa 240
catttgagaa aattttgttg ttctctcttt tcattggtca aaaacaatag agagagaaaa 300
aggaagaggg agaataaaaa cataatgtga gtatgagaga gaaagttgta caaaagttgt 360
accaaaatag ttgtacaaat atcattgagg aatttgacaa aagctacaca aataagggtt 420
aattgctgta aataaataag gatgacgcat tagagagatg taccattaga gaatttttgg 480
caagtcatta aaaagaaaga ataaattatt tttaaaatta aaagttgagt catttgatta 540
aacatgtgat tatttaatga attgatgaaa gagttggatt aaagttgtat tagtaattag 600
aatttggtgt caaatttaat ttgacatttg atcttttcct atatattgcc ccatagagtc 660
agttaactca tttttatatt tcatagatca aataagagaa ataacggtat attaatccct 720
ccaaaaaaaa aaaacggtat atttactaaa aaatctaagc cacgtaggag gataacagga 780
tccccgtagg aggataacat ccaatccaac caatcacaac aatcctgatg agataaccca 840
ctttaagccc acgcatctgt ggcacatcta cattatctaa atcacacatt cttccacaca 900
tctgagccac acaaaaacca atccacatct ttatcaccca ttctataaaa aatcacactt 960
tgtgagtcta cactttgatt cccttcaaac acatacaaag agaagagact aattaattaa 1020
ttaatcatct tgagagaaaa tggcgaaaaa cgttgcgatt ttcggcttat tgttttctct 1080
tcttgtgttg gttccttctc agatcttcgc tgacacaata tgtataggct accatgccaa 1140
caactcaacc gacactgttg acacagtact tgagaagaat gtgacagtga cacactctgt 1200
caacctactt gaggacagtc acaatggaaa actatgtcta ctaaaaggaa tagccccact 1260
acaattgggt aattgcagcg ttgccggatg gatcttagga aacccagaat gcgaattact 1320
gatttccaag gaatcatggt cctacattgt agaaacacca aatcctgaga atggaacatg 1380
ttacccaggg agtttcaacg actatgaaga actgaaacac ctattgagca gaataaacca 1440
ttttgagaaa attcaaatca tccccaaaag ttcttggtcc gatcatgaag cctcatcagg 1500
agttagctca gcatgtccat acctgggaag tccctccttt tttagaaatg tggtatggct 1560
tatcaaaaag aacagtacat acccaacaat aaagaaaagc tacaataata ccaaccaaga 1620
ggatcttttg gtactgtggg gaattcacca tcctaatgat gcggcagagc agacaaggct 1680
atatcaaaac ccaaccacct atatttccat tgggacatca acactaaacc agagattggt 1740
accaaaaata gctactagat ccaaagtaaa cgggcaaagt ggaaggatgg agttcttctg 1800
gacaatttta aaacctaatg atgcaatcaa cttcgagagt aatggaaatt tcattgctcc 1860
agaatatgca tacaaaattg tcaagaaagg ggactcagca atcatcacct caaatgcacc 1920
aatggatgaa tgtgatgcga agtgtcaaac acctcaggga gctataaaca gcagtcttcc 1980
tttccagaat gtacacccag tcacaatagg agagtgtcca aagtatgtca ggagtgcaaa 2040
attaaggatg gttacaggac taaggaacat cccatccatt caatccagag gtttgtttgg 2100
agccattgcc ggtttcattg aagggggggtg gactggaatg gtagatgggt ggtatggtta 2160
tcatcatcag aatgagcaag gatctggcta tgctgcagat caaaaaagta cacaaaatgc 2220
cattaacggg attacaaaca aggtcaattc tgtaattgag aaaatgaaca ctcaattcac 2280
agctgtgggc aaagagttca acaaattgga aagaaggatg gaaaacttaa ataaaaaagt 2340
tgatgatggg tttctagaca tttggacata taatgcagaa ttgttggttc tactggaaaa 2400
tgaaaggact ttggatttcc atgactccaa tgtgaagaat ctgtatgaga aagtaaaaag 2460
ccaattaaag aataatgcca aagaaatagg aaacgggtgt tttgagttct atcacaagtg 2520
taacaatgaa tgcatggaga gtgtgaaaaa tggtacctat gactatccaa aatattccga 2580
agaatcaaag ttaaacaggg agaaaattga tggagtgaaa ttggaatcaa tgggagtata 2640
ccagattctg gcgatctact caactgtcgc cagttccctg gttcttttgg tctccctggg 2700
ggcaatcagc ttctggatgt gttccaatgg gtctttgcag tgtagaatat gcatctaaga 2760
gctctaagtt aaaatgcttc ttcgtctcct atttataata tggtttgtta ttgttaattt 2820
tgttcttgta gaagagctta attaatcgtt gttgttatga aatactattt gtatgagatg 2880
aactggtgta atgtaattca tttacataag tggagtcaga atcagaatgt ttcctccata 2940
actaactaga catgaagacc tgccgcgtac aattgtctta tatttgaaca actaaaattg 3000
aacatctttt gccacaactt tataagtggt taatatagct caaatatatg gtcaagttca 3060
atagattaat aatggaaata tcagttatcg aaattcatta acaatcaact taacgttatt 3120
aactactaat tttatatcat ccccttttgat aaatgatagt acaccaatta ggaaggagca 3180
tgctcgaggc ctggctggcc gaattc 3206

<210> SEQ ID NO 66
<211> LENGTH: 3058
<212> TYPE: DNA
<213> ORGANISM: Artificial Sequence
<220> FEATURE:
<223> OTHER INFORMATION: Synthesized Construct 732, from PacI to AscI

<400> SEQUENCE: 66
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780

-continued

```
acagagtttt cccgtggttt tcgaacttgg agaaagattg ttaagcttct gtatattctg    840
cccaaatttg tcgggcccat gaaagtaaaa ctactggtcc tgttatgcac atttacagct    900
acatatgcag acacaatatg tataggctac catgctaaca actcgaccga cactgttgac    960
acagtacttg aaaagaatgt gacagtgaca cactctgtca acctgcttga gaacagtcac   1020
aatggaaaac tatgtctatt aaaaggaata gccccactac aattgggtaa ttgcagcgtt   1080
gccgggtgga tcttaggaaa cccagaatgc gaattactga tttccaagga gtcatggtcc   1140
tacattgtag aaaaaccaaa tcctgagaat ggaacatgtt acccagggca tttcgctgac   1200
tatgaggaac tgagggagca attgagttca gtatcttcat ttgagaggtt cgaaatattc   1260
cccaaagaaa gctcatggcc caaccacacc gtaaccggag tgtcagcatc atgctcccat   1320
aatggggaaa gcagtttttta cagaaatttg ctatggctga cggggaagaa tggtttgtac   1380
ccaaacctga gcaagtccta tgcaaacaac aaagaaaaag aagtccttgt actatggggt   1440
gttcatcacc cgccaaacat aggtgaccaa aaggccctct atcatacaga aaatgcttat   1500
gtctctgtag tgtcttcaca ttatagcaga aaattcaccc cagaaatagc caaaagaccc   1560
aaagtaagag atcaagaagg aagaatcaat tactactgga ctctgcttga acccggggat   1620
acaataatat ttgaggcaaa tggaaatcta atagcgccaa gatatgcttt cgcactgagt   1680
agaggctttg gatcaggaat catcaactca aatgcaccaa tggataaatg tgatgcgaag   1740
tgccaaacac ctcagggagc tataaacagc agtcttcctt tccagaacgt acacccagtc   1800
acaataggag agtgtccaaa gtatgtcagg agtgcaaaat taaggatggt tacaggacta   1860
aggaacatcc catccattca atccagaggt ttgtttggag ccattgccgg tttcattgaa   1920
ggggggtgga ctggaatggt agatggttgg tatggttatc atcatcagaa tgagcaagga   1980
tctggctatg ctgcagatca aaaaagcaca caaaatgcca ttaatgggat tacaaacaag   2040
gtcaattctg taattgagaa aatgaacact caattcacag cagtgggcaa agagttcaac   2100
aaattggaaa gaaggatgga aaacttgaat aaaaaagttg atgatgggtt tatagacatt   2160
tggacatata atgcagaact gttggttcta ctggaaaatg aaaggacttt ggatttccat   2220
gactccaatg tgaagaatct gtatgagaaa gtaaaaagcc agttaaagaa taatgctaaa   2280
gaaataggaa atgggtgttt tgagttctat cacaagtgta acgatgaatg catggagagt   2340
gtaaagaatg gaacttatga ctatccaaaa tattccgaag aatcaaagtt aaacagggag   2400
aaaattgatg gagtgaaatt ggaatcaatg ggagtctatc agattctggc gatctactca   2460
acagtcgcca gttctctggt tcttttggtc tccctggggg caatcagctt ctggatgtgt   2520
tccaatgggt ctttacagtg tagaatatgc atctaaaggc ctattttctt tagtttgaat   2580
ttactgttat tcggtgtgca tttctatgtt tggtgagcgg ttttctgtgc tcagagtgtg   2640
tttattttat gtaatttaat ttctttgtga gctcctgttt agcaggtcgt cccttcagca   2700
aggacacaaa aagattttaa ttttattaaa aaaaaaaaaa aaaaagaccg ggaattcgat   2760
atcaagctta tcgacctgca gatcgttcaa acatttggca ataaagtttc ttaagattga   2820
atcctgttgc cggtcttgcg atgattatca tataatttct gttgaattac gttaagcatg   2880
taataattaa catgtaatgc atgacgttat ttatgagatg ggtttttatg attagagtcc   2940
cgcaattata catttaatac gcgatagaaa acaaaatata gcgcgcaaac taggataaat   3000
tatcgcgcgc ggtgtcatct atgttactag attctagagt ctcaagcttc ggcgcgcc     3058
```

<210> SEQ ID NO 67
<211> LENGTH: 1719

-continued

<212> TYPE: DNA
<213> ORGANISM: Artificial Sequence
<220> FEATURE:
<223> OTHER INFORMATION: Synthesized construct number 787

<400> SEQUENCE: 67

```
atggcgaaaa acgttgcgat tttcggctta ttgttttctc ttcttgtgtt ggttccttct     60

cagatcttcg ctgacacaat atgtataggc taccatgcta acaactcgac cgacactgtt    120

gacacagtac ttgaaaagaa tgtgacagtg acacactctg tcaacctgct tgagaacagt    180

cacaatggaa aactatgtct attaaaagga atagccccac tacaattggg taattgcagc    240

gttgccgggt ggatcttagg aaacccagaa tgcgaattac tgatttccaa ggagtcatgg    300

tcctacattg tagaaaaacc aaatcctgag aatggaacat gttacccagg gcatttcgct    360

gactatgagg aactgaggga gcaattgagt tcagtatctt catttgagag gttcgaaata    420

ttccccaaag aaagctcatg gcccaaccac accgtaaccg gagtgtcagc atcatgctcc    480

cataatgggg aaagcagttt ttacagaaat ttgctatggc tgacggggaa gaatggtttg    540

tacccaaacc tgagcaagtc ctatgcaaac aacaaagaaa aagaagtcct tgtactatgg    600

ggtgttcatc acccgccaaa cataggtgac caaaaggccc tctatcatac agaaaatgct    660

tatgtctctg tagtgtcttc acattatagc agaaaattca ccccagaaat agccaaaaga    720

cccaaagtaa gagatcaaga aggaagaatc aattactact ggactctgct tgaacccggg    780

gatacaataa tatttgaggc aaatggaaat ctaatagcgc caagatatgc tttcgcactg    840

agtagaggct ttggatcagg aatcatcaac tcaaatgcac caatggataa atgtgatgcg    900

aagtgccaaa cacctcaggg agctataaac agcagtcttc ctttccagaa cgtacaccca    960

gtcacaatag gagagtgtcc aaagtatgtc aggagtgcaa aattaaggat ggttacagga   1020

ctaaggaaca tcccatccat tcaatccaga ggtttgtttg gagccattgc cggtttcatt   1080

gaagggggtt ggactggaat ggtagatggt tggtatggtt atcatcatca gaatgagcaa   1140

ggatctggct atgctgcaga tcaaaaaagc acacaaaatg ccattaatgg gattacaaac   1200

aaggtcaatt ctgtaattga gaaaatgaac actcaattca cagcagtggg caaagagttc   1260

aacaaattgg aaagaaggat ggaaaacttg aataaaaaag ttgatgatgg gtttatagac   1320

atttggacat ataatgcaga actgttggtt ctactggaaa atgaaaggac tttggatttc   1380

catgactcca atgtgaagaa tctgtatgag aaagtaaaaa gccagttaaa gaataatgct   1440

aaagaaatag gaaatgggtg ttttgagttc tatcacaagt gtaacgatga atgcatggag   1500

agtgtaaaga atggaactta tgactatcca aaatattccg aagaatcaaa gttaaacagg   1560

gagaaaattg atggagtgaa attggaatca atgggagtct atcagattct ggcgatctac   1620

tcaacagtcg ccagttctct ggttcttttg gtctccctgg gggcaatcag cttctggatg   1680

tgttccaatg ggtctttaca gtgtagaata tgcatctaa                          1719
```

<210> SEQ ID NO 68
<211> LENGTH: 3079
<212> TYPE: DNA
<213> ORGANISM: Artificial Sequence
<220> FEATURE:
<223> OTHER INFORMATION: Synthesized Construct number 733, from PacI to
AscI

<400> SEQUENCE: 68

```
ttaattaaga attcgagctc caccgcggaa acctcctcgg attccattgc ccagctatct     60

gtcactttat tgagaagata gtggaaaagg aaggtggctc ctacaaatgc catcattgcg    120
```

-continued

```
ataaaggaaa ggccatcgtt gaagatgcct ctgccgacag tggtcccaaa gatggacccc    180
cacccacgag gagcatcgtg gaaaaagaag acgttccaac cacgtcttca aagcaagtgg    240
attgatgtga tatctccact gacgtaaggg atgacgcaca atcccactat ccttcgcaag    300
acccttcctc tatataagga agttcatttc atttggagag gtattaaaat cttaataggt    360
tttgataaaa gcgaacgtgg ggaaacccga accaaacctt cttctaaact ctctctcatc    420
tctcttaaag caaacttctc tcttgtcttt cttgcgtgag cgatcttcaa cgttgtcaga    480
tcgtgcttcg gcaccagtac aacgttttct ttcactgaag cgaaatcaaa gatctctttg    540
tggacacgta gtgcggcgcc attaaataac gtgtacttgt cctattcttg tcggtgtggt    600
cttgggaaaa gaaagcttgc tggaggctgc tgttcagccc catacattac ttgttacgat    660
tctgctgact ttcggcgggt gcaatatctc tacttctgct tgacgaggta ttgttgcctg    720
tacttctttc ttcttcttct tgctgattgg ttctataaga aatctagtat tttctttgaa    780
acagagtttt cccgtggttt tcgaacttgg agaaagattg ttaagcttct gtatattctg    840
cccaaatttg tcgggcccat ggcgaaaaac gttgcgattt tcggcttatt gttttctctt    900
cttgtgttgg ttccttctca gatcttcgct gacacaatat gtataggcta ccatgctaac    960
aactcgaccg acactgttga cacagtactt gaaaagaatg tgacagtgac acactctgtc   1020
aacctgcttg agaacagtca caatggaaaa ctatgtctat taaaaggaat agccccacta   1080
caattgggta attgcagcgt tgccgggtgg atcttaggaa acccagaatg cgaattactg   1140
atttccaagg agtcatggtc ctacattgta gaaaaaccaa atcctgagaa tggaacatgt   1200
tacccagggc atttcgctga ctatgaggaa ctgagggagc aattgagttc agtatcttca   1260
tttgagaggt tcgaaatatt ccccaaagaa agctcatggc ccaaccacac cgtaaccgga   1320
gtgtcagcat catgctccca taatggggaa agcagttttt acagaaattt gctatggctg   1380
acggggaaga atggtttgta cccaaacctg agcaagtcct atgcaaacaa caaagaaaaa   1440
gaagtccttg tactatgggg tgttcatcac ccgccaaaca taggtgacca aaaggccctc   1500
tatcatacag aaaatgctta tgtctctgta gtgtcttcac attatagcag aaaattcacc   1560
ccagaaatag ccaaaagacc caaagtaaga gatcaagaag gaagaatcaa ttactactgg   1620
actctgcttg aacccgggga tacaataata tttgaggcaa atggaaatct aatagcgcca   1680
agatatgctt tcgcactgag tagaggcttt ggatcaggaa tcatcaactc aaatgcacca   1740
atggataaat gtgatgcgaa gtgccaaaca cctcagggag ctataaacag cagtcttcct   1800
ttccagaacg tacacccagt cacaatagga gagtgtccaa agtatgtcag gagtgcaaaa   1860
ttaaggatgg ttacaggact aaggaacatc ccatccattc aatccagagg tttgtttgga   1920
gccattgccg gtttcattga aggggggtgg actggaatgg tagatggttg gtatggttat   1980
catcatcaga atgagcaagg atctggctat gctgcagatc aaaaaagcac acaaaatgcc   2040
attaatggga ttacaaacaa ggtcaattct gtaattgaga aaatgaacac tcaattcaca   2100
gcagtgggca aagagttcaa caaattggaa agaaggatgg aaaacttgaa taaaaaagtt   2160
gatgatgggt ttatagacat ttggacatat aatgcagaac tgttggttct actggaaaat   2220
gaaaggactt tggatttcca tgactccaat gtgaagaatc tgtatgagaa agtaaaaagc   2280
cagttaaaga ataatgctaa agaaatagga aatgggtgtt ttgagttcta tcacaagtgt   2340
aacgatgaat gcatggagag tgtaaagaat ggaacttatg actatccaaa atattccgaa   2400
gaatcaaagt taaacaggga gaaaattgat ggagtgaaat tggaatcaat gggagtctat   2460
```

-continued

```
cagattctgg cgatctactc aacagtcgcc agttctctgg ttcttttggt ctccctgggg   2520

gcaatcagct tctggatgtg ttccaatggg tctttacagt gtagaatatg catctaaagg   2580

cctattttct ttagtttgaa tttactgtta ttcggtgtgc atttctatgt ttggtgagcg   2640

gttttctgtg ctcagagtgt gtttatttta tgtaatttaa tttctttgtg agctcctgtt   2700

tagcaggtcg tcccttcagc aaggacacaa aaagatttta attttattaa aaaaaaaaaa   2760

aaaaaagacc gggaattcga tatcaagctt atcgacctgc agatcgttca aacatttggc   2820

aataaagttt cttaagattg aatcctgttg ccggtcttgc gatgattatc atataatttc   2880

tgttgaatta cgttaagcat gtaataatta acatgtaatg catgacgtta tttatgagat   2940

gggtttttat gattagagtc ccgcaattat acatttaata cgcgatagaa aacaaaatat   3000

agcgcgcaaa ctaggataaa ttatcgcgcg cggtgtcatc tatgttacta gattctagag   3060

tctcaagctt cggcgcgcc                                                3079
```

<210> SEQ ID NO 69
<211> LENGTH: 3067
<212> TYPE: DNA
<213> ORGANISM: Artificial Sequence
<220> FEATURE:
<223> OTHER INFORMATION: Synthesized Construct 734, from PacI to AscI

<400> SEQUENCE: 69

```
ttaattaaga attcgagctc caccgcggaa acctcctcgg attccattgc ccagctatct     60

gtcactttat tgagaagata gtggaaaagg aaggtggctc ctacaaatgc catcattgcg    120

ataaaggaaa ggccatcgtt gaagatgcct ctgccgacag tggtcccaaa gatggacccc    180

cacccacgag gagcatcgtg gaaaaagaag acgttccaac cacgtcttca aagcaagtgg    240

attgatgtga tatctccact gacgtaaggg atgacgcaca atcccactat ccttcgcaag    300

acccttcctc tatataagga agttcatttc atttggagag gtattaaaat cttaataggt    360

tttgataaaa gcgaacgtgg ggaaacccga accaaacctt cttctaaact ctctctcatc    420

tctcttaaag caaacttctc tcttgtcttt cttgcgtgag cgatcttcaa cgttgtcaga    480

tcgtgcttcg gcaccagtac aacgttttct ttcactgaag cgaaatcaaa gatctctttg    540

tggacacgta gtgcggcgcc attaaataac gtgtacttgt cctattcttg tcggtgtggt    600

cttgggaaaa gaaagcttgc tggaggctgc tgttcagccc catacattac ttgttacgat    660

tctgctgact ttcggcgggt gcaatatctc tacttctgct tgacgaggta ttgttgcctg    720

tacttctttc ttcttcttct tgctgattgg ttctataaga aatctagtat tttctttgaa    780

acagagtttt cccgtggttt tcgaacttgg agaaagattg ttaagcttct gtatattctg    840

cccaaatttg tcgggcccat ggagaaaata gtgcttcttc ttgcaatagt cagtcttgtt    900

aaaagtgatc agatttgcat tggttaccat gcaaacaatt caacagagca ggttgacaca    960

atcatggaaa agaacgttac tgttacacat gcccaagaca tactggaaaa gacacacaac   1020

gggaagctct gcgatctaga tggagtgaag cctctaattt taagagattg tagtgtagct   1080

ggatggctcc tcgggaaccc aatgtgtgac gaattcatca atgtaccgga atggtcttac   1140

atagtggaga aggccaatcc aaccaatgac ctctgttacc cagggcattt cgctgactat   1200

gaggaactga gggagcaatt gagttcagta tcttcatttg agaggttcga aatattcccc   1260

aaagaaagct catggcccaa ccacaccgta accggagtgt cagcatcatg ctcccataat   1320

ggggaaagca gtttttacag aaatttgcta tggctgacgg ggaagaatgg tttgtaccca   1380

aacctgagca agtcctatgc aaacaacaaa gaaaaagaag tccttgtact atggggtgtt   1440
```

-continued catcacccgc caaacatagg tgaccaaaag gccctctatc atacagaaaa tgcttatgtc 1500
tctgtagtgt cttcacatta tagcagaaaa ttcaccccag aaatagccaa aagacccaaa 1560
gtaagagatc aagaaggaag aatcaattac tactggactc tgcttgaacc cggggataca 1620
ataatatttg aggcaaatgg aaatctaata gcgccaagat atgctttcgc actgagtaga 1680
ggctttggat caggaattat gaaaagtgaa ttggaatatg gtaactgcaa caccaagtgt 1740
caaactccaa tgggggcgat aaactctagt atgccattcc acaacataca ccctctcacc 1800
atcggggaat gccccaaata tgtgaaatca aacagattag tccttgcaac agggctcaga 1860
aatagccctc aaagagagag cagaagaaaa aagagaggac tatttggagc tatagcaggt 1920
tttatagagg gaggatggca gggaatggta gatggttggt atgggtacca ccatagcaat 1980
gagcagggga gtgggtacgc tgcagacaaa gaatccactc aaaaggcaat agatggagtc 2040
accaataagg tcaactcaat cattgacaaa atgaacactc agtttgaggc cgttggaagg 2100
gaatttaata acttagaaag gagaatagag aatttaaaca agaagatgga agacgggttt 2160
ctagatgtct ggacttataa tgccgaactt ctggttctca tggaaaatga gagaactcta 2220
gactttcatg actcaaatgt taagaacctc tacgacaagg tccgactaca gcttagggat 2280
aatgcaaagg agctgggtaa cggttgtttc gagttctatc acaaatgtga taatgaatgt 2340
atggaaagta taagaaacgg aacgtacaac tatccgcagt attcagaaga agcaagatta 2400
aaaagagagg aaataagtgg ggtaaaattg gaatcaatag gaacttacca aatactgtca 2460
atttattcaa cagtggcgag ttccctagca ctggcaatca tgatggctgg tctatcttta 2520
tggatgtgct ccaatggatc gttacaatgc agaatttgca tttaaaggcc tattttcttt 2580
agtttgaatt tactgttatt cggtgtgcat ttctatgttt ggtgagcggt tttctgtgct 2640
cagagtgtgt ttattttatg taatttaatt tctttgtgag ctcctgttta gcaggtcgtc 2700
ccttcagcaa ggacacaaaa agattttaat tttattaaaa aaaaaaaaaa aaaagaccgg 2760
gaattcgata tcaagcttat cgacctgcag atcgttcaaa catttggcaa taaagtttct 2820
taagattgaa tcctgttgcc ggtcttgcga tgattatcat ataatttctg ttgaattacg 2880
ttaagcatgt aataattaac atgtaatgca tgacgttatt tatgagatgg gtttttatga 2940
ttagagtccc gcaattatac atttaatacg cgatagaaaa caaaatatag cgcgcaaact 3000
aggataaatt atcgcgcgcg gtgtcatcta tgttactaga ttctagagtc tcaagcttcg 3060
gcgcgcc 3067

<210> SEQ ID NO 70
<211> LENGTH: 1791
<212> TYPE: DNA
<213> ORGANISM: Artificial Sequence
<220> FEATURE:
<223> OTHER INFORMATION: Synthesized fragment DraIII-Plasto(-84+1)-H3 A/Brisbane/10/07-SacI

<400> SEQUENCE: 70
cactttgtga gtctacactt tgattccctt caaacacata caaagagaag agactaatta 60
attaattaat catcttgaga gaaaatgaag actatcattg ctttgagcta cattctatgt 120
ctggttttca ctcaaaaact tcccggaaat gacaacagca cggcaacgct gtgccttggg 180
caccatgcag taccaaacgg aacgatagtg aaaacaatca cgaatgacca aattgaagtt 240
actaatgcta ctgagctggt tcagagttcc tcaacaggtg aaatatgcga cagtcctcat 300
cagatccttg atggagaaaa ctgcacacta atagatgctc tattgggaga ccctcagtgt 360
gatggcttcc aaaataagaa atgggacctt tttgttgaac gcagcaaagc ctacagcaac 420
tgttaccctt atgatgtgcc ggattatgcc tcccttaggt cactagttgc ctcatccggc 480
acactggagt ttaacaatga aagtttcaat tggactggag tcactcaaaa cggaacaagc 540
tctgcttgca taaggagatc taataacagt ttctttagta gattgaattg gttgacccac 600
ttaaaattca aatacccagc attgaacgtg actatgccaa acaatgaaaa atttgacaaa 660
ttgtacattt ggggggttca ccacccgggt acggacaatg accaaatctt cctgtatgct 720
caagcatcag gaagaatcac agtctctacc aaaagaagcc aacaaactgt aatcccgaat 780
atcggatcta gacccagagt aaggaatatc cccagcagaa taagcatcta ttggacaata 840
gtaaaaccgg gagacatact tttgattaac agcacaggga atctaattgc tcctaggggt 900
tacttcaaaa tacgaagtgg gaaaagctca ataatgagat cagatgcacc cattggcaaa 960
tgcaattctg aatgcatcac tccaaacgga agcattccca atgacaaacc attccaaaat 1020
gtaaacagga tcacatacgg ggcctgtccc agatatgtta agcaaaacac tctgaaattg 1080
gcaacaggga tgcgaaatgt accagagaaa caaactagag gcatatttgg cgcaatcgcg 1140
ggtttcatag aaaatggttg ggagggaatg gtggatggtt ggtatggttt caggcatcaa 1200
aattctgagg gaataggaca agcagcagat ctcaaaagca ctcaagcagc aatcgatcaa 1260
atcaatggga agctgaatag gttgatcggg aaaaccaacg agaaattcca tcagattgaa 1320
aaagagttct cagaagtcga agggagaatc caggaccttg agaaatatgt tgaggacacc 1380
aaaatagatc tctggtcata caacgcggag cttcttgttg ccctggagaa ccaacataca 1440
attgatctaa ctgactcaga aatgaacaaa ctgtttgaaa aaacaaagaa gcaactgagg 1500
gaaaatgctg aggatatggg caatggttgt ttcaaaatat accacaaatg tgacaatgcc 1560
tgcataggat caatcagaaa tggaacttat gaccacgatg tatacagaga tgaagcatta 1620
aacaaccggt tccagatcaa gggcgttgag ctgaagtcag gatacaaaga ttggatacta 1680
tggatttcct ttgccatatc atgttttttg ctttgtgttg ctttgttggg gttcatcatg 1740
tgggcctgcc aaaaaggcaa cattaggtgc aacatttgca tttgagagct c 1791

<210> SEQ ID NO 71
<211> LENGTH: 3085
<212> TYPE: DNA
<213> ORGANISM: Artificial Sequence
<220> FEATURE:
<223> OTHER INFORMATION: Synthesized Construct 736, from PacI to AscI

<400> SEQUENCE: 71
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600

-continued

```
cttgggaaaa gaaagcttgc tggaggctgc tgttcagccc catacattac ttgttacgat    660
tctgctgact ttcggcgggt gcaatatctc tacttctgct tgacgaggta ttgttgcctg    720
tacttctttc ttcttcttct tgctgattgg ttctataaga aatctagtat tttctttgaa    780
acagagtttt cccgtggttt tcgaacttgg agaaagattg ttaagcttct gtatattctg    840
cccaaatttg tcgggcccat ggcgaaaaac gttgcgattt tcggcttatt gttttctctt    900
cttgtgttgg ttccttctca gatcttcgct caaaaacttc ccggaaatga caacagcacg    960
gcaacgctgt gccttgggca ccatgcagta ccaaacggaa cgatagtgaa aacaatcacg   1020
aatgaccaaa ttgaagttac taatgctact gagctggttc agagttcctc aacaggtgaa   1080
atatgcgaca gtcctcatca gatccttgat ggagaaaact gcacactaat agatgctcta   1140
ttgggagacc ctcagtgtga tggcttccaa aataagaaat gggacctttt tgttgaacgc   1200
agcaaagcct acagcaactg ttacccttat gatgtgccgg attatgcctc ccttaggtca   1260
ctagttgcct catccggcac actggagttt aacaatgaaa gtttcaattg gactggagtc   1320
actcaaaacg gaacaagctc tgcttgcata aggagatcta ataacagttt ctttagtaga   1380
ttgaattggt tgacccactt aaaattcaaa tacccagcat tgaacgtgac tatgccaaac   1440
aatgaaaaat ttgacaaatt gtacatttgg ggggttcacc acccgggtac ggacaatgac   1500
caaatcttcc tgtatgctca agcatcagga agaatcacag tctctaccaa aagaagccaa   1560
caaactgtaa tcccgaatat cggatctaga cccagagtaa ggaatatccc cagcagaata   1620
agcatctatt ggacaatagt aaaaccggga gacatacttt tgattaacag cacagggaat   1680
ctaattgctc ctaggggtta cttcaaaata cgaagtggga aaagctcaat aatgagatca   1740
gatgcaccca ttggcaaatg caattctgaa tgcatcactc caaacggaag cattcccaat   1800
gacaaaccat tccaaaatgt aaacaggatc acatacgggg cctgtcccag atatgttaag   1860
caaaacactc tgaaattggc aacagggatg cgaaatgtac cagagaaaca aactagaggc   1920
atatttggcg caatcgcggg tttcatagaa aatggttggg agggaatggt ggatggttgg   1980
tatggtttca ggcatcaaaa ttctgaggga ataggacaag cagcagatct caaaagcact   2040
caagcagcaa tcgatcaaat caatgggaag ctgaataggt tgatcgggaa aaccaacgag   2100
aaattccatc agattgaaaa agagttctca gaagtcgaag ggagaatcca ggaccttgag   2160
aaatatgttg aggacaccaa aatagatctc tggtcataca acgcggagct tcttgttgcc   2220
ctggagaacc aacatacaat tgatctaact gactcagaaa tgaacaaact gtttgaaaaa   2280
acaaagaagc aactgaggga aaatgctgag gatatgggca atggttgttt caaaatatac   2340
cacaaatgtg acaatgcctg cataggatca atcagaaatg gaacttatga ccacgatgta   2400
tacagagatg aagcattaaa caaccggttc cagatcaagg gcgttgagct gaagtcagga   2460
tacaaagatt ggatactatg gatttccttt gccatatcat gtttttttgct ttgtgttgct   2520
ttgttggggt tcatcatgtg ggcctgccaa aaaggcaaca ttaggtgcaa catttgcatt   2580
tgaaggccta ttttctttag tttgaattta ctgttattcg gtgtgcattt ctatgtttgg   2640
tgagcggttt tctgtgctca gagtgtgttt attttatgta atttaatttc tttgtgagct   2700
cctgtttagc aggtcgtccc ttcagcaagg acacaaaaag attttaattt tattaaaaaa   2760
aaaaaaaaaa aagaccggga attcgatatc aagcttatcg acctgcagat cgttcaaaca   2820
tttggcaata aagtttctta agattgaatc ctgttgccgg tcttgcgatg attatcatat   2880
aatttctgtt gaattacgtt aagcatgtaa taattaacat gtaatgcatg acgttattta   2940
tgagatgggt ttttatgatt agagtcccgc aattatacat ttaatacgcg atagaaaaca   3000
```

aaatatagcg cgcaaactag gataaattat cgcgcgcggt gtcatctatg ttactagatt 3060
ctagagtctc aagcttcggc gcgcc 3085

<210> SEQ ID NO 72
<211> LENGTH: 3088
<212> TYPE: DNA
<213> ORGANISM: Artificial Sequence
<220> FEATURE:
<223> OTHER INFORMATION: Synthesized Construct 737, from PacI to AscI

<400> SEQUENCE: 72
ttaattaaga attcgagctc caccgcggaa acctcctcgg attccattgc ccagctatct 60
gtcactttat tgagaagata gtggaaaagg aaggtggctc ctacaaatgc catcattgcg 120
ataaaggaaa ggccatcgtt gaagatgcct ctgccgacag tggtcccaaa gatggacccc 180
cacccacgag gagcatcgtg gaaaaagaag acgttccaac cacgtcttca aagcaagtgg 240
attgatgtga tatctccact gacgtaaggg atgacgcaca atcccactat ccttcgcaag 300
acccttcctc tatataagga agttcatttc atttggagag gtattaaaat cttaataggt 360
tttgataaaa gcgaacgtgg ggaaacccga accaaacctt cttctaaact ctctctcatc 420
tctcttaaag caaacttctc tcttgtcttt cttgcgtgag cgatcttcaa cgttgtcaga 480
tcgtgcttcg gcaccagtac aacgttttct ttcactgaag cgaaatcaaa gatctctttg 540
tggacacgta gtgcggcgcc attaaataac gtgtacttgt cctattcttg tcggtgtggt 600
cttgggaaaa gaaagcttgc tggaggctgc tgttcagccc catacattac ttgttacgat 660
tctgctgact ttcggcgggt gcaatatctc tacttctgct tgacgaggta ttgttgcctg 720
tacttctttc ttcttcttct tgctgattgg ttctataaga aatctagtat tttctttgaa 780
acagagtttt cccgtggttt tcgaacttgg agaaagattg ttaagcttct gtatattctg 840
cccaaatttg tcgggcccat ggcgaaaaac gttgcgattt tcggcttatt gttttctctt 900
cttgtgttgg ttccttctca gatcttcgct caaaaacttc ccggaaatga caacagcacg 960
gcaacgctgt gccttgggca ccatgcagta ccaaacggaa cgatagtgaa aacaatcacg 1020
aatgaccaaa ttgaagttac taatgctact gagctggttc agagttcctc aacaggtgaa 1080
atatgcgaca gtcctcatca gatccttgat ggagaaaact gcacactaat agatgctcta 1140
ttgggagacc ctcagtgtga tggcttccaa aataagaaat gggacctttt tgttgaacgc 1200
agcaaagcct acagcaactg ttacccttat gatgtgccgg attatgcctc ccttaggtca 1260
ctagttgcct catccggcac actggagttt aacaatgaaa gtttcaattg gactggagtc 1320
actcaaaacg gaacaagctc tgcttgcata aggagatcta ataacagttt ctttagtaga 1380
ttgaattggt tgacccactt aaaattcaaa tacccagcat tgaacgtgac tatgccaaac 1440
aatgaaaaat ttgacaaatt gtacatttgg ggggttcacc acccgggtac ggacaatgac 1500
caaatcttcc tgtatgctca agcatcagga agaatcacag tctctaccaa aagaagccaa 1560
caaactgtaa tcccgaatat cggatctaga cccagagtaa ggaatatccc cagcagaata 1620
agcatctatt ggacaatagt aaaaccggga gacatacttt tgattaacag cacagggaat 1680
ctaattgctc ctaggggtta cttcaaaata cgaagtggga aaagctcaat aatgagatca 1740
gatgcaccca ttggcaaatg caattctgaa tgcatcactc caaacggaag cattcccaat 1800
gacaaaccat tccaaaatgt aaacaggatc acatacgggg cctgtcccag atatgttaag 1860
caaaacactc tgaaattggc aacagggatg cgaaatgtac cagagaaaca aactagaggc 1920
atatttggcg caatcgcggg tttcatagaa aatggttggg agggaatggt ggatggttgg 1980
tatggtttca ggcatcaaaa ttctgaggga ataggacaag cagcagatct caaaagcact 2040
caagcagcaa tcgatcaaat caatgggaag ctgaataggt tgatcgggaa aaccaacgag 2100
aaattccatc agattgaaaa agagttctca gaagtcgaag ggagaatcca ggaccttgag 2160
aaatatgttg aggacaccaa aatagatctc tggtcataca acgcggagct tcttgttgcc 2220
ctggagaacc aacatacaat tgatctaact gactcagaaa tgaacaaact gtttgaaaaa 2280
acaaagaagc aactgaggga aaatgctgag gatatgggca atggttgttt caaaatatac 2340
cacaaatgtg acaatgcctg cataggatca atcagaaatg gaacttatga ccacgatgta 2400
tacagagatg aagcattaaa caaccggttc cagatcaagg gcgttgagct gaagtcaata 2460
ggaacttacc aaatactgtc aatttattca acagtggcga gttccctagc actggcaatc 2520
atgatggctg gtctatcttt atggatgtgc tccaatggat cgttacaatg cagaatttgc 2580
atttaaaggc ctattttctt tagtttgaat ttactgttat tcggtgtgca tttctatgtt 2640
tggtgagcgg ttttctgtgc tcagagtgtg tttattttat gtaatttaat ttctttgtga 2700
gctcctgttt agcaggtcgt cccttcagca aggacacaaa aagattttaa ttttattaaa 2760
aaaaaaaaaa aaaaagaccg ggaattcgat atcaagctta tcgacctgca gatcgttcaa 2820
acatttggca ataaagtttc ttaagattga atcctgttgc cggtcttgcg atgattatca 2880
tataatttct gttgaattac gttaagcatg taataattaa catgtaatgc atgacgttat 2940
ttatgagatg ggtttttatg attagagtcc cgcaattata catttaatac gcgatagaaa 3000
acaaaatata gcgcgcaaac taggataaat tatcgcgcgc ggtgtcatct atgttactag 3060
attctagagt ctcaagcttc ggcgcgcc 3088

<210> SEQ ID NO 73
<211> LENGTH: 1845
<212> TYPE: DNA
<213> ORGANISM: Artificial Sequence
<220> FEATURE:
<223> OTHER INFORMATION: Synthesized fragment DraIII-Plasto(-84+1)-HA B/Florida/4/06-SacI

<400> SEQUENCE: 73
cactttgtga gtctacactt tgattccctt caaacacata caaagagaag agactaatta 60
attaattaat catcttgaga gaaaatgaag gcaataattg tactactcat ggtagtaaca 120
tccaatgcag atcgaatctg cactggaata acatcttcaa actcacctca tgtggtcaaa 180
acagccactc aaggggaggt caatgtgact ggtgtgatac cactaacaac aacaccaaca 240
aaatcttatt ttgcaaatct caaaggaaca aggaccagag ggaaactatg cccagactgt 300
ctcaactgca cagatctgga tgtggctttg ggcagaccaa tgtgtgtggg gaccacacct 360
tcggcgaagg cttcaatact ccacgaagtc aaacctgtta catccgggtg ctttcctata 420
atgcacgaca gaacaaaaat caggcaacta cccaatcttc tcagaggata tgaaaatatc 480
aggctatcaa cccaaaacgt catcgatgcg gaaaaggcac caggaggacc ctacagactt 540
ggaacctcag gatcttgccc taacgctacc agtaagagcg gatttttcgc aacaatggct 600
tgggctgtcc caaaggacaa caacaaaaat gcaacgaacc cactaacagt agaagtacca 660
tacatttgta cagaagggga agaccaaatc actgtttggg ggttccattc agataacaaa 720
acccaaatga agaacctcta tggagactca aatcctcaaa agttcacctc atctgctaat 780
ggagtaacca cacactatgt ttctcagatt ggcagcttcc cagatcaaac agaagacgga 840

-continued

```
ggactaccac aaagcggcag gattgttgtt gattacatga tgcaaaaacc tgggaaaaca    900

ggaacaattg tctaccaaag aggtgttttg ttgcctcaaa aggtgtggtg cgcgagtggc    960

aggagcaaag taataaaagg gtccttgcct ttaattggtg aagcagattg ccttcatgaa   1020

aaatacggtg gattaaacaa aagcaagcct tactacacag gagaacatgc aaaagccata   1080

ggaaattgcc caatatgggt gaaaacacct ttgaagctcg ccaatggaac caaatataga   1140

cctcctgcaa aactattaaa ggaaaggggt ttcttcggag ctattgctgg tttcctagaa   1200

ggaggatggg aaggaatgat tgcaggctgg cacggataca catctcacgg agcacatgga   1260

gtggcagtgg cggcggacct taagagtacg caagaagcta taaacaagat aacaaaaaat   1320

ctcaattctt tgagtgagct agaagtaaag aatcttcaaa gactaagtgg tgccatggat   1380

gaactccaca acgaaatact cgagctggat gagaaagtgg atgatctcag agctgacact   1440

ataagctcgc aaatagaact tgcagtcttg ctttccaacg aaggaataat aaacagtgaa   1500

gatgagcatc tattggcact tgagagaaaa ctaaagaaaa tgctgggtcc ctctgctgta   1560

gagataggaa atggatgctt cgaaaccaaa cacaagtgca accagacctg cttagacagg   1620

atagctgctg gcacctttaa tgcaggagaa ttttctctcc ccacttttga ttcactgaac   1680

attactgctg catctttaaa tgatgatgga ttggataacc atactatact gctctattac   1740

tcaactgctg cttctagttt ggctgtaaca ttgatgctag ctatttttat tgtttatatg   1800

gtctccagag acaacgtttc atgctccatc tgtctataag agctc                   1845
```

<210> SEQ ID NO 74
<211> LENGTH: 3142
<212> TYPE: DNA
<213> ORGANISM: Artificial Sequence
<220> FEATURE:
<223> OTHER INFORMATION: Synthesized Construct 739, from PacI to AscI

<400> SEQUENCE: 74

```
ttaattaaga attcgagctc caccgcggaa acctcctcgg attccattgc ccagctatct     60

gtcactttat tgagaagata gtggaaaagg aaggtggctc ctacaaatgc catcattgcg    120

ataaaggaaa ggccatcgtt gaagatgcct ctgccgacag tggtcccaaa gatggacccc    180

cacccacgag gagcatcgtg gaaaaagaag acgttccaac cacgtcttca aagcaagtgg    240

attgatgtga tatctccact gacgtaaggg atgacgcaca atcccactat ccttcgcaag    300

acccttcctc tatataagga agttcatttc atttggagag gtattaaaat cttaataggt    360

tttgataaaa gcgaacgtgg ggaaacccga accaaacctt cttctaaact ctctctcatc    420

tctcttaaag caaacttctc tcttgtcttt cttgcgtgag cgatcttcaa cgttgtcaga    480

tcgtgcttcg gcaccagtac aacgttttct ttcactgaag cgaaatcaaa gatctctttg    540

tggacacgta gtgcggcgcc attaaataac gtgtacttgt cctattcttg tcggtgtggt    600

cttgggaaaa gaaagcttgc tggaggctgc tgttcagccc catacattac ttgttacgat    660

tctgctgact ttcggcgggt gcaatatctc tacttctgct tgacgaggta ttgttgcctg    720

tacttctttc ttcttcttct tgctgattgg ttctataaga aatctagtat tttctttgaa    780

acagagtttt cccgtggttt tcgaacttgg agaaagattg ttaagcttct gtatattctg    840

cccaaatttg tcgggcccat ggcgaaaaac gttgcgattt tcggcttatt gttttctctt    900

cttgtgttgg ttccttctca gatcttcgct gatcgaatct gcactggaat aacatcttca    960

aactcacctc atgtggtcaa aacagccact caaggggagg tcaatgtgac tggtgtgata   1020

ccactaacaa caacaccaac aaaatcttat tttgcaaatc tcaaaggaac aaggaccaga   1080
```

-continued

```
gggaaactat gcccagactg tctcaactgc acagatctgg atgtggcttt gggcagacca   1140

atgtgtgtgg ggaccacacc ttcggcgaag gcttcaatac tccacgaagt caaacctgtt   1200

acatccgggt gctttcctat aatgcacgac agaacaaaaa tcaggcaact acccaatctt   1260

ctcagaggat atgaaaatat caggctatca acccaaaacg tcatcgatgc ggaaaaggca   1320

ccaggaggac cctacagact tggaacctca ggatcttgcc ctaacgctac cagtaagagc   1380

ggatttttcg caacaatggc ttgggctgtc ccaaaggaca acaacaaaaa tgcaacgaac   1440

ccactaacag tagaagtacc atacatttgt acagaagggg aagaccaaat cactgtttgg   1500

gggttccatt cagataacaa aacccaaatg aagaacctct atggagactc aaatcctcaa   1560

aagttcacct catctgctaa tggagtaacc acacactatg tttctcagat tggcagcttc   1620

ccagatcaaa cagaagacgg aggactacca caaagcggca ggattgttgt tgattacatg   1680

atgcaaaaac ctgggaaaac aggaacaatt gtctaccaaa gaggtgtttt gttgcctcaa   1740

aaggtgtggt gcgcgagtgg caggagcaaa gtaataaaag ggtccttgcc tttaattggt   1800

gaagcagatt gccttcatga aaaatacggt ggattaaaca aaagcaagcc ttactacaca   1860

ggagaacatg caaaagccat aggaaattgc ccaatatggg tgaaaacacc tttgaagctc   1920

gccaatggaa ccaaatatag acctcctgca aaactattaa aggaaagggg tttcttcgga   1980

gctattgctg gtttcctaga aggaggatgg gaaggaatga ttgcaggctg gcacggatac   2040

acatctcacg gagcacatgg agtggcagtg gcggcggacc ttaagagtac gcaagaagct   2100

ataaacaaga taacaaaaaa tctcaattct ttgagtgagc tagaagtaaa gaatcttcaa   2160

agactaagtg gtgccatgga tgaactccac aacgaaatac tcgagctgga tgagaaagtg   2220

gatgatctca gagctgacac tataagctcg caaatagaac ttgcagtctt gctttccaac   2280

gaaggaataa taaacagtga agatgagcat ctattggcac ttgagagaaa actaaagaaa   2340

atgctgggtc cctctgctgt agagatagga aatggatgct tcgaaaccaa acacaagtgc   2400

aaccagacct gcttagacag gatagctgct ggcaccttta atgcaggaga attttctctc   2460

cccacttttg attcactgaa cattactgct gcatctttaa atgatgatgg attggataac   2520

catactatac tgctctatta ctcaactgct gcttctagtt tggctgtaac attgatgcta   2580

gctattttta ttgtttatat ggtctccaga gacaacgttt catgctccat ctgtctataa   2640

aggcctattt tctttagttt gaatttactg ttattcggtg tgcatttcta tgtttggtga   2700

gcggttttct gtgctcagag tgtgtttatt ttatgtaatt taatttcttt gtgagctcct   2760

gtttagcagg tcgtcccttc agcaaggaca caaaaagatt ttaattttat taaaaaaaaa   2820

aaaaaaaaag accgggaatt cgatatcaag cttatcgacc tgcagatcgt tcaaacattt   2880

ggcaataaag tttcttaaga ttgaatcctg ttgccggtct tgcgatgatt atcatataat   2940

ttctgttgaa ttacgttaag catgtaataa ttaacatgta atgcatgacg ttatttatga   3000

gatgggtttt tatgattaga gtcccgcaat tatacattta atacgcgata gaaaacaaaa   3060

tatagcgcgc aaactaggat aaattatcgc gcgcggtgtc atctatgtta ctagattcta   3120

gagtctcaag cttcggcgcg cc                                             3142
```

```
<210> SEQ ID NO 75
<211> LENGTH: 3142
<212> TYPE: DNA
<213> ORGANISM: Artificial Sequence
<220> FEATURE:
<223> OTHER INFORMATION: Construct 745, from PacI to AscI
```

<400> SEQUENCE: 75

```
ttaattaaga attcgagctc caccgcggaa acctcctcgg attccattgc ccagctatct      60
gtcactttat tgagaagata gtggaaaagg aaggtggctc ctacaaatgc catcattgcg     120
ataaaggaaa ggccatcgtt gaagatgcct ctgccgacag tggtcccaaa gatggacccc     180
cacccacgag gagcatcgtg gaaaaagaag acgttccaac cacgtcttca aagcaagtgg     240
attgatgtga tatctccact gacgtaaggg atgacgcaca atcccactat ccttcgcaag     300
acccttcctc tatataagga agttcatttc atttggagag gtattaaaat cttaataggt     360
tttgataaaa gcgaacgtgg ggaaacccga accaaacctt cttctaaact ctctctcatc     420
tctcttaaag caaacttctc tcttgtcttt cttgcgtgag cgatcttcaa cgttgtcaga     480
tcgtgcttcg gcaccagtac aacgttttct ttcactgaag cgaaatcaaa gatctctttg     540
tggacacgta gtgcggcgcc attaaataac gtgtacttgt cctattcttg tcggtgtggt     600
cttgggaaaa gaaagcttgc tggaggctgc tgttcagccc catacattac ttgttacgat     660
tctgctgact ttcggcgggt gcaatatctc tacttctgct tgacgaggta ttgttgcctg     720
tacttctttc ttcttcttct tgctgattgg ttctataaga aatctagtat tttctttgaa     780
acagagtttt cccgtggttt tcgaacttgg agaaagattg ttaagcttct gtatattctg     840
cccaaatttg tcgggcccat ggcgaaaaac gttgcgattt tcggcttatt gttttctctt     900
cttgtgttgg ttccttctca gatcttcgct gatcgaatct gcactggaat aacatcttca     960
aactcacctc atgtggtcaa aacagccact caaggggagg tcaatgtgac tggtgtgata    1020
ccactaacaa caacaccaac aaaatcttat tttgcaaatc tcaaaggaac aaggaccaga    1080
gggaaactat gcccagactg tctcaactgc acagatctgg atgtggcttt gggcagacca    1140
atgtgtgtgg ggaccacacc ttcggcgaag gcttcaatac tccacgaagt caaacctgtt    1200
acatccgggt gctttcctat aatgcacgac agaacaaaaa tcaggcaact acccaatctt    1260
ctcagaggat atgaaaatat caggctatca acccaaaacg tcatcgatgc ggaaaaggca    1320
ccaggaggac cctacagact tggaacctca ggatcttgcc ctaacgctac cagtaagagc    1380
ggatttttcg caacaatggc ttgggctgtc ccaaaggaca acaacaaaaa tgcaacgaac    1440
ccactaacag tagaagtacc atacatttgt acagaagggg aagaccaaat cactgtttgg    1500
gggttccatt cagataacaa aacccaaatg aagaacctct atggagactc aaatcctcaa    1560
aagttcacct catctgctaa tggagtaacc acacactatg tttctcagat tggcagcttc    1620
ccagatcaaa cagaagacgg aggactacca caaagcggca ggattgttgt tgattacatg    1680
atgcaaaaac ctgggaaaac aggaacaatt gtctaccaaa gaggtgtttt gttgcctcaa    1740
aaggtgtggt gcgcgagtgg caggagcaaa gtaataaaag ggtccttgcc tttaattggt    1800
gaagcagatt gccttcatga aaaatacggt ggattaaaca aaagcaagcc ttactacaca    1860
ggagaacatg caaaagccat aggaaattgc ccaatatggg tgaaaacacc tttgaagctc    1920
gccaatggaa ccaaatatag acctcctgca aaactattaa aggaaagggg tttcttcgga    1980
gctattgctg gtttcctaga aggaggatgg gaaggaatga ttgcaggctg gcacggatac    2040
acatctcacg gagcacatgg agtggcagtg gcggcggacc ttaagagtac gcaagaagct    2100
ataaacaaga taacaaaaaa tctcaattct ttgagtgagc tagaagtaaa gaatcttcaa    2160
agactaagtg gtgccatgga tgaactccac aacgaaatac tcgagctgga tgagaaagtg    2220
gatgatctca gagctgacac tataagctcg caaatagaac ttgcagtctt gctttccaac    2280
gaaggaataa taaacagtga agatgagcat ctattggcac ttgagagaaa actaaagaaa    2340
```

```
atgctgggtc cctctgctgt agagatagga aatggatgct tcgaaaccaa acacaagtgc   2400

aaccagacct gcttagacag gatagctgct ggcaccttta atgcaggaga attttctctc   2460

cccacttttg attcactgaa cattactgct gcatctttaa atgatgatgg attggataac   2520

taccaaatac tgtcaattta ttcaacagtg gcgagttccc tagcactggc aatcatgatg   2580

gctggtctat ctttatggat gtgctccaat ggatcgttac aatgcagaat ttgcatttaa   2640

aggcctattt tctttagttt gaatttactg ttattcggtg tgcatttcta tgtttggtga   2700

gcggttttct gtgctcagag tgtgtttatt ttatgtaatt taatttcttt gtgagctcct   2760

gtttagcagg tcgtcccttc agcaaggaca caaaaagatt ttaattttat taaaaaaaaa   2820

aaaaaaaaag accgggaatt cgatatcaag cttatcgacc tgcagatcgt tcaaacattt   2880

ggcaataaag tttcttaaga ttgaatcctg ttgccggtct tgcgatgatt atcatataat   2940

ttctgttgaa ttacgttaag catgtaataa ttaacatgta atgcatgacg ttatttatga   3000

gatgggtttt tatgattaga gtcccgcaat tatacattta atacgcgata gaaaacaaaa   3060

tatagcgcgc aaactaggat aaattatcgc gcgcggtgtc atctatgtta ctagattcta   3120

gagtctcaag cttcggcgcg cc                                            3142
```

<210> SEQ ID NO 76
<211> LENGTH: 1272
<212> TYPE: DNA
<213> ORGANISM: Artificial Sequence
<220> FEATURE:
<223> OTHER INFORMATION: Synthesized Msj1 coding sequence

<400> SEQUENCE: 76

```
atgtttgggc gcggaccaac aaggaagagt gataacacca aatattacga tattcttggt     60

gtttcaaaaa gtgctagtga agatgaaatc aagaaagcct atagaaaggc agcgatgaag    120

aaccatccag ataagggtgg ggatcctgag aagttcaagg agttgggcca agcatatgaa    180

gtgttgagcg atcctgaaaa gaaagaactg tatgatcaat atggtgaaga tgcccttaaa    240

gaaggaatgg ggggaggcgc aggaagctca tttcataatc cgtttgatat tttcgaatca    300

ttttttggtg caggctttgg tggtggtggt ccttcacgcg caagaagaca gaagcaagga    360

gaagatgtgg tgcattctat aaaggtttcc ttggaggatg tgtataacgg cactacaaag    420

aagctatcac tttctaggaa tgcactgtgc tcaaaatgta aagggaaagg ttcaaaaagt    480

ggaactgctg gaaggtgttt tggatgccag ggcacaggta tgaagattac cagaaggcaa    540

attggactgg gcatgattca acaaatgcaa cacgtctgtc ctgactgcaa aggaacaggc    600

gaggtcatta gtgagagaga tagatgccct caatgcaagg gaaacaagat tactcaagaa    660

aagaaggtgc tggaggtgca tgtggaaaag gggatgcagc agggtcacaa gattgtattc    720

gaaggacaag ctgatgaagc tcctgataca atcacaggag acatagtttt tgtcttgcaa    780

gtaaagggac atccgaagtt tcggagggag cgtgatgacc tccacattga acacaatttg    840

agcttaactg aggctctctg tggcttccag tttaatgtca cacatcttga tggaaggcaa    900

ctattggtca aatcgaaccc cggcgaagtc atcaagccag gtcaacataa agctataaat    960

gatgagggaa tgccacaaca tggtaggccg ttcatgaagg gacgcctata catcaagttt   1020

agtgttgatt tcccggattc gggttttctt tccccaagcc aaagcctgga attagaaaag   1080

atattacctc aaaagacaag caagaacttg tcccaaaagg aggtagatga ttgtgaggag   1140

accaccctgc atgatgtcaa tattgcagag gagatgagtc gaaagaagca acaataccgt   1200
```

-continued

```
gaggcatatg atgacgatga tgatgaagat gatgagcact cgcagcctcg ggtgcaatgc   1260

gctcaacagt ag                                                       1272


<210> SEQ ID NO 77
<211> LENGTH: 4402
<212> TYPE: DNA
<213> ORGANISM: Artificial Sequence
<220> FEATURE:
<223> OTHER INFORMATION: Synthesized Construct number R850, from HindIII

<400> SEQUENCE: 77

aagcttgcat gcctgcaggt cgactctaga ggatccccgg gctggtctgt acattcatct     60

tgccgccttt gcattcactt ggccacaaag agtagagaga aggaagagaa gagcccagac    120

ttcaagaagc gaccttgcaa gtgcactcga gggtcagaaa ctgtatatca tatctatgtg    180

agagaaaggg gaacatttga gatggagtcc atttacttga ggtatactta ttattttgat    240

caataaattt gtatacttct tatttagatc aataaatttg tcattaagct ataatccaaa    300

ataaattacg atcaaatatg caaatgttag ccagtacttg tgttaaactt gatggcatct    360

cttggtttct ttggcaatca catgcctaag aaataaatag tatcatatga ttgtgtttgg    420

tcagacttca gagtcagatg actctgtttg gataaacagc ttaattaagc gcttatagaa    480

tatcatatga ttgtgtttgg tcagacttca gagcatctct tggtttctct ggcaatcata    540

tgcctaagaa ataaatagta tcatatgatt gtgtttggtc agacttcaga gtcagatgac    600

cctgtttggg taaacagctt aattaagtgc ttatagaata agcgcttatc atataagtgc    660

ttttgtacag ttatttctat gaaagtagaa gaaatagtca tattgtttta atataagcta    720

tcctggagag cttgtggaaa taaccagaaa agaacttatg gacacgtcat gagctgttta    780

cataagatct ccctaacagt ctcaaaagtg tttatgccag tagataaatt caaataagtc    840

aatctaaaca gaccctaaat ccattatggt acctatcatt ttagcttatt ccatctttat    900

taagaatgtc atgagataac ataatgataa cacattattt tgacacaaat gggcagatct    960

agcaatttaa ctctggagtc cttcaagact gctgttctta cgaagttcac gtccctgaat   1020

catgttcctg tatggaagcc tgaaagacct caaattctaa aaggtggcga taaattgaag   1080

gtttacaaaa tataccctgc gggcttgaca cagaggcaag ctctttatac cttccagttc   1140

aacggggatg ttgatttcag aagtcacttg gagagcaatc cttgtgccaa gtttgaagta   1200

atttttgtgt agcatatgtt gagctaccta caatttacat gatcacctag cattagctct   1260

ttcacttaac tgagagaatg aagttttagg aatgagtatg accatggagt cggcatggct   1320

ttgtaatgcc taccctactt tggccaactc atcggggatt tacattcaga aaatatacat   1380

gacttcaacc atacttaaac cccttttgt aagataactg aatgttcata tttaatgttg   1440

ggttgtagtg tttttacttg attatatcca gacagttaca agttggacaa caagattgtg   1500

ggtctgtact gttatttatt tattttttt ttagcagaaa caccttatct tttgtttcgt   1560

ttgaatgtag aatgaaaata aaagaaagaa aatataacat catcggccgc gcttgtctaa   1620

tttcgggcag ttaggatcct ctccggtcac cggaaagttt cagtagaaga aacaaaacac   1680

cgtgactaaa atgatactat tattttattt attgtgtttt tcttttttct accggaactt   1740

tttagaacgg atcccaactc gttccggggc cgctacaact gaaacaaaag aagatatttt   1800

ctctctcttc agaaatgtaa gttttccttt acagataccc attcaccatt tgattcagat   1860

gtggtgacta gagataaagc atactaattt gactcttgga aacccataaa gtttatgtta   1920

tccgtgttct ggaccaatcc acttgggggc ataacctgtg tctatgtgtg gtttggtttc   1980
```

-continued

```
cattctgatt tatgcggcga cttgtaattt aaaatctagg aggggcagac attgaacaat   2040
cccaatattt taataactta tgcaagattt tttttattaa tgagatgatg tgtttgtgac   2100
tgagattgag tcatacattt cactaagaaa tggttccaag taccaaacta tcatgaccca   2160
gttgcaaaca tgacgttcgg gagtggtcac tttgatagtt caatttcatc ttggcttctt   2220
attcctttta taattctaat tcttcttgtg taaactattt catgtattat ttttctttaa   2280
aatttacatg tcatttattt tgcctcacta actcaatttt gcatataaca atgataagtg   2340
atattttgac tcacaaaatt tacatcaaat ttcgacatcg tttattatgt tcattggatg   2400
attaacaaat ataacaaact ttgcaactaa ttaaccacca actgaatata attaactata   2460
actgtgaaag tagttaactc atttttatat ttcatagatc aaataagaga aataacggta   2520
tattaatccc tccaaaaaaa aaaaacggta tatttactaa aaaatctaag ccacgtagga   2580
ggataacagg atccccgtag gaggataaca tccaatccaa ccaatcacaa caatcctgat   2640
gagataaccc actttaagcc cacgcatctg tggcacatct acattatcta aatcacacat   2700
tcttccacac atctgagcca cacaaaaacc aatccacatc tttatcaccc attctataaa   2760
aaatcacact ttgtgagtct acactttgat tcccttcaaa cacatacaaa gagaagagac   2820
taattaatta attaatcatc ttgagagaaa atgtttgggc gcggaccaac aaggaagagt   2880
gataacacca aatattacga tattcttggt gtttcaaaaa gtgctagtga agatgaaatc   2940
aagaaagcct atagaaaggc agcgatgaag aaccatccag ataagggtgg ggatcctgag   3000
aagttcaagg agttgggcca agcatatgaa gtgttgagcg atcctgaaaa gaaagaactg   3060
tatgatcaat atggtgaaga tgcccttaaa gaaggaatgg ggggaggcgc aggaagctca   3120
tttcataatc cgtttgatat tttcgaatca ttttttggtg caggctttgg tggtggtggt   3180
ccttcacgcg caagaagaca gaagcaagga gaagatgtgg tgcattctat aaaggtttcc   3240
ttggaggatg tgtataacgg cactacaaag aagctatcac tttctaggaa tgcactgtgc   3300
tcaaaatgta aagggaaagg ttcaaaaagt ggaactgctg gaaggtgttt tggatgccag   3360
ggcacaggta tgaagattac cagaaggcaa attggactgg gcatgattca acaaatgcaa   3420
cacgtctgtc ctgactgcaa aggaacaggc gaggtcatta gtgagagaga tagatgccct   3480
caatgcaagg gaaacaagat tactcaagaa aagaaggtgc tggaggtgca tgtggaaaag   3540
gggatgcagc agggtcacaa gattgtattc gaaggacaag ctgatgaagc tcctgataca   3600
atcacaggag acatagtttt tgtcttgcaa gtaaagggac atccgaagtt tcggagggag   3660
cgtgatgacc tccacattga acacaatttg agcttaactg aggctctctg tggcttccag   3720
tttaatgtca cacatcttga tggaaggcaa ctattggtca aatcgaaccc cggcgaagtc   3780
atcaagccag gtcaacataa agctataaat gatgagggaa tgccacaaca tggtaggccg   3840
ttcatgaagg gacgcctata catcaagttt agtgttgatt tcccggattc gggttttctt   3900
tccccaagcc aaagcctgga attagaaaag atattacctc aaaagacaag caagaacttg   3960
tcccaaaagg aggtagatga ttgtgaggag accaccctgc atgatgtcaa tattgcagag   4020
gagatgagtc gaaagaagca acaataccgt gaggcatatg atgacgatga tgatgaagat   4080
gatgagcact cgcagcctcg ggtgcaatgc gctcaacagt aggagctcag ctcgaatttc   4140
cccgatcgtt caaacatttg gcaataaagt ttcttaagat tgaatcctgt tgccggtctt   4200
gcgatgatta tcatataatt tctgttgaat tacgttaagc atgtaataat taacatgtaa   4260
tgcatgacgt tatttatgag atgggttttt atgattagag tcccgcaatt atacatttaa   4320
```

```
tacgcgatag aaaacaaaat atagcgcgca aactaggata aattatcgcg cgcggtgtca   4380

tctatgttac tagatcgaat tc                                            4402


<210> SEQ ID NO 78
<211> LENGTH: 5086
<212> TYPE: DNA
<213> ORGANISM: Artificial Sequence
<220> FEATURE:
<223> OTHER INFORMATION: Synthesized Construct number R860, from
      HindIII to EcoRI

<400> SEQUENCE: 78

aagcttgcat gcctgcaggt cgactctaga ggatccccgg gctggtctgt acattcatct     60

tgccgccttt gcattcactt ggccacaaag agtagagaga aggaagagaa gagcccagac    120

ttcaagaagc gaccttgcaa gtgcactcga gggtcagaaa ctgtatatca tatctatgtg    180

agagaaaggg gaacatttga gatggagtcc atttacttga ggtatactta ttattttgat    240

caataaattt gtatacttct tatttagatc aataaatttg tcattaagct ataatccaaa    300

ataaattacg atcaaatatg caaatgttag ccagtacttg tgttaaactt gatggcatct    360

cttggtttct ttggcaatca catgcctaag aaataaatag tatcatatga ttgtgtttgg    420

tcagacttca gagtcagatg actctgtttg gataaacagc ttaattaagc gcttatagaa    480

tatcatatga ttgtgtttgg tcagacttca gagcatctct tggtttctct ggcaatcata    540

tgcctaagaa ataaatagta tcatatgatt gtgtttggtc agacttcaga gtcagatgac    600

cctgtttggg taaacagctt aattaagtgc ttatagaata agcgcttatc atataagtgc    660

ttttgtacag ttatttctat gaaagtagaa gaaatagtca tattgtttta atataagcta    720

tcctggagag cttgtggaaa taaccagaaa agaacttatg gacacgtcat gagctgttta    780

cataagatct ccctaacagt ctcaaaagtg tttatgccag tagataaatt caaataagtc    840

aatctaaaca gaccctaaat ccattatggt acctatcatt ttagcttatt ccatctttat    900

taagaatgtc atgagataac ataatgataa cacattattt tgacacaaat gggcagatct    960

agcaatttaa ctctggagtc cttcaagact gctgttctta cgaagttcac gtccctgaat   1020

catgttcctg tatggaagcc tgaaagacct caaattctaa aaggtggcga taaattgaag   1080

gtttacaaaa tataccctgc gggcttgaca cagaggcaag ctctttatac cttccagttc   1140

aacggggatg ttgatttcag aagtcacttg gagagcaatc cttgtgccaa gtttgaagta   1200

atttttgtgt agcatatgtt gagctaccta caatttacat gatcacctag cattagctct   1260

ttcacttaac tgagagaatg aagttttagg aatgagtatg accatggagt cggcatggct   1320

ttgtaatgcc taccctactt tggccaactc atcggggatt tacattcaga aaatatacat   1380

gacttcaacc atacttaaac cccttttttgt aagataactg aatgttcata tttaatgttg   1440

ggttgtagtg tttttacttg attatatcca gacagttaca agttggacaa caagattgtg   1500

ggtctgtact gttatttatt tatttttttt ttagcagaaa caccttatct tttgtttcgt   1560

ttgaatgtag aatgaaaata aaagaaagaa aatataacat catcggccgc gcttgtctaa   1620

tttcgggcag ttaggatcct ctccggtcac cggaaagttt cagtagaaga aacaaaacac   1680

cgtgactaaa atgatactat tattttattt attgtgtttt tcttttttct accggaactt   1740

tttagaacgg atcccaactc gttccggggc cgctacaact gaaacaaaag aagatatttt   1800

ctctctcttc agaaatgtaa gttttccttt acagataccc attcaccatt tgattcagat   1860

gtggtgacta gagataaagc atactaattt gactcttgga aacccataaa gtttatgtta   1920
```

-continued

```
tccgtgttct ggaccaatcc acttgggggc ataacctgtg tctatgtgtg gtttggtttc   1980
cattctgatt tatgcggcga cttgtaattt aaaatctagg aggggcagac attgaacaat   2040
cccaatattt taataactta tgcaagattt tttttattaa tgagatgatg tgtttgtgac   2100
tgagattgag tcatacattt cactaagaaa tggttccaag taccaaacta tcatgaccca   2160
gttgcaaaca tgacgttcgg gagtggtcac tttgatagtt caatttcatc ttggcttctt   2220
attcctttta taattctaat tcttcttgtg taaactattt catgtattat ttttctttaa   2280
aatttacatg tcatttattt tgcctcacta actcaatttt gcatataaca atgataagtg   2340
atattttgac tcacaaaatt tacatcaaat ttcgacatcg tttattatgt tcattggatg   2400
attaacaaat ataacaaact ttgcaactaa ttaaccacca actgaatata attaactata   2460
actgtgaaag tagttaactc atttttatat ttcatagatc aaataagaga aataacggta   2520
tattaatccc tccaaaaaaa aaaaacggta tatttactaa aaaatctaag ccacgtagga   2580
ggataacagg atccccgtag gaggataaca tccaatccaa ccaatcacaa caatcctgat   2640
gagataaccc actttaagcc cacgcatctg tggcacatct acattatcta aatcacacat   2700
tcttccacac atctgagcca cacaaaaacc aatccacatc tttatcaccc attctataaa   2760
aaatcacact ttgtgagtct acactttgat tcccttcaaa cacatacaaa gagaagagac   2820
taattaatta attaatcatc ttgagagaaa atgtcgggta aaggagaagg accagctatc   2880
ggtatcgatc ttggtaccac ttactcttgc gtcggagtat ggcaacacga ccgtgttgag   2940
atcattgcta atgatcaagg aaacagaacc acgccatctt acgttgcttt caccgactcc   3000
gagaggttga tcggtgacgc agctaagaat caggtcgcca tgaaccccgt taacaccgtt   3060
ttcgacgcta agaggttgat cggtcgtcgt ttctctgaca gctctgttca gagtgacatg   3120
aaattgtggc cattcaagat tcaagccgga cctgccgata agccaatgat ctacgtcgaa   3180
tacaagggtg aagagaaaga gttcgcagct gaggagattt cttccatggt tcttattaag   3240
atgcgtgaga ttgctgaggc ttaccttggt gtcacaatca agaacgccgt tgttaccgtt   3300
ccagcttact tcaacgactc tcagcgtcag gctacaaagg atgctggtgt catcgctggt   3360
ttgaacgtta tgcgaatcat caacgagcct acagccgccg ctattgccta cggtcttgac   3420
aaaaaggcta ccagcgttgg agagaagaat gttcttatct tcgatcttgg tggtggcact   3480
tttgatgtct ctcttcttac cattgaagag ggtatctttg aggtgaaggc aactgctggt   3540
gacacccatc ttggtgggga agattttgac aacagaatgg ttaaccactt tgtccaagag   3600
ttcaagagga agagtaagaa ggatatcacc ggtaacccaa gagctcttag gaggttgaga   3660
acttcctgtg agagagcgaa gaggactctt tcttccactg ctcagaccac catcgagatt   3720
gactctctat acgagggtat cgacttctac tccaccatca cccgtgctag atttgaggag   3780
ctcaacatgg atctcttcag gaagtgtatg gagccagttg agaagtgtct tcgtgatgct   3840
aagatggaca agagcactgt tcatgatgtt gtccttgttg gtggttctac ccgtatccct   3900
aaggttcagc aattgctcca ggacttcttc aacggcaaag agctttgcaa gtctattaac   3960
cctgatgagg ctgttgccta cggtgctgct gtccagggag ctattctcag cggtgaagga   4020
aacgagaagg ttcaagatct tctattgctc gatgtcactc ctctctccct tggtttggaa   4080
actgccggtg gtgtcatgac cactttgatc ccaaggaaca caaccatccc aaccaagaag   4140
gaacaagtct tctccaccta ctcagacaac caacccggtg tgttgatcca ggtgtacgaa   4200
ggagagagag ccagaaccaa ggacaacaac cttcttggta aatttgagct ctccggaatt   4260
cctccagctc ctcgtggtgt cccccagatc acagtctgct ttgacattga tgccaatggt   4320
```

```
atcctcaatg tctctgctga ggacaagacc accggacaga agaacaagat caccatcacc   4380
aatgacaagg gtcgtctctc caaggatgag attgagaaga tggttcaaga ggctgagaag   4440
tacaagtccg aagacgagga gcacaagaag aaggttgaag ccaagaacgc tctcgagaac   4500
tacgcttaca acatgaggaa caccatccaa gacgagaaga ttggtgagaa gctcccggct   4560
gcagacaaga agaagatcga ggattctatt gagcaggcga ttcaatggct cgagggtaac   4620
cagttggctg aggctgatga gttcgaagac aagatgaagg aattggagag catctgcaac   4680
ccaatcattg ccaagatgta ccaaggagct ggtggtgaag ccggtggtcc aggtgcctct   4740
ggtatggacg atgatgctcc ccctgcttca ggcggtgctg gacctaagat cgaggaggtc   4800
gactaagagc tcagctcgaa tttccccgat cgttcaaaca tttggcaata aagtttctta   4860
agattgaatc ctgttgccgg tcttgcgatg attatcatat aatttctgtt gaattacgtt   4920
aagcatgtaa taattaacat gtaatgcatg acgttattta tgagatgggt ttttatgatt   4980
agagtcccgc aattatacat ttaatacgcg atagaaaaca aaatatagcg cgcaaactag   5040
gataaattat cgcgcgcggt gtcatctatg ttactagatc gaattc                  5086
```

<210> SEQ ID NO 79
<211> LENGTH: 9493
<212> TYPE: DNA
<213> ORGANISM: Artificial Sequence
<220> FEATURE:
<223> OTHER INFORMATION: Synthesized Construct number R870, from HindIII to EcoRI

<400> SEQUENCE: 79

```
aagcttgcat gcctgcaggt cgactctaga ggatccccgg gctggtctgt acattcatct     60
tgccgccttt gcattcactt ggccacaaag agtagagaga aggaagagaa gagcccagac    120
ttcaagaagc gaccttgcaa gtgcactcga gggtcagaaa ctgtatatca tatctatgtg    180
agagaaaggg gaacatttga gatggagtcc atttacttga ggtatactta ttattttgat    240
caataaattt gtatacttct tatttagatc aataaatttg tcattaagct ataatccaaa    300
ataaattacg atcaaatatg caaatgttag ccagtacttg tgttaaactt gatggcatct    360
cttggtttct ttggcaatca catgcctaag aaataaatag tatcatatga ttgtgtttgg    420
tcagacttca gagtcagatg actctgtttg gataaacagc ttaattaagc gcttatagaa    480
tatcatatga ttgtgtttgg tcagacttca gagcatctct tggtttctct ggcaatcata    540
tgcctaagaa ataaatagta tcatatgatt gtgtttggtc agacttcaga gtcagatgac    600
cctgtttggg taaacagctt aattaagtgc ttatagaata agcgcttatc atataagtgc    660
ttttgtacag ttatttctat gaaagtagaa gaaatagtca tattgtttta atataagcta    720
tcctggagag cttgtggaaa taaccagaaa agaacttatg gacacgtcat gagctgttta    780
cataagatct ccctaacagt ctcaaaagtg tttatgccag tagataaatt caaataagtc    840
aatctaaaca gaccctaaat ccattatggt acctatcatt ttagcttatt ccatctttat    900
taagaatgtc atgagataac ataatgataa cacattattt tgacacaaat gggcagatct    960
agcaatttaa ctctggagtc cttcaagact gctgttctta cgaagttcac gtccctgaat   1020
catgttcctg tatggaagcc tgaaagacct caaattctaa aaggtggcga taaattgaag   1080
gtttacaaaa tataccctgc gggcttgaca cagaggcaag ctctttatac cttccagttc   1140
aacggggatg ttgatttcag aagtcacttg gagagcaatc cttgtgccaa gtttgaagta   1200
atttttgtgt agcatatgtt gagctaccta caatttacat gatcacctag cattagctct   1260
```

-continued

```
ttcacttaac tgagagaatg aagttttagg aatgagtatg accatggagt cggcatggct   1320
ttgtaatgcc taccctactt tggccaactc atcggggatt tacattcaga aaatatacat   1380
gacttcaacc atacttaaac cccttttttgt aagataactg aatgttcata tttaatgttg   1440
ggttgtagtg tttttacttg attatatcca gacagttaca agttggacaa caagattgtg   1500
ggtctgtact gttatttatt tatttttttt ttagcagaaa caccttatct tttgtttcgt   1560
ttgaatgtag aatgaaaata aaagaaagaa aatataacat catcggccgc gcttgtctaa   1620
tttcgggcag ttaggatcct ctccggtcac cggaaagttt cagtagaaga aacaaaacac   1680
cgtgactaaa atgatactat tattttattt attgtgtttt tcttttttct accggaactt   1740
tttagaacgg atcccaactc gttccggggc cgctacaact gaaacaaaag aagatatttt   1800
ctctctcttc agaaatgtaa gttttccttt acagataccc attcaccatt tgattcagat   1860
gtggtgacta gagataaagc atactaattt gactcttgga aacccataaa gtttatgtta   1920
tccgtgttct ggaccaatcc acttgggggc ataacctgtg tctatgtgtg gtttggtttc   1980
cattctgatt tatgcggcga cttgtaattt aaaatctagg aggggcagac attgaacaat   2040
cccaatattt taataactta tgcaagattt tttttattaa tgagatgatg tgtttgtgac   2100
tgagattgag tcatacattt cactaagaaa tggttccaag taccaaacta tcatgaccca   2160
gttgcaaaca tgacgttcgg gagtggtcac tttgatagtt caatttcatc ttggcttctt   2220
attcctttta taattctaat tcttcttgtg taaactattt catgtattat ttttctttaa   2280
aatttacatg tcatttattt tgcctcacta actcaatttt gcatataaca atgataagtg   2340
atattttgac tcacaaaatt tacatcaaat ttcgacatcg tttattatgt tcattggatg   2400
attaacaaat ataacaaact ttgcaactaa ttaaccacca actgaatata attaactata   2460
actgtgaaag tagttaactc atttttatat ttcatagatc aaataagaga aataacggta   2520
tattaatccc tccaaaaaaa aaaaacggta tatttactaa aaaatctaag ccacgtagga   2580
ggataacagg atccccgtag gaggataaca tccaatccaa ccaatcacaa caatcctgat   2640
gagataaccc actttaagcc cacgcatctg tggcacatct acattatcta aatcacacat   2700
tcttccacac atctgagcca cacaaaaacc aatccacatc tttatcaccc attctataaa   2760
aaatcacact ttgtgagtct acactttgat tcccttcaaa cacatacaaa gagaagagac   2820
taattaatta attaatcatc ttgagagaaa atgtcgggta aaggagaagg accagctatc   2880
ggtatcgatc ttggtaccac ttactcttgc gtcggagtat ggcaacacga ccgtgttgag   2940
atcattgcta atgatcaagg aaacagaacc acgccatctt acgttgcttt caccgactcc   3000
gagaggttga tcggtgacgc agctaagaat caggtcgcca tgaaccccgt taacaccgtt   3060
ttcgacgcta agaggttgat cggtcgtcgt ttctctgaca gctctgttca gagtgacatg   3120
aaattgtggc cattcaagat tcaagccgga cctgccgata agccaatgat ctacgtcgaa   3180
tacaagggtg aagagaaaga gttcgcagct gaggagattt cttccatggt tcttattaag   3240
atgcgtgaga ttgctgaggc ttaccttggt gtcacaatca agaacgccgt tgttaccgtt   3300
ccagcttact tcaacgactc tcagcgtcag gctacaaagg atgctggtgt catcgctggt   3360
ttgaacgtta tgcgaatcat caacgagcct acagccgccg ctattgccta cggtcttgac   3420
aaaaaggcta ccagcgttgg agagaagaat gttcttatct tcgatcttgg tggtggcact   3480
tttgatgtct ctcttcttac cattgaagag ggtatctttg aggtgaaggc aactgctggt   3540
gacacccatc ttggtgggga agattttgac aacagaatgg ttaaccactt tgtccaagag   3600
```

-continued

```
ttcaagagga agagtaagaa ggatatcacc ggtaacccaa gagctcttag gaggttgaga   3660
acttcctgtg agagagcgaa gaggactctt tcttccactg ctcagaccac catcgagatt   3720
gactctctat acgagggtat cgacttctac tccaccatca cccgtgctag atttgaggag   3780
ctcaacatgg atctcttcag gaagtgtatg gagccagttg agaagtgtct tcgtgatgct   3840
aagatggaca agagcactgt tcatgatgtt gtccttgttg gtggttctac ccgtatccct   3900
aaggttcagc aattgctcca ggacttcttc aacggcaaag agctttgcaa gtctattaac   3960
cctgatgagg ctgttgccta cggtgctgct gtccagggag ctattctcag cggtgaagga   4020
aacgagaagg ttcaagatct tctattgctc gatgtcactc ctctctccct tggtttggaa   4080
actgccggtg gtgtcatgac cactttgatc ccaaggaaca caaccatccc aaccaagaag   4140
gaacaagtct tctccaccta ctcagacaac caacccggtg tgttgatcca ggtgtacgaa   4200
ggagagagag ccagaaccaa ggacaacaac cttcttggta aatttgagct ctccggaatt   4260
cctccagctc ctcgtggtgt cccccagatc acagtctgct ttgacattga tgccaatggt   4320
atcctcaatg tctctgctga ggacaagacc accggacaga agaacaagat caccatcacc   4380
aatgacaagg gtcgtctctc caaggatgag attgagaaga tggttcaaga ggctgagaag   4440
tacaagtccg aagacgagga gcacaagaag aaggttgaag ccaagaacgc tctcgagaac   4500
tacgcttaca acatgaggaa caccatccaa gacgagaaga ttggtgagaa gctcccggct   4560
gcagacaaga agaagatcga ggattctatt gagcaggcga ttcaatggct cgagggtaac   4620
cagttggctg aggctgatga gttcgaagac aagatgaagg aattggagag catctgcaac   4680
ccaatcattg ccaagatgta ccaaggagct ggtggtgaag ccggtggtcc aggtgcctct   4740
ggtatggacg atgatgctcc ccctgcttca ggcggtgctg gacctaagat cgaggaggtc   4800
gactaagagc tcagctcgaa tttccccgat cgttcaaaca tttggcaata aagtttctta   4860
agattgaatc ctgttgccgg tcttgcgatg attatcatat aatttctgtt gaattacgtt   4920
aagcatgtaa taattaacat gtaatgcatg acgttattta tgagatgggt ttttatgatt   4980
agagtcccgc aattatacat ttaatacgcg atagaaaaca aaatatagcg cgcaaactag   5040
gataaattat cgcgcgcggt gtcatctatg ttactagatc gaattcgtaa tcatggtcat   5100
agctgtttcc tgtgtgaaat tgttatccgg ggctggtctg tacattcatc ttgccgcctt   5160
tgcattcact tggccacaaa gagtagagag aaggaagaga agagcccaga cttcaagaag   5220
cgaccttgca agtgcactcg agggtcagaa actgtatatc atatctatgt gagagaaagg   5280
ggaacatttg agatggagtc catttacttg aggtatactt attattttga tcaataaatt   5340
tgtatacttc ttatttagat caataaattt gtcattaagc tataatccaa aataaattac   5400
gatcaaatat gcaaatgtta gccagtactt gtgttaaact tgatggcatc tcttggtttc   5460
tttggcaatc acatgcctaa gaaataaata gtatcatatg attgtgtttg gtcagacttc   5520
agagtcagat gactctgttt ggataaacag cttaattaag cgcttataga atatcatatg   5580
attgtgtttg gtcagacttc agagcatctc ttggtttctc tggcaatcat atgcctaaga   5640
aataaatagt atcatatgat tgtgtttggt cagacttcag agtcagatga ccctgtttgg   5700
gtaaacagct taattaagtg cttatagaat aagcgcttat catataagtg cttttgtaca   5760
gttatttcta tgaaagtaga agaaatagtc atattgtttt aatataagct atcctggaga   5820
gcttgtggaa ataaccagaa aagaacttat ggacacgtca tgagctgttt acataagatc   5880
tccctaacag tctcaaaagt gtttatgcca gtagataaat tcaaataagt caatctaaac   5940
agaccctaaa tccattatgg tacctatcat tttagcttat tccatcttta ttaagaatgt   6000
```

-continued

```
catgagataa cataatgata acacattatt ttgacacaaa tgggcagatc tagcaattta   6060
actctggagt ccttcaagac tgctgttctt acgaagttca cgtccctgaa tcatgttcct   6120
gtatggaagc ctgaaagacc tcaaattcta aaaggtggcg ataaattgaa ggtttacaaa   6180
atataccctg cgggcttgac acagaggcaa gctctttata ccttccagtt caacggggat   6240
gttgatttca gaagtcactt ggagagcaat ccttgtgcca agtttgaagt aatttttgtg   6300
tagcatatgt tgagctacct acaatttaca tgatcaccta gcattagctc tttcacttaa   6360
ctgagagaat gaagttttag gaatgagtat gaccatggag tcggcatggc tttgtaatgc   6420
ctaccctact ttggccaact catcggggat ttacattcag aaaatataca tgacttcaac   6480
catacttaaa ccccttttg taagataact gaatgttcat atttaatgtt gggttgtagt   6540
gtttttactt gattatatcc agacagttac aagttggaca acaagattgt gggtctgtac   6600
tgttatttat ttattttttt tttagcagaa acaccttatc ttttgtttcg tttgaatgta   6660
gaatgaaaat aaaagaaaga aaatataaca tcatcggccg cgcttgtcta atttcgggca   6720
gttaggatcc tctccggtca ccggaaagtt tcagtagaag aaacaaaaca ccgtgactaa   6780
aatgatacta ttattttatt tattgtgttt ttcttttttc taccggaact ttttagaacg   6840
gatcccaact cgttccgggg ccgctacaac tgaaacaaaa gaagatattt tctctctctt   6900
cagaaatgta agttttcctt tacagatacc cattcaccat ttgattcaga tgtggtgact   6960
agagataaag catactaatt tgactcttgg aaacccataa agtttatgtt atccgtgttc   7020
tggaccaatc cacttggggg cataacctgt gtctatgtgt ggtttggttt ccattctgat   7080
ttatgcggcg acttgtaatt taaaatctag gaggggcaga cattgaacaa tcccaatatt   7140
ttaataactt atgcaagatt ttttttatta atgagatgat gtgtttgtga ctgagattga   7200
gtcatacatt tcactaagaa atggttccaa gtaccaaact atcatgaccc agttgcaaac   7260
atgacgttcg ggagtggtca ctttgatagt tcaatttcat cttggcttct tattcctttt   7320
ataattctaa ttcttcttgt gtaaactatt tcatgtatta tttttcttta aaatttacat   7380
gtcatttatt ttgcctcact aactcaattt tgcatataac aatgataagt gatattttga   7440
ctcacaaaat ttacatcaaa tttcgacatc gtttattatg ttcattggat gattaacaaa   7500
tataacaaac tttgcaacta attaaccacc aactgaatat aattaactat aactgtgaaa   7560
gtagttaact catttttata tttcatagat caaataagag aaataacggt atattaatcc   7620
ctccaaaaaa aaaaaacggt atatttacta aaaaatctaa gccacgtagg aggataacag   7680
gatccccgta ggaggataac atccaatcca accaatcaca acaatcctga tgagataacc   7740
cactttaagc ccacgcatct gtggcacatc tacattatct aaatcacaca ttcttccaca   7800
catctgagcc acacaaaaac caatccacat ctttatcacc cattctataa aaaatcacac   7860
tttgtgagtc tacactttga ttcccttcaa acacatacaa agagaagaga ctaattaatt   7920
aattaatcat cttgagagaa aatgtttggg cgcggaccaa caaggaagag tgataacacc   7980
aaatattacg atattcttgg tgtttcaaaa agtgctagtg aagatgaaat caagaaagcc   8040
tatagaaagg cagcgatgaa gaaccatcca gataagggtg gggatcctga gaagttcaag   8100
gagttgggcc aagcatatga agtgttgagc gatcctgaaa agaaagaact gtatgatcaa   8160
tatggtgaag atgcccttaa agaaggaatg gggggaggcg caggaagctc atttcataat   8220
ccgtttgata ttttcgaatc attttttggt gcaggctttg gtggtggtgg tccttcacgc   8280
gcaagaagac agaagcaagg agaagatgtg gtgcattcta taaaggtttc cttggaggat   8340
```

-continued

```
gtgtataacg gcactacaaa gaagctatca ctttctagga atgcactgtg ctcaaaatgt   8400
aaagggaaag gttcaaaaag tggaactgct ggaaggtgtt ttggatgcca gggcacaggt   8460
atgaagatta ccagaaggca aattggactg ggcatgattc aacaaatgca acacgtctgt   8520
cctgactgca aaggaacagg cgaggtcatt agtgagagag atagatgccc tcaatgcaag   8580
ggaaacaaga ttactcaaga aaagaaggtg ctggaggtgc atgtggaaaa ggggatgcag   8640
cagggtcaca agattgtatt cgaaggacaa gctgatgaag ctcctgatac aatcacagga   8700
gacatagttt ttgtcttgca agtaaaggga catccgaagt ttcggaggga gcgtgatgac   8760
ctccacattg aacacaattt gagcttaact gaggctctct gtggcttcca gtttaatgtc   8820
acacatcttg atggaaggca actattggtc aaatcgaacc ccggcgaagt catcaagcca   8880
ggtcaacata aagctataaa tgatgaggga atgccacaac atggtaggcc gttcatgaag   8940
ggacgcctat acatcaagtt tagtgttgat ttcccggatt cgggttttct ttccccaagc   9000
caaagcctgg aattagaaaa gatattacct caaaagacaa gcaagaactt gtcccaaaag   9060
gaggtagatg attgtgagga gaccaccctg catgatgtca atattgcaga ggagatgagt   9120
cgaaagaagc aacaataccg tgaggcatat gatgacgatg atgatgaaga tgatgagcac   9180
tcgcagcctc gggtgcaatg cgctcaacag taggagctca gctcgaattt ccccgatcgt   9240
tcaaacattt ggcaataaag tttcttaaga ttgaatcctg ttgccggtct tgcgatgatt   9300
atcatataat ttctgttgaa ttacgttaag catgtaataa ttaacatgta atgcatgacg   9360
ttatttatga gatgggtttt tatgattaga gtcccgcaat tatacattta atacgcgata   9420
gaaaacaaaa tatagcgcgc aaactaggat aaattatcgc gcgcggtgtc atctatgtta   9480
ctagatcgaa ttc                                                      9493
```

```
<210> SEQ ID NO 80
<211> LENGTH: 568
<212> TYPE: PRT
<213> ORGANISM: Artificial Sequence
<220> FEATURE:
<223> OTHER INFORMATION: Synthesized amino acid translation of coding
      sequence in construct 690 expression cassette

<400> SEQUENCE: 80

Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Asp Leu Asp Gly Val Lys
    50                  55                  60

Pro Leu Ile Leu Arg Asp Cys Ser Val Ala Gly Trp Leu Leu Gly Asn
65                  70                  75                  80

Pro Met Cys Asp Glu Phe Ile Asn Val Pro Glu Trp Ser Tyr Ile Val
                85                  90                  95

Glu Lys Ala Asn Pro Thr Asn Asp Leu Cys Tyr Pro Gly His Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Glu Ser Ser Trp Pro Asn His Thr Val
    130                 135                 140

Thr Gly Val Ser Ala Ser Cys Ser His Asn Gly Glu Ser Ser Phe Tyr
```

-continued

```
145                 150                 155                 160

Arg Asn Leu Leu Trp Leu Thr Gly Lys Asn Gly Leu Tyr Pro Asn Leu
                165                 170                 175

Ser Lys Ser Tyr Ala Asn Asn Lys Glu Lys Glu Val Leu Val Leu Trp
            180                 185                 190

Gly Val His His Pro Pro Asn Ile Gly Asp Gln Lys Ala Leu Tyr His
        195                 200                 205

Thr Glu Asn Ala Tyr Val Ser Val Val Ser Ser His Tyr Ser Arg Lys
    210                 215                 220

Phe Thr Pro Glu Ile Ala Lys Arg Pro Lys Val Arg Asp Gln Glu Gly
225                 230                 235                 240

Arg Ile Asn Tyr Tyr Trp Thr Leu Leu Glu Pro Gly Asp Thr Ile Ile
                245                 250                 255

Phe Glu Ala Asn Gly Asn Leu Ile Ala Pro Arg Tyr Ala Phe Ala Leu
            260                 265                 270

Ser Arg Gly Phe Gly Ser Gly Ile Met Lys Ser Glu Leu Glu Tyr Gly
        275                 280                 285

Asn Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565
```

<210> SEQ ID NO 81
<211> LENGTH: 568
<212> TYPE: PRT
<213> ORGANISM: Artificial Sequence
<220> FEATURE:
<223> OTHER INFORMATION: Synthesized Amino acid translation of coding sequence in construct 691 expression cassette

<400> SEQUENCE: 81

```
Met Glu Lys Ile Val Leu Leu Leu Ala Ile Val Ser Leu Val Lys Ser
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Thr His Asn Gly Lys Leu Cys Leu Leu Lys Gly Ile Ala
    50                  55                  60

Pro Leu Gln Leu Gly Asn Cys Ser Val Ala Gly Trp Ile Leu Gly Asn
65                  70                  75                  80

Pro Glu Cys Glu Leu Leu Ile Ser Lys Glu Ser Trp Ser Tyr Ile Val
                85                  90                  95

Glu Lys Pro Asn Pro Glu Asn Gly Thr Cys Tyr Pro Gly His Phe Ala
            100                 105                 110

Asp Tyr Glu Glu Leu Arg Glu Gln Leu Ser Ser Val Ser Ser Phe Glu
        115                 120                 125

Arg Phe Glu Ile Phe Pro Lys Glu Ser Ser Trp Pro Asn His Thr Val
    130                 135                 140

Thr Gly Val Ser Ala Ser Cys Ser His Asn Gly Glu Ser Ser Phe Tyr
145                 150                 155                 160

Arg Asn Leu Leu Trp Leu Thr Gly Lys Asn Gly Leu Tyr Pro Asn Leu
                165                 170                 175

Ser Lys Ser Tyr Ala Asn Asn Lys Glu Lys Glu Val Leu Val Leu Trp
            180                 185                 190

Gly Val His His Pro Pro Asn Ile Gly Asp Gln Lys Ala Leu Tyr His
        195                 200                 205

Thr Glu Asn Ala Tyr Val Ser Val Val Ser Ser His Tyr Ser Arg Lys
    210                 215                 220

Phe Thr Pro Glu Ile Ala Lys Arg Pro Lys Val Arg Asp Gln Glu Gly
225                 230                 235                 240

Arg Ile Asn Tyr Tyr Trp Thr Leu Leu Glu Pro Gly Asp Thr Ile Ile
                245                 250                 255

Phe Glu Ala Asn Gly Asn Leu Ile Ala Pro Arg Tyr Ala Phe Ala Leu
            260                 265                 270

Ser Arg Gly Phe Gly Ser Gly Ile Ile Asn Ser Asn Ala Pro Met Asp
        275                 280                 285

Lys Cys Asn Thr Lys Cys Gln Thr Pro Met Gly Ala Ile Asn Ser Ser
    290                 295                 300

Met Pro Phe His Asn Ile His Pro Leu Thr Ile Gly Glu Cys Pro Lys
305                 310                 315                 320

Tyr Val Lys Ser Asn Arg Leu Val Leu Ala Thr Gly Leu Arg Asn Ser
                325                 330                 335

Pro Gln Arg Glu Ser Arg Arg Lys Lys Arg Gly Leu Phe Gly Ala Ile
            340                 345                 350

Ala Gly Phe Ile Glu Gly Gly Trp Gln Gly Met Val Asp Gly Trp Tyr
```

```
        355                 360                 365

Gly Tyr His His Ser Asn Glu Gln Gly Ser Gly Tyr Ala Ala Asp Lys
    370                 375                 380

Glu Ser Thr Gln Lys Ala Ile Asp Gly Val Thr Asn Lys Val Asn Ser
385                 390                 395                 400

Ile Ile Asp Lys Met Asn Thr Gln Phe Glu Ala Val Gly Arg Glu Phe
                405                 410                 415

Asn Asn Leu Glu Arg Arg Ile Glu Asn Leu Asn Lys Lys Met Glu Asp
            420                 425                 430

Gly Phe Leu Asp Val Trp Thr Tyr Asn Ala Glu Leu Leu Val Leu Met
        435                 440                 445

Glu Asn Glu Arg Thr Leu Asp Phe His Asp Ser Asn Val Lys Asn Leu
    450                 455                 460

Tyr Asp Lys Val Arg Leu Gln Leu Arg Asp Asn Ala Lys Glu Leu Gly
465                 470                 475                 480

Asn Gly Cys Phe Glu Phe Tyr His Lys Cys Asp Asn Glu Cys Met Glu
                485                 490                 495

Ser Ile Arg Asn Gly Thr Tyr Asn Tyr Pro Gln Tyr Ser Glu Glu Ala
            500                 505                 510

Arg Leu Lys Arg Glu Glu Ile Ser Gly Val Lys Leu Glu Ser Ile Gly
        515                 520                 525

Thr Tyr Gln Ile Leu Ser Ile Tyr Ser Thr Val Ala Ser Ser Leu Ala
    530                 535                 540

Leu Ala Ile Met Met Ala Gly Leu Ser Leu Trp Met Cys Ser Asn Gly
545                 550                 555                 560

Ser Leu Gln Cys Arg Ile Cys Ile
                565


<210> SEQ ID NO 82
<211> LENGTH: 572
<212> TYPE: PRT
<213> ORGANISM: Artificial Sequence
<220> FEATURE:
<223> OTHER INFORMATION: Synthesized Amino acid translation of coding
      sequence in construct 696 expression cassette

<400> SEQUENCE: 82

Met Ala Lys Asn Val Ala Ile Phe Gly Leu Leu Phe Ser Leu Leu Val
1               5                   10                  15

Leu Val Pro Ser Gln Ile Phe Ala Asp Thr Ile Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Ser His Asn Gly Lys
    50                  55                  60

Leu Cys Leu Leu Lys Gly Ile Ala Pro Leu Gln Leu Gly Asn Cys Ser
65                  70                  75                  80

Val Ala Gly Trp Ile Leu Gly Asn Pro Glu Cys Glu Leu Leu Ile Ser
                85                  90                  95

Lys Glu Ser Trp Ser Tyr Ile Val Glu Thr Pro Asn Pro Glu Asn Gly
            100                 105                 110

Thr Cys Tyr Pro Gly Ser Phe Asn Asp Tyr Glu Glu Leu Lys His Leu
        115                 120                 125

Leu Ser Arg Ile Asn His Phe Glu Lys Ile Gln Ile Ile Pro Lys Ser
    130                 135                 140
```

-continued

```
Ser Trp Ser Asp His Glu Ala Ser Ser Gly Val Ser Ser Ala Cys Pro
145                 150                 155                 160

Tyr Leu Gly Ser Pro Ser Phe Phe Arg Asn Val Val Trp Leu Ile Lys
                165                 170                 175

Lys Asn Ser Thr Tyr Pro Thr Ile Lys Lys Ser Tyr Asn Asn Thr Asn
            180                 185                 190

Gln Glu Asp Leu Leu Val Leu Trp Gly Ile His His Pro Asn Asp Ala
        195                 200                 205

Ala Glu Gln Thr Arg Leu Tyr Gln Asn Pro Thr Thr Tyr Ile Ser Ile
    210                 215                 220

Gly Thr Ser Thr Leu Asn Gln Arg Leu Val Pro Lys Ile Ala Thr Arg
225                 230                 235                 240

Ser Lys Val Asn Gly Gln Ser Gly Arg Met Glu Phe Phe Trp Thr Ile
                245                 250                 255

Leu Lys Pro Asn Asp Ala Ile Asn Phe Glu Ser Asn Gly Asn Phe Ile
            260                 265                 270

Ala Pro Glu Tyr Ala Tyr Lys Ile Val Lys Lys Gly Asp Ser Ala Ile
        275                 280                 285

Ile Thr Ser Asn Ala Pro Met Asp Glu Cys Asp Ala Lys Cys Gln Thr
    290                 295                 300

Pro Gln Gly Ala Ile Asn Ser Ser Leu Pro Phe Gln Asn Val His Pro
305                 310                 315                 320

Val Thr Ile Gly Glu Cys Pro Lys Tyr Val Arg Ser Ala Lys Leu Arg
                325                 330                 335

Met Val Thr Gly Leu Arg Asn Ile Pro Ser Ile Gln Ser Arg Gly Leu
            340                 345                 350

Phe Gly Ala Ile Ala Gly Phe Ile Glu Gly Gly Trp Thr Gly Met Val
        355                 360                 365

Asp Gly Trp Tyr Gly Tyr His His Gln Asn Glu Gln Gly Ser Gly Tyr
    370                 375                 380

Ala Ala Asp Gln Lys Ser Thr Gln Asn Ala Ile Asn Gly Ile Thr Asn
385                 390                 395                 400

Lys Val Asn Ser Val Ile Glu Lys Met Asn Thr Gln Phe Thr Ala Val
                405                 410                 415

Gly Lys Glu Phe Asn Lys Leu Glu Arg Arg Met Glu Asn Leu Asn Lys
            420                 425                 430

Lys Val Asp Asp Gly Phe Leu Asp Ile Trp Thr Tyr Asn Ala Glu Leu
        435                 440                 445

Leu Val Leu Leu Glu Asn Glu Arg Thr Leu Asp Phe His Asp Ser Asn
    450                 455                 460

Val Lys Asn Leu Tyr Glu Lys Val Lys Ser Gln Leu Lys Asn Asn Ala
465                 470                 475                 480

Lys Glu Ile Gly Asn Gly Cys Phe Glu Phe Tyr His Lys Cys Asn Asn
                485                 490                 495

Glu Cys Met Glu Ser Val Lys Asn Gly Thr Tyr Asp Tyr Pro Lys Tyr
            500                 505                 510

Ser Glu Glu Ser Lys Leu Asn Arg Glu Lys Ile Asp Gly Val Lys Leu
        515                 520                 525

Glu Ser Met Gly Val Tyr Gln Ile Leu Ala Ile Tyr Ser Thr Val Ala
    530                 535                 540

Ser Ser Leu Val Leu Leu Val Ser Leu Gly Ala Ile Ser Phe Trp Met
545                 550                 555                 560

Cys Ser Asn Gly Ser Leu Gln Cys Arg Ile Cys Ile
```

565 570

<210> SEQ ID NO 83
<211> LENGTH: 575
<212> TYPE: PRT
<213> ORGANISM: Artificial Sequence
<220> FEATURE:
<223> OTHER INFORMATION: Synthesized amino acid translation of coding sequence in construct 737 expression cassette

<400> SEQUENCE: 83

Met Ala Lys Asn Val Ala Ile Phe Gly Leu Leu Phe Ser Leu Leu Val
1 5 10 15

Leu Val Pro Ser Gln Ile Phe Ala Gln Lys Leu Pro Gly Asn Asp Asn
20 25 30

Ser Thr Ala Thr Leu Cys Leu Gly His His Ala Val Pro Asn Gly Thr
35 40 45

Ile Val Lys Thr Ile Thr Asn Asp Gln Ile Glu Val Thr Asn Ala Thr
50 55 60

Glu Leu Val Gln Ser Ser Ser Thr Gly Glu Ile Cys Asp Ser Pro His
65 70 75 80

Gln Ile Leu Asp Gly Glu Asn Cys Thr Leu Ile Asp Ala Leu Leu Gly
85 90 95

Asp Pro Gln Cys Asp Gly Phe Gln Asn Lys Lys Trp Asp Leu Phe Val
100 105 110

Glu Arg Ser Lys Ala Tyr Ser Asn Cys Tyr Pro Tyr Asp Val Pro Asp
115 120 125

Tyr Ala Ser Leu Arg Ser Leu Val Ala Ser Ser Gly Thr Leu Glu Phe
130 135 140

Asn Asn Glu Ser Phe Asn Trp Thr Gly Val Thr Gln Asn Gly Thr Ser
145 150 155 160

Ser Ala Cys Ile Arg Arg Ser Asn Asn Ser Phe Phe Ser Arg Leu Asn
165 170 175

Trp Leu Thr His Leu Lys Phe Lys Tyr Pro Ala Leu Asn Val Thr Met
180 185 190

Pro Asn Asn Glu Lys Phe Asp Lys Leu Tyr Ile Trp Gly Val His His
195 200 205

Pro Gly Thr Asp Asn Asp Gln Ile Phe Leu Tyr Ala Gln Ala Ser Gly
210 215 220

Arg Ile Thr Val Ser Thr Lys Arg Ser Gln Gln Thr Val Ile Pro Asn
225 230 235 240

Ile Gly Ser Arg Pro Arg Val Arg Asn Ile Pro Ser Arg Ile Ser Ile
245 250 255

Tyr Trp Thr Ile Val Lys Pro Gly Asp Ile Leu Leu Ile Asn Ser Thr
260 265 270

Gly Asn Leu Ile Ala Pro Arg Gly Tyr Phe Lys Ile Arg Ser Gly Lys
275 280 285

Ser Ser Ile Met Arg Ser Asp Ala Pro Ile Gly Lys Cys Asn Ser Glu
290 295 300

Cys Ile Thr Pro Asn Gly Ser Ile Pro Asn Asp Lys Pro Phe Gln Asn
305 310 315 320

Val Asn Arg Ile Thr Tyr Gly Ala Cys Pro Arg Tyr Val Lys Gln Asn
325 330 335

Thr Leu Lys Leu Ala Thr Gly Met Arg Asn Val Pro Glu Lys Gln Thr
340 345 350

```
Arg Gly Ile Phe Gly Ala Ile Ala Gly Phe Ile Glu Asn Gly Trp Glu
        355                 360                 365

Gly Met Val Asp Gly Trp Tyr Gly Phe Arg His Gln Asn Ser Glu Gly
    370                 375                 380

Ile Gly Gln Ala Ala Asp Leu Lys Ser Thr Gln Ala Ala Ile Asp Gln
385                 390                 395                 400

Ile Asn Gly Lys Leu Asn Arg Leu Ile Gly Lys Thr Asn Glu Lys Phe
                405                 410                 415

His Gln Ile Glu Lys Glu Phe Ser Glu Val Glu Gly Arg Ile Gln Asp
            420                 425                 430

Leu Glu Lys Tyr Val Glu Asp Thr Lys Ile Asp Leu Trp Ser Tyr Asn
        435                 440                 445

Ala Glu Leu Leu Val Ala Leu Glu Asn Gln His Thr Ile Asp Leu Thr
    450                 455                 460

Asp Ser Glu Met Asn Lys Leu Phe Glu Lys Thr Lys Lys Gln Leu Arg
465                 470                 475                 480

Glu Asn Ala Glu Asp Met Gly Asn Gly Cys Phe Lys Ile Tyr His Lys
                485                 490                 495

Cys Asp Asn Ala Cys Ile Gly Ser Ile Arg Asn Gly Thr Tyr Asp His
            500                 505                 510

Asp Val Tyr Arg Asp Glu Ala Leu Asn Asn Arg Phe Gln Ile Lys Gly
        515                 520                 525

Val Glu Leu Lys Ser Ile Gly Thr Tyr Gln Ile Leu Ser Ile Tyr Ser
    530                 535                 540

Thr Val Ala Ser Ser Leu Ala Leu Ala Ile Met Met Ala Gly Leu Ser
545                 550                 555                 560

Leu Trp Met Cys Ser Asn Gly Ser Leu Gln Cys Arg Ile Cys Ile
                565                 570                 575


<210> SEQ ID NO 84
<211> LENGTH: 593
<212> TYPE: PRT
<213> ORGANISM: Artificial Sequence
<220> FEATURE:
<223> OTHER INFORMATION: Synthesized amino acid translation of coding
      sequence in construct 745 expression cassette

<400> SEQUENCE: 84

Met Ala Lys Asn Val Ala Ile Phe Gly Leu Leu Phe Ser Leu Leu Val
1               5                   10                  15

Leu Val Pro Ser Gln Ile Phe Ala Asp Arg Ile Cys Thr Gly Ile Thr
            20                  25                  30

Ser Ser Asn Ser Pro His Val Val Lys Thr Ala Thr Gln Gly Glu Val
        35                  40                  45

Asn Val Thr Gly Val Ile Pro Leu Thr Thr Thr Pro Thr Lys Ser Tyr
    50                  55                  60

Phe Ala Asn Leu Lys Gly Thr Arg Thr Arg Gly Lys Leu Cys Pro Asp
65                  70                  75                  80

Cys Leu Asn Cys Thr Asp Leu Asp Val Ala Leu Gly Arg Pro Met Cys
                85                  90                  95

Val Gly Thr Thr Pro Ser Ala Lys Ala Ser Ile Leu His Glu Val Lys
            100                 105                 110

Pro Val Thr Ser Gly Cys Phe Pro Ile Met His Asp Arg Thr Lys Ile
        115                 120                 125

Arg Gln Leu Pro Asn Leu Leu Arg Gly Tyr Glu Asn Ile Arg Leu Ser
    130                 135                 140
```

-continued

```
Thr Gln Asn Val Ile Asp Ala Glu Lys Ala Pro Gly Gly Pro Tyr Arg
145                 150                 155                 160

Leu Gly Thr Ser Gly Ser Cys Pro Asn Ala Thr Ser Lys Ser Gly Phe
                165                 170                 175

Phe Ala Thr Met Ala Trp Ala Val Pro Lys Asp Asn Asn Lys Asn Ala
            180                 185                 190

Thr Asn Pro Leu Thr Val Glu Val Pro Tyr Ile Cys Thr Glu Gly Glu
        195                 200                 205

Asp Gln Ile Thr Val Trp Gly Phe His Ser Asp Asn Lys Thr Gln Met
    210                 215                 220

Lys Asn Leu Tyr Gly Asp Ser Asn Pro Gln Lys Phe Thr Ser Ser Ala
225                 230                 235                 240

Asn Gly Val Thr Thr His Tyr Val Ser Gln Ile Gly Ser Phe Pro Asp
                245                 250                 255

Gln Thr Glu Asp Gly Gly Leu Pro Gln Ser Gly Arg Ile Val Val Asp
            260                 265                 270

Tyr Met Met Gln Lys Pro Gly Lys Thr Gly Thr Ile Val Tyr Gln Arg
        275                 280                 285

Gly Val Leu Leu Pro Gln Lys Val Trp Cys Ala Ser Gly Arg Ser Lys
    290                 295                 300

Val Ile Lys Gly Ser Leu Pro Leu Ile Gly Glu Ala Asp Cys Leu His
305                 310                 315                 320

Glu Lys Tyr Gly Gly Leu Asn Lys Ser Lys Pro Tyr Tyr Thr Gly Glu
                325                 330                 335

His Ala Lys Ala Ile Gly Asn Cys Pro Ile Trp Val Lys Thr Pro Leu
            340                 345                 350

Lys Leu Ala Asn Gly Thr Lys Tyr Arg Pro Pro Ala Lys Leu Leu Lys
        355                 360                 365

Glu Arg Gly Phe Phe Gly Ala Ile Ala Gly Phe Leu Glu Gly Gly Trp
    370                 375                 380

Glu Gly Met Ile Ala Gly Trp His Gly Tyr Thr Ser His Gly Ala His
385                 390                 395                 400

Gly Val Ala Val Ala Ala Asp Leu Lys Ser Thr Gln Glu Ala Ile Asn
                405                 410                 415

Lys Ile Thr Lys Asn Leu Asn Ser Leu Ser Glu Leu Glu Val Lys Asn
            420                 425                 430

Leu Gln Arg Leu Ser Gly Ala Met Asp Glu Leu His Asn Glu Ile Leu
        435                 440                 445

Glu Leu Asp Glu Lys Val Asp Asp Leu Arg Ala Asp Thr Ile Ser Ser
    450                 455                 460

Gln Ile Glu Leu Ala Val Leu Leu Ser Asn Glu Gly Ile Ile Asn Ser
465                 470                 475                 480

Glu Asp Glu His Leu Leu Ala Leu Glu Arg Lys Leu Lys Lys Met Leu
                485                 490                 495

Gly Pro Ser Ala Val Glu Ile Gly Asn Gly Cys Phe Glu Thr Lys His
            500                 505                 510

Lys Cys Asn Gln Thr Cys Leu Asp Arg Ile Ala Ala Gly Thr Phe Asn
        515                 520                 525

Ala Gly Glu Phe Ser Leu Pro Thr Phe Asp Ser Leu Asn Ile Thr Ala
    530                 535                 540

Ala Ser Leu Asn Asp Asp Gly Leu Asp Asn Tyr Gln Ile Leu Ser Ile
545                 550                 555                 560
```

-continued

```
Tyr Ser Thr Val Ala Ser Ser Leu Ala Leu Ala Ile Met Met Ala Gly
                565                 570                 575

Leu Ser Leu Trp Met Cys Ser Asn Gly Ser Leu Gln Cys Arg Ile Cys
            580                 585                 590

Ile


<210> SEQ ID NO 85
<211> LENGTH: 405
<212> TYPE: DNA
<213> ORGANISM: Artificial Sequence
<220> FEATURE:
<223> OTHER INFORMATION: Synthesized SacI-Plasto 3'UTR sequence

<400> SEQUENCE: 85

gagctctaag ttaaaatgct tcttcgtctc ctatttataa tatggtttgt tattgttaat      60

tttgttcttg tagaagagct taattaatcg ttgttgttat gaaatactat ttgtatgaga     120

tgaactggtg taatgtaatt catttacata agtggagtca gaatcagaat gtttcctcca     180

taactaacta gacatgaaga cctgccgcgt acaattgtct tatatttgaa caactaaaat     240

tgaacatctt ttgccacaac tttataagtg gttaatatag ctcaaatata tggtcaagtt     300

caatagatta ataatggaaa tatcagttat cgaaattcat taacaatcaa cttaacgtta     360

ttaactacta attttatatc atcccctttg ataaatgata gtaca                     405


<210> SEQ ID NO 86
<211> LENGTH: 1718
<212> TYPE: DNA
<213> ORGANISM: Artificial Sequence
<220> FEATURE:
<223> OTHER INFORMATION: Synthesized PDI sp - A/California/04/09

<400> SEQUENCE: 86

atggcgaaaa acgttgcgat tttcggctta ttgttttctc ttcttgtgtt ggttcctctc      60

agatcttcgc tgacacatta tgtataggtt atcatgcgaa caattcaaca gacactgtag     120

acacagtact agaaaagaat gtaacagtaa cacactctgt taaccttcta gaagacaagc     180

ataacgggaa actatgcaaa ctaagagggg tagccccatt gcatttgggt aaatgtaaca     240

ttgctggctg gatcctggga aatccagagt gtgaatcact ctccacagca agctcatggt     300

cctacattgt ggaaacacct agttcagaca atggaacgtg ttacccagga gatttcatcg     360

attatgagga gctaagagag caattaagct cagtgtcatc atttgaaagg tttgagatat     420

tccccaagac aagttcatgg cccaatcatg actcgaacaa aggtgtaacg gcagcatgtc     480

ctcatgctgg agcaaaaagc ttctacaaaa atttaatatg gctagttaaa aaaggaaatt     540

catacccaaa gctcagcaaa tcctacatta atgataaagg gaaagaagtc ctcgtgctat     600

ggggcattca ccatccatct actagtgctg accaacaaag tctctatcag aatgcagata     660

catatgtttt tgtggggtca tcaagataca gcaagaagtt caagccggaa atagcaataa     720

gacccaaagt gagggatcaa gaagggagaa tgaactatta ctggacacta gtagagccgg     780

gagacaaaat aacattcgaa gcaactggaa atctagtggt accgagatat gcattcgcaa     840

tggaaagaaa tgctggatct ggtattatca tttcagatac accagtccac gattgcaata     900

caacttgtca aacacccaag ggtgctataa acaccagcct cccatttcag aatatacatc     960

cgatcacaat tggaaaatgt ccaaaatatg taaaaagcac aaaattgaga ctggccacag    1020

gattgaggaa tatcccgtct attcaatcta gaggactatt tggggccatt gccggtttca    1080

ttgaaggggg gtggacaggg atggtagatg gatggtacgg ttatcaccat caaaatgagc    1140
```

-continued

```
aggggtcagg atatgcagcc gacctgaaga gcacacagaa tgccattgac gagattacta   1200

acaaagtaaa ttctgttatt gaaaagatga atacacagtt cacagcagta ggtaaagagt   1260

tcaaccacct ggaaaaaaga atagagaatt taaataaaaa agttgatgat ggtttcctgg   1320

acatttggac ttacaatgcc gaactgttgg ttctattgga aaatgaaaga actttggact   1380

accacgattc aaatgtgaag aacttatatg aaaaggtaag aagccagcta aaaaacaatg   1440

ccaaggaaat tggaaacggc tgctttgaat tttaccacaa atgcgataac acgtgcatgg   1500

aaagtgtcaa aaatgggact tatgactacc caaaatactc agaggaagca aaattaaaca   1560

gagaagaaat agatggggta aagctggaat caacaaggat ttaccagatt ttggcgatct   1620

attcaactgt cgccagttca ttggtactgg tagtctccct gggggcaatc agtttctgga   1680

tgtgctctaa tgggtctcta cagtgtagaa tatgtatt                           1718
```

<210> SEQ ID NO 87
<211> LENGTH: 573
<212> TYPE: PRT
<213> ORGANISM: Artificial Sequence
<220> FEATURE:
<223> OTHER INFORMATION: Synthesized PDI sp - A/California 04/09

<400> SEQUENCE: 87

```
Met Ala Lys Asn Val Ala Ile Phe Gly Leu Leu Phe Ser Leu Leu Val
1               5                   10                  15

Leu Val Pro Ser Gln Ile Phe Ala Asp Thr Leu Cys Ile Gly Tyr His
            20                  25                  30

Ala Asn Asn Ser Thr Asp Thr Val Asp Thr Val Leu Glu Lys Asn Val
        35                  40                  45

Thr Val Thr His Ser Val Asn Leu Leu Glu Asp Lys His Asn Gly Lys
    50                  55                  60

Leu Cys Lys Leu Arg Gly Val Ala Pro Leu His Leu Gly Lys Cys Asn
65                  70                  75                  80

Ile Ala Gly Trp Ile Leu Gly Asn Pro Glu Cys Glu Ser Leu Ser Thr
                85                  90                  95

Ala Ser Ser Trp Ser Tyr Ile Val Glu Thr Pro Ser Ser Asp Asn Gly
            100                 105                 110

Thr Cys Tyr Pro Gly Asp Phe Ile Asp Tyr Glu Glu Leu Arg Glu Gln
        115                 120                 125

Leu Ser Ser Val Ser Ser Phe Glu Arg Phe Glu Ile Phe Pro Lys Thr
    130                 135                 140

Ser Ser Trp Pro Asn His Asp Ser Asn Lys Gly Val Thr Ala Ala Cys
145                 150                 155                 160

Pro His Ala Gly Ala Lys Ser Phe Tyr Lys Asn Leu Ile Trp Leu Val
                165                 170                 175

Lys Lys Gly Asn Ser Tyr Pro Lys Leu Ser Lys Ser Tyr Ile Asn Asp
            180                 185                 190

Lys Gly Lys Glu Val Leu Val Leu Trp Gly Ile His His Pro Ser Thr
        195                 200                 205

Ser Ala Asp Gln Gln Ser Leu Tyr Gln Asn Ala Asp Thr Tyr Val Phe
    210                 215                 220

Val Gly Ser Ser Arg Tyr Ser Lys Lys Phe Lys Pro Glu Ile Ala Ile
225                 230                 235                 240

Arg Pro Lys Val Arg Asp Gln Glu Gly Arg Met Asn Tyr Tyr Trp Thr
                245                 250                 255
```

```
Leu Val Glu Pro Gly Asp Lys Ile Thr Phe Glu Ala Thr Gly Asn Leu
            260                 265                 270

Val Val Pro Arg Tyr Ala Phe Ala Met Glu Arg Asn Ala Gly Ser Gly
        275                 280                 285

Ile Ile Ile Ser Asp Thr Pro Val His Asp Cys Asn Thr Thr Cys Gln
    290                 295                 300

Thr Pro Lys Gly Ala Ile Asn Thr Ser Leu Pro Phe Gln Asn Ile His
305                 310                 315                 320

Pro Ile Thr Ile Gly Lys Cys Pro Lys Tyr Val Lys Ser Thr Lys Leu
                325                 330                 335

Arg Leu Ala Thr Gly Leu Arg Asn Ile Pro Ser Ile Gln Ser Arg Gly
            340                 345                 350

Leu Phe Gly Ala Ile Ala Gly Phe Ile Glu Gly Gly Trp Thr Gly Met
        355                 360                 365

Val Asp Gly Trp Tyr Gly Tyr His His Gln Asn Glu Gln Gly Ser Gly
    370                 375                 380

Tyr Ala Ala Asp Leu Lys Ser Thr Gln Asn Ala Ile Asp Glu Ile Thr
385                 390                 395                 400

Asn Lys Val Asn Ser Val Ile Glu Lys Met Asn Thr Gln Phe Thr Ala
                405                 410                 415

Val Gly Lys Glu Phe Asn His Leu Glu Lys Arg Ile Glu Asn Leu Asn
            420                 425                 430

Lys Lys Val Asp Asp Gly Phe Leu Asp Ile Trp Thr Tyr Asn Ala Glu
        435                 440                 445

Leu Leu Val Leu Leu Glu Asn Glu Arg Thr Leu Asp Tyr His Asp Ser
    450                 455                 460

Asn Val Lys Asn Leu Tyr Glu Lys Val Arg Ser Gln Leu Lys Asn Asn
465                 470                 475                 480

Ala Lys Glu Ile Gly Asn Gly Cys Phe Glu Phe Tyr His Lys Cys Asp
                485                 490                 495

Asn Thr Cys Met Glu Ser Val Lys Asn Gly Thr Tyr Asp Tyr Pro Lys
            500                 505                 510

Tyr Ser Glu Glu Ala Lys Leu Asn Arg Glu Glu Ile Asp Gly Val Lys
        515                 520                 525

Leu Glu Ser Thr Arg Ile Tyr Gln Ile Leu Ala Ile Tyr Ser Thr Val
    530                 535                 540

Ala Ser Ser Leu Val Leu Val Val Ser Leu Gly Ala Ile Ser Phe Trp
545                 550                 555                 560

Met Cys Ser Asn Gly Ser Leu Gln Cys Arg Ile Cys Ile
                565                 570
```

<210> SEQ ID NO 88
<211> LENGTH: 747
<212> TYPE: DNA
<213> ORGANISM: Artificial Sequence
<220> FEATURE:
<223> OTHER INFORMATION: Synthesized 2X35S promoter sequence

<400> SEQUENCE: 88

```
gtcaacatgg tggagcacga cacacttgtc tactccaaaa atatcaaaga tacagtctca      60

gaagaccaaa gggcaattga gacttttcaa caaagggtaa tatccggaaa cctcctcgga     120

ttccattgcc cagctatctg tcactttatt gtgaagatag tggaaaagga aggtggctcc     180

tacaaatgcc atcattgcga taaaggaaag gccatcgttg aagatgcctc tgccgacagt     240

ggtcccaaag atggaccccc acccacgagg agcatcgtgg aaaaagaaga cgttccaacc     300
```

-continued acgtcttcaa agcaagtgga ttgatgtgat aacatggtgg agcacgacac acttgtctac 360
tccaaaaata tcaaagatac agtctcagaa gaccaaaggg caattgagac ttttcaacaa 420
agggtaatat ccggaaacct cctcggattc cattgcccag ctatctgtca ctttattgtg 480
aagatagtgg aaaaggaagg tggctcctac aaatgccatc attgcgataa aggaaaggcc 540
atcgttgaag atgcctctgc cgacagtggt cccaaagatg gacccccacc cacgaggagc 600
atcgtggaaa aagaagacgt tccaaccacg tcttcaaagc aagtggattg atgtgatatc 660
tccactgacg taagggatga cgcacaatcc cactatcctt cgcaagaccc ttcctctata 720
taaggaagtt catttcattt ggagagg 747

<210> SEQ ID NO 89
<211> LENGTH: 43
<212> TYPE: DNA
<213> ORGANISM: Artificial Sequence
<220> FEATURE:
<223> OTHER INFORMATION: Synthesized PacI-MCS-2X35S.c

<400> SEQUENCE: 89
aattgttaat taagtcgaca agcttgcatg cctgcaggtc aac 43

<210> SEQ ID NO 90
<211> LENGTH: 48
<212> TYPE: DNA
<213> ORGANISM: Artificial Sequence
<220> FEATURE:
<223> OTHER INFORMATION: Synthesized CPMV 5'UTR-2X35S.r

<400> SEQUENCE: 90
tcaaaaccta ttaagatttt aatacctctc caaatgaaat gaacttcc 48

<210> SEQ ID NO 91
<211> LENGTH: 49
<212> TYPE: DNA
<213> ORGANISM: Artificial Sequence
<220> FEATURE:
<223> OTHER INFORMATION: Synthesized 2X35S-CPMV 5'UTR.c

<400> SEQUENCE: 91
ttggagaggt attaaaatct taataggttt tgataaaagc gaacgtggg 49

<210> SEQ ID NO 92
<211> LENGTH: 44
<212> TYPE: DNA
<213> ORGANISM: Artificial Sequence
<220> FEATURE:
<223> OTHER INFORMATION: Synthesized ApaI-M prot.r

<400> SEQUENCE: 92
tctccatggg cccgacaaat ttgggcagaa tatacagaag ctta 44

<210> SEQ ID NO 93
<211> LENGTH: 3580
<212> TYPE: DNA
<213> ORGANISM: Artificial Sequence
<220> FEATURE:
<223> OTHER INFORMATION: Synthesized Construct 747, from PacI to AscI

<400> SEQUENCE: 93
ttaattaagt cgacaagctt gcatgcctgc aggtcaacat ggtggagcac gacacacttg 60
tctactccaa aaatatcaaa gatacagtct cagaagacca aagggcaatt gagacttttc 120

-continued

```
aacaaagggt aatatccgga aacctcctcg gattccattg cccagctatc tgtcacttta    180
ttgtgaagat agtggaaaag gaaggtggct cctacaaatg ccatcattgc gataaaggaa    240
aggccatcgt tgaagatgcc tctgccgaca gtggtcccaa agatggaccc ccacccacga    300
ggagcatcgt ggaaaaagaa gacgttccaa ccacgtcttc aaagcaagtg gattgatgtg    360
ataacatggt ggagcacgac acacttgtct actccaaaaa tatcaaagat acagtctcag    420
aagaccaaag ggcaattgag acttttcaac aaagggtaat atccggaaac ctcctcggat    480
tccattgccc agctatctgt cactttattg tgaagatagt ggaaaaggaa ggtggctcct    540
acaaatgcca tcattgcgat aaaggaaagg ccatcgttga agatgcctct gccgacagtg    600
gtcccaaaga tggaccccca cccacgagga gcatcgtgga aaaagaagac gttccaacca    660
cgtcttcaaa gcaagtggat tgatgtgata tctccactga cgtaagggat gacgcacaat    720
cccactatcc ttcgcaagac ccttcctcta tataaggaag ttcatttcat ttggagaggt    780
attaaaatct taataggttt tgataaaagc gaacgtgggg aaacccgaac caaaccttct    840
tctaaactct ctctcatctc tcttaaagca aacttctctc ttgtctttct tgcgtgagcg    900
atcttcaacg ttgtcagatc gtgcttcggc accagtacaa cgttttcttt cactgaagcg    960
aaatcaaaga tctctttgtg gacacgtagt gcggcgccat taaataacgt gtacttgtcc   1020
tattcttgtc ggtgtggtct tgggaaaaga aagcttgctg gaggctgctg ttcagcccca   1080
tacattactt gttacgattc tgctgacttt cggcgggtgc aatatctcta cttctgcttg   1140
acgaggtatt gttgcctgta cttctttctt cttcttcttg ctgattggtt ctataagaaa   1200
tctagtattt tctttgaaac agagttttcc cgtggttttc gaacttggag aaagattgtt   1260
aagcttctgt atattctgcc caaatttgtc gggcccatgg cgaaaaacgt tgcgattttc   1320
ggcttattgt tttctcttct tgtgttggtt ccttctcaga tcttcgctga tcgaatctgc   1380
actggaataa catcttcaaa ctcacctcat gtggtcaaaa cagccactca aggggaggtc   1440
aatgtgactg gtgtgatacc actaacaaca acaccaacaa aatcttattt tgcaaatctc   1500
aaaggaacaa ggaccagagg gaaactatgc ccagactgtc tcaactgcac agatctggat   1560
gtggctttgg gcagaccaat gtgtgtgggg accacacctt cggcgaaggc ttcaatactc   1620
cacgaagtca aacctgttac atccgggtgc tttcctataa tgcacgacag aacaaaaatc   1680
aggcaactac ccaatcttct cagaggatat gaaaatatca ggctatcaac ccaaaacgtc   1740
atcgatgcgg aaaaggcacc aggaggaccc tacagacttg gaacctcagg atcttgccct   1800
aacgctacca gtaagagcgg atttttcgca acaatggctt gggctgtccc aaaggacaac   1860
aacaaaaatg caacgaaccc actaacagta gaagtaccat acatttgtac agaaggggaa   1920
gaccaaatca ctgtttgggg gttccattca gataacaaaa cccaaatgaa gaacctctat   1980
ggagactcaa atcctcaaaa gttcacctca tctgctaatg gagtaaccac acactatgtt   2040
tctcagattg gcagcttccc agatcaaaca gaagacggag gactaccaca aagcggcagg   2100
attgttgttg attacatgat gcaaaaacct gggaaaacag gaacaattgt ctaccaaaga   2160
ggtgttttgt tgcctcaaaa ggtgtggtgc gcgagtggca ggagcaaagt aataaaaggg   2220
tccttgcctt taattggtga agcagattgc cttcatgaaa aatacggtgg attaaacaaa   2280
agcaagcctt actacacagg agaacatgca aaagccatag gaaattgccc aatatgggtg   2340
aaaacacctt tgaagctcgc caatggaacc aaatatagac ctcctgcaaa actattaaag   2400
gaaaggggtt tcttcggagc tattgctggt ttcctagaag gaggatggga aggaatgatt   2460
gcaggctggc acggatacac atctcacgga gcacatggag tggcagtggc ggcggacctt   2520
```

-continued

```
aagagtacgc aagaagctat aaacaagata acaaaaaatc tcaattcttt gagtgagcta   2580

gaagtaaaga atcttcaaag actaagtggt gccatggatg aactccacaa cgaaatactc   2640

gagctggatg agaaagtgga tgatctcaga gctgacacta taagctcgca aatagaactt   2700

gcagtcttgc tttccaacga aggaataata aacagtgaag atgagcatct attggcactt   2760

gagagaaaac taaagaaaat gctgggtccc tctgctgtag agataggaaa tggatgcttc   2820

gaaaccaaac acaagtgcaa ccagacctgc ttagacagga tagctgctgg cacctttaat   2880

gcaggagaat tttctctccc cacttttgat tcactgaaca ttactgctgc atctttaaat   2940

gatgatggat tggataacta ccaaatactg tcaatttatt caacagtggc gagttcccta   3000

gcactggcaa tcatgatggc tggtctatct ttatggatgt gctccaatgg atcgttacaa   3060

tgcagaattt gcatttaaag gcctattttc tttagtttga atttactgtt attcggtgtg   3120

catttctatg tttggtgagc ggttttctgt gctcagagtg tgtttatttt atgtaattta   3180

atttctttgt gagctcctgt ttagcaggtc gtcccttcag caaggacaca aaaagatttt   3240

aattttatta aaaaaaaaaa aaaaaaagac cgggaattcg atatcaagct tatcgacctg   3300

cagatcgttc aaacatttgg caataaagtt tcttaagatt gaatcctgtt gccggtcttg   3360

cgatgattat catataattt ctgttgaatt acgttaagca tgtaataatt aacatgtaat   3420

gcatgacgtt atttatgaga tgggttttta tgattagagt cccgcaatta tacatttaat   3480

acgcgataga aaacaaaata tagcgcgcaa actaggataa attatcgcgc gcggtgtcat   3540

ctatgttact agattctaga gtctcaagct tcggcgcgcc                         3580
```

<210> SEQ ID NO 94
<211> LENGTH: 569
<212> TYPE: PRT
<213> ORGANISM: Artificial Sequence
<220> FEATURE:
<223> OTHER INFORMATION: Synthesized Influenza B virus B/Florida/4/2006

<400> SEQUENCE: 94

```
Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser Tyr Phe Ala Asn Leu Lys Gly Thr Arg
        35                  40                  45

Thr Arg Gly Lys Leu Cys Pro Asp Cys Leu Asn Cys Thr Asp Leu Asp
    50                  55                  60

Val Ala Leu Gly Arg Pro Met Cys Val Gly Thr Thr Pro Ser Ala Lys
65                  70                  75                  80

Ala Ser Ile Leu His Glu Val Lys Pro Val Thr Ser Gly Cys Phe Pro
                85                  90                  95

Ile Met His Asp Arg Thr Lys Ile Arg Gln Leu Pro Asn Leu Leu Arg
            100                 105                 110

Gly Tyr Glu Asn Ile Arg Leu Ser Thr Gln Asn Val Ile Asp Ala Glu
        115                 120                 125

Lys Ala Pro Gly Gly Pro Tyr Arg Leu Gly Thr Ser Gly Ser Cys Pro
    130                 135                 140

Asn Ala Thr Ser Lys Ser Gly Phe Phe Ala Thr Met Ala Trp Ala Val
145                 150                 155                 160

Pro Lys Asp Asn Asn Lys Asn Ala Thr Asn Pro Leu Thr Val Glu Val
                165                 170                 175
```

```
Pro Tyr Ile Cys Thr Glu Gly Glu Asp Gln Ile Thr Val Trp Gly Phe
            180                 185                 190

His Ser Asp Asp Lys Thr Gln Met Lys Asn Leu Tyr Gly Asp Ser Asn
        195                 200                 205

Pro Gln Lys Phe Thr Ser Ser Ala Asn Gly Val Thr Thr His Tyr Val
    210                 215                 220

Ser Gln Ile Gly Ser Phe Pro Asp Gln Thr Glu Asp Gly Gly Leu Pro
225                 230                 235                 240

Gln Ser Gly Arg Ile Val Val Asp Tyr Met Met Gln Lys Pro Gly Lys
                245                 250                 255

Thr Gly Thr Ile Val Tyr Gln Arg Gly Val Leu Leu Pro Gln Lys Val
            260                 265                 270

Trp Cys Ala Ser Gly Arg Ser Lys Val Ile Lys Gly Ser Leu Pro Leu
        275                 280                 285

Ile Gly Glu Ala Asp Cys Leu His Glu Lys Tyr Gly Gly Leu Asn Lys
    290                 295                 300

Ser Lys Pro Tyr Tyr Thr Gly Glu His Ala Lys Ala Ile Gly Asn Cys
305                 310                 315                 320

Pro Ile Trp Val Lys Thr Pro Leu Lys Leu Ala Asn Gly Thr Lys Tyr
                325                 330                 335

Arg Pro Pro Ala Lys Leu Leu Lys Glu Arg Gly Phe Phe Gly Ala Ile
            340                 345                 350

Ala Gly Phe Leu Glu Gly Gly Trp Glu Gly Met Ile Ala Gly Trp His
        355                 360                 365

Gly Tyr Thr Ser His Gly Ala His Gly Val Ala Val Ala Ala Asp Leu
    370                 375                 380

Lys Ser Thr Gln Glu Ala Ile Asn Lys Ile Thr Lys Asn Leu Asn Ser
385                 390                 395                 400

Leu Ser Glu Leu Glu Val Lys Asn Leu Gln Arg Leu Ser Gly Ala Met
                405                 410                 415

Asp Glu Leu His Asn Glu Ile Leu Glu Leu Asp Glu Lys Val Asp Asp
            420                 425                 430

Leu Arg Ala Asp Thr Ile Ser Ser Gln Ile Glu Leu Ala Val Leu Leu
        435                 440                 445

Ser Asn Glu Gly Ile Ile Asn Ser Glu Asp Glu His Leu Leu Ala Leu
    450                 455                 460

Glu Arg Lys Leu Lys Lys Met Leu Gly Pro Ser Ala Val Glu Ile Gly
465                 470                 475                 480

Asn Gly Cys Phe Glu Thr Lys His Lys Cys Asn Gln Thr Cys Leu Asp
                485                 490                 495

Arg Ile Ala Ala Gly Thr Phe Asn Ala Gly Glu Phe Ser Leu Pro Thr
            500                 505                 510

Phe Asp Ser Leu Asn Ile Thr Ala Ala Ser Leu Asn Asp Asp Gly Leu
        515                 520                 525

Asp Asn His Thr Ile Leu Leu Tyr Tyr Ser Thr Ala Ala Ser Ser Leu
    530                 535                 540

Ala Val Thr Leu Met Leu Ala Ile Phe Ile Val Tyr Met Val Ser Arg
545                 550                 555                 560

Asp Asn Val Ser Cys Ser Ile Cys Leu
                565
```

<210> SEQ ID NO 95
<211> LENGTH: 570

<212> TYPE: PRT
<213> ORGANISM: Artificial Sequence
<220> FEATURE:
<223> OTHER INFORMATION: Synthesized Influenza B virus
      B/Malaysia/2506/2004

<400> SEQUENCE: 95

```
Asp Arg Ile Cys Thr Gly Ile Thr Ser Ser Asn Ser Pro His Val Val
1               5                   10                  15

Lys Thr Ala Thr Gln Gly Glu Val Asn Val Thr Gly Val Ile Pro Leu
            20                  25                  30

Thr Thr Thr Pro Thr Lys Ser His Phe Ala Asn Leu Lys Gly Thr Glu
        35                  40                  45

Thr Arg Gly Lys Leu Cys Pro Lys Cys Leu Asn Cys Thr Asp Leu Asp
    50                  55                  60

Val Ala Leu Gly Arg Pro Lys Cys Thr Gly Asn Ile Pro Ser Ala Arg
65                  70                  75                  80

Val Ser Ile Leu His Glu Val Arg Pro Val Thr Ser Gly Cys Phe Pro
                85                  90                  95

Ile Met His Asp Arg Thr Lys Ile Arg Gln Leu Pro Lys Leu Leu Arg
            100                 105                 110

Gly Tyr Glu His Ile Arg Leu Ser Thr His Asn Val Ile Asn Ala Glu
        115                 120                 125

Asn Ala Pro Gly Gly Pro Tyr Lys Ile Gly Thr Ser Gly Ser Cys Pro
    130                 135                 140

Asn Val Thr Asn Gly Asn Gly Phe Phe Ala Thr Met Ala Trp Ala Val
145                 150                 155                 160

Pro Lys Asn Asp Asn Asn Lys Thr Ala Thr Asn Ser Leu Thr Ile Glu
                165                 170                 175

Val Pro Tyr Ile Cys Thr Glu Gly Glu Asp Gln Ile Thr Val Trp Gly
            180                 185                 190

Phe His Ser Asp Asn Glu Thr Gln Met Ala Lys Leu Tyr Gly Asp Ser
        195                 200                 205

Lys Pro Gln Lys Phe Thr Ser Ser Ala Asn Gly Val Thr Thr His Tyr
    210                 215                 220

Val Ser Gln Ile Gly Gly Phe Pro Asn Gln Thr Glu Asp Gly Gly Leu
225                 230                 235                 240

Pro Gln Ser Gly Arg Ile Val Val Asp Tyr Met Val Gln Lys Ser Gly
                245                 250                 255

Lys Thr Gly Thr Ile Thr Tyr Gln Arg Gly Ile Leu Leu Pro Gln Lys
            260                 265                 270

Val Trp Cys Ala Ser Gly Arg Ser Lys Val Ile Lys Gly Ser Leu Pro
        275                 280                 285

Leu Ile Gly Glu Ala Asp Cys Leu His Glu Lys Tyr Gly Gly Leu Asn
    290                 295                 300

Lys Ser Lys Pro Tyr Tyr Thr Gly Glu His Ala Lys Ala Ile Gly Asn
305                 310                 315                 320

Cys Pro Ile Trp Val Lys Thr Pro Leu Lys Leu Ala Asn Gly Thr Lys
                325                 330                 335

Tyr Arg Pro Pro Ala Lys Leu Leu Lys Glu Arg Gly Phe Phe Gly Ala
            340                 345                 350

Ile Ala Gly Phe Leu Glu Gly Gly Trp Glu Gly Met Ile Ala Gly Trp
        355                 360                 365

His Gly Tyr Thr Ser His Gly Ala His Gly Val Ala Val Ala Ala Asp
    370                 375                 380
```

-continued

Leu Lys Ser Thr Gln Glu Ala Ile Asn Lys Ile Thr Lys Asn Leu Asn
385 390 395 400

Ser Leu Ser Glu Leu Glu Val Lys Asn Leu Gln Arg Leu Ser Gly Ala
405 410 415

Met Asp Glu Leu His Asn Glu Ile Leu Glu Leu Asp Glu Lys Val Asp
420 425 430

Asp Leu Arg Ala Asp Thr Ile Ser Ser Gln Ile Glu Leu Ala Val Leu
435 440 445

Leu Ser Asn Glu Gly Ile Ile Asn Ser Glu Asp Glu His Leu Leu Ala
450 455 460

Leu Glu Arg Lys Leu Lys Lys Met Leu Gly Pro Ser Ala Val Glu Ile
465 470 475 480

Gly Asn Gly Cys Phe Glu Thr Lys His Lys Cys Asn Gln Thr Cys Leu
485 490 495

Asp Arg Ile Ala Ala Gly Thr Phe Asp Ala Gly Glu Phe Ser Leu Pro
500 505 510

Thr Phe Asp Ser Leu Asn Ile Thr Ala Ala Ser Leu Asn Asp Asp Gly
515 520 525

Leu Asp Asn His Thr Ile Leu Leu Tyr Tyr Ser Thr Ala Ala Ser Ser
530 535 540

Leu Ala Val Thr Leu Met Ile Ala Ile Phe Val Val Tyr Met Val Ser
545 550 555 560

Arg Asp Asn Val Ser Cys Ser Ile Cys Leu
565 570

<210> SEQ ID NO 96
<211> LENGTH: 548
<212> TYPE: PRT
<213> ORGANISM: Artificial Sequence
<220> FEATURE:
<223> OTHER INFORMATION: Synthesized Influenza A virus A/Brisbane/59/2007(H1N1)

<400> SEQUENCE: 96

Asp Thr Ile Cys Ile Gly Tyr His Ala Asn Asn Ser Thr Asp Thr Val
1 5 10 15

Asp Thr Val Leu Glu Lys Asn Val Thr Val Thr His Ser Val Asn Leu
20 25 30

Leu Glu Asn Ser His Asn Gly Lys Leu Cys Leu Leu Lys Gly Ile Ala
35 40 45

Pro Leu Gln Leu Gly Asn Cys Ser Val Ala Gly Trp Ile Leu Gly Asn
50 55 60

Pro Glu Cys Glu Leu Leu Ile Ser Lys Glu Ser Trp Ser Tyr Ile Val
65 70 75 80

Glu Lys Pro Asn Pro Glu Asn Gly Thr Cys Tyr Pro Gly His Phe Ala
85 90 95

Asp Tyr Glu Glu Leu Arg Glu Gln Leu Ser Ser Val Ser Ser Phe Glu
100 105 110

Arg Phe Glu Ile Phe Pro Lys Glu Ser Ser Trp Pro Asn His Thr Val
115 120 125

Thr Gly Val Ser Ala Ser Cys Ser His Asn Gly Glu Ser Ser Phe Tyr
130 135 140

Arg Asn Leu Leu Trp Leu Thr Gly Lys Asn Gly Leu Tyr Pro Asn Leu
145 150 155 160

Ser Lys Ser Tyr Ala Asn Asn Lys Glu Lys Glu Val Leu Val Leu Trp

```
                165                 170                 175

Gly Val His His Pro Pro Asn Ile Gly Asn Gln Lys Ala Leu Tyr His
            180                 185                 190

Thr Glu Asn Ala Tyr Val Ser Val Val Ser Ser His Tyr Ser Arg Lys
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                245                 250                 255

Ser Arg Gly Phe Gly Ser Gly Ile Ile Asn Ser Asn Ala Pro Met Asp
            260                 265                 270

Lys Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Ile Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asp Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Val Lys Leu Glu Ser Met Gly Val Tyr Gln Ile
            500                 505                 510

Leu Ala Ile Tyr Ser Thr Val Ala Ser Ser Leu Val Leu Leu Val Ser
        515                 520                 525

Leu Gly Ala Ile Ser Phe Trp Met Cys Ser Asn Gly Ser Leu Gln Cys
    530                 535                 540

Arg Ile Cys Ile
545
```

<210> SEQ ID NO 97
<211> LENGTH: 548
<212> TYPE: PRT
<213> ORGANISM: Artificial Sequence

```
<220> FEATURE:
<223> OTHER INFORMATION: Synthesized Influenza A virus A/Solomon
      Islands/3/2006(H1N1)

<400> SEQUENCE: 97

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Arg Glu Ser Trp Ser Tyr Ile Val
65                  70                  75                  80

Glu Lys Pro Asn Pro Glu Asn Gly Thr Cys Tyr Pro Gly His Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Thr
        115                 120                 125

Thr Gly Val Ser Ala Ser Cys Ser His Asn Gly Glu Ser Ser Phe Tyr
    130                 135                 140

Lys Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                165                 170                 175

Gly Val His His Pro Pro Asn Ile Gly Asp Gln Arg Ala Leu Tyr His
            180                 185                 190

Lys Glu Asn Ala Tyr Val Ser Val Val Ser Ser His Tyr Ser Arg Lys
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                245                 250                 255

Ser Arg Gly Phe Gly Ser Gly Ile Ile Asn Ser Asn Ala Pro Met Asp
            260                 265                 270

Glu Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
```

-continued

```
385                 390                 395                 400

Arg Arg Met Glu Asn Leu Asn Lys Lys Val Asp Asp Gly Phe Ile Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asp Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Val Lys Leu Glu Ser Met Gly Val Tyr Gln Ile
            500                 505                 510

Leu Ala Ile Tyr Ser Thr Val Ala Ser Ser Leu Val Leu Leu Val Ser
        515                 520                 525

Leu Gly Ala Ile Ser Phe Trp Met Cys Ser Asn Gly Ser Leu Gln Cys
    530                 535                 540

Arg Ile Cys Ile
545


<210> SEQ ID NO 98
<211> LENGTH: 548
<212> TYPE: PRT
<213> ORGANISM: Artificial Sequence
<220> FEATURE:
<223> OTHER INFORMATION: Synthesized Influenza A virus A/New
      Caledonia/20/1999(H1N1)

<400> SEQUENCE: 98

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Thr Pro Asn Pro Glu Asn Gly Thr Cys Tyr Pro Gly Tyr Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Lys Ser Ser Phe Tyr
    130                 135                 140

Arg Asn Leu Leu Trp Leu Thr Gly Lys Asn Gly Leu Tyr Pro Asn Leu
145                 150                 155                 160

Ser Lys Ser Tyr Val Asn Asn Lys Glu Lys Glu Val Leu Val Leu Trp
                165                 170                 175

Gly Val His His Pro Pro Asn Ile Gly Asn Gln Arg Ala Leu Tyr His
            180                 185                 190
```

```
Thr Glu Asn Ala Tyr Val Ser Val Val Ser Ser His Tyr Ser Arg Arg
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Trp Tyr Ala Phe Ala Leu
                245                 250                 255

Ser Arg Gly Phe Gly Ser Gly Ile Ile Thr Ser Asn Ala Pro Met Asp
            260                 265                 270

Glu Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asn Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Val Lys Leu Glu Ser Met Gly Val Tyr Gln Ile
            500                 505                 510

Leu Ala Ile Tyr Ser Thr Val Ala Ser Ser Leu Val Leu Leu Val Ser
        515                 520                 525

Leu Gly Ala Ile Ser Phe Trp Met Cys Ser Asn Gly Ser Leu Gln Cys
    530                 535                 540

Arg Ile Cys Ile
545
```

<210> SEQ ID NO 99
<211> LENGTH: 547
<212> TYPE: PRT
<213> ORGANISM: Artificial Sequence
<220> FEATURE:
<223> OTHER INFORMATION: Synthesized Influenza A virus
A/Singapore/1/1957(H2N2)

<400> SEQUENCE: 99

-continued

```
Asp Gln Ile Cys Ile Gly Tyr His Ala Asn Asn Ser Thr Glu Lys Val
1               5                   10                  15

Asp Thr Ile Leu Glu Arg Asn Val Thr Val Thr His Ala Lys Asp Ile
            20                  25                  30

Leu Glu Lys Thr His Asn Gly Lys Leu Cys Lys Leu Asn Gly Ile Pro
        35                  40                  45

Pro Leu Glu Leu Gly Asp Cys Ser Ile Ala Gly Trp Leu Leu Gly Asn
    50                  55                  60

Pro Glu Cys Asp Arg Leu Leu Ser Val Pro Glu Trp Ser Tyr Ile Met
65                  70                  75                  80

Glu Lys Glu Asn Pro Arg Asp Gly Leu Cys Tyr Pro Gly Ser Phe Asn
                85                  90                  95

Asp Tyr Glu Glu Leu Lys His Leu Leu Ser Ser Val Lys His Phe Glu
            100                 105                 110

Lys Val Lys Ile Leu Pro Lys Asp Arg Trp Thr Gln His Thr Thr Thr
        115                 120                 125

Gly Gly Ser Arg Ala Cys Ala Val Ser Gly Asn Pro Ser Phe Phe Arg
    130                 135                 140

Asn Met Val Trp Leu Thr Lys Lys Glu Ser Asn Tyr Pro Val Ala Lys
145                 150                 155                 160

Gly Ser Tyr Asn Asn Thr Ser Gly Glu Gln Met Leu Ile Ile Trp Gly
                165                 170                 175

Val His His Pro Asn Asp Glu Thr Glu Gln Arg Thr Leu Tyr Gln Asn
            180                 185                 190

Val Gly Thr Tyr Val Ser Val Gly Thr Ser Thr Leu Asn Lys Arg Ser
        195                 200                 205

Thr Pro Asp Ile Ala Thr Arg Pro Lys Val Asn Gly Leu Gly Ser Arg
    210                 215                 220

Met Glu Phe Ser Trp Thr Leu Leu Asp Met Trp Asp Thr Ile Asn Phe
225                 230                 235                 240

Glu Ser Thr Gly Asn Leu Ile Ala Pro Glu Tyr Gly Phe Lys Ile Ser
                245                 250                 255

Lys Arg Gly Ser Ser Gly Ile Met Lys Thr Glu Gly Thr Leu Glu Asn
            260                 265                 270

Cys Glu Thr Lys Cys Gln Thr Pro Leu Gly Ala Ile Asn Thr Thr Leu
        275                 280                 285

Pro Phe His Asn Val His Pro Leu Thr Ile Gly Glu Cys Pro Lys Tyr
    290                 295                 300

Val Lys Ser Glu Lys Leu Val Leu Ala Thr Gly Leu Arg Asn Val Pro
305                 310                 315                 320

Gln Ile Glu Ser Arg Gly Leu Phe Gly Ala Ile Ala Gly Phe Ile Glu
                325                 330                 335

Gly Gly Trp Gln Gly Met Val Asp Gly Trp Tyr Gly Tyr His His Ser
            340                 345                 350

Asn Asp Gln Gly Ser Gly Tyr Ala Ala Asp Lys Glu Ser Thr Gln Lys
        355                 360                 365

Ala Phe Asp Gly Ile Thr Asn Lys Val Asn Ser Val Ile Glu Lys Met
    370                 375                 380

Asn Thr Gln Phe Glu Ala Val Gly Lys Glu Phe Ser Asn Leu Glu Arg
385                 390                 395                 400

Arg Leu Glu Asn Leu Asn Lys Lys Met Glu Asp Gly Phe Leu Asp Val
                405                 410                 415
```

-continued

```
Trp Thr Tyr Asn Ala Glu Leu Leu Val Leu Met Glu Asn Glu Arg Thr
            420                 425                 430

Leu Asp Phe His Asp Ser Asn Val Lys Asn Leu Tyr Asp Lys Val Arg
        435                 440                 445

Met Gln Leu Arg Asp Asn Val Lys Glu Leu Gly Asn Gly Cys Phe Glu
    450                 455                 460

Phe Tyr His Lys Cys Asp Asp Glu Cys Met Asn Ser Val Lys Asn Gly
465                 470                 475                 480

Thr Tyr Asp Tyr Pro Lys Tyr Glu Glu Glu Ser Lys Leu Asn Arg Asn
                485                 490                 495

Glu Ile Lys Gly Val Lys Leu Ser Ser Met Gly Val Tyr Gln Ile Leu
            500                 505                 510

Ala Ile Tyr Ala Thr Val Ala Gly Ser Leu Ser Leu Ala Ile Met Met
        515                 520                 525

Ala Gly Ile Ser Phe Trp Met Cys Ser Asn Gly Ser Leu Gln Cys Arg
    530                 535                 540

Ile Cys Ile
545


<210> SEQ ID NO 100
<211> LENGTH: 541
<212> TYPE: PRT
<213> ORGANISM: Artificial Sequence
<220> FEATURE:
<223> OTHER INFORMATION: Synthesized [Influenza A virus
      A/Brisbane/10/2007(H3N2)

<400> SEQUENCE: 100

Thr Ala Thr Leu Cys Leu Gly His His Ala Val Pro Asn Gly Thr Ile
1               5                   10                  15

Val Lys Thr Ile Thr Asn Asp Gln Ile Glu Val Thr Asn Ala Thr Glu
            20                  25                  30

Leu Val Gln Ser Ser Ser Thr Gly Glu Ile Cys Asp Ser Pro His Gln
        35                  40                  45

Ile Leu Asp Gly Glu Asn Cys Thr Leu Ile Asp Ala Leu Leu Gly Asp
    50                  55                  60

Pro Gln Cys Asp Gly Phe Gln Asn Lys Lys Trp Asp Leu Phe Val Glu
65                  70                  75                  80

Arg Ser Lys Ala Tyr Ser Asn Cys Tyr Pro Tyr Asp Val Pro Asp Tyr
                85                  90                  95

Ala Ser Leu Arg Ser Leu Val Ala Ser Ser Gly Thr Leu Glu Phe Asn
            100                 105                 110

Asn Glu Ser Phe Asn Trp Thr Gly Val Thr Gln Asn Gly Thr Ser Ser
        115                 120                 125

Ala Cys Ile Arg Arg Ser Asn Asn Ser Phe Phe Ser Arg Leu Asn Trp
    130                 135                 140

Leu Thr His Leu Lys Phe Lys Tyr Pro Ala Leu Asn Val Thr Met Pro
145                 150                 155                 160

Asn Asn Glu Lys Phe Asp Lys Leu Tyr Ile Trp Gly Val His His Pro
                165                 170                 175

Gly Thr Asp Asn Asp Gln Ile Phe Leu Tyr Ala Gln Ala Ser Gly Arg
            180                 185                 190

Ile Thr Val Ser Thr Lys Arg Ser Gln Gln Thr Val Ile Pro Asn Ile
        195                 200                 205

Gly Ser Arg Pro Arg Val Arg Asn Ile Pro Ser Arg Ile Ser Ile Tyr
    210                 215                 220
```

Trp Thr Ile Val Lys Pro Gly Asp Ile Leu Leu Ile Asn Ser Thr Gly
225 230 235 240

Asn Leu Ile Ala Pro Arg Gly Tyr Phe Lys Ile Arg Ser Gly Lys Ser
245 250 255

Ser Ile Met Arg Ser Asp Ala Pro Ile Gly Lys Cys Asn Ser Glu Cys
260 265 270

Ile Thr Pro Asn Gly Ser Ile Pro Asn Asp Lys Pro Phe Gln Asn Val
275 280 285

Asn Arg Ile Thr Tyr Gly Ala Cys Pro Arg Tyr Val Lys Gln Asn Thr
290 295 300

Leu Lys Leu Ala Thr Gly Met Arg Asn Val Pro Glu Lys Gln Thr Arg
305 310 315 320

Gly Ile Phe Gly Ala Ile Ala Gly Phe Ile Glu Asn Gly Trp Glu Gly
325 330 335

Met Val Asp Gly Trp Tyr Gly Phe Arg His Gln Asn Ser Glu Gly Ile
340 345 350

Gly Gln Ala Ala Asp Leu Lys Ser Thr Gln Ala Ala Ile Asp Gln Ile
355 360 365

Asn Gly Lys Leu Asn Arg Leu Ile Gly Lys Thr Asn Glu Lys Phe His
370 375 380

Gln Ile Glu Lys Glu Phe Ser Glu Val Glu Gly Arg Ile Gln Asp Leu
385 390 395 400

Glu Lys Tyr Val Glu Asp Thr Lys Ile Asp Leu Trp Ser Tyr Asn Ala
405 410 415

Glu Leu Leu Val Ala Leu Glu Asn Gln His Thr Ile Asp Leu Thr Asp
420 425 430

Ser Glu Met Asn Lys Leu Phe Glu Lys Thr Lys Lys Gln Leu Arg Glu
435 440 445

Asn Ala Glu Asp Met Gly Asn Gly Cys Phe Lys Ile Tyr His Lys Cys
450 455 460

Asp Asn Ala Cys Ile Gly Ser Ile Arg Asn Gly Thr Tyr Asp His Asp
465 470 475 480

Val Tyr Arg Asp Glu Ala Leu Asn Asn Arg Phe Gln Ile Lys Gly Val
485 490 495

Glu Leu Lys Ser Gly Tyr Lys Asp Trp Ile Leu Trp Ile Ser Phe Ala
500 505 510

Ile Ser Cys Phe Leu Leu Cys Val Ala Leu Leu Gly Phe Ile Met Trp
515 520 525

Ala Cys Gln Lys Gly Asn Ile Arg Cys Asn Ile Cys Ile
530 535 540

<210> SEQ ID NO 101
<211> LENGTH: 541
<212> TYPE: PRT
<213> ORGANISM: Artificial Sequence
<220> FEATURE:
<223> OTHER INFORMATION: Synthesized A/Wisconsin/67e5/2005(H3)

<400> SEQUENCE: 101

Thr Ala Thr Leu Cys Leu Gly His His Ala Val Pro Asn Gly Thr Ile
1 5 10 15

Val Lys Thr Ile Thr Asn Asp Gln Ile Glu Val Thr Asn Ala Thr Glu
20 25 30

Leu Val Gln Ser Ser Ser Thr Gly Gly Ile Cys Asp Ser Pro His Gln
35 40 45

-continued

```
Ile Leu Asp Gly Glu Asn Cys Thr Leu Ile Asp Ala Leu Leu Gly Asp
    50                  55                  60

Pro Gln Cys Asp Gly Phe Gln Asn Lys Lys Trp Asp Leu Phe Val Glu
65                  70                  75                  80

Arg Ser Lys Ala Tyr Ser Asn Cys Tyr Pro Tyr Asp Val Pro Asp Tyr
                85                  90                  95

Ala Ser Leu Arg Ser Leu Val Ala Ser Ser Gly Thr Leu Glu Phe Asn
            100                 105                 110

Asp Glu Ser Phe Asn Trp Thr Gly Val Thr Gln Asn Gly Thr Ser Ser
        115                 120                 125

Ala Cys Lys Arg Arg Ser Asn Asn Ser Phe Phe Ser Arg Leu Asn Trp
    130                 135                 140

Leu Thr His Leu Lys Phe Lys Tyr Pro Ala Leu Asn Val Thr Met Pro
145                 150                 155                 160

Asn Asn Glu Lys Phe Asp Lys Leu Tyr Ile Trp Gly Val His His Pro
                165                 170                 175

Gly Thr Asp Asn Asp Gln Ile Phe Leu His Ala Gln Ala Ser Gly Arg
            180                 185                 190

Ile Thr Val Ser Thr Lys Arg Ser Gln Gln Thr Val Ile Pro Asn Ile
        195                 200                 205

Gly Ser Arg Pro Arg Ile Arg Asn Ile Pro Ser Arg Ile Ser Ile Tyr
    210                 215                 220

Trp Thr Ile Val Lys Pro Gly Asp Ile Leu Leu Ile Asn Ser Thr Gly
225                 230                 235                 240

Asn Leu Ile Ala Pro Arg Gly Tyr Phe Lys Ile Arg Ser Gly Lys Ser
                245                 250                 255

Ser Ile Met Arg Ser Asp Ala Pro Ile Gly Lys Cys Asn Ser Glu Cys
            260                 265                 270

Ile Thr Pro Asn Gly Ser Ile Pro Asn Asp Lys Pro Phe Gln Asn Val
        275                 280                 285

Asn Arg Ile Thr Tyr Gly Ala Cys Pro Arg Tyr Val Lys Gln Asn Thr
    290                 295                 300

Leu Lys Leu Ala Thr Gly Met Arg Asn Val Pro Glu Lys Gln Thr Arg
305                 310                 315                 320

Gly Ile Phe Gly Ala Ile Ala Gly Phe Ile Glu Asn Gly Trp Glu Gly
                325                 330                 335

Met Val Asp Gly Trp Tyr Gly Phe Arg His Gln Asn Ser Glu Gly Ile
            340                 345                 350

Gly Gln Ala Ala Asp Leu Lys Ser Thr Gln Ala Ala Ile Asn Gln Ile
        355                 360                 365

Asn Gly Lys Leu Asn Arg Leu Ile Gly Lys Thr Asn Glu Lys Phe His
    370                 375                 380

Gln Ile Glu Lys Glu Phe Ser Glu Val Glu Gly Arg Ile Gln Asp Leu
385                 390                 395                 400

Glu Lys Tyr Val Glu Asp Thr Lys Ile Asp Leu Trp Ser Tyr Asn Ala
                405                 410                 415

Glu Leu Leu Val Ala Leu Glu Asn Gln His Thr Ile Asp Leu Thr Asp
            420                 425                 430

Ser Glu Met Asn Lys Leu Phe Glu Arg Thr Lys Lys Gln Leu Arg Glu
        435                 440                 445

Asn Ala Glu Asp Met Gly Asn Gly Cys Phe Lys Ile Tyr His Lys Cys
    450                 455                 460
```

-continued

Asp Asn Ala Cys Ile Gly Ser Ile Arg Asn Gly Thr Tyr Asp His Asp
465 470 475 480

Val Tyr Arg Asp Glu Ala Leu Asn Asn Arg Phe Gln Ile Lys Gly Val
485 490 495

Glu Leu Lys Ser Gly Tyr Lys Asp Trp Ile Leu Trp Ile Ser Phe Ala
500 505 510

Ile Ser Cys Phe Leu Leu Cys Val Ala Leu Leu Gly Phe Ile Met Trp
515 520 525

Ala Cys Gln Lys Gly Asn Ile Arg Cys Asn Ile Cys Ile
530 535 540

<210> SEQ ID NO 102
<211> LENGTH: 551
<212> TYPE: PRT
<213> ORGANISM: Artificial Sequence
<220> FEATURE:
<223> OTHER INFORMATION: Synthesized Influenza A virus
A/Anhui/1/2005(H5N1)

<400> SEQUENCE: 102

Asp Gln Ile Cys Ile Gly Tyr His Ala Asn Asn Ser Thr Glu Gln Val
1 5 10 15

Asp Thr Ile Met Glu Lys Asn Val Thr Val Thr His Ala Gln Asp Ile
20 25 30

Leu Glu Lys Thr His Asn Gly Lys Leu Cys Asp Leu Asp Gly Val Lys
35 40 45

Pro Leu Ile Leu Arg Asp Cys Ser Val Ala Gly Trp Leu Leu Gly Asn
50 55 60

Pro Met Cys Asp Glu Phe Ile Asn Val Pro Glu Trp Ser Tyr Ile Val
65 70 75 80

Glu Lys Ala Asn Pro Ala Asn Asp Leu Cys Tyr Pro Gly Asn Phe Asn
85 90 95

Asp Tyr Glu Glu Leu Lys His Leu Leu Ser Arg Ile Asn His Phe Glu
100 105 110

Lys Ile Gln Ile Ile Pro Lys Ser Ser Trp Ser Asp His Glu Ala Ser
115 120 125

Ser Gly Val Ser Ser Ala Cys Pro Tyr Gln Gly Thr Pro Ser Phe Phe
130 135 140

Arg Asn Val Val Trp Leu Ile Lys Lys Asn Asn Thr Tyr Pro Thr Ile
145 150 155 160

Lys Arg Ser Tyr Asn Asn Thr Asn Gln Glu Asp Leu Leu Ile Leu Trp
165 170 175

Gly Ile His His Ser Asn Asp Ala Ala Glu Gln Thr Lys Leu Tyr Gln
180 185 190

Asn Pro Thr Thr Tyr Ile Ser Val Gly Thr Ser Thr Leu Asn Gln Arg
195 200 205

Leu Val Pro Lys Ile Ala Thr Arg Ser Lys Val Asn Gly Gln Ser Gly
210 215 220

Arg Met Asp Phe Phe Trp Thr Ile Leu Lys Pro Asn Asp Ala Ile Asn
225 230 235 240

Phe Glu Ser Asn Gly Asn Phe Ile Ala Pro Glu Tyr Ala Tyr Lys Ile
245 250 255

Val Lys Lys Gly Asp Ser Ala Ile Val Lys Ser Glu Val Glu Tyr Gly
260 265 270

Asn Cys Asn Thr Lys Cys Gln Thr Pro Ile Gly Ala Ile Asn Ser Ser
275 280 285

Met Pro Phe His Asn Ile His Pro Leu Thr Ile Gly Glu Cys Pro Lys
290 295 300

Tyr Val Lys Ser Asn Lys Leu Val Leu Ala Thr Gly Leu Arg Asn Ser
305 310 315 320

Pro Leu Arg Glu Arg Arg Arg Lys Arg Gly Leu Phe Gly Ala Ile Ala
325 330 335

Gly Phe Ile Glu Gly Gly Trp Gln Gly Met Val Asp Gly Trp Tyr Gly
340 345 350

Tyr His His Ser Asn Glu Gln Gly Ser Gly Tyr Ala Ala Asp Lys Glu
355 360 365

Ser Thr Gln Lys Ala Ile Asp Gly Val Thr Asn Lys Val Asn Ser Ile
370 375 380

Ile Asp Lys Met Asn Thr Gln Phe Glu Ala Val Gly Arg Glu Phe Asn
385 390 395 400

Asn Leu Glu Arg Arg Ile Glu Asn Leu Asn Lys Lys Met Glu Asp Gly
405 410 415

Phe Leu Asp Val Trp Thr Tyr Asn Ala Glu Leu Leu Val Leu Met Glu
420 425 430

Asn Glu Arg Thr Leu Asp Phe His Asp Ser Asn Val Lys Asn Leu Tyr
435 440 445

Asp Lys Val Arg Leu Gln Leu Arg Asp Asn Ala Lys Glu Leu Gly Asn
450 455 460

Gly Cys Phe Glu Phe Tyr His Lys Cys Asp Asn Glu Cys Met Glu Ser
465 470 475 480

Val Arg Asn Gly Thr Tyr Asp Tyr Pro Gln Tyr Ser Glu Glu Ala Arg
485 490 495

Leu Lys Arg Glu Glu Ile Ser Gly Val Lys Leu Glu Ser Ile Gly Thr
500 505 510

Tyr Gln Ile Leu Ser Ile Tyr Ser Thr Val Ala Ser Ser Leu Ala Leu
515 520 525

Ala Ile Met Val Ala Gly Leu Ser Leu Trp Met Cys Ser Asn Gly Ser
530 535 540

Leu Gln Cys Arg Ile Cys Ile
545 550

<210> SEQ ID NO 103
<211> LENGTH: 552
<212> TYPE: PRT
<213> ORGANISM: Artificial Sequence
<220> FEATURE:
<223> OTHER INFORMATION: Synthesized [Influenza A virus
A/Vietnam/1194/2004(H5N1)

<400> SEQUENCE: 103

Asp Gln Ile Cys Ile Gly Tyr His Ala Asn Asn Ser Thr Glu Gln Val
1 5 10 15

Asp Thr Ile Met Glu Lys Asn Val Thr Val Thr His Ala Gln Asp Ile
20 25 30

Leu Glu Lys Thr His Asn Gly Lys Leu Cys Asp Leu Asp Gly Val Lys
35 40 45

Pro Leu Ile Leu Arg Asp Cys Ser Val Ala Gly Trp Leu Leu Gly Asn
50 55 60

Pro Met Cys Asp Glu Phe Ile Asn Val Pro Glu Trp Ser Tyr Ile Val
65 70 75 80

Glu Lys Ala Asn Pro Val Asn Asp Leu Cys Tyr Pro Gly Asp Phe Asn

-continued

```
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Ser His Glu Ala Ser
        115                 120                 125

Leu Gly Val Ser Ser Ala Cys Pro Tyr Gln Gly Lys Ser Ser Phe Phe
    130                 135                 140

Arg Asn Val Val Trp Leu Ile Lys Lys Asn Ser Thr Tyr Pro Thr Ile
145                 150                 155                 160

Lys Arg Ser Tyr Asn Asn Thr Asn Gln Glu Asp Leu Leu Val Leu Trp
                165                 170                 175

Gly Ile His His Pro Lys Asp Ala Ala Glu Gln Thr Lys Leu Tyr Gln
            180                 185                 190

Asn Pro Thr Thr Tyr Ile Ser Val Gly Thr Ser Thr Leu Asn Gln Arg
        195                 200                 205

Leu Val Pro Arg Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Thr Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Arg Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Val Arg Asn Gly Thr Tyr Asp Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510
```

```
Ile Tyr Gln Ile Leu Ser Ile Tyr Ser Thr Val Ala Ser Ser Leu Ala
        515                 520                 525

Leu Ala Ile Met Val Ala Gly Leu Ser Leu Trp Met Cys Ser Asn Gly
    530                 535                 540

Ser Leu Gln Cys Arg Ile Cys Ile
545                 550


<210> SEQ ID NO 104
<211> LENGTH: 553
<212> TYPE: PRT
<213> ORGANISM: Artificial sequence
<220> FEATURE:
<223> OTHER INFORMATION: Synthesized A/Indonesia/5/2005(H5N1)

<400> SEQUENCE: 104

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320
```

```
Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
        515                 520                 525

Leu Ala Ile Met Met Ala Gly Leu Ser Leu Trp Met Cys Ser Asn Gly
    530                 535                 540

Ser Leu Gln Cys Arg Ile Cys Ile Lys
545                 550


<210> SEQ ID NO 105
<211> LENGTH: 548
<212> TYPE: PRT
<213> ORGANISM: Artificial Sequence
<220> FEATURE:
<223> OTHER INFORMATION: Construct 900

<400> SEQUENCE: 105

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Tyr Asp Val Pro
                85                  90                  95

Asp Tyr Ala Ser Leu Arg Ser Leu Val Ala Ser Ser Gly Thr Leu Glu
            100                 105                 110

Phe Asn Asn Glu Ser Phe Asn Trp Thr Gly Val Thr Gln Asn Gly Thr
        115                 120                 125
```

-continued

```
Ser Ser Ala Cys Ile Arg Arg Ser Asn Asn Ser Phe Phe Ser Arg Leu
    130                 135                 140

Asn Trp Leu Thr His Leu Lys Phe Lys Tyr Pro Ala Leu Asn Val Thr
145                 150                 155                 160

Met Pro Asn Asn Glu Lys Phe Asp Lys Leu Tyr Ile Trp Gly Val His
                165                 170                 175

His Pro Gly Thr Asp Asn Asp Gln Ile Phe Leu Tyr Ala Gln Ala Ser
            180                 185                 190

Gly Arg Ile Thr Val Ser Thr Lys Arg Ser Gln Gln Thr Val Ile Pro
        195                 200                 205

Asn Ile Gly Ser Arg Pro Arg Val Arg Asn Ile Pro Ser Arg Ile Ser
    210                 215                 220

Ile Tyr Trp Thr Ile Val Lys Pro Gly Asp Ile Leu Leu Ile Asn Ser
225                 230                 235                 240

Thr Gly Asn Leu Ile Ala Pro Arg Gly Tyr Phe Lys Ile Arg Ser Gly
                245                 250                 255

Lys Ser Ser Ile Met Lys Ser Glu Leu Glu Tyr Gly Asn Cys Asn Thr
            260                 265                 270

Lys Cys Gln Thr Pro Met Gly Ala Ile Asn Ser Ser Met Pro Phe His
        275                 280                 285

Asn Ile His Pro Leu Thr Ile Gly Glu Cys Pro Lys Tyr Val Lys Ser
    290                 295                 300

Asn Arg Leu Val Leu Ala Thr Gly Leu Arg Asn Ser Pro Gln Arg Glu
305                 310                 315                 320

Ser Arg Arg Lys Lys Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Val Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Ile Arg Asn
465                 470                 475                 480

Gly Thr Tyr Asn Tyr Pro Gln Tyr Ser Glu Glu Ala Arg Leu Lys Arg
                485                 490                 495

Glu Glu Ile Ser Gly Val Lys Leu Glu Ser Ile Gly Thr Tyr Gln Ile
            500                 505                 510

Leu Ser Ile Tyr Ser Thr Val Ala Ser Ser Leu Ala Leu Ala Ile Met
        515                 520                 525

Met Ala Gly Leu Ser Leu Trp Met Cys Ser Asn Gly Ser Leu Gln Cys
    530                 535                 540
```

Arg Ile Cys Ile
545

<210> SEQ ID NO 106
<211> LENGTH: 565
<212> TYPE: PRT
<213> ORGANISM: Artificial Sequence
<220> FEATURE:
<223> OTHER INFORMATION: Construct 745

<400> SEQUENCE: 106

Asp Gln Ile Cys Ile Gly Tyr His Ala Asn Asn Ser Thr Glu Gln Val
1 5 10 15

Asp Thr Ile Met Glu Lys Asn Val Thr Val Thr His Ala Gln Asp Ile
20 25 30

Leu Glu Lys Thr His Asn Gly Lys Leu Cys Asp Leu Asp Gly Val Lys
35 40 45

Pro Leu Ile Leu Arg Asp Cys Ser Val Ala Gly Trp Leu Leu Gly Asn
50 55 60

Pro Met Cys Asp Glu Phe Ile Asn Val Pro Glu Trp Ser Tyr Ile Val
65 70 75 80

Glu Lys Ala Asn Pro Thr Asn Asp Leu Cys Tyr Pro Ile Met His Asp
85 90 95

Arg Thr Lys Ile Arg Gln Leu Pro Asn Leu Leu Arg Gly Tyr Glu Asn
100 105 110

Ile Arg Leu Ser Thr Gln Asn Val Ile Asp Ala Glu Lys Ala Pro Gly
115 120 125

Gly Pro Tyr Arg Leu Gly Thr Ser Gly Ser Cys Pro Asn Ala Thr Ser
130 135 140

Lys Ser Gly Phe Phe Ala Thr Met Ala Trp Ala Val Pro Lys Asp Asn
145 150 155 160

Asn Lys Asn Ala Thr Asn Pro Leu Thr Val Glu Val Pro Tyr Ile Cys
165 170 175

Thr Glu Gly Glu Asp Gln Ile Thr Val Trp Gly Phe His Ser Asp Asn
180 185 190

Lys Thr Gln Met Lys Asn Leu Tyr Gly Asp Ser Asn Pro Gln Lys Phe
195 200 205

Thr Ser Ser Ala Asn Gly Val Thr Thr His Tyr Val Ser Gln Ile Gly
210 215 220

Ser Phe Pro Asp Gln Thr Glu Asp Gly Gly Leu Pro Gln Ser Gly Arg
225 230 235 240

Ile Val Val Asp Tyr Met Met Gln Lys Pro Gly Lys Thr Gly Thr Ile
245 250 255

Val Tyr Gln Arg Gly Val Leu Leu Pro Gln Lys Val Trp Cys Ala Ser
260 265 270

Gly Arg Ser Lys Ile Met Lys Ser Glu Leu Glu Tyr Gly Asn Cys Asn
275 280 285

Thr Lys Cys Gln Thr Pro Met Gly Ala Ile Asn Ser Ser Met Pro Phe
290 295 300

His Asn Ile His Pro Leu Thr Ile Gly Glu Cys Pro Lys Tyr Val Lys
305 310 315 320

Ser Asn Arg Leu Val Leu Ala Thr Gly Leu Arg Asn Ser Pro Gln Arg
325 330 335

Glu Ser Arg Arg Lys Lys Arg Gly Leu Phe Gly Ala Ile Ala Gly Phe
340 345 350

```
Ile Glu Gly Gly Trp Gln Gly Met Val Asp Gly Trp Tyr Gly Tyr His
        355                 360                 365

His Ser Asn Glu Gln Gly Ser Gly Tyr Ala Ala Asp Lys Glu Ser Thr
    370                 375                 380

Gln Lys Ala Ile Asp Gly Val Thr Asn Lys Val Asn Ser Ile Ile Asp
385                 390                 395                 400

Lys Met Asn Thr Gln Phe Glu Ala Val Gly Arg Glu Phe Asn Asn Leu
                405                 410                 415

Glu Arg Arg Ile Glu Asn Leu Asn Lys Lys Met Glu Asp Gly Phe Leu
            420                 425                 430

Asp Val Trp Thr Tyr Asn Ala Glu Leu Leu Val Leu Met Glu Asn Glu
        435                 440                 445

Arg Thr Leu Asp Phe His Asp Ser Asn Val Lys Asn Leu Tyr Asp Lys
    450                 455                 460

Val Arg Leu Gln Leu Arg Asp Asn Ala Lys Glu Leu Gly Asn Gly Cys
465                 470                 475                 480

Phe Glu Phe Tyr His Lys Cys Asp Asn Glu Cys Met Glu Ser Ile Arg
                485                 490                 495

Asn Gly Thr Tyr Asn Tyr Pro Gln Tyr Ser Glu Glu Ala Arg Leu Lys
            500                 505                 510

Arg Glu Glu Ile Ser Gly Val Lys Leu Glu Ser Ile Gly Thr Tyr Gln
        515                 520                 525

Ile Leu Ser Ile Tyr Ser Thr Val Ala Ser Ser Leu Ala Leu Ala Ile
    530                 535                 540

Met Met Ala Gly Leu Ser Leu Trp Met Cys Ser Asn Gly Ser Leu Gln
545                 550                 555                 560

Cys Arg Ile Cys Ile
                565


<210> SEQ ID NO 107
<211> LENGTH: 545
<212> TYPE: PRT
<213> ORGANISM: Artificial Sequence
<220> FEATURE:
<223> OTHER INFORMATION: Construct 910

<400> SEQUENCE: 107

Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Asp Ser Pro His Gln Ile
        35                  40                  45

Leu Asp Gly Glu Asn Cys Thr Leu Ile Asp Ala Leu Leu Gly Asp Pro
    50                  55                  60

Gln Cys Asp Gly Phe Gln Asn Lys Lys Trp Asp Leu Phe Val Glu Arg
65                  70                  75                  80

Ser Lys Ala Tyr Ser Asn Cys Tyr Pro Tyr Asp Val Pro Asp Tyr Ala
                85                  90                  95

Ser Leu Arg Ser Leu Val Ala Ser Ser Gly Thr Leu Glu Phe Asn Asn
            100                 105                 110

Glu Ser Phe Asn Trp Thr Gly Val Thr Gln Asn Gly Thr Ser Ser Ala
        115                 120                 125

Cys Ile Arg Arg Ser Asn Asn Ser Phe Phe Ser Arg Leu Asn Trp Leu
    130                 135                 140
```

-continued

```
Thr His Leu Lys Phe Lys Tyr Pro Ala Leu Asn Val Thr Met Pro Asn
145                 150                 155                 160

Asn Glu Lys Phe Asp Lys Leu Tyr Ile Trp Gly Val His His Pro Gly
                165                 170                 175

Thr Asp Asn Asp Gln Ile Phe Leu Tyr Ala Gln Ala Ser Gly Arg Ile
            180                 185                 190

Thr Val Ser Thr Lys Arg Ser Gln Gln Thr Val Ile Pro Asn Ile Gly
        195                 200                 205

Ser Arg Pro Arg Val Arg Asn Ile Pro Ser Arg Ile Ser Ile Tyr Trp
    210                 215                 220

Thr Ile Val Lys Pro Gly Asp Ile Leu Leu Ile Asn Ser Thr Gly Asn
225                 230                 235                 240

Leu Ile Ala Pro Arg Gly Tyr Phe Lys Ile Arg Ser Gly Lys Ser Ser
                245                 250                 255

Ile Met Arg Ser Asp Ala Pro Ile Gly Lys Cys Asn Thr Lys Cys Gln
            260                 265                 270

Thr Pro Met Gly Ala Ile Asn Ser Ser Met Pro Phe His Asn Ile His
        275                 280                 285

Pro Leu Thr Ile Gly Glu Cys Pro Lys Tyr Val Lys Ser Asn Arg Leu
    290                 295                 300

Val Leu Ala Thr Gly Leu Arg Asn Ser Pro Gln Arg Glu Ser Arg Arg
305                 310                 315                 320

Lys Lys Arg Gly Leu Phe Gly Ala Ile Ala Gly Phe Ile Glu Gly Gly
                325                 330                 335

Trp Gln Gly Met Val Asp Gly Trp Tyr Gly Tyr His His Ser Asn Glu
            340                 345                 350

Gln Gly Ser Gly Tyr Ala Ala Asp Lys Glu Ser Thr Gln Lys Ala Ile
        355                 360                 365

Asp Gly Val Thr Asn Lys Val Asn Ser Ile Ile Asp Lys Met Asn Thr
    370                 375                 380

Gln Phe Glu Ala Val Gly Arg Glu Phe Asn Asn Leu Glu Arg Arg Ile
385                 390                 395                 400

Glu Asn Leu Asn Lys Lys Met Glu Asp Gly Phe Leu Asp Val Trp Thr
                405                 410                 415

Tyr Asn Ala Glu Leu Leu Val Leu Met Glu Asn Glu Arg Thr Leu Asp
            420                 425                 430

Phe His Asp Ser Asn Val Lys Asn Leu Tyr Asp Lys Val Arg Leu Gln
        435                 440                 445

Leu Arg Asp Asn Ala Lys Glu Leu Gly Asn Gly Cys Phe Glu Phe Tyr
    450                 455                 460

His Lys Cys Asp Asn Glu Cys Met Glu Ser Ile Arg Asn Gly Thr Tyr
465                 470                 475                 480

Asn Tyr Pro Gln Tyr Ser Glu Glu Ala Arg Leu Lys Arg Glu Glu Ile
                485                 490                 495

Ser Gly Val Lys Leu Glu Ser Ile Gly Thr Tyr Gln Ile Leu Ser Ile
            500                 505                 510

Tyr Ser Thr Val Ala Ser Ser Leu Ala Leu Ala Ile Met Met Ala Gly
        515                 520                 525

Leu Ser Leu Trp Met Cys Ser Asn Gly Ser Leu Gln Cys Arg Ile Cys
    530                 535                 540

Ile
545
```

-continued

<210> SEQ ID NO 108
<211> LENGTH: 556
<212> TYPE: PRT
<213> ORGANISM: Artificial Sequence
<220> FEATURE:
<223> OTHER INFORMATION: Construct 920

<400> SEQUENCE: 108

```
Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Pro Asp Cys Leu Asn Cys
        35                  40                  45

Thr Asp Leu Asp Val Ala Leu Gly Arg Pro Met Cys Val Gly Thr Thr
    50                  55                  60

Pro Ser Ala Lys Ala Ser Ile Leu His Glu Val Lys Pro Val Thr Ser
65                  70                  75                  80

Gly Cys Phe Pro Ile Met His Asp Arg Thr Lys Ile Arg Gln Leu Pro
                85                  90                  95

Asn Leu Leu Arg Gly Tyr Glu Asn Ile Arg Leu Ser Thr Gln Asn Val
            100                 105                 110

Ile Asp Ala Glu Lys Ala Pro Gly Gly Pro Tyr Arg Leu Gly Thr Ser
        115                 120                 125

Gly Ser Cys Pro Asn Ala Thr Ser Lys Ser Gly Phe Phe Ala Thr Met
    130                 135                 140

Ala Trp Ala Val Pro Lys Asp Asn Asn Lys Asn Ala Thr Asn Pro Leu
145                 150                 155                 160

Thr Val Glu Val Pro Tyr Ile Cys Thr Glu Gly Glu Asp Gln Ile Thr
                165                 170                 175

Val Trp Gly Phe His Ser Asp Asn Lys Thr Gln Met Lys Asn Leu Tyr
            180                 185                 190

Gly Asp Ser Asn Pro Gln Lys Phe Thr Ser Ser Ala Asn Gly Val Thr
        195                 200                 205

Thr His Tyr Val Ser Gln Ile Gly Ser Phe Pro Asp Gln Thr Glu Asp
    210                 215                 220

Gly Gly Leu Pro Gln Ser Gly Arg Ile Val Val Asp Tyr Met Met Gln
225                 230                 235                 240

Lys Pro Gly Lys Thr Gly Thr Ile Val Tyr Gln Arg Gly Val Leu Leu
                245                 250                 255

Pro Gln Lys Val Trp Cys Ala Ser Gly Arg Ser Lys Val Ile Lys Gly
            260                 265                 270

Ser Leu Pro Leu Ile Gly Glu Ala Asp Cys Gln Thr Pro Met Gly Ala
        275                 280                 285

Ile Asn Ser Ser Met Pro Phe His Asn Ile His Pro Leu Thr Ile Gly
    290                 295                 300

Glu Cys Pro Lys Tyr Val Lys Ser Asn Arg Leu Val Leu Ala Thr Gly
305                 310                 315                 320

Leu Arg Asn Ser Pro Gln Arg Glu Ser Arg Arg Lys Lys Arg Gly Leu
                325                 330                 335

Phe Gly Ala Ile Ala Gly Phe Ile Glu Gly Gly Trp Gln Gly Met Val
            340                 345                 350

Asp Gly Trp Tyr Gly Tyr His His Ser Asn Glu Gln Gly Ser Gly Tyr
        355                 360                 365

Ala Ala Asp Lys Glu Ser Thr Gln Lys Ala Ile Asp Gly Val Thr Asn
```

```
        370                 375                 380

Lys Val Asn Ser Ile Ile Asp Lys Met Asn Thr Gln Phe Glu Ala Val
385                 390                 395                 400

Gly Arg Glu Phe Asn Asn Leu Glu Arg Arg Ile Glu Asn Leu Asn Lys
                405                 410                 415

Lys Met Glu Asp Gly Phe Leu Asp Val Trp Thr Tyr Asn Ala Glu Leu
            420                 425                 430

Leu Val Leu Met Glu Asn Glu Arg Thr Leu Asp Phe His Asp Ser Asn
        435                 440                 445

Val Lys Asn Leu Tyr Asp Lys Val Arg Leu Gln Leu Arg Asp Asn Ala
    450                 455                 460

Lys Glu Leu Gly Asn Gly Cys Phe Glu Phe Tyr His Lys Cys Asp Asn
465                 470                 475                 480

Glu Cys Met Glu Ser Ile Arg Asn Gly Thr Tyr Asn Tyr Pro Gln Tyr
                485                 490                 495

Ser Glu Glu Ala Arg Leu Lys Arg Glu Glu Ile Ser Gly Val Lys Leu
            500                 505                 510

Glu Ser Ile Gly Thr Tyr Gln Ile Leu Ser Ile Tyr Ser Thr Val Ala
        515                 520                 525

Ser Ser Leu Ala Leu Ala Ile Met Met Ala Gly Leu Ser Leu Trp Met
    530                 535                 540

Cys Ser Asn Gly Ser Leu Gln Cys Arg Ile Cys Ile
545                 550                 555


<210> SEQ ID NO 109
<211> LENGTH: 548
<212> TYPE: PRT
<213> ORGANISM: Artificial Sequence
<220> FEATURE:
<223> OTHER INFORMATION: Construct 930

<400> SEQUENCE: 109

Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Asp Leu Asp Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Asn Pro Thr Asn Asp Leu Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
```

```
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Lys Ser Glu Leu Glu Tyr Gly
            260                 265                 270

Asn Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asn Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Val Lys Leu Glu Ser Met Gly Val Tyr Gln Ile
            500                 505                 510

Leu Ala Ile Tyr Ser Thr Val Ala Ser Ser Leu Val Leu Leu Val Ser
        515                 520                 525

Leu Gly Ala Ile Ser Phe Trp Met Cys Ser Asn Gly Ser Leu Gln Cys
    530                 535                 540

Arg Ile Cys Ile
545
```

<210> SEQ ID NO 110
<211> LENGTH: 30
<212> TYPE: PRT
<213> ORGANISM: Artificial Sequence
<220> FEATURE:
<223> OTHER INFORMATION: Consensus sequence

<400> SEQUENCE: 110

Thr Thr Thr Thr Thr Thr Thr Thr Thr Thr Thr Thr Thr Thr Thr Thr
1 5 10 15

Thr Thr Thr Thr Thr Thr Thr Thr Thr Thr Thr Thr Thr Thr
20 25 30

<210> SEQ ID NO 111
<211> LENGTH: 552
<212> TYPE: PRT
<213> ORGANISM: Artificial Sequence
<220> FEATURE:
<223> OTHER INFORMATION: Construct 690 and 734

<400> SEQUENCE: 111

Asp Gln Ile Cys Ile Gly Tyr His Ala Asn Asn Ser Thr Glu Gln Val
1 5 10 15

Asp Thr Ile Met Glu Lys Asn Val Thr Val Thr His Ala Gln Asp Ile
20 25 30

Leu Glu Lys Thr His Asn Gly Lys Leu Cys Asp Leu Asp Gly Val Lys
35 40 45

Pro Leu Ile Leu Arg Asp Cys Ser Val Ala Gly Trp Leu Leu Gly Asn
50 55 60

Pro Met Cys Asp Glu Phe Ile Asn Val Pro Glu Trp Ser Tyr Ile Val
65 70 75 80

Glu Lys Ala Asn Pro Thr Asn Asp Leu Cys Tyr Pro Gly His Phe Ala
85 90 95

Asp Tyr Glu Glu Leu Arg Glu Gln Leu Ser Ser Val Ser Ser Phe Glu
100 105 110

Arg Phe Glu Ile Phe Pro Lys Glu Ser Ser Trp Pro Asn His Thr Val
115 120 125

Thr Gly Val Ser Ala Ser Cys Ser His Asn Gly Glu Ser Ser Phe Tyr
130 135 140

Arg Asn Leu Leu Trp Leu Thr Gly Lys Asn Gly Leu Tyr Pro Asn Leu
145 150 155 160

Ser Lys Ser Tyr Ala Asn Asn Lys Glu Lys Glu Val Leu Val Leu Trp
165 170 175

Gly Val His His Pro Pro Asn Ile Gly Asp Gln Lys Ala Leu Tyr His
180 185 190

Thr Glu Asn Ala Tyr Val Ser Val Val Ser Ser His Tyr Ser Arg Lys
195 200 205

Phe Thr Pro Glu Ile Ala Lys Arg Pro Lys Val Arg Asp Gln Glu Gly
210 215 220

Arg Ile Asn Tyr Tyr Trp Thr Leu Leu Glu Pro Gly Asp Thr Ile Ile
225 230 235 240

Phe Glu Ala Asn Gly Asn Leu Ile Ala Pro Arg Tyr Ala Phe Ala Leu
245 250 255

Ser Arg Gly Phe Gly Ser Gly Ile Met Lys Ser Glu Leu Glu Tyr Gly
260 265 270

Asn Cys Asn Thr Lys Cys Gln Thr Pro Met Gly Ala Ile Asn Ser Ser
275 280 285

Met Pro Phe His Asn Ile His Pro Leu Thr Ile Gly Glu Cys Pro Lys
290 295 300

Tyr Val Lys Ser Asn Arg Leu Val Leu Ala Thr Gly Leu Arg Asn Ser
305 310 315 320

Pro Gln Arg Glu Ser Arg Arg Lys Lys Arg Gly Leu Phe Gly Ala Ile

```
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365

Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
        515                 520                 525

Leu Ala Ile Met Met Ala Gly Leu Ser Leu Trp Met Cys Ser Asn Gly
    530                 535                 540

Ser Leu Gln Cys Arg Ile Cys Ile
545                 550
```

<210> SEQ ID NO 112
<211> LENGTH: 548
<212> TYPE: PRT
<213> ORGANISM: Artificial Sequence
<220> FEATURE:
<223> OTHER INFORMATION: Construct 696

<400> SEQUENCE: 112

```
Asp Thr Ile Cys Ile Gly Tyr His Ala Asn Asn Ser Thr Asp Thr Val
1               5                   10                  15

Asp Thr Val Leu Glu Lys Asn Val Thr Val Thr His Ser Val Asn Leu
            20                  25                  30

Leu Glu Asp Ser His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Thr Pro Asn Pro Glu Asn Gly Thr Cys Tyr Pro Gly Ser Phe Asn
                85                  90                  95

Asp Tyr Glu Glu Leu Lys His Leu Leu Ser Arg Ile Asn His Phe Glu
            100                 105                 110

Lys Ile Gln Ile Ile Pro Lys Ser Ser Trp Ser Asp His Glu Ala Ser
        115                 120                 125

Ser Gly Val Ser Ser Ala Cys Pro Tyr Leu Gly Ser Pro Ser Phe Phe
```

-continued

```
    130                 135                 140

Arg Asn Val Val Trp Leu Ile Lys Lys Asn Ser Thr Tyr Pro Thr Ile
145                 150                 155                 160

Lys Lys Ser Tyr Asn Asn Thr Asn Gln Glu Asp Leu Leu Val Leu Trp
                165                 170                 175

Gly Ile His His Pro Asn Asp Ala Ala Glu Gln Thr Arg Leu Tyr Gln
            180                 185                 190

Asn Pro Thr Thr Tyr Ile Ser Ile Gly Thr Ser Thr Leu Asn Gln Arg
        195                 200                 205

Leu Val Pro Lys Ile Ala Thr Arg Ser Lys Val Asn Gly Gln Ser Gly
    210                 215                 220

Arg Met Glu Phe Phe Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Ile Thr Ser Asn Ala Pro Met Asp
            260                 265                 270

Glu Cys Asp Ala Lys Cys Gln Thr Pro Gln Gly Ala Ile Asn Ser Ser
        275                 280                 285

Leu Pro Phe Gln Asn Val His Pro Val Thr Ile Gly Glu Cys Pro Lys
    290                 295                 300

Tyr Val Arg Ser Ala Lys Leu Arg Met Val Thr Gly Leu Arg Asn Ile
305                 310                 315                 320

Pro Ser Ile Gln Ser Arg Gly Leu Phe Gly Ala Ile Ala Gly Phe Ile
                325                 330                 335

Glu Gly Gly Trp Thr Gly Met Val Asp Gly Trp Tyr Gly Tyr His His
            340                 345                 350

Gln Asn Glu Gln Gly Ser Gly Tyr Ala Ala Asp Gln Lys Ser Thr Gln
        355                 360                 365

Asn Ala Ile Asn Gly Ile Thr Asn Lys Val Asn Ser Val Ile Glu Lys
    370                 375                 380

Met Asn Thr Gln Phe Thr Ala Val Gly Lys Glu Phe Asn Lys Leu Glu
385                 390                 395                 400

Arg Arg Met Glu Asn Leu Asn Lys Lys Val Asp Asp Gly Phe Leu Asp
                405                 410                 415

Ile Trp Thr Tyr Asn Ala Glu Leu Leu Val Leu Leu Glu Asn Glu Arg
            420                 425                 430

Thr Leu Asp Phe His Asp Ser Asn Val Lys Asn Leu Tyr Glu Lys Val
        435                 440                 445

Lys Ser Gln Leu Lys Asn Asn Ala Lys Glu Ile Gly Asn Gly Cys Phe
    450                 455                 460

Glu Phe Tyr His Lys Cys Asn Asn Glu Cys Met Glu Ser Val Lys Asn
465                 470                 475                 480

Gly Thr Tyr Asp Tyr Pro Lys Tyr Ser Glu Glu Ser Lys Leu Asn Arg
                485                 490                 495

Glu Lys Ile Asp Gly Val Lys Leu Glu Ser Met Gly Val Tyr Gln Ile
            500                 505                 510

Leu Ala Ile Tyr Ser Thr Val Ala Ser Ser Leu Val Leu Leu Val Ser
        515                 520                 525

Leu Gly Ala Ile Ser Phe Trp Met Cys Ser Asn Gly Ser Leu Gln Cys
    530                 535                 540

Arg Ile Cys Ile
545
```

<210> SEQ ID NO 113
<211> LENGTH: 552
<212> TYPE: PRT
<213> ORGANISM: Artificial Sequence
<220> FEATURE:
<223> OTHER INFORMATION: Construct 691

<400> SEQUENCE: 113

```
Asp Gln Ile Cys Ile Gly Tyr His Ala Asn Asn Ser Thr Glu Gln Val
1               5                   10                  15

Asp Thr Ile Met Glu Lys Asn Val Thr Val Thr His Ala Gln Asp Ile
            20                  25                  30

Leu Glu Lys Thr His Asn Gly Lys Leu Cys Leu Leu Lys Gly Ile Ala
        35                  40                  45

Pro Leu Gln Leu Gly Asn Cys Ser Val Ala Gly Trp Ile Leu Gly Asn
    50                  55                  60

Pro Glu Cys Glu Leu Leu Ile Ser Lys Glu Ser Trp Ser Tyr Ile Val
65                  70                  75                  80

Glu Lys Pro Asn Pro Glu Asn Gly Thr Cys Tyr Pro Gly His Phe Ala
                85                  90                  95

Asp Tyr Glu Glu Leu Arg Glu Gln Leu Ser Ser Val Ser Ser Phe Glu
            100                 105                 110

Arg Phe Glu Ile Phe Pro Lys Glu Ser Ser Trp Pro Asn His Thr Val
        115                 120                 125

Thr Gly Val Ser Ala Ser Cys Ser His Asn Gly Glu Ser Ser Phe Tyr
    130                 135                 140

Arg Asn Leu Leu Trp Leu Thr Gly Lys Asn Gly Leu Tyr Pro Asn Leu
145                 150                 155                 160

Ser Lys Ser Tyr Ala Asn Asn Lys Glu Lys Glu Val Leu Val Leu Trp
                165                 170                 175

Gly Val His His Pro Pro Asn Ile Gly Asp Gln Lys Ala Leu Tyr His
            180                 185                 190

Thr Glu Asn Ala Tyr Val Ser Val Val Ser Ser His Tyr Ser Arg Lys
        195                 200                 205

Phe Thr Pro Glu Ile Ala Lys Arg Pro Lys Val Arg Asp Gln Glu Gly
    210                 215                 220

Arg Ile Asn Tyr Tyr Trp Thr Leu Leu Glu Pro Gly Asp Thr Ile Ile
225                 230                 235                 240

Phe Glu Ala Asn Gly Asn Leu Ile Ala Pro Arg Tyr Ala Phe Ala Leu
                245                 250                 255

Ser Arg Gly Phe Gly Ser Gly Ile Ile Asn Ser Asn Ala Pro Met Asp
            260                 265                 270

Lys Cys Asn Thr Lys Cys Gln Thr Pro Met Gly Ala Ile Asn Ser Ser
        275                 280                 285

Met Pro Phe His Asn Ile His Pro Leu Thr Ile Gly Glu Cys Pro Lys
    290                 295                 300

Tyr Val Lys Ser Asn Arg Leu Val Leu Ala Thr Gly Leu Arg Asn Ser
305                 310                 315                 320

Pro Gln Arg Glu Ser Arg Arg Lys Lys Arg Gly Leu Phe Gly Ala Ile
                325                 330                 335

Ala Gly Phe Ile Glu Gly Gly Trp Gln Gly Met Val Asp Gly Trp Tyr
            340                 345                 350

Gly Tyr His His Ser Asn Glu Gln Gly Ser Gly Tyr Ala Ala Asp Lys
        355                 360                 365
```

```
Glu Ser Thr Gln Lys Ala Ile Asp Gly Val Thr Asn Lys Val Asn Ser
    370                 375                 380

Ile Ile Asp Lys Met Asn Thr Gln Phe Glu Ala Val Gly Arg Glu Phe
385                 390                 395                 400

Asn Asn Leu Glu Arg Arg Ile Glu Asn Leu Asn Lys Lys Met Glu Asp
                405                 410                 415

Gly Phe Leu Asp Val Trp Thr Tyr Asn Ala Glu Leu Leu Val Leu Met
            420                 425                 430

Glu Asn Glu Arg Thr Leu Asp Phe His Asp Ser Asn Val Lys Asn Leu
        435                 440                 445

Tyr Asp Lys Val Arg Leu Gln Leu Arg Asp Asn Ala Lys Glu Leu Gly
    450                 455                 460

Asn Gly Cys Phe Glu Phe Tyr His Lys Cys Asp Asn Glu Cys Met Glu
465                 470                 475                 480

Ser Ile Arg Asn Gly Thr Tyr Asn Tyr Pro Gln Tyr Ser Glu Glu Ala
                485                 490                 495

Arg Leu Lys Arg Glu Glu Ile Ser Gly Val Lys Leu Glu Ser Ile Gly
            500                 505                 510

Thr Tyr Gln Ile Leu Ser Ile Tyr Ser Thr Val Ala Ser Ser Leu Ala
        515                 520                 525

Leu Ala Ile Met Met Ala Gly Leu Ser Leu Trp Met Cys Ser Asn Gly
    530                 535                 540

Ser Leu Gln Cys Arg Ile Cys Ile
545                 550


<210> SEQ ID NO 114
<211> LENGTH: 10
<212> TYPE: PRT
<213> ORGANISM: Artificial Sequence
<220> FEATURE:
<223> OTHER INFORMATION: Construct 745 H5/Indo

<400> SEQUENCE: 114

Gln Ile Leu Ser Ile Tyr Ser Thr Val Ala
1               5                   10


<210> SEQ ID NO 115
<211> LENGTH: 8
<212> TYPE: PRT
<213> ORGANISM: Artificial Sequence
<220> FEATURE:
<223> OTHER INFORMATION: Construct No. 745 B/Florida

<400> SEQUENCE: 115

Leu Asn Asp Asp Gly Leu Asp Asn
1               5


<210> SEQ ID NO 116
<211> LENGTH: 7
<212> TYPE: PRT
<213> ORGANISM: Artificial Sequence
<220> FEATURE:
<223> OTHER INFORMATION: Construct No. 737 H3/Brisbane

<400> SEQUENCE: 116

Lys Gly Val Glu Leu Lys Ser
1               5


<210> SEQ ID NO 117
<211> LENGTH: 4
```

```
<212> TYPE: PRT
<213> ORGANISM: Artificial Sequence
<220> FEATURE:
<223> OTHER INFORMATION: Construct No. 737 H5/Indo

<400> SEQUENCE: 117

Ile Gly Thr Tyr
1


<210> SEQ ID NO 118
<211> LENGTH: 9
<212> TYPE: PRT
<213> ORGANISM: Artificial Sequence
<220> FEATURE:
<223> OTHER INFORMATION: H1/Brisbane on H5/Indo stem F1 + E1 H5/Indo

<400> SEQUENCE: 118

Asn Pro Thr Asn Asp Leu Cys Tyr Pro
1               5


<210> SEQ ID NO 119
<211> LENGTH: 8
<212> TYPE: PRT
<213> ORGANISM: Artificial Sequence
<220> FEATURE:
<223> OTHER INFORMATION: H1/Brisbane on H5/Indo stem RB H1/Bri

<400> SEQUENCE: 119

Gly His Phe Ala Asp Tyr Glu Glu
1               5


<210> SEQ ID NO 120
<211> LENGTH: 5
<212> TYPE: PRT
<213> ORGANISM: Artificial Sequence
<220> FEATURE:
<223> OTHER INFORMATION: H1/Brisbane on H5/Indo stem RB H1/Bri

<400> SEQUENCE: 120

Gly Phe Gly Ser Gly
1               5


<210> SEQ ID NO 121
<211> LENGTH: 8
<212> TYPE: PRT
<213> ORGANISM: Artificial Sequence
<220> FEATURE:
<223> OTHER INFORMATION: H1/Brisbane on H5/Indo stem E2 + F2 stop
      H5/Indo

<400> SEQUENCE: 121

Ile Met Lys Ser Glu Leu Glu Tyr
1               5


<210> SEQ ID NO 122
<211> LENGTH: 8
<212> TYPE: PRT
<213> ORGANISM: Artificial Sequence
<220> FEATURE:
<223> OTHER INFORMATION: H3/Brisbane on H5/Indo stem - RB H3/Bri

<400> SEQUENCE: 122

Tyr Asp Val Pro Asp Tyr Ala Ser
1               5


<210> SEQ ID NO 123
<211> LENGTH: 6
```

<212> TYPE: PRT
<213> ORGANISM: Artificial Sequence
<220> FEATURE:
<223> OTHER INFORMATION: B/Florida on H5/Indo stem - RB B/Flo

<400> SEQUENCE: 123

Arg Ser Gly Lys Ser Ser
1 5

<210> SEQ ID NO 124
<211> LENGTH: 9
<212> TYPE: PRT
<213> ORGANISM: Artificial Sequence
<220> FEATURE:
<223> OTHER INFORMATION: B/Florida on H5/Indo stem - RB B/Flo

<400> SEQUENCE: 124

Ile Met His Asp Arg Thr Lys Ile Arg
1 5

<210> SEQ ID NO 125
<211> LENGTH: 7
<212> TYPE: PRT
<213> ORGANISM: Artificial Sequence
<220> FEATURE:
<223> OTHER INFORMATION: B/Florida on H5/Indo stem - RB B/Flo

<400> SEQUENCE: 125

Cys Ala Ser Gly Arg Ser Lys
1 5

<210> SEQ ID NO 126
<211> LENGTH: 8
<212> TYPE: PRT
<213> ORGANISM: Artificial Sequence
<220> FEATURE:
<223> OTHER INFORMATION: H5/Indo on H1/New Cal stem - F1 + E1 H1/NC

<400> SEQUENCE: 126

Pro Glu Asn Gly Thr Cys Tyr Pro
1 5

<210> SEQ ID NO 127
<211> LENGTH: 5
<212> TYPE: PRT
<213> ORGANISM: Artificial Sequence
<220> FEATURE:
<223> OTHER INFORMATION: H5/Indo on H1/New Cal stem - RB H5/Indo

<400> SEQUENCE: 127

Gly Ser Phe Asn Asp
1 5

<210> SEQ ID NO 128
<211> LENGTH: 6
<212> TYPE: PRT
<213> ORGANISM: Artificial Sequence
<220> FEATURE:
<223> OTHER INFORMATION: H5/Indo on H1/New Cal stem - RB H5/Indo

<400> SEQUENCE: 128

Lys Lys Gly Asp Ser Ala
1 5

<210> SEQ ID NO 129
<211> LENGTH: 9
<212> TYPE: PRT

<213> ORGANISM: Artificial Sequence
<220> FEATURE:
<223> OTHER INFORMATION: H5/Indo on H1/New Cal stem - E2 + F2-stop H1/NC

<400> SEQUENCE: 129

Cys Asp Ala Lys Cys Gln Thr Pro Gln
1 5

<210> SEQ ID NO 130
<211> LENGTH: 12
<212> TYPE: PRT
<213> ORGANISM: Artificial Sequence
<220> FEATURE:
<223> OTHER INFORMATION: H1/Brisbane on H5/Indo Stem - F1 H5/Indo

<400> SEQUENCE: 130

Asp Ile Leu Glu Lys Thr His Asn Gly Lys Leu Cys
1 5 10

<210> SEQ ID NO 131
<211> LENGTH: 9
<212> TYPE: PRT
<213> ORGANISM: Artificial Sequence
<220> FEATURE:
<223> OTHER INFORMATION: H1/Brisbane on H5/Indo stem - E1-RB-E2 H1/Bri

<400> SEQUENCE: 131

Leu Leu Lys Gly Ile Ala Pro Leu Gln
1 5

<210> SEQ ID NO 132
<211> LENGTH: 7
<212> TYPE: PRT
<213> ORGANISM: Artificial Sequence
<220> FEATURE:
<223> OTHER INFORMATION: H1/Brisbane on H5/Indo stem - E1-RB-E2 H1/Bri

<400> SEQUENCE: 132

Ser Asn Ala Pro Met Asp Lys
1 5

<210> SEQ ID NO 133
<211> LENGTH: 6
<212> TYPE: PRT
<213> ORGANISM: Artificial Sequence
<220> FEATURE:
<223> OTHER INFORMATION: H1/Brisbane on H5/Indo stem - F2-stop H5/Indo

<400> SEQUENCE: 133

Cys Asn Thr Lys Cys Gln
1 5

<210> SEQ ID NO 134
<211> LENGTH: 9
<212> TYPE: PRT
<213> ORGANISM: Artificial Sequence
<220> FEATURE:
<223> OTHER INFORMATION: H3/Brisbane on H5/Indo stem - E1-RB-E2 H3/Bri

<400> SEQUENCE: 134

Asp Ser Pro His Gln Ile Leu Asp Gly
1 5

<210> SEQ ID NO 135
<211> LENGTH: 8
<212> TYPE: PRT
<213> ORGANISM: Artificial Sequence
<220> FEATURE:
<223> OTHER INFORMATION: H3/Brisbane on H5/Indo stem - E1-RB-E2 H3/Bri

<400> SEQUENCE: 135

Arg Ser Asp Ala Pro Ile Gly Lys
1               5

<210> SEQ ID NO 136
<211> LENGTH: 7
<212> TYPE: PRT
<213> ORGANISM: Artificial Sequence
<220> FEATURE:
<223> OTHER INFORMATION: B/Florida on H5/Indo stem - E1-RB-E2 B/Flo

<400> SEQUENCE: 136

Pro Asp Cys Leu Asn Cys Thr
1               5

<210> SEQ ID NO 137
<211> LENGTH: 9
<212> TYPE: PRT
<213> ORGANISM: Artificial Sequence
<220> FEATURE:
<223> OTHER INFORMATION: B/Florida on H5/Indo stem - E1-RB-E2 B/Flo

<400> SEQUENCE: 137

Ser Leu Pro Leu Ile Gly Glu Ala Asp
1               5

<210> SEQ ID NO 138
<211> LENGTH: 8
<212> TYPE: PRT
<213> ORGANISM: Artificial Sequence
<220> FEATURE:
<223> OTHER INFORMATION: B/Florida on H5/Indo stem - F2-stop H5/Indo

<400> SEQUENCE: 138

Cys Gln Thr Pro Met Gly Ala Ile
1               5

<210> SEQ ID NO 139
<211> LENGTH: 11
<212> TYPE: PRT
<213> ORGANISM: Artificial Sequence
<220> FEATURE:
<223> OTHER INFORMATION: H5/Indo on N1/New Cal stem - F1 H1/NC

<400> SEQUENCE: 139

Leu Leu Glu Asp Ser His Asn Gly Lys Leu Cys
1               5                   10

<210> SEQ ID NO 140
<211> LENGTH: 7
<212> TYPE: PRT
<213> ORGANISM: Artificial Sequence
<220> FEATURE:
<223> OTHER INFORMATION: H5/Indo on H1/New Cal stem - E1-RB-E2 H5/Indo

<400> SEQUENCE: 140

Asp Leu Asp Gly Val Lys Pro
1               5

<210> SEQ ID NO 141
<211> LENGTH: 7
<212> TYPE: PRT
<213> ORGANISM: Artificial Sequence
<220> FEATURE:

-continued

<223> OTHER INFORMATION: H5/Indo on H1/New Cal Stem - E1-RB-E2 H5/Indo

<400> SEQUENCE: 141

Ser Glu Leu Glu Tyr Gly Asn
1               5

<210> SEQ ID NO 142
<211> LENGTH: 9
<212> TYPE: PRT
<213> ORGANISM: Artificial Sequence
<220> FEATURE:
<223> OTHER INFORMATION: H5/Indo on H1/New Cal stem - F2-stop H1/NC

<400> SEQUENCE: 142

Cys Asp Ala Lys Cys Gln Thr Pro Gln
1               5

<210> SEQ ID NO 143
<211> LENGTH: 26
<212> TYPE: PRT
<213> ORGANISM: Artificial Sequence
<220> FEATURE:
<223> OTHER INFORMATION: Signal peptide of alfalfa protein disulfide isomerase gene

<400> SEQUENCE: 143

Met Ala Lys Asn Val Ala Ile Phe Gly Leu Leu Phe Ser Leu Leu Leu
1               5                   10                  15

Leu Val Pro Ser Gln Ile Phe Ala Glu Glu
            20                  25